(12) United States Patent
Howell et al.

(10) Patent No.: US 11,624,751 B2
(45) Date of Patent: Apr. 11, 2023

(54) BIOMARKERS FOR VITILIGO

(71) Applicant: Incyte Corporation, Wilmington, DE (US)

(72) Inventors: Michael D. Howell, Kennett Square, PA (US); Sherry Owens, Wilmington, DE (US); Beth Rumberger, Quarryville, PA (US); Huiqing Liu, Berwyn, PA (US)

(73) Assignee: Incyte Corporation, Wilmington, DE (US)

( * ) Notice: Subject to any disclaimer, the term of this patent is extended or adjusted under 35 U.S.C. 154(b) by 150 days.

(21) Appl. No.: 16/823,085

(22) Filed: Mar. 18, 2020

(65) Prior Publication Data

US 2020/0348313 A1    Nov. 5, 2020

Related U.S. Application Data

(60) Provisional application No. 62/820,647, filed on Mar. 19, 2019, provisional application No. 62/893,532, filed on Aug. 29, 2019.

(51) Int. Cl.
  *A61K 31/519*   (2006.01)
  *G01N 33/68*    (2006.01)
  *A61P 17/00*    (2006.01)

(52) U.S. Cl.
  CPC ....... *G01N 33/6863* (2013.01); *A61K 31/519* (2013.01); *A61P 17/00* (2018.01); *G01N 33/6866* (2013.01); *G01N 33/6869* (2013.01); *G01N 2800/207* (2013.01)

(58) Field of Classification Search
  CPC .... G01N 33/6863; A61P 17/00; A61K 31/519
  See application file for complete search history.

(56) References Cited

FOREIGN PATENT DOCUMENTS

| WO | 2018067422 A1 | 4/2018 |
| WO | 2018087202 A1 | 5/2018 |
| WO | 2018200786 A1 | 11/2018 |

OTHER PUBLICATIONS

Liu et al., "Repigmentation in vitiligo using the Janus kinase inhibitor tofacitinib may require concomitant light exposure", American Academy of Dermatalogy Inc., vol. 77, No. 4 (Aug. 17, 2017).

*Primary Examiner* — Paul V Ward
(74) *Attorney, Agent, or Firm* — Finnegan, Henderson, Farabow, Garrett & Dunner, LLP

(57) ABSTRACT

Biomarkers are provided that are associated with or predictive of a subject's responsiveness to a JAK inhibitor. The biomarkers, compositions, and methods described herein are useful in selecting appropriate treatment modalities for a subject having, suspected of having, or at risk of developing vitiligo.

8 Claims, 2 Drawing Sheets

| Protein | Name | Uniprot | Spearman Correlation (r) | p-value |
|---|---|---|---|---|
| FUCA1 | Alpha-L-fucosidase 1 | P04066 | 0.29793 | 0.0009 |
| GFRA2 | Neurturin receptor | O00451 | 0.26738 | 0.0029 |
| LDL receptor | Low-density lipoprotein (LDL) receptor | P01130 | 0.26536 | 0.0031 |
| AXL | AXL receptor tyrosine kinase | P30530 | 0.26184 | 0.0036 |
| t-PA | tissue plasminogen activator | P00750 | 0.24054 | 0.0076 |
| IL-1RT1 | Interleukin-1 receptor type 1 precursor | P14778 | 0.23947 | 0.0079 |
| EPHB4 | Ephrin type-B receptor 4 precursor | P54760 | 0.23673 | 0.0087 |
| TR-AP | Acid phosphatase 5, tartrate resistant | P13686 | 0.33356 | 0.0096 |
| PTPRF | Protein tyrosine phosphatase receptor type F | P10586 | 0.23339 | 0.0097 |
| PON2 | Paraoxonase/arylesterase 2 | Q62086 | 0.23263 | 0.0099 |
| DLK-1 | Protein delta homolog 1 precursor | P80370 | 0.22537 | 0.0126 |
| IL-20RA | Interleukin-20 receptor subunit alpha | Q9UHF4 | 0.21208 | 0.019 |

Fig. 3

| | Vehicle | | 0.15% QD | | 0.5% QD | | 1.5% QD | | 1.5% BID | |
|---|---|---|---|---|---|---|---|---|---|---|
| Assay | Fold Change | p-value | Fold Change | p-value | Fold Change | p-value | Fold Change | p-value | Fold Change | p-value |
| CXCL9 | 1.08 | 0.134 | 0.88 | 0.284 | 0.93 | 0.593 | 0.81 | 0.064 | 0.73 | <0.001 |
| CXCL10 | 1.04 | 0.337 | 0.92 | 0.336 | 0.89 | 0.183 | 0.70 | 0.002 | 0.68 | <0.001 |
| CCL19 | 1.04 | 0.262 | 0.94 | 0.340 | 0.92 | 0.088 | 0.70 | <0.001 | 0.71 | <0.001 |
| IL2-RA | 1.03 | 0.296 | 0.97 | 0.282 | 0.92 | 0.017 | 0.82 | 0.001 | 0.79 | <0.001 |
| CCL18 | 1.00 | 0.959 | 1.06 | 0.163 | 0.99 | 0.748 | 0.85 | 0.017 | 0.76 | 0.001 |
| IL12 | 1.01 | 0.831 | 0.94 | 0.239 | 0.99 | 0.936 | 0.80 | <0.001 | 0.85 | 0.001 |
| MMP12 | 1.07 | 0.154 | 0.98 | 0.727 | 0.92 | 0.116 | 0.86 | 0.021 | 0.81 | 0.001 |
| GZMB | 1.02 | 0.702 | 0.96 | 0.414 | 0.98 | 0.823 | 0.79 | 0.013 | 0.80 | 0.002 |
| Gal-9 | 1.01 | 0.686 | 1.00 | 0.904 | 1.02 | 0.688 | 0.96 | 0.269 | 0.95 | 0.017 |

BID, twice daily; CCL, chemokine C-C motif ligand; CXCL, C-X-C motif chemokine ligand; Gal-9, galectin-9; GZMB, granzyme B; IL, interleukin; IL2-RA, interleukin 2 receptor antagonist; MMP, matrix metalloprotease; QD, once daily.

Fig. 4

BIOMARKERS FOR VITILIGO

CROSS-REFERENCE TO RELATED APPLICATIONS

This application claims priority to U.S. Provisional Application No. 62/820,647, filed Mar. 19, 2019, and U.S. Provisional Application No. 62/893,532, filed Aug. 29, 2019. The content of each of the foregoing applications are incorporated by reference herein in their entirety.

TECHNICAL FIELD

The present invention relates generally to biomarkers and vitiligo.

BACKGROUND

Vitiligo occurs when the cells that produce melanin die or stop functioning, resulting in patchy loss of skin pigmentation. Nonsegmental vitiligo involves depigmentation in patches of skin all over the body. Depigmentation typically occurs on the face, neck, and scalp, and around body openings. Loss of pigmentation is also frequently seen in areas that tend to experience rubbing, impact, or other trauma, such as the hands, and arms. Segmental vitiligo is associated with smaller patches of depigmented skin that appear on one side of the body in a limited area.

Janus kinase (JAK) inhibitors have been developed as agents for the treatment of vitiligo. However, as for any therapeutic, JAK inhibitors may not be equally effective in all subjects that have vitiligo. There is a need for means of identifying those subjects having vitiligo that could most benefit from treatment with a JAK inhibitor as well as identifying those subjects that exhibit a therapeutic response to treatment with a JAK inhibitor.

SUMMARY

The present application is based, at least in part, on the identification of biomarkers that identify a subject that has undergone a therapeutic response to a JAK inhibitor and biomarkers that are predictive of a vitiligo subject's responsiveness to a JAK inhibitor. The change in level of certain proteins during the course of treatment is identified as a useful identifier of responsiveness to a JAK inhibitor. In addition, the baseline level of certain proteins and the baseline expression level of certain genes prior to treatment are identified as useful predictors of responsiveness to a JAK inhibitor. Thus, the biomarkers and compositions described herein are useful, for example, in identifying, stratifying, and/or selecting a patient or a subset of patients having, suspected of having, or at risk of developing vitiligo that could benefit, or have benefitted, from treatment with a JAK inhibitor. In addition, the methods described herein are useful, for example, in selecting appropriate treatment modalities (e.g., a JAK inhibitor) for a subject suffering from, suspected of having, or at risk of developing vitiligo.

The disclosure features a method of treating a human subject having, suspected of having, or at risk of developing vitiligo by: measuring, in a first biological sample obtained from the human subject prior to administering a JAK inhibitor, the concentration of CXCL9 and/or CXCL10; administering the JAK inhibitor to the human subject; and measuring, in a second biological sample obtained from the human subject after administering the JAK inhibitor, a reduced concentration, as compared to the first biological sample, of CXCL9 and/or CXCL10. In some embodiments, administration of the JAK inhibitor is continued.

In some embodiments, the method entails: measuring, in the first biological sample obtained from the human subject prior to administering the JAK inhibitor, the concentration of CXCL9; administering the JAK inhibitor to the human subject; and measuring, in the second biological sample obtained from the human subject after administering the JAK inhibitor, a reduced concentration, as compared to the first biological sample, of CXCL9. In some embodiments, administration of the JAK inhibitor is continued.

In some embodiments, the concentration of CXCL9 is reduced by at least 5% in the second biological sample as compared to the first biological sample.

In some embodiments, the concentration of CXCL9 is reduced by at least 10% in the second biological sample as compared to the first biological sample.

In some embodiments, the concentration of CXCL9 is reduced by at least 15% in the second biological sample as compared to the first biological sample.

In some embodiments, the method entails: measuring, in the first biological sample obtained from the human subject prior to administering the JAK inhibitor, the concentration of CXCL10; administering the JAK inhibitor to the human subject; and measuring, in the second biological sample obtained from the human subject after administering the JAK inhibitor, a reduced concentration, as compared to the first biological sample, of CXCL10. In some embodiments, administration of the JAK inhibitor is continued.

In some embodiments, the concentration of CXCL10 is reduced by at least 5% in the second biological sample as compared to the first biological sample.

In some embodiments, the concentration of CXCL10 is reduced by at least 10% in the second biological sample as compared to the first biological sample.

In some embodiments, the concentration of CXCL10 is reduced by at least 15% in the second biological sample as compared to the first biological sample.

In some embodiments, the method entails: measuring, in the first biological sample obtained from the human subject prior to administering the JAK inhibitor, the concentration of CXCL9 and CXCL10; administering the JAK inhibitor to the human subject; and measuring, in the second biological sample obtained from the human subject after administering the JAK inhibitor, a reduced concentration, as compared to the first biological sample, of CXCL9 and CXCL10. In some embodiments, administration of the JAK inhibitor is continued.

In some embodiments, the concentration of CXCL9 and CXCL10 are each reduced by at least 5% in the second biological sample as compared to the first biological sample.

In some embodiments, the concentration of CXCL9 and CXCL10 are each reduced by at least 10% in the second biological sample as compared to the first biological sample.

In some embodiments, the concentration of CXCL9 and CXCL10 are each reduced by at least 15% in the second biological sample as compared to the first biological sample.

In some embodiments, the JAK inhibitor is administered to the human subject at least once a week for a period of, e.g., at least 12 weeks (e.g., at least 3 months, at least 4 months, at least 5 months, at least 6 months, at least 7 months, at least 8 months, at least 9 months, at least 10 months, at least 11 months, or at least 12 months).

In some embodiments, the JAK inhibitor is administered to the human subject at least once a day for a period of, e.g., at least 12 weeks (e.g., at least 3 months, at least 4 months, at least 5 months, at least 6 months, at least 7 months, at least 8 months, at least 9 months, at least 10 months, at least 11 months, or at least 12 months).

In some embodiments, the JAK inhibitor is administered to the human subject at least two times each day for a period of, e.g., at least 12 weeks (e.g., at least 3 months, at least 4 months, at least 5 months, at least 6 months, at least 7 months, at least 8 months, at least 9 months, at least 10 months, at least 11 months, or at least 12 months).

In some embodiments, wherein the JAK inhibitor is topically administered to the human subject.

In some embodiments, the second biological sample is obtained from the human subject at least 12 weeks after the first administration of the JAK inhibitor.

In some embodiments, the second biological sample is obtained from the human subject at least 24 weeks after the first administration of the JAK inhibitor.

In some embodiments, a second therapeutic agent is administered to the human subject in combination with the JAK inhibitor.

In another aspect, the disclosure features a method of identifying a therapeutic response (e.g., prior to visible skin improvement) of a human subject having, suspected of having, or at risk of developing vitiligo to a JAK inhibitor by: measuring the concentration of CXCL9 and/or CXCL10 in a first biological sample obtained from the human subject before administering the JAK inhibitor; and measuring the concentration of CXCL9 and/or CXCL10 in a second biological sample obtained from the subject after administering the JAK inhibitor, wherein a reduced concentration in the second biological sample, as compared to the first biological sample, of CXCL9 and/or CXCL10 indicates that the human subject has undergone a therapeutic response (e.g., prior to visible skin improvement) to the JAK inhibitor.

In some embodiments, the concentration of CXCL9 is reduced by at least 5% in the second biological sample as compared to the first biological sample. In some embodiments, the concentration of CXCL10 is reduced by at least 5% in the second biological sample as compared to the first biological sample. In some embodiments, the concentration of CXCL9 and CXCL10 are each reduced by at least 5% in the second biological sample as compared to the first biological sample.

In some embodiments, the concentration of CXCL9 is reduced by at least 10% in the second biological sample as compared to the first biological sample. In some embodiments, the concentration of CXCL10 is reduced by at least 10% in the second biological sample as compared to the first biological sample. In some embodiments, the concentration of CXCL9 and CXCL10 are each reduced by at least 10% in the second biological sample as compared to the first biological sample.

In some embodiments, the concentration of CXCL9 is reduced by at least 15% in the second biological sample as compared to the first biological sample. In some embodiments, the concentration of CXCL10 is reduced by at least 15% in the second biological sample as compared to the first biological sample. In some embodiments, the concentration of CXCL9 and CXCL10 are each reduced by at least 15% in the second biological sample as compared to the first biological sample.

In another aspect, the disclosure features a method of treating a human subject having, suspected of having, or at risk of developing vitiligo by: measuring, in a first biological sample obtained from the human subject prior to administering a JAK inhibitor, the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of FAP, RET, CNTN5, FUCA1, ITGAV, ITGB5, THBS4, CD207, GDF-8, CDH6, MRC2, ICOSLG, TNXB, EDIL3, OSMR, GPC1, MIC-A/B, TGFR-2, LRRN1, TLR3, KIM1, ROBO2, CD70, CLMP, N-CDase, FCRL5, CTSV, SCARF2, PLXDC1, PRTG, ERBB4, MAGED1, CEACAM1, TSHB, PTK7, TGFR-2, ADAM 22, CTSC, DLK-1, USP8, SCARF2, TNFRSF13B, MB, TMPRSS5, NUDT5, MMP-3, MAEA, NEMO, IFN-gamma, IL18, AKT1S1, CASP-8, PPP1R2, ST2, VSIG4, SCGB3A2, HDGF, ICA1, IL13, PEBP1, PARK7, MAP4K5, FLI1, MMP-10, CCL24, TIMP4, MBL2, REG4, and CPA2; administering the JAK inhibitor to the human subject; and measuring, in a second biological sample obtained from the human subject after administering the JAK inhibitor, a reduced concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of FAP, RET, CNTN5, FUCA1, ITGAV, ITGB5, THBS4, CD207, GDF-8, CDH6, MRC2, ICOSLG, TNXB, EDIL3, OSMR, GPC1, MIC-A/B, TGFR-2, LRRN1, TLR3, KIM1, ROBO2, CD70, CLMP, N-CDase, FCRL5, CTSV, SCARF2, PLXDC1, PRTG, ERBB4, MAGED1, CEACAM1, TSHB, PTK7, TGFR-2, ADAM 22, CTSC, DLK-1, USP8, SCARF2, TNFRSF13B, MB, and TMPRSS5, and/or an increased concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of NUDT5, MMP-3, MAEA, NEMO, IFN-gamma, IL18, AKT1S1, CASP-8, PPP1R2, ST2, VSIG4, SCGB3A2, HDGF, ICA1, IL13, PEBP1, PARK7, MAP4K5, FLI1, MMP-10, CCL24, TIMP4, MBL2, REG4, and CPA2. In some embodiments, administration of the JAK inhibitor is continued.

In some embodiments, the method entails measuring, in a first biological sample obtained from the human subject prior to administering a JAK inhibitor, the concentration of at least one protein (e.g., at least 1, 2, 3, 4, 5, or 6 proteins) selected from the group consisting of FAP, RET, CNTN5, NUDT5, MMP-3, and MAEA; administering the JAK inhibitor to the human subject; and measuring, in a second biological sample obtained from the human subject after administering the JAK inhibitor, a reduced concentration, as compared to the first biological sample, of at least one protein (e.g., at least 1, 2, or 3 proteins) selected from the group consisting of FAP, RET, and CNTN5, and/or an increased concentration, as compared to the first biological sample, of at least one protein (e.g., at least 1, 2, or 3 proteins) selected from the group consisting of NUDT5, MMP-3, and MAEA. In some embodiments, administration of the JAK inhibitor is continued.

In some embodiments, the method entails measuring, in a first biological sample obtained from the human subject prior to administering a JAK inhibitor, the concentration of at least one protein (e.g., at least 1, 2, 3, or 4 proteins) selected from the group consisting of FAP, RET, NUDT5, and MMP-3; administering the JAK inhibitor to the human subject; and measuring, in a second biological sample obtained from the human subject after administering the JAK inhibitor, a reduced concentration, as compared to the first biological sample, of at least one protein (e.g., at least 1 or 2 proteins) selected from the group consisting of FAP and RET, and/or an increased concentration, as compared to the first biological sample, of at least one protein (e.g., at least 1 or 2 proteins) selected from the group consisting of NUDT5 and MMP-3. In some embodiments, administration of the JAK inhibitor is continued.

In another aspect, the disclosure features a method of identifying a therapeutic response (e.g., prior to visible skin improvement) of a human subject having, suspected of having, or at risk of developing vitiligo to a JAK inhibitor by: measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of FAP, RET, CNTN5, FUCA1, ITGAV, ITGB5, THBS4, CD207, GDF-8, CDH6, MRC2, ICOSLG, TNXB, EDIL3, OSMR, GPC1, MIC-A/B, TGFR-2, LRRN1, TLR3, KIM1, ROBO2, CD70, CLMP, N-CDase, FCRL5, CTSV, SCARF2, PLXDC1, PRTG, ERBB4, MAGED1, CEACAM1, TSHB, PTK7, TGFR-2, ADAM 22, CTSC, DLK-1, USP8, SCARF2, TNFRSF13B, MB, TMPRSS5, NUDT5, MMP-3, MAEA, NEMO, IFN-gamma, IL18, AKT1S1, CASP-8, PPP1R2, ST2, VSIG4, SCGB3A2, HDGF, ICA1, IL13, PEBP1, PARK7, MAP4K5, FLI1, MMP-10, CCL24, TIMP4, MBL2, REG4, and CPA2 in a first biological sample obtained from the human subject before administering the JAK inhibitor; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of FAP, RET, CNTN5, FUCA1, ITGAV, ITGB5, THBS4, CD207, GDF-8, CDH6, MRC2, ICOSLG, TNXB, EDIL3, OSMR, GPC1, MIC-A/B, TGFR-2, LRRN1, TLR3, KIM1, ROBO2, CD70, CLMP, N-CDase, FCRL5, CTSV, SCARF2, PLXDC1, PRTG, ERBB4, MAGED1, CEACAM1, TSHB, PTK7, TGFR-2, ADAM 22, CTSC, DLK-1, USP8, SCARF2, TNFRSF13B, MB, TMPRSS5, NUDT5, MMP-3, MAEA, NEMO, IFN-gamma, IL18, AKT1S1, CASP-8, PPP1R2, ST2, VSIG4, SCGB3A2, HDGF, ICA1, IL13, PEBP1, PARK7, MAP4K5, FLI1, MMP-10, CCL24, TIMP4, MBL2, REG4, and CPA2 in a second biological sample obtained from the subject after administering the JAK inhibitor, wherein a reduced concentration in the second biological sample, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of FAP, RET, CNTN5, FUCA1, ITGAV, ITGB5, THBS4, CD207, GDF-8, CDH6, MRC2, ICOSLG, TNXB, EDIL3, OSMR, GPC1, MIC-A/B, TGFR-2, LRRN1, TLR3, KIM1, ROBO2, CD70, CLMP, N-CDase, FCRL5, CTSV, SCARF2, PLXDC1, PRTG, ERBB4, MAGED1, CEACAM1, TSHB, PTK7, TGFR-2, ADAM 22, CTSC, DLK-1, USP8, SCARF2, TNFRSF13B, MB, and TMPRSS5, and/or an increased concentration in the second biological sample, as compared to the first biological sample of at least one protein (e.g., at least 1, 2, 3, 4, 5, 6, 7, 8, 9, 10, 11, 12, 13, 14, 15, 16, 17, 18, 19, or 20 proteins) selected from the group consisting of NUDT5, MMP-3, MAEA, NEMO, IFN-gamma, IL18, AKT1S1, CASP-8, PPP1R2, ST2, VSIG4, SCGB3A2, HDGF, ICA1, IL13, PEBP1, PARK7, MAP4K5, FLI1, MMP-10, CCL24, TIMP4, MBL2, REG4, and CPA2 indicates that the human subject has undergone a therapeutic response (e.g., prior to visible skin improvement) to the JAK inhibitor.

In some embodiments, the method entails measuring the concentration of at least one protein (e.g., at least 1, 2, 3, 4, 5, or 6 proteins) selected from the group consisting of FAP, RET, CNTN5, NUDT5, MMP-3, and MAEA in a first biological sample obtained from the human subject before administering the JAK inhibitor; and measuring the concentration of at least one protein (e.g., at least 1, 2, 3, 4, 5, or 6 proteins) selected from the group consisting of FAP, RET, CNTN5, NUDT5, MMP-3, and MAEA in a second biological sample obtained from the subject after administering the JAK inhibitor, wherein a reduced concentration in the second biological sample, as compared to the first biological sample, of at least one protein (e.g., at least 1, 2, or 3 proteins) selected from the group consisting of FAP, RET, and CNTN5, and/or an increased concentration in the second biological sample, as compared to the first biological sample of at least one protein (e.g., at least 1, 2, or 3 proteins) selected from the group consisting of NUDT5, MMP-3, and MAEA indicates that the human subject has undergone a therapeutic response (e.g., prior to visible skin improvement) to the JAK inhibitor.

In some embodiments, the method entails measuring the concentration of at least one protein (e.g., at least 1, 2, 3, or 4 proteins) selected from the group consisting of FAP, RET, NUDT5, and MMP-3 in a first biological sample obtained from the human subject before administering the JAK inhibitor; and measuring the concentration of at least one protein (e.g., at least 1, 2, 3, or 4 proteins) selected from the group consisting of FAP, RET, NUDT5, and MMP-3 in a second biological sample obtained from the subject after administering the JAK inhibitor, wherein a reduced concentration in the second biological sample, as compared to the first biological sample, of at least one protein (e.g., at least 1 or 2 proteins) selected from the group consisting of FAP and RET, and/or an increased concentration in the second biological sample, as compared to the first biological sample of at least one protein (e.g., at least 1 or 2 proteins) selected from the group consisting of NUDT5 and MMP-3 indicates that the human subject has undergone a therapeutic response (e.g., prior to visible skin improvement) to the JAK inhibitor.

In another aspect, the disclosure features a method of treating a human subject having, suspected of having, or at risk of developing vitiligo by: measuring, in a first biological sample obtained from the human subject prior to administering a JAK inhibitor, the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of DDR1, NTRK2, CES2, SCARA5, GDF-8, BOC, PAEP, ARTN, CDNF, TMPRSS5, FLRT2, ROBO2, SIGLEC10, PRTG, SCARF2, CDH3, GFR-alpha-1, TSHB, CD200R1, RGMB, KYNU, HS3ST3B1, CHRDL2, CNTN1, VSIG4, ARHGAP1, B4GAT1, STX8, CRELD2, ARSA, BCAM, SCARF1, CA13, DAG1, LAIR1, GUSB, PMVK, PEAR1, GP1BA, TACC3, PARK7, ARHGEF12, SEMA7A, ESAM, FKBP5, ARHGAP1, SCAMP3, ABL1, EGF, TACC3, FKBP5, BID, PRDX5, STX8, CD63, SCARF1, PTPN1, CLEC1B, ARSB, FKBP1B, YES1, SRC, TNFSF14, PLXNB3, LRMP, CD164, DAG, PVALB, NAA10, TRIM5, ARHGEF12, HGF, CA13, SNAP23, SORT1, GP6, CTSS, PPIB, CRKL, MAP2K6, MANF, PMVK, ABHD14B, GUSB, FATC1, MAD1L1, EDAR, CEACAM8, GLB1, ST3GAL1, ARSA, ADAM 8, CD40, IFI30, ECE1, AXIN1, WFDC2, TBCB, CXCL13, ST1A1, KIF1BP, DPP7, VEGFA, CETN2, TGF-alpha, CD84, SNAP29, CASP-8, S100A11, GSTP1, CRADD, PRKAB1, HGF, STK4, RNASE3, SERPINB6, OSM, MK, FADD, CLEC11A, CD69, LOX-1, ITGA6, CLEC5A, BCAM, FES, TXNDC5, LAT2, CXCL11, PARP-1, APBB1IP, GZMB, and CRNN; administering the JAK inhibitor to the human subject; and measuring, in a second biological sample obtained from the human subject after administering the JAK inhibitor, a reduced concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of DDR1, NTRK2, CES2, SCARA5, GDF-8, BOC, PAEP, ARTN, CDNF, TMPRSS5, FLRT2, ROBO2, SIGLEC10, PRTG, SCARF2, CDH3, GFR-alpha-1, TSHB, CD200R1, RGMB, KYNU, HS3ST3B1, CHRDL2, and CNTN1, and/or an increased concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of VSIG4, ARHGAP1, B4GAT1, STX8, CRELD2, ARSA, BCAM, SCARF, CA13, DAG1, LAIR1, GUSB, PMVK, PEAR1, GP1BA, TACC3, PARK7, ARHGEF12, SEMA7A, ESAM, FKBP5, ARHGAP1, SCAMP3, ABL1, EGF, TACC3, FKBP5, BID, PRDX5, STX8, CD63, SCARF1, PTPN1, CLEC1B, ARSB, FKBP1B, YES1, SRC, TNFSF14, PLXNB3, LRMP, CD164, DAG1, PVALB, NAA10, TRIM5, ARHGEF12, HGF, CA13, SNAP23, SORT1, GP6, CTSS, PPIB, CRKL, MAP2K6, MANF, PMVK, ABHD14B, GUSB, FATC1, MAD1L1, EDAR, CEACAM8, GLB1, ST3GAL1, ARSA, ADAM 8, CD40, IFI30, ECE1, AXIN1, WFDC2, TBCB, CXCL13, ST1A1, KIF1BP, DPP7, VEGFA, CETN2, TGF-alpha, CD84, SNAP29, CASP-8, S100A11, GSTP1, CRADD, PRKAB1, HGF, STK4, RNASE3, SERPINB6, OSM, MK, FADD, CLEC11A, CD69, LOX-1, ITGA6, CLEC5A, BCAM, FES, TXNDC5, LAT2, CXCL11, PARP-1, APBB1IP, GZMB, and CRNN.

In some embodiments, the method entails measuring, in a first biological sample obtained from the human subject prior to administering a JAK inhibitor, the concentration of at least one protein (e.g., at least 1, 2, 3, 4, 5, or 6 proteins) selected from the group consisting of DDR1, NTRK2, CES2, VSIG4, ARHGAP1, and B4GAT1; administering the JAK inhibitor to the human subject; and measuring, in a second biological sample obtained from the human subject after administering the JAK inhibitor, a reduced concentration, as compared to the first biological sample, of at least one protein (e.g., at least 1, 2, or 3 proteins) selected from the group consisting of DDR1, NTRK2, and CES2, and/or an increased concentration, as compared to the first biological sample, of at least one protein (e.g., at least 1, 2, or 3 proteins) selected from the group consisting of VSIG4, ARHGAP1, and B4GAT1.

In some embodiments, the method entails measuring, in a first biological sample obtained from the human subject prior to administering a JAK inhibitor, the concentration of at least one protein (e.g., at least 1, 2, 3, or 4 proteins) selected from the group consisting of DDR1, NTRK2, VSIG4, and ARHGAP1; administering the JAK inhibitor to the human subject; and measuring, in a second biological sample obtained from the human subject after administering the JAK inhibitor, a reduced concentration, as compared to the first biological sample, of at least one protein (e.g., at least 1 or 2 proteins) selected from the group consisting of DDR1 and NTRK2, and/or an increased concentration, as compared to the first biological sample, of at least one protein (e.g., at least 1 or 2 proteins) selected from the group consisting of VSIG4 and ARHGAP1.

In another aspect, the disclosure features a method of identifying a therapeutic response of a human subject having, suspected of having, or at risk of developing vitiligo to a JAK inhibitor by: measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of DDR1, NTRK2, CES2, SCARA5, GDF-8, BOC, PAEP, ARTN, CDNF, TMPRSS5, FLRT2, ROBO2, SIGLEC10, PRTG, SCARF2, CDH3, GFR-alpha-1, TSHB, CD200R1, RGMB, KYNU, HS3ST3B1, CHRDL2, CNTN1, VSIG4, ARHGAP1, B4GAT1, STX8, CRELD2, ARSA, BCAM, SCARF1, CA13, DAG1, LAIR1, GUSB, PMVK, PEAR1, GP1BA, TACC3, PARK7, ARHGEF12, SEMA7A, ESAM, FKBP5, ARHGAP1, SCAMP3, ABL1, EGF, TACC3, FKBP5, BID, PRDX5, STX8, CD63, SCARF1, PTPN1, CLEC1B, ARSB, FKBP1B, YES1, SRC, TNFSF14, PLXNB3, LRMP, CD164, DAG1, PVALB, NAA10, TRIM5, ARHGEF12, HGF, CA13, SNAP23, SORT1, GP6, CTSS, PPIB, CRKL, MAP2K6, MANF, PMVK, ABHD14B, GUSB, FATC1, MAD1L1, EDAR, CEACAM8, GLB1, ST3GAL1, ARSA, ADAM 8, CD40, IFI30, ECE1, AXIN1, WFDC2, TBCB, CXCL13, ST1A1, KIF1BP, DPP7, VEGFA, CETN2, TGF-alpha, CD84, SNAP29, CASP-8, S100A11, GSTP1, CRADD, PRKAB1, HGF, STK4, RNASE3, SERPINB6, OSM, MK, FADD, CLEC11A, CD69, LOX-1, ITGA6, CLEC5A, BCAM, FES, TXNDC5, LAT2, CXCL11, PARP-1, APBB1IP, GZMB, and CRNN in a first biological sample obtained from the human subject before administering the JAK inhibitor; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of DDR1, NTRK2, CES2, SCARA5, GDF-8, BOC, PAEP, ARTN, CDNF, TMPRSS5, FLRT2, ROBO2, SIGLEC10, PRTG, SCARF2, CDH3, GFR-alpha-1, TSHB, CD200R1, RGMB, KYNU, HS3ST3B1, CHRDL2, CNTN1, VSIG4, ARHGAP1, B4GAT1, STX8, CRELD2, ARSA, BCAM, SCARF1, CA13, DAG1, LAIR1, GUSB, PMVK, PEAR1, GP1BA, TACC3, PARK7, ARHGEF12, SEMA7A, ESAM, FKBP5, ARHGAP1, SCAMP3, ABL1, EGF, TACC3, FKBP5, BID, PRDX5, STX8, CD63, SCARF1, PTPN1, CLEC1B, ARSB, FKBP1B, YES1, SRC, TNFSF14, PLXNB3, LRMP, CD164, DAG1, PVALB, NAA10, TRIM5, ARHGEF12, HGF, CA13, SNAP23, SORT1, GP6, CTSS, PPIB, CRKL, MAP2K6, MANF, PMVK, ABHD14B, GUSB, FATC1, MAD1L1, EDAR, CEACAM8, GLB1, ST3GAL1, ARSA, ADAM 8, CD40, IFI30, ECE1, AXIN1, WFDC2, TBCB, CXCL13, ST1A1, KIF1BP, DPP7, VEGFA, CETN2, TGF-alpha, CD84, SNAP29, CASP-8, S100A11, GSTP1, CRADD, PRKAB1, HGF, STK4, RNASE3, SERPINB6, OSM, MK, FADD, CLEC11A, CD69, LOX-1, ITGA6, CLEC5A, BCAM, FES, TXNDC5, LAT2, CXCL11, PARP-1, APBB1IP, GZMB, and CRNN in a second biological sample obtained from the subject after administering the JAK inhibitor, wherein a reduced concentration in the second biological sample, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of DDR1, NTRK2, CES2, SCARA5, GDF-8, BOC, PAEP, ARTN, CDNF, TMPRSS5, FLRT2, ROBO2, SIGLEC10, PRTG, SCARF2, CDH3, GFR-alpha-1, TSHB, CD200R1, RGMB, KYNU, HS3ST3B1, CHRDL2, and CNTN1, and/or an increased concentration in the second biological sample, as compared to the first biological sample of at least one protein (e.g., at least 1, 2, 3, 4, 5, 6, 7, 8, 9, 10, 11, 12, 13, 14, 15, 16, 17, 18, 19, or 20 proteins) selected from the group consisting of VSIG4, ARHGAP1, B4GAT1, STX8, CRELD2, ARSA, BCAM, SCARF1, CA13, DAG1, LAIR1, GUSB, PMVK, PEAR1, GP1BA, TACC3, PARK7, ARHGEF12, SEMA7A, ESAM, FKBP5, ARHGAP1, SCAMP3, ABL1, EGF, TACC3, FKBP5, BID, PRDX5, STX8, CD63, SCARF1, PTPN1, CLEC1B, ARSB, FKBP1B, YES1, SRC, TNFSF14, PLXNB3, LRMP, CD164, DAG1, PVALB, NAA10, TRIM5, ARHGEF12, HGF, CA13, SNAP23, SORT1, GP6, CTSS, PPIB, CRKL, MAP2K6, MANF, PMVK, ABHD14B, GUSB, FATC1, MAD1L1, EDAR, CEACAM8, GLB1, ST3GAL1, ARSA, ADAM 8, CD40, IFI30, ECE1, AXIN1, WFDC2, TBCB, CXCL13, ST1A1, KIF1BP, DPP7, VEGFA, CETN2, TGF-alpha, CD84, SNAP29, CASP-8, S100A11, GSTP1, CRADD, PRKAB1, HGF, STK4, RNASE3, SERPINB6, OSM, MK, FADD, CLEC11A, CD69, LOX-1, ITGA6, CLEC5A, BCAM, FES, TXNDC5, LAT2, CXCL11, PARP-1, APBB1IP, GZMB, and CRNN indicates that the human subject has not undergone a therapeutic response to the JAK inhibitor.

In some embodiments, the method entails measuring the concentration of at least one protein (e.g., at least 1, 2, 3, 4, 5, or 6 proteins) selected from the group consisting of DDR1, NTRK2, CES2, VSIG4, ARHGAP1, and B4GAT1 in a first biological sample obtained from the human subject before administering the JAK inhibitor; and measuring the concentration of at least one protein (e.g., at least 1, 2, 3, 4, 5, or 6 proteins) selected from the group consisting of DDR1, NTRK2, CES2, VSIG4, ARHGAP1, and B4GAT1 in a second biological sample obtained from the subject after administering the JAK inhibitor, wherein a reduced concentration in the second biological sample, as compared to the first biological sample, of at least one protein (e.g., at least 1, 2, or 3 proteins) selected from the group consisting of DDR1, NTRK2, and CES2, and/or an increased concentration in the second biological sample, as compared to the first biological sample of at least one protein (e.g., at least 1, 2, or 3 proteins) selected from the group consisting of VSIG4, ARHGAP1, and B4GAT1 indicates that the human subject has not undergone a therapeutic response to the JAK inhibitor.

In some embodiments, the method entails measuring the concentration of at least one protein (e.g., at least 1, 2, 3, or 4 proteins) selected from the group consisting of DDR1, NTRK2, VSIG4, and ARHGAP1 in a first biological sample obtained from the human subject before administering the JAK inhibitor; and measuring the concentration of at least one protein (e.g., at least 1, 2, 3, or 4 proteins) selected from the group consisting of DDR1, NTRK2, VSIG4, and ARHGAP1 in a second biological sample obtained from the subject after administering the JAK inhibitor, wherein a reduced concentration in the second biological sample, as compared to the first biological sample, of at least one protein (e.g., at least 1 or 2 proteins) selected from the group consisting of DDR1 and NTRK2, and/or an increased concentration in the second biological sample, as compared to the first biological sample of at least one protein (e.g., at least 1 or 2 proteins) selected from the group consisting of VSIG4 and ARHGAP1 indicates that the human subject has not undergone a therapeutic response to the JAK inhibitor.

In another aspect, the disclosure features a method of treating a human subject having, suspected of having, or at risk of developing vitiligo, comprising administering to the human subject a JAK inhibitor, wherein the human subject has been previously determined to have (i) a baseline concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of SCF, CPA2, P4HB, SPARCL1, ST2, SCF, CNDP1, TRAIL, KIRREL2, EGFR, ISLR2, PPP3R1, FCGR3B, MMP-3, IL-18BP, Flt3L, PPY, LTA4H, ITGB2, PTN, GPNMB, SIRPB1, PLTP, PSP-D, COMP, PAMR1, VASN, F11, IL10, CA3, CXCL10, Notch 3, NCAM1, PROC, CLEC14A, IL-12B, IL10, CD40, and IFN-gamma in a biological sample obtained from the human subject that is lower than a control, and/or (ii) a baseline concentration of at least one protein (e.g., at least 1, 2, 3, 4, or 5 proteins) selected from the group consisting of SERPINA12, GHRL, PREB, IL-20RA, and PON2 in a biological sample obtained from the human subject that is higher than a control.

In some embodiments, the method entails administering to the human subject a JAK inhibitor, wherein the human subject has been previously determined to have (i) a baseline concentration of at least one protein (e.g., at least 1, 2, or 3 proteins) selected from the group consisting of SCF, CPA2, and P4HB in a biological sample obtained from the human subject that is lower than a control, and/or (ii) a baseline concentration of at least one protein (e.g., at least 1, 2, or 3 proteins) selected from the group consisting of SERPINA12, GHRL, and PREB in a biological sample obtained from the human subject that is higher than a control.

In some embodiments, the method entails administering to the human subject a JAK inhibitor, wherein the human subject has been previously determined to have a baseline concentration of at least one protein (e.g., at least 1 or 2 proteins) selected from the group consisting of IL-20RA and PON2 in a biological sample obtained from the human subject that is higher than a control.

In another aspect, the disclosure features a method of treating a human subject having, suspected of having, or at risk of developing vitiligo, by: measuring in a biological sample obtained from the human subject a reduced concentration, as compared to a control, of at least one protein (e.g., at least 1, 2, 3, 4, 5, 6, 7, 8, 9, 10, 11, 12, 13, 14, 15, 16, 17, 18, 19, or 20 proteins) selected from the group consisting of SCF, CPA2, P4HB, SPARCL1, ST2, SCF, CNDP1, TRAIL, KIRREL2, EGFR, ISLR2, PPP3R1, FCGR3B, MMP-3, IL-18BP, Flt3L, PPY, LTA4H, ITGB2, PTN, GPNMB, SIRPB1, PLTP, PSP-D, COMP, PAMR1, VASN, F11, IL10, CA3, CXCL10, Notch 3, NCAM1, PROC, CLEC14A, IL-12B, IL10, CD40, and IFN-gamma, and/or an increased concentration, as compared to a control, of at least one protein (e.g., at least 1, 2, 3, 5, or 5 proteins) selected from the group consisting of SERPINA12, GHRL, PREB, IL-20RA, and PON2; and administering a JAK inhibitor to the human subject.

In some embodiments, the method entails measuring in a biological sample obtained from the human subject a reduced concentration, as compared to a control, of at least one protein (e.g., at least 1, 2, or 3 proteins) selected from the group consisting of SCF, CPA2, and P4HB, and/or an increased concentration, as compared to a control, of at least one protein (e.g., at least 1, 2, or 3 proteins) selected from the group consisting of SERPINA12, GHRL, and PREB; and administering a JAK inhibitor to the human subject.

In some embodiments, the method entails measuring in a biological sample obtained from the human subject an increased concentration, as compared to a control, of at least one protein (e.g., at least 1 or 2 proteins) selected from the group consisting of IL-20RA and PON2; and administering a JAK inhibitor to the human subject.

In another aspect, the disclosure features a method of predicting the response of a human subject having, suspected of having, or at risk of developing vitiligo to a JAK inhibitor by: measuring, in a biological sample obtained from the human subject before administration of the JAK inhibitor, the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of SCF, CPA2, P4HB, SPARCL1, ST2, SCF, CNDP1, TRAIL, KIRREL2, EGFR, ISLR2, PPP3R1, FCGR3B, MMP-3, IL-18BP, Flt3L, PPY, LTA4H, ITGB2, PTN, GPNMB, SIRPB1, PLTP, PSP-D, COMP, PAMR1, VASN, F11, IL10, CA3, CXCL10, Notch 3, NCAM1, PROC, CLEC14A, IL-12B, IL10, CD40, IFN-gamma, SERPINA12, GHRL, PREB, IL-20RA, and PON2, wherein a reduced concentration, as compared to a control, of at least one of (e.g., at least 1, 2, 3, 4, 5, 6, 7, 8, 9, 10, 11, 12, 13, 14, 15, 16, 17, 18, 19, or 20 of) SCF, CPA2, P4HB, SPARCL1, ST2, SCF, CNDP1, TRAIL, KIRREL2, EGFR, ISLR2, PPP3R1, FCGR3B, MMP-3, IL-18BP, Flt3L, PPY, LTA4H, ITGB2, PTN, GPNMB, SIRPB1, PLTP, PSP-D, COMP, PAMR1, VASN, F11, IL10, CA3, CXCL10, Notch 3, NCAM1, PROC, CLEC14A, IL-12B, IL10, CD40, and IFN-gamma and/or an increased concentration, as compared to a control, of at least one of (e.g., at least 1, 2, 3, 4, or 5 of) SERPINA12, GHRL, PREB, IL-20RA, or PON2 is predictive that the subject will respond to the JAK inhibitor.

In some embodiments, the method entails measuring, in a biological sample obtained from the human subject before administration of the JAK inhibitor, the concentration of at least one protein (e.g., at least 1, 2, 3, 4, 5, or 6 proteins) selected from the group consisting of SCF, CPA2, P4HB, SERPINA12, GHRL, and PREB, wherein a reduced concentration, as compared to a control, of at least one of (e.g., at least 1, 2, or 3 of) SCF, CPA2, or P4HB, and/or an increased concentration, as compared to a control, of at least one of (e.g., at least 1, 2, or 3 of) SERPINA12, GHRL, or PREB is predictive that the subject will respond to the JAK inhibitor.

In some embodiments, the method entails measuring, in a biological sample obtained from the human subject before administration of the JAK inhibitor, the concentration of at least one protein (e.g., at least 1 or 2 proteins) selected from the group consisting of IL-20RA and PON2, wherein increased concentration, as compared to a control, of at least one of (e.g., at least 1 or 2 of) IL-20RA and PON2 is predictive that the subject will respond to the JAK inhibitor.

In another aspect, the disclosure features a method of predicting the response of a human subject having, suspected of having, or at risk of developing vitiligo to a JAK inhibitor by: measuring, in a biological sample obtained from the human subject before administration of the JAK inhibitor, the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of EPHA10, GH2, PARP-1, GLRX, ARSB, SCAMP3, t-PA, LDL receptor, DLK-1, SELE, EPHB4, GFRA2, PLC, LTBR, PAMR1, TACSTD2, FS, ICAM-2, AXL, PRSS8, SPINK5, AMN, NOMO1, PAI, and CPM, wherein a reduced concentration, as compared to a control, of at least one of (e.g., at least 1, 2, 3, 4, 5, or 6 of) EPHA10, GH2, PARP-1, GLRX, ARSB, and SCAMP3 and/or an increased concentration, as compared to a control, of at least one of (e.g., at least 1, 2, 3, 4, 5, 6, 7, 8, 9, 10, 11, 12, 13, 14, 15, 16, 17, 18, 19, or 20 of) t-PA, LDL receptor, DLK-1, SELE, EPHB4, GFRA2, PLC, LTBR, PAMR1, TACSTD2, FS, ICAM-2, AXL, PRSS8, SPINK5, AMN, NOMO1, PAI, and CPM is predictive that the subject will not respond to the JAK inhibitor.

In some embodiments, the method entails measuring, in a biological sample obtained from the human subject before administration of the JAK inhibitor, the concentration of at least one protein (e.g., at least 1, 2, 3, 4, 5, or 6 proteins) selected from the group consisting of EPHA10, GH2, PARP-1, t-PA, LDL receptor, DLK-1, and SELE, wherein a reduced concentration, as compared to a control, of at least one of (e.g., at least 1, 2, or 3 of) EPHA10, GH2, or PARP-1 and/or an increased concentration, as compared to a control, of at least one of (e.g., at least 1, 2, or 3 of) t-PA, LDL receptor, or DLK-1 is predictive that the subject will not respond to the JAK inhibitor.

The disclosure also features a method for measuring the amount of a protein in a sample, by: providing a biological sample obtained from a human subject having, suspected of having, or at risk of developing vitiligo; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of FAP, RET, CNTN5, FUCA1, ITGAV, ITGB5, THBS4, CD207, GDF-8, CDH6, MRC2, ICOSLG, TNXB, EDIL3, OSMR, GPC1, MIC-A/B, TGFR-2, LRRN1, TLR3, KIM1, ROBO2, CD70, CLMP, N-CDase, FCRL5, CTSV, SCARF2, PLXDC1, PRTG, ERBB4, MAGED1, CEACAM1, TSHB, PTK7, TGFR-2, ADAM 22, CTSC, DLK-1, USP8, SCARF2, TNFRSF13B, MB, TMPRSS5, NUDT5, MMP-3, MAEA, NEMO, IFN-gamma, IL18, AKT1S1, CASP-8, PPP1R2, ST2, VSIG4, SCGB3A2, HDGF, ICA1, IL13, PEBP1, PARK7, MAP4K5, FLI1, MMP-10, CCL24, TIMP4, MBL2, REG4, and CPA2 in the biological sample. In some embodiments of the methods described herein, the concentrations of no more than 50, 40, 30, 20, 15, 10, or 5 proteins are measured.

The disclosure also features a method for measuring the amount of a protein in a sample, by: providing a biological sample obtained from a human subject having, suspected of having, or at risk of developing vitiligo; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of DDR1, NTRK2, CES2, SCARA5, GDF-8, BOC, PAEP, ARTN, CDNF, TMPRSS5, FLRT2, ROBO2, SIGLEC10, PRTG, SCARF2, CDH3, GFR-alpha-1, TSHB, CD200R1, RGMB, KYNU, HS3ST3B1, CHRDL2, CNTN1, VSIG4, ARHGAP1, B4GAT1, STX8, CRELD2, ARSA, BCAM, SCARF1, CA13, DAG1, LAIR1, GUSB, PMVK, PEAR1, GP1BA, TACC3, PARK7, ARHGEF12, SEMA7A, ESAM, FKBP5, ARHGAP1, SCAMP3, ABL1, EGF, TACC3, FKBP5, BID, PRDX5, STX8, CD63, SCARF1, PTPN1, CLEC1B, ARSB, FKBP1B, YES1, SRC, TNFSF14, PLXNB3, LRMP, CD164, DAG1, PVALB, NAA10, TRIM5, ARHGEF12, HGF, CA13, SNAP23, SORT1, GP6, CTSS, PPIB, CRKL, MAP2K6, MANF, PMVK, ABHD14B, GUSB, FATC1, MAD1L1, EDAR, CEACAM8, GLB1, ST3GAL1, ARSA, ADAM 8, CD40, IFI30, ECE1, AXIN1, WFDC2, TBCB, CXCL13, ST1A1, KIF1BP, DPP7, VEGFA, CETN2, TGF-alpha, CD84, SNAP29, CASP-8, S100A11, GSTP1, CRADD, PRKAB1, HGF, STK4, RNASE3, SERPINB6, OSM, MK, FADD, CLEC11A, CD69, LOX-1, ITGA6, CLEC5A, BCAM, FES, TXNDC5, LAT2, CXCL11, PARP-1, APBB1IP, GZMB, and CRNN in the biological sample. In some embodiments of the methods described herein, the concentrations of no more than 50, 40, 30, 20, 15, 10, or 5 proteins are measured.

The disclosure also features a method for measuring the amount of a protein in a sample, by: providing a biological sample obtained from a human subject having, suspected of having, or at risk of developing vitiligo; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of SCF, CPA2, P4HB, SPARCL1, ST2, SCF, CNDP1, TRAIL, KIRREL2, EGFR, ISLR2, PPP3R1, FCGR3B, MMP-3, IL-18BP, Flt3L, PPY, LTA4H, ITGB2, PTN, GPNMB, SIRPB1, PLTP, PSP-D, COMP, PAMR1, VASN, F11, IL10, CA3, CXCL10, Notch 3, NCAM1, PROC, CLEC14A, IL-12B, IL10, CD40, IFN-gamma, SERPINA12, GHRL, PREB, IL-20RA, and PON2 in the biological sample. In some embodiments of the methods described herein, the concentrations of no more than 50, 40, 30, 20, 15, 10, or 5 proteins are measured.

The disclosure also features a method for measuring the amount of a protein in a sample, by: providing a biological sample obtained from a human subject having, suspected of having, or at risk of developing vitiligo; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of EPHA10, GH2, PARP-1, GLRX, ARSB, SCAMP3, t-PA, LDL receptor, DLK-1, SELE, EPHB4, GFRA2, PLC, LTBR, PAMR1, TACSTD2, FS, ICAM-2, AXL, PRSS8, SPINK5, AMN, NOMO1, PAI, and CPM in the biological sample. In some embodiments of the methods described herein, the concentrations of no more than 50, 40, 30, 20, 15, 10, or 5 proteins are measured.

In another aspect, the disclosure features a method of treating a human subject having, suspected of having, or at risk of developing vitiligo, comprising administering to the human subject a JAK inhibitor, wherein the human subject has been previously determined to have (i) a baseline expression level of at least one gene (e.g., at least 1, 2, 3, 4, 5, 6, 7, 8, 9, 10, 11, 12, 13, 14, 15, 16, 17, 18, 19, or 20 genes) selected from the group consisting of SLFN12, DLEU1, EDARADD, SH3BGR, IGFN1, APOBEC3G, TRPM2, RNF148, HMMR, SKA1, AHRR, LDHAL6A, SHCBP1, GBP3, RFC4, CTF1, RAB3IL1, GINS1, CD5, PRKG1, SRSF12, FAXC, PDIA5, TGIF2, EED, GORAB, NPAS3, AVPR1A, C9orf64, C1orf74, ACAN, RNF180, BCL2L12, XK, IQCG, and ZNF43 in a biological sample obtained from the human subject that is lower than a control, and/or (ii) a baseline expression level of at least one gene (e.g., at least 1, 2, 3, 4, 5, 6, 7, 8, 9, 10, 11, 12, 13, 14, 15, 16, 17, 18, 19, or 20 genes) selected from the group consisting of OVCH2, ANKRD2, KCNJ1, TAS1R3, PPIAL4G, ZSCAN1, CACNA1F, IL17B, C1QL1, OR10A4, TAF1L, STK16, RFNG, CSAG1, PRR21, NHSL2, ZNF787, ZNRF1, PALD1, ZNF444, FAM219A, TMEM208, NMRK1, ARID3B, MPLKIP, CAB39L, ALKBH3, PLCE1, C12orf29, LSAMP, SMIM5, UQCC2, FAM96B, GID4, AKAP10, HMGCL, and C11orf49 in a biological sample obtained from the human subject that is higher than a control.

The disclosure also features a method of treating a human subject having, suspected of having, or at risk of developing vitiligo, comprising: measuring in a biological sample obtained from the human subject a reduced expression level, as compared to a control, of at least one gene (e.g., at least 1, 2, 3, 4, 5, 6, 7, 8, 9, 10, 11, 12, 13, 14, 15, 16, 17, 18, 19, or 20 genes) selected from the group consisting of SLFN12, DLEU1, EDARADD, SH3BGR, IGFN1, APOBEC3G, TRPM2, RNF148, HMMR, SKA1, AHRR, LDHAL6A, SHCBP1, GBP3, RFC4, CTF1, RAB3IL1, GINS1, CD5, PRKG1, SRSF12, FAXC, PDIA5, TGIF2, EED, GORAB, NPAS3, AVPR1A, C9orf64, C1orf74, ACAN, RNF180, BCL2L12, XK, IQCG, and ZNF43, and/or an increased expression level, as compared to a control, of at least one gene (e.g., at least 1, 2, 3, 4, 5, 6, 7, 8, 9, 10, 11, 12, 13, 14, 15, 16, 17, 18, 19, or 20 genes) selected from the group consisting of OVCH2, ANKRD2, KCNJ1, TAS1R3, PPIAL4G, ZSCAN1, CACNA1F, IL17B, C1QL1, OR10A4, TAF1L, STK16, RFNG, CSAG1, PRR21, NHSL2, ZNF787, ZNRF1, PALD1, ZNF444, FAM219A, TMEM208, NMRK1, ARID3B, MPLKIP, CAB39L, ALKBH3, PLCE1, C12orf29, LSAMP, SMIM5, UQCC2, FAM96B, GID4, AKAP10, HMGCL, and C11orf49; and administering a JAK inhibitor to the human subject.

The disclosure also features a method of predicting the response of a human subject having, suspected of having, or at risk of developing vitiligo to a JAK inhibitor, comprising: measuring, in a biological sample obtained from the human subject before administration of the JAK inhibitor, the expression level of at least one gene (e.g., at least 1, 2, 3, 4, 5, 6, 7, 8, 9, 10, 11, 12, 13, 14, 15, 16, 17, 18, 19, or 20 genes) selected from the group consisting of OVCH2, ANKRD2, KCNJ1, TAS1R3, PPIAL4G, ZSCAN1, CACNA1F, IL17B, C1QL1, OR10A4, TAF1L, STK16, RFNG, CSAG1, PRR21, NHSL2, ZNF787, ZNRF1, PALD1, ZNF444, FAM219A, TMEM208, NMRK1, ARID3B, MPLKIP, CAB39L, ALKBH3, PLCE1, C12orf29, LSAMP, SMIM5, UQCC2, FAM96B, GID4, AKAP10, HMGCL, C11orf49, SLFN12, DLEU1, EDARADD, SH3BGR, IGFN1, APOBEC3G, TRPM2, RNF148, HMMR, SKA1, AHRR, LDHAL6A, SHCBP1, GBP3, RFC4, CTF1, RAB3IL1, GINS1, CD5, PRKG1, SRSF12, FAXC, PDIA5, TGIF2, EED, GORAB, NPAS3, AVPR1A, C9orf64, C1orf74, ACAN, RNF180, BCL2L12, XK, IQCG, and ZNF43, wherein a reduced expression level, as compared to a control, of at least one of SLFN12, DLEU1, EDARADD, SH3BGR, IGFN1, APOBEC3G, TRPM2, RNF148, HMMR, SKA1, AHRR, LDHAL6A, SHCBP1, GBP3, RFC4, CTF1, RAB3IL1, GINS1, CD5, PRKG1, SRSF12, FAXC, PDIA5, TGIF2, EED, GORAB, NPAS3, AVPR1A, C9orf64, C1orf74, ACAN, RNF180, BCL2L12, XK, IQCG, and ZNF43 and/or an increased expression level, as compared to a control, of at least one of OVCH2, ANKRD2, KCNJ1, TAS1R3, PPIAL4G, ZSCAN1, CACNA1F, IL17B, C1QL1, OR10A4, TAF1L, STK16, RFNG, CSAG1, PRR21, NHSL2, ZNF787, ZNRF1, PALD1, ZNF444, FAM219A, TMEM208, NMRK1, ARID3B, MPLKIP, CAB39L, ALKBH3, PLCE1, C12orf29, LSAMP, SMIM5, UQCC2, FAM96B, GID4, AKAP10, HMGCL, and C11orf49 is predictive that the subject will respond to the JAK inhibitor.

The disclosure also features a method of predicting the response of a human subject having, suspected of having, or at risk of developing vitiligo to a JAK inhibitor, comprising: measuring, in a biological sample obtained from the human subject before administration of the JAK inhibitor, the expression level of at least one gene (e.g., at least 1, 2, 3, 4, 5, 6, 7, 8, 9, 10, 11, 12, 13, 14, 15, 16, 17, 18, 19, or 20 genes) selected from the group consisting of OVCH2, ANKRD2, KCNJ1, TAS1R3, PPIAL4G, ZSCAN1, CACNA1F, IL17B, C1QL1, OR10A4, TAF1L, STK16, RFNG, CSAG1, PRR21, NHSL2, ZNF787, ZNRF1, PALD1, ZNF444, FAM219A, TMEM208, NMRK1, ARID3B, MPLKIP, CAB39L, ALKBH3, PLCE1, C12orf29, LSAMP, SMIM5, UQCC2, FAM96B, GID4, AKAP10, HMGCL, C11orf49, SLFN12, DLEU1, EDARADD, SH3BGR, IGFN1, APOBEC3G, TRPM2, RNF148, HMMR, SKA1, AHRR, LDHAL6A, SHCBP1, GBP3, RFC4, CTF1, RAB3IL1, GINS1, CD5, PRKG1, SRSF12, FAXC, PDIA5, TGIF2, EED, GORAB, NPAS3, AVPR1A, C9orf64, C1orf74, ACAN, RNF180, BCL2L12, XK, IQCG, and ZNF43, wherein a reduced expression level, as compared to a control, of at least one of OVCH2, ANKRD2, KCNJ1, TAS1R3, PPIAL4G, ZSCAN1, CACNA1F, IL17B, C1QL1, OR10A4, TAF1L, STK16, RFNG, CSAG1, PRR21, NHSL2, ZNF787, ZNRF1, PALD1, ZNF444, FAM219A, TMEM208, NMRK1, ARID3B, MPLKIP, CAB39L, ALKBH3, PLCE1, C12orf29, LSAMP, SMIM5, UQCC2, FAM96B, GID4, AKAP10, HMGCL, and C11orf49 and/or an increased expression level, as compared to a control, of at least one of SLFN12, DLEU1, EDARADD, SH3BGR, IGFN1, APOBEC3G, TRPM2, RNF148, HMMR, SKA1, AHRR, LDHAL6A, SHCBP1, GBP3, RFC4, CTF1, RAB3IL1, GINS1, CD5, PRKG1, SRSF12, FAXC, PDIA5, TGIF2, EED, GORAB, NPAS3, AVPR1A, C9orf64, C1orf74, ACAN, RNF180, BCL2L12, XK, IQCG, and ZNF43 is predictive that the subject will not respond to the JAK inhibitor.

In another aspect, the disclosure features a method of treating a human subject having, suspected of having, or at risk of developing vitiligo, comprising administering to the human subject a JAK inhibitor, wherein the human subject has been previously determined to have (i) a baseline expression level of at least one gene (e.g., at least 1, 2, 3, 4, 5, 6, 7, 8, 9, 10, 11, or 12 genes) selected from the group consisting of STK16, RFNG, ZNRF1, ARID3B, WSB2, JAK1, IL1RL2, PALD1, S100A1, BCL2L12, FAM219A, and TSHZ1 in a biological sample obtained from the human subject that is lower than a control, and/or (ii) a baseline expression level of at least one gene (e.g., at least 1, 2, 3, 4, 5, 6, or 7 genes) selected from the group consisting of PPIAL4G, CD5, IFI6, CCR4, CNTF, CD28, and RAB3IL1 in a biological sample obtained from the human subject that is higher than a control.

The disclosure also features a method of treating a human subject having, suspected of having, or at risk of developing vitiligo, comprising: measuring in a biological sample obtained from the human subject a reduced expression level, as compared to a control, of at least one gene (e.g., at least 1, 2, 3, 4, 5, 6, 7, 8, 9, 10, 11, or 12 genes) selected from the group consisting of STK16, RFNG, ZNRF1, ARID3B, WSB2, JAK1, IL1RL2, PALD1, S100A1, BCL2L12, FAM219A, and TSHZ1, and/or an increased expression level, as compared to a control, of at least one gene (e.g., at least 1, 2, 3, 4, 5, 6, or 7 genes) selected from the group consisting of PPIAL4G, CD5, IFI6, CCR4, CNTF, CD28, and RAB3IL1; and administering a JAK inhibitor to the human subject.

The disclosure also features a method of predicting the response of a human subject having, suspected of having, or at risk of developing vitiligo to a JAK inhibitor, comprising: measuring, in a biological sample obtained from the human subject before administration of the JAK inhibitor, the expression level of at least one gene (e.g., at least 1, 2, 3, 4, 5, 6, 7, 8, 9, 10, 11, 12, 13, 14, 15, 16, 17, 18, or 19 genes) selected from the group consisting of PPIAL4G, CD5, IFI6, CCR4, CNTF, CD28, RAB3IL1, STK16, RFNG, ZNRF1, ARID3B, WSB2, JAK1, IL1RL2, PALD1, S100A1, BCL2L12, FAM219A, and TSHZ1, wherein a reduced expression level, as compared to a control, of at least one of STK16, RFNG, ZNRF1, ARID3B, WSB2, JAK1, IL1RL2, PALD1, S100A1, BCL2L12, FAM219A, and TSHZ1 and/or an increased expression level, as compared to a control, of at least one of PPIAL4G, CD5, IFI6, CCR4, CNTF, CD28, and RAB3IL1 is predictive that the subject will respond to the JAK inhibitor.

The disclosure also features a method of predicting the response of a human subject having, suspected of having, or at risk of developing vitiligo to a JAK inhibitor, comprising: measuring, in a biological sample obtained from the human subject before administration of the JAK inhibitor, the expression level of at least one gene (e.g., at least 1, 2, 3, 4, 5, 6, 7, 8, 9, 10, 11, 12, 13, 14, 15, 16, 17, 18, or 19 genes) selected from the group consisting of PPIAL4G, CD5, IFI6, CCR4, CNTF, CD28, RAB3IL1, STK16, RFNG, ZNRF1, ARID3B, WSB2, JAK1, IL1RL2, PALD1, S100A1, BCL2L12, FAM219A, and TSHZ1, wherein a reduced expression level, as compared to a control, of at least one of PPIAL4G, CD5, IFI6, CCR4, CNTF, CD28, and RAB3IL1 and/or an increased expression level, as compared to a control, of at least one of STK16, RFNG, ZNRF1, ARID3B, WSB2, JAK1, IL1RL2, PALD1, S100A1, BCL2L12, FAM219A, and TSHZ1 is predictive that the subject will not respond to the JAK inhibitor.

In some embodiments of the methods described herein, the biological sample is blood, serum, plasma, urine, spinal fluid, saliva, lacrimal fluid, or sweat. In some embodiments, the biological sample is blood, serum, or plasma.

In some embodiments of the methods described herein, the concentration of the protein is measured by an immunological method (e.g., selected from the group consisting of enzyme-linked immunosorbent assay, enzyme immunoassay, radioimmunoassay, chemiluminescent immunoassay, electrochemiluminescence immunoassay, latex turbidimetric immunoassay, latex photometric immunoassay, immunochromatographic assay, and western blotting).

In some embodiments of the methods described herein, the concentration of the protein is measured by mass spectrometry.

In some embodiments of the methods described herein, the expression level of the gene is measured by RNA sequencing or quantitative PCR.

In some embodiments of the methods described herein, the JAK inhibitor is ruxolitinib. In some embodiments, ruxolitinib is topically administered to the human subject at least once a day in a cream comprising at least 0.15% ruxolitinib. In some embodiments, ruxolitinib is topically administered to the human subject at least two times each day in a cream comprising at least 0.15% ruxolitinib. In some embodiments, ruxolitinib is topically administered to the human subject at least once a day in a cream comprising at least 0.5% ruxolitinib. In some embodiments, ruxolitinib is topically administered to the human subject at least two times each day in a cream comprising at least 0.5% ruxolitinib. In some embodiments, ruxolitinib is topically administered to the human subject at least once a day in a cream comprising at least 1.5% ruxolitinib. In some embodiments, ruxolitinib is topically administered to the human subject at least two times each day in a cream comprising at least 1.5% ruxolitinib.

In some embodiments of the methods described herein, the JAK inhibitor is itacitinib, 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide or a pharmaceutically acceptable salt thereof, or ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile or a pharmaceutically acceptable salt thereof.

The term "baseline concentration" of protein refers to the concentration of a protein in a subject prior to initiation of treatment with a JAK inhibitor.

The term "baseline expression level" of a gene refers to the expression level of a gene in a subject prior to initiation of treatment with a JAK inhibitor.

The term "reduced concentration" means a concentration of the protein being analyzed that is lower than the concentration of that protein in a control or in a previous sample. For example, the concentration of the protein being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the concentration of that protein in a control.

The term "reduced expression level" means an expression level of the gene being analyzed that is lower than the expression level of that gene in a control. For example, the expression level of the gene being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the expression level of that gene in a control.

The term "increased concentration" means a concentration of the protein being analyzed that is higher than the concentration of that protein in a control or in a previous sample. For example, the concentration of the protein being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the concentration of that protein in a control.

The term "increased expression level" means an expression level of the gene being analyzed that is higher than the expression level of that gene in a control. For example, the expression level of the gene being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the expression level of that gene in a control.

The term "respond to a therapy" means that the subject administered with the therapy shows a positive response to the JAK inhibitor therapy provided.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 3 depicts proteins in circulation that positively correlated with baseline F-VASI.

FIG. 4 depicts fold change and p-values of paired t-tests from baseline to week 24 in select inflammatory mediators, by treatment group.

DETAILED DESCRIPTION

Figure 1:
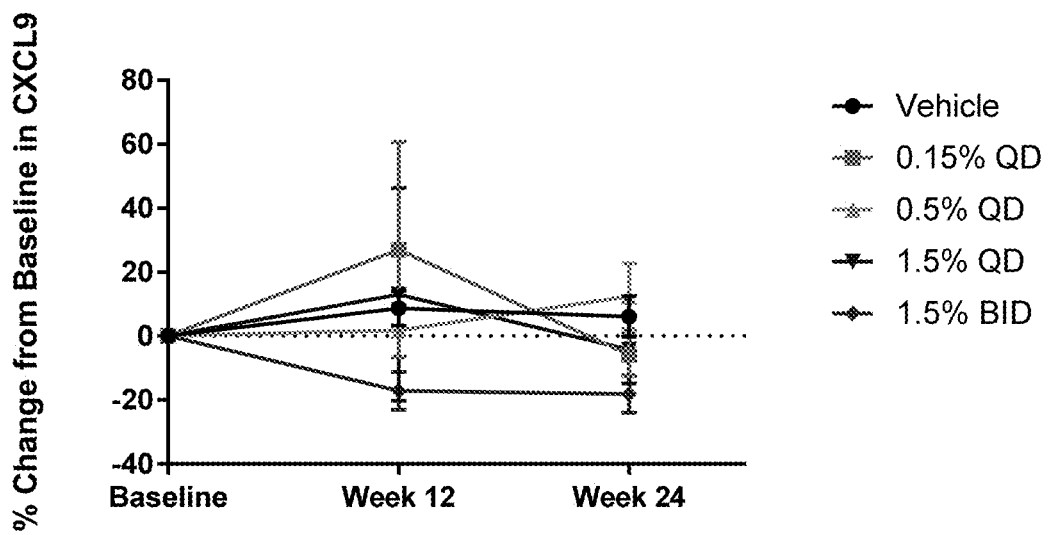
FIG. 1 is a graph depicting percent changes from baseline in CXCL9 levels at weeks 12 and 24 following treatment with a vehicle control or ruxolitinib-containing compositions.

This disclosure provides methods and compositions for treating a subject having, suspected of having, or at risk of developing vitiligo with a JAK inhibitor. The disclosure provides pharmacodynamics biomarkers (e.g., protein expression levels) to identify those subjects having vitiligo that have undergone a therapeutic response (e.g., prior to visible skin improvement) to a JAK inhibitor. The disclosure also provides predictive biomarkers (e.g., protein expression levels) to identify those subjects having, suspected of having, or at risk of developing vitiligo for whom administering a JAK inhibitor is likely to be effective.

Methods of Identifying Therapeutic Responsiveness to a JAK Inhibitor

As described in Example 1, treatment of subjects having vitiligo with a JAK inhibitor resulted in a decrease in circulating CXCL9 and CXCL10 levels. Changes in CXCL9 and CXCL10 levels during the course of treatment can therefore be used in identifying therapeutic responsiveness (e.g., improvement in disease scores and/or disease resolution) of a subject having vitiligo to a JAK inhibitor. A reduced CXCL9 and/or CXCL10 protein concentration in a biological sample (e.g., plasma or serum) obtained from a subject after treatment with a JAK inhibitor, as compared to the baseline CXCL9 and/or CXCL10 expression level in a biological sample obtained from the subject before treatment with the JAK inhibitor, is indicative that the subject has undergone a therapeutic response (e.g., prior to visible skin improvement) to the JAK inhibitor.

As described in Examples 2-4, proteomic profiling identified numerous proteins whose expression levels, in subjects who respond to treatment with a JAK inhibitor, change during the course of treatment and are therefore useful in identifying therapeutic responsiveness (e.g., improvement in disease scores and/or disease resolution) of a subject having vitiligo to a JAK inhibitor. In addition, numerous proteins were identified whose expression levels, in subjects who did not respond to treatment with a JAK inhibitor, change during the course of treatment and are therefore useful in identifying non-responsiveness (e.g., non-improvement in disease scores and/or lack of disease resolution) of a subject having vitiligo to a JAK inhibitor.

A reduced protein concentration in a biological sample (e.g., plasma or serum) obtained from a subject after treatment with a JAK inhibitor, as compared to the baseline expression level in a biological sample obtained from the subject before treatment with the JAK inhibitor, of one or more (e.g., at least 1, 2, 3, 4, 5, 6, 7, 8, 9, 10, 11, 12, 13, 14, 15, 16, 17, 18, 19, or 20) of FAP, RET, CNTN5, FUCA1, ITGAV, ITGB5, THBS4, CD207, GDF-8, CDH6, MRC2, ICOSLG, TNXB, EDIL3, OSMR, GPC1, MIC-A/B, TGFR-2, LRRN1, TLR3, KIM1, ROBO2, CD70, CLMP, N-CDase, FCRL5, CTSV, SCARF2, PLXDC1, PRTG, ERBB4, MAGED1, CEACAM1, TSHB, PTK7, TGFR-2, ADAM 22, CTSC, DLK-1, USP8, SCARF2, TNFRSF13B, MB, or TMPRSS5 is indicative that the subject has undergone a therapeutic response (e.g., prior to visible skin improvement) to the JAK inhibitor.

An increased protein concentration in a biological sample (e.g., plasma or serum) obtained from a subject after treatment with a JAK inhibitor, as compared to the baseline expression level in a biological sample obtained from the subject before treatment with the JAK inhibitor, of one or more (e.g., at least 1, 2, 3, 4, 5, 6, 7, 8, 9, 10, 11, 12, 13, 14, 15, 16, 17, 18, 19, or 20) of NUDT5, MMP-3, MAEA, NEMO, IFN-gamma, IL18, AKT1S1, CASP-8, PPP1R2, ST2, VSIG4, SCGB3A2, HDGF, ICA1, IL13, PEBP1, PARK7, MAP4K5, FLI1, MMP-10, CCL24, TIMP4, MBL2, REG4, or CPA2 is indicative that the subject has undergone a therapeutic response (e.g., prior to visible skin improvement) to the JAK inhibitor.

A reduced protein concentration in a biological sample (e.g., plasma or serum) obtained from a subject after treatment with a JAK inhibitor, as compared to the baseline expression level in a biological sample obtained from the subject before treatment with the JAK inhibitor, of one or more (e.g., at least 1, 2, 3, 4, 5, 6, 7, 8, 9, 10, 11, 12, 13, 14, 15, 16, 17, 18, 19, or 20) of FAP, RET, CNTN5, FUCA1, ITGAV, ITGB5, THBS4, CD207, GDF-8, CDH6, MRC2, ICOSLG, TNXB, EDIL3, OSMR, GPC1, MIC-A/B, TGFR-2, LRRN1, TLR3, KIM1, ROBO2, CD70, CLMP, N-CDase, FCRL5, CTSV, SCARF2, PLXDC1, PRTG, ERBB4, MAGED1, CEACAM1, TSHB, PTK7, TGFR-2, ADAM 22, CTSC, DLK-1, USP8, SCARF2, TNFRSF13B, MB, or TMPRSS5 combined with an increased protein concentration in a biological sample (e.g., plasma or serum) obtained from the subject after treatment with a JAK inhibitor, as compared to the baseline expression level in a biological sample obtained from the subject before treatment with the JAK inhibitor, of one or more (e.g., at least 1, 2, 3, 4, 5, 6, 7, 8, 9, 10, 11, 12, 13, 14, 15, 16, 17, 18, 19, or 20) of NUDT5, MMP-3, MAEA, NEMO, IFN-gamma, IL18, AKT1S1, CASP-8, PPP1R2, ST2, VSIG4, SCGB3A2, HDGF, ICA1, IL13, PEBP1, PARK7, MAP4K5, FLI1, MMP-10, CCL24, TIMP4, MBL2, REG4, or CPA2 is indicative that the subject has undergone a therapeutic response (e.g., prior to visible skin improvement) to the JAK inhibitor.

A reduced protein concentration in a biological sample (e.g., plasma or serum) obtained from a subject after treatment with a JAK inhibitor, as compared to the baseline expression level in a biological sample obtained from the subject before treatment with the JAK inhibitor, of one or more (e.g., at least 1, 2, 3, 4, 5, 6, 7, 8, 9, 10, 11, 12, 13, 14, 15, 16, 17, 18, 19, or 20) of DDR1, NTRK2, CES2, SCARA5, GDF-8, BOC, PAEP, ARTN, CDNF, TMPRSS5, FLRT2, ROBO2, SIGLEC10, PRTG, SCARF2, CDH3, GFR-alpha-1, TSHB, CD200R1, RGMB, KYNU, HS3ST3B1, CHRDL2, or CNTN1 is indicative that the subject has not undergone a therapeutic response to the JAK inhibitor.

An increased protein concentration in a biological sample (e.g., plasma or serum) obtained from a subject after treatment with a JAK inhibitor, as compared to the baseline expression level in a biological sample obtained from the subject before treatment with the JAK inhibitor, of one or more (e.g., at least 1, 2, 3, 4, 5, 6, 7, 8, 9, 10, 11, 12, 13, 14, 15, 16, 17, 18, 19, or 20) of VSIG4, ARHGAP1, B4GAT1, STX8, CRELD2, ARSA, BCAM, SCARF1, CA13, DAG1, LAIR1, GUSB, PMVK, PEAR1, GP1BA, TACC3, PARK7, ARHGEF12, SEMA7A, ESAM, FKBP5, ARHGAP1, SCAMP3, ABL1, EGF, TACC3, FKBP5, BID, PRDX5, STX8, CD63, SCARF1, PTPN1, CLEC1B, ARSB, FKBP1B, YES1, SRC, TNFSF14, PLXNB3, LRMP, CD164, DAG1, PVALB, NAA10, TRIM5, ARHGEF12, HGF, CA13, SNAP23, SORT1, GP6, CTSS, PPIB, CRKL, MAP2K6, MANF, PMVK, ABHD14B, GUSB, FATC1, MAD1L1, EDAR, CEACAM8, GLB1, ST3GAL1, ARSA, ADAM 8, CD40, IFI30, ECE1, AXIN1, WFDC2, TBCB, CXCL13, ST1A1, KIF1BP, DPP7, VEGFA, CETN2, TGF-alpha, CD84, SNAP29, CASP-8, S100A11, GSTP1, CRADD, PRKAB1, HGF, STK4, RNASE3, SERPINB6, OSM, MK, FADD, CLEC11A, CD69, LOX-1, ITGA6, CLEC5A, BCAM, FES, TXNDC5, LAT2, CXCL11, PARP-1, APBB1IP, GZMB, or CRNN is indicative that the subject has not undergone a therapeutic response to the JAK inhibitor.

A reduced protein concentration in a biological sample (e.g., plasma or serum) obtained from a subject after treatment with a JAK inhibitor, as compared to the baseline expression level in a biological sample obtained from the subject before treatment with the JAK inhibitor, of one or more (e.g., at least 1, 2, 3, 4, 5, 6, 7, 8, 9, 10, 11, 12, 13, 14, 15, 16, 17, 18, 19, or 20) of DDR1, NTRK2, CES2, SCARA5, GDF-8, BOC, PAEP, ARTN, CDNF, TMPRSS5, FLRT2, ROBO2, SIGLEC10, PRTG, SCARF2, CDH3, GFR-alpha-1, TSHB, CD200R1, RGMB, KYNU, HS3ST3B1, CHRDL2, or CNTN1 combined with an increased protein concentration in a biological sample (e.g., plasma or serum) obtained from the subject after treatment with a JAK inhibitor, as compared to the baseline expression level in a biological sample obtained from the subject before treatment with the JAK inhibitor, of one or more (e.g., at least 1, 2, 3, 4, 5, 6, 7, 8, 9, 10, 11, 12, 13, 14, 15, 16, 17, 18, 19, or 20) of VSIG4, ARHGAP1, B4GAT1, STX8, CRELD2, ARSA, BCAM, SCARF1, CA13, DAG1, LAIR1, GUSB, PMVK, PEAR1, GP1BA, TACC3, PARK7, ARHGEF12, SEMA7A, ESAM, FKBP5, ARHGAP1, SCAMP3, ABL1, EGF, TACC3, FKBP5, BID, PRDX5, STX8, CD63, SCARF1, PTPN1, CLEC1B, ARSB, FKBP1B, YES1, SRC, TNFSF14, PLXNB3, LRMP, CD164, DAG1, PVALB, NAA10, TRIM5, ARHGEF12, HGF, CA13, SNAP23, SORT1, GP6, CTSS, PPIB, CRKL, MAP2K6, MANF, PMVK, ABHD14B, GUSB, FATC1, MAD1L1, EDAR, CEACAM8, GLB1, ST3GAL1, ARSA, ADAM 8, CD40, IFI30, ECE1, AXIN1, WFDC2, TBCB, CXCL13, ST1A1, KIF1BP, DPP7, VEGFA, CETN2, TGF-alpha, CD84, SNAP29, CASP-8, S100A11, GSTP1, CRADD, PRKAB1, HGF, STK4, RNASE3, SERPINB6, OSM, MK, FADD, CLEC11A, CD69, LOX-1, ITGA6, CLEC5A, BCAM, FES, TXNDC5, LAT2, CXCL11, PARP-1, APBB1IP, GZMB, or CRNN is indicative that the subject has not undergone a therapeutic response to the JAK inhibitor.

In some embodiments, the vitiligo is nonsegmental vitiligo. In other embodiments, the vitiligo is segmental vitiligo.

Methods of Predicting Therapeutic Responsiveness to a JAK Inhibitor

Several proteins have been identified in the Examples whose baseline expression levels are useful in predicting responsiveness (e.g., improvement in disease scores and/or disease resolution) of a subject having vitiligo to a JAK inhibitor. In addition, several proteins have been identified whose baseline expression levels are useful in predicting non-responsiveness (e.g., non-improvement in disease scores and/or lack of disease resolution) of a subject having vitiligo to a JAK inhibitor.

A reduced baseline protein concentration (e.g., in plasma or serum) compared to a control of one or more (e.g., at least 1, 2, 3, 4, 5, 6, 7, 8, 9, 10, 11, 12, 13, or 14) of SCF, CPA2, P4HB, SPARCL1, ST2, SCF, CNDP1, TRAIL, KIRREL2, EGFR, ISLR2, PPP3R1, FCGR3B, MMP-3, IL-18BP, Flt3L, PPY, LTA4H, ITGB2, PTN, GPNMB, SIRPB1, PLTP, PSP-D, COMP, PAMR1, VASN, F11, IL10, CA3, CXCL10, Notch 3, NCAM1, PROC, CLEC14A, IL-12B, IL10, CD40, or IFN-gamma is indicative/predictive that a subject that has, is suspected of having, or is at risk of developing vitiligo will respond to a JAK inhibitor. For example, low concentrations (compared to a control) of SPARCL1 protein in a biological sample obtained from a subject prior to treatment with the JAK inhibitor are predictive that the subject will respond to the JAK inhibitor.

An increased baseline protein concentration (e.g., in plasma or serum) compared to a control of one or more (e.g., at least 1, 2, or 3) of SERPINA12, GHRL, PREB, IL-20RA, or PON2 is indicative/predictive that a subject that has, is suspected of having, or is at risk of developing vitiligo will respond to a JAK inhibitor. For example, increased concentrations (compared to a control) of SERPINA12 protein in a biological sample obtained from a subject prior to treatment with the JAK inhibitor are predictive that the subject will respond to the JAK inhibitor.

A reduced baseline protein concentration (e.g., in plasma or serum) compared to a control of one or more (e.g., at least 1, 2, 3, 4, 5, 6, 7, 8, 9, 10, 11, 12, 13, or 14) of SCF, CPA2, P4HB, SPARCL1, ST2, SCF, CNDP1, TRAIL, KIRREL2, EGFR, ISLR2, PPP3R1, FCGR3B, MMP-3, IL-18BP, Flt3L, PPY, LTA4H, ITGB2, PTN, GPNMB, SIRPB1, PLTP, PSP-D, COMP, PAMR1, VASN, F11, IL10, CA3, CXCL10, Notch 3, NCAM1, PROC, CLEC14A, IL-12B, IL10, CD40, or IFN-gamma combined with an increased baseline protein concentration compared to a control of one or more (e.g., at least 1, 2, or 3) of SERPINA12, GHRL, PREB, IL-20RA, or PON2 is indicative/predictive that a subject that has, is suspected of having, or is at risk of developing vitiligo will respond to a JAK inhibitor. For example, low concentrations (compared to a control) of SPARCL1 protein and increased concentrations (compared to a control) of SERPINA12 protein in a biological sample obtained from a subject prior to treatment with the JAK inhibitor are predictive that the subject will respond to the JAK inhibitor.

A reduced baseline protein concentration (e.g., in plasma or serum) compared to a control of one or more (e.g., at least 1, 2, 3, 4, 5, or 6) of EPHA10, GH2, PARP-1, GLRX, ARSB, or SCAMP3 is indicative/predictive that a subject that has, is suspected of having, or is at risk of developing vitiligo will not respond to a JAK inhibitor. For example, low concentrations (compared to a control) of EPHA10 protein in a biological sample obtained from a subject prior to treatment with the JAK inhibitor are predictive that the subject will not respond to the JAK inhibitor.

An increased baseline protein concentration (e.g., in plasma or serum) compared to a control of one or more (e.g., at least 1, 2, 3, 4, 5, 6, 7, 8, 9, 10, 11, 12, 13, or 14) of t-PA, LDL receptor, DLK-1, SELE, EPHB4, GFRA2, PLC, LTBR, PAMR1, TACSTD2, FS, ICAM-2, AXL, PRSS8, SPINK5, AMN, NOMO1, PAI, or CPM is indicative/predictive that a subject that has, is suspected of having, or is at risk of developing vitiligo will not respond to a JAK inhibitor. For example, increased concentrations (compared to a control) of EPHB4 protein in a biological sample obtained from a subject prior to treatment with the JAK inhibitor are predictive that the subject will not respond to the JAK inhibitor.

A reduced baseline protein concentration (e.g., in plasma or serum) compared to a control of one or more (e.g., at least 1, 2, 3, 4, 5, or 6) of EPHA10, GH2, PARP-1, GLRX, ARSB, or SCAMP3 combined with an increased baseline protein concentration (e.g., in plasma or serum) compared to a control of one or more (e.g., at least 1, 2, 3, 4, 5, 6, 7, 8, 9, 10, 11, 12, 13, or 14) of t-PA, LDL receptor, DLK-1, SELE, EPHB4, GFRA2, PLC, LTBR, PAMR1, TACSTD2, FS, ICAM-2, AXL, PRSS8, SPINK5, AMN, NOMO1, PAI, or CPM is indicative/predictive that a subject that has, is suspected of having, or is at risk of developing vitiligo will not respond to a JAK inhibitor. For example, low concentrations (compared to a control) of EPHA10 protein and increased concentrations (compared to a control) of EPHB4 protein in a biological sample obtained from a subject prior to treatment with the JAK inhibitor are predictive that the subject will not respond to the JAK inhibitor.

In some embodiments, the vitiligo is nonsegmental vitiligo. In other embodiments, the vitiligo is segmental vitiligo.

Controls

As described above, the methods of the present invention can involve measuring the concentration of one or more proteins in a biological sample from a subject having, suspected of having or at risk of developing vitiligo, wherein the concentration of one or more proteins, compared to a control, predicts the response of a subject to a JAK inhibitor. In certain embodiments, when the concentration of a protein described herein in a biological sample from a subject having, suspected of having or at risk of developing vitiligo is lower than the control, the subject is identified as likely to respond to a JAK inhibitor. In other embodiments, when the concentration of a protein described herein in a biological sample from a subject having, suspected of having or at risk of developing vitiligo is higher than the control, the subject is identified as likely to respond to a JAK inhibitor. In this context, the term "control" includes a sample (from the same tissue type) obtained from a subject who is known to not respond to a JAK inhibitor. The term "control" also includes a sample (from the same tissue type) obtained in the past from a subject who is known to not respond to a JAK inhibitor and used as a reference for future comparisons to test samples taken from subjects for which therapeutic responsiveness is to be predicted. The "control" expression level/concentration for a particular protein in a particular cell type or tissue may be pre-established by an analysis of protein expression in one or more (e.g., 2, 3, 4, 5, 6, 7, 8, 9, 10, 15, 20, 25, 30, 35, or 40 or more) subjects, of the same species, that have not responded to treatment with a JAK inhibitor. This pre-established reference value (which may be an average or median expression level/concentration taken from multiple subjects that have not responded to the therapy) may then be used for the "control" concentration/expression level of the protein in the comparison with the test sample. In such a comparison, the subject is predicted to respond to a JAK inhibitor if the expression level of the protein being analyzed is lower or higher than the pre-established reference.

The "control" concentration for a particular protein in a particular cell type or tissue may alternatively be pre-established by an analysis of protein expression in one or more subjects that have responded to treatment with a JAK inhibitor. This pre-established reference value (which may be an average or median expression level taken from multiple subjects that have responded to the therapy) may then be used as the "control" expression level in the comparison with the test sample. In such a comparison, the subject is predicted to respond to a JAK inhibitor if the concentration of the protein being analyzed is the same as, or comparable to (e.g., at least 85% but less than 100% of), the pre-established reference.

In certain embodiments, the "control" is a pre-established cut-off value. A cut-off value is typically a concentration of a protein above or below which is considered predictive of responsiveness of a subject to a therapy of interest. Thus, in accordance with the methods and compositions described herein, a reference protein concentration is identified as a cut-off value, above or below of which is predictive of responsiveness to a JAK inhibitor. Cut-off values determined for use in the methods described herein can be compared with, e.g., published ranges of concentrations but can be individualized to the methodology used and patient population.

In some embodiments, the concentration of the protein being analyzed is reduced as compared to the concentration of that protein in a control. For example, the concentration of the protein being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the concentration of that protein in a control.

In some embodiments, the concentration of the protein being analyzed is increased as compared to the concentration of that protein in a control. For example, the concentration of the protein being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the concentration of that protein in a control.

Biological Samples

Suitable biological samples for the methods described herein include any biological fluid, cell, tissue, or fraction thereof, which includes proteins of interest. A biological sample can be, for example, a specimen obtained from a human subject or can be derived from such a subject. For example, a biological sample can be a biological fluid such as blood, serum, plasma, urine, spinal fluid, saliva, lacrimal fluid, or sweat, or such a sample absorbed onto a substrate (e.g., glass, polymer, or paper).

A biological sample can be obtained from a subject having, suspected of having, or at risk of developing, vitiligo. In certain embodiments, the subject has nonsegmental vitiligo. In some embodiments, the subject has segmental vitiligo.

Methods for obtaining and/or storing samples that preserve the activity or integrity of molecules (e.g., proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules in the sample.

Determining Expression Levels/Concentrations of Biomarkers

The expression level (amount) of a gene product can be determined by detecting and/or measuring the level of protein expression of the gene.

In one embodiment, the expression of a gene can be determined by detecting and/or measuring expression or concentration of a protein encoded by the gene. Methods of determining protein expression/concentration are well known in the art. A generally used method involves the use of antibodies specific for the target protein of interest. For example, methods of determining protein expression include, but are not limited to, western blot or dot blot analysis, immunohistochemistry (e.g., quantitative immunohistochemistry), immunocytochemistry, enzyme-linked immunosorbent assay (ELISA), enzyme-linked immunosorbent spot (ELISPOT; Coligan, J. E., et al., eds. (1995) Current Protocols in Immunology. Wiley, New York), radioimmunoassay, chemiluminescent immunoassay, electrochemiluminescence immunoassay, latex turbidimetric immunoassay, latex photometric immunoassay, immunochromatographic assay, and antibody array analysis (see, e.g., U.S. Publication Nos. 20030013208 and 2004171068, the disclosures of each of which are incorporated herein by reference in their entirety).

In one example, the presence or amount of protein expression of a gene can be determined using a western blotting technique. For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of a gene. As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, sepharose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here as above, the presence or amount of bound detectably-labeled antibody indicates the presence or amount of protein in the biological sample.

There is no particular restriction as to the form of the antibody and the present disclosure includes polyclonal antibodies, as well as monoclonal antibodies. The antiserum obtained by immunizing animals, such as rabbits with a protein or fragment thereof, as well polyclonal and monoclonal antibodies of all classes, human antibodies, and humanized antibodies produced by genetic recombination, are also included. Antibodies or antibody fragments specific for a protein encoded by one or more biomarkers can also be generated by in vitro methods such as phage display. Moreover, the antibody may be an antibody fragment or modified-antibody, so long as it binds to a protein encoded by a biomarker of the invention. For instance, Fab, F (ab') 2, Fv, or single chain Fv (scFv) in which the H chain Fv and the L chain Fv are suitably linked by a linker (Huston et al., *Proc. Natl. Acad. Sci. USA,* 85:5879-5883, (1988)) can be given as antibody fragments.

The antibodies may be conjugated to various molecules, such as fluorescent substances, radioactive substances, and luminescent substances. Methods to attach such moieties to an antibody are already established and conventional in the field (see, e.g., U.S. Pat. Nos. 5,057,313 and 5,156,840).

Examples of methods that assay the antigen-binding activity of the antibodies include, for example, measurement of absorbance, enzyme-linked immunosorbent assay (ELISA), enzyme immunoassay (EIA), radioimmunoassay (RIA), and/or immunofluorescence. For example, when using ELISA, a protein encoded by a biomarker of the invention is added to a plate coated with the antibodies of the present disclosure, and then, the antibody sample, for example, culture supernatants of antibody-producing cells, or purified antibodies are added. Then, secondary antibody recognizing the primary antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (GE Healthcare) may be used.

By using these methods, the antibody and a sample presumed to contain a protein of interest are contacted, and the protein encoded by a biomarker of the invention is detected or assayed by detecting or assaying the immune complex formed between the above-mentioned antibody and the protein.

Mass spectrometry based quantitation assay methods, for example, but not limited to, multiple reaction monitoring (MRM)-based approaches in combination with stable-isotope labeled internal standards, are an alternative to immunoassays for quantitative measurement of proteins. These approaches do not require the use of antibodies (see, for example, Addona et al., *Nat. Biotechnol.*, 27:633-641, 2009; Kuzyk et al., *Mol. Cell Proteomics*, 8:1860-1877, 2009; Paulovich et al., *Proteomics Clin. Appl.*, 2:1386-1402, 2008). In addition, MRM offers superior multiplexing capabilities, allowing for the simultaneous quantification of numerous proteins in parallel. The basic theory of these methods has been well-established and widely utilized for drug metabolism and pharmacokinetics analysis of small molecules.

In some embodiments, the concentration of two proteins, three proteins, four proteins, five proteins, six proteins, seven proteins, eight proteins, nine proteins, 10 proteins, 11 proteins, 12 proteins, 13 proteins, or 14 proteins, or at least two proteins, at least three proteins, at least four proteins, at least five proteins, at least six proteins, at least seven proteins, at least eight proteins, at least nine proteins, at least 10 proteins, at least 11 proteins, at least 12 proteins, at least 13 proteins, at least 14 proteins, at least 15 proteins, at least 16 proteins, at least 17 proteins, at least 18 proteins, at least 19 proteins, or at least 20 proteins can be assessed and/or measured.

JAK Inhibitors

In some embodiments, the JAK inhibitor is a compound that inhibits JAK1, JAK2, JAK3, and/or TYK2. In some embodiments, the JAK inhibitor is selective for JAK1 and JAK2 over JAK3 and TYK2. In some embodiments, the JAK inhibitor is selective for JAK1 over JAK2, JAK3, and TYK2. For example, some of the compounds described herein, or a pharmaceutically acceptable salt thereof, preferentially inhibit JAK1 over one or more of JAK2, JAK3, and TYK2. In some embodiments, the compounds or salts inhibit JAK1 preferentially over JAK2 (e.g., have a JAK2/JAK1 $IC_{50}$ ratio >1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring $IC_{50}$ at 1 mM ATP.

In some embodiments, the JAK inhibitor is 3-cyclopentyl-3-[4-(7H-pyrrolo[2,3-d]pyrimidin-4-yl)-1H-pyrazol-1-yl] propanenitrile.

In some embodiments, the JAK inhibitor is (3R)-3-cyclopentyl-3-[4-(7H-pyrrolo[2,3-d]pyrimidin-4-yl)-1H-pyrazol-1-yl]propanenitrile (ruxolitinib; also known as INCB018424).

3-Cyclopentyl-3-[4-(7H-pyrrolo[2,3-d]pyrimidin-4-yl)-1H-pyrazol-1-yl]propanenitrile and ruxolitinib can be made by the procedure described in U.S. Pat. No. 7,598,257 (Example 67), filed Dec. 12, 2006, which is incorporated herein by reference in its entirety.

In some embodiments, the JAK inhibitor is (3R)-3-cyclopentyl-3-[4-(7H-pyrrolo[2,3-d]pyrimidin-4-yl)-1H-pyrazol-1-yl]propanenitrile phosphoric acid salt.

In some embodiments, the JAK inhibitor is barcitinib, tofacitinib, oclacitinib, filgotinib, gandotinib, lestaurtinib, momelotinib, bacritinib, PF-04965842, upadacitinib, peficitinib, fedratinib, cucurbitacin I, ATI-501 (Aclaris), ATI-502 (Aclaris), JTE052 (Leo Pharma and Japan Tobacco), or CHZ868.

In some embodiments, the JAK inhibitor can be an isotopically-labeled compound, or a pharmaceutically acceptable salt thereof. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$).

One or more constituent atoms of the compounds described herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

Accordingly, in some embodiments, the JAK inhibitor is a compound, wherein one or more hydrogen atoms in the compound are replaced by deuterium atoms, or a pharmaceutically acceptable salt thereof.

In some embodiments, the JAK inhibitor is ruxolitinib, wherein one or more hydrogen atoms are replaced by deuterium atoms, or a pharmaceutically acceptable salt thereof. In some embodiments, the JAK inhibitor is any of the compounds in U.S. Pat. No. 9,249,149 (which is incorporated herein by reference in its entirety), or a pharmaceutically acceptable salt thereof. In some embodiments, the JAK inhibitor is CTP-543, or a pharmaceutically acceptable salt thereof. In some embodiments, the compound is a compound of Formula I

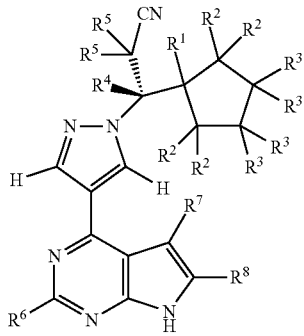

or a pharmaceutically acceptable salt thereof, wherein.

$R^1$ is selected from H and D;

each $R^2$ is independently selected from H and D, provided that each $R^2$ attached to a common carbon is the same;

each $R^3$ is independently selected from H and D, provided that each $R^3$ attached to a common carbon is the same;

$R^4$ is selected from H and D;

each $R^5$ is the same and is selected from H and D; and $R^6$, $R^7$, and $R^8$ are each independently selected from H and D; provided that when $R^1$ is H, each $R^2$ and each $R^3$ are H, $R^4$ is H, and each of $R^6$, $R^7$, and $R^8$ is H, then each $R^5$ is D.

In some embodiments, the JAK inhibitor is a compound of Formula I selected from the following compounds 100-130 in the table below (wherein $R^6$, $R^7$, and $R^8$ are each H), or a pharmaceutically acceptable salt thereof. In some embodiments, the JAK inhibitor is a compound of Formula I selected from the following compounds 200-231 in the table below (wherein $R^6$, $R^7$, and $R^8$ are each D), or a pharmaceutically acceptable salt thereof.

| Compound | $R^1$ | Each $R^2$ | Each $R^3$ | $R^4$ | Each $R^5$ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | H | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | D | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK inhibitor is baricitinib, wherein one or more hydrogen atoms are replaced by deuterium atoms, or a pharmaceutically acceptable salt thereof. In some embodiments, the JAK inhibitor is any of the compounds in U.S. Pat. No. 9,540,367 (which is incorporated herein by reference in its entirety), or a pharmaceutically acceptable salt thereof.

In some embodiments, the JAK inhibitor is a compound of Table A, or a pharmaceutically acceptable salt thereof. The compounds in Table A are selective JAK1 inhibitors (selective over JAK2, JAK3, and TYK2).

TABLE A

| Comp. No. | Prep. | Name | Structure |
|---|---|---|---|
| 1 | US 2011/0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile (itacitinib; also known as INCB039110) | 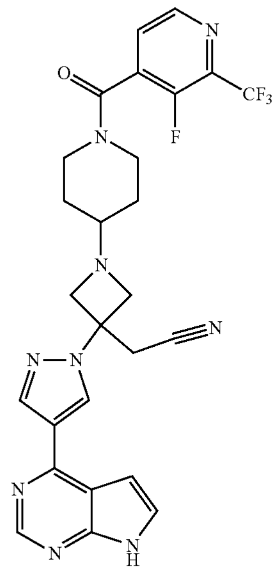 [SMILES: N#CCC1(n2cc(-c3ncnc4[nH]ccc34)cn2)CN(C2CCN(C(=O)c3ccnc(C(F)(F)F)c3F)CC2)C1] |
| 2 | US 2011/0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 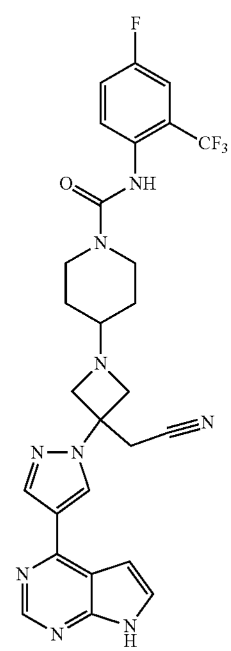 [SMILES: N#CCC1(n2cc(-c3ncnc4[nH]ccc34)cn2)CN(C2CCN(C(=O)Nc3ccc(F)cc3C(F)(F)F)CC2)C1] |

TABLE A-continued

Examples of JAK inhibitors

| Comp. No. | Prep. | Name | Structure |
|---|---|---|---|
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 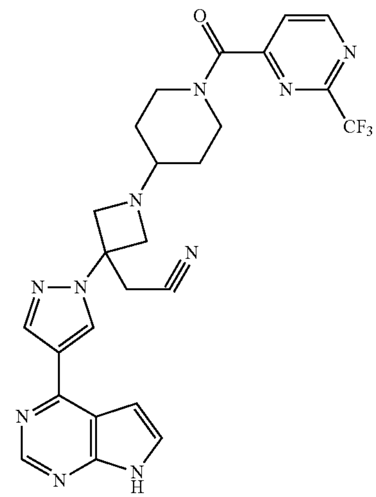 [SMILES: N#CCC1(n2cc(-c3ncnc4[nH]ccc34)cn2)CN(C2CCN(C(=O)c3ccnc(C(F)(F)F)n3)CC2)C1] |
| 4 | US 2014/ 0343030 (Example 7) | 4-[3-(cyanomethyl)-3-(3′,5′-dimethyl-1H,1′H-4,4′-bipyrazol-1-yl)azetidin-1-yl]-2,5-difluoro-N-[(1S)-2,2,2-trifluoro-1-methylethyl]benzamide | 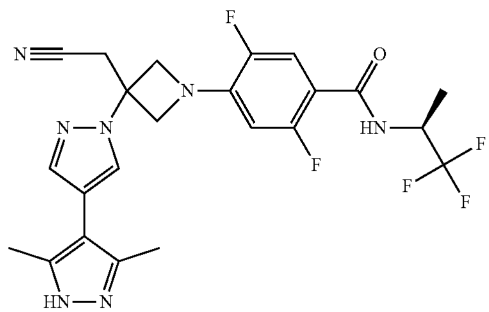 [SMILES: Cc1n[nH]c(C)c1-c1cnn(C2(CC#N)CN(c3cc(F)c(C(=O)N[C@@H](C)C(F)(F)F)cc3F)C2)c1] |
| 5 | US 2014/ 0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 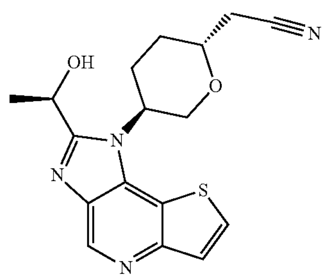 [SMILES: C[C@@H](O)c1nc2cnc3ccsc3c2n1[C@H]1CC[C@H](CC#N)OC1] |
| 6 | US 2010/ 0298334 (Example 2) | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 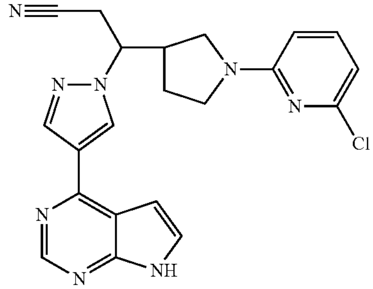 [SMILES: N#CCC(C1CCN(c2cccc(Cl)n2)C1)n1cc(-c2ncnc3[nH]ccc23)cn1] |

TABLE A-continued

Examples of JAK inhibitors

| Comp. No. | Prep. | Name | Structure |
|---|---|---|---|
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 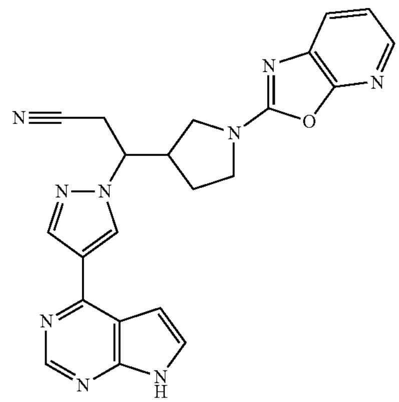 [SMILES: N#CCC(C1CCN(c2nc3cccnc3o2)C1)n1cc(-c2ncnc3[nH]ccc23)cn1] |
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 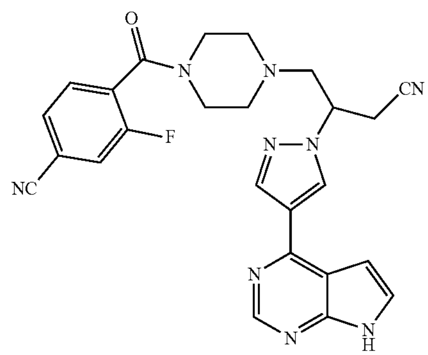 [SMILES: N#CCC(CN1CCN(C(=O)c2ccc(C#N)cc2F)CC1)n1cc(-c2ncnc3[nH]ccc23)cn1] |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 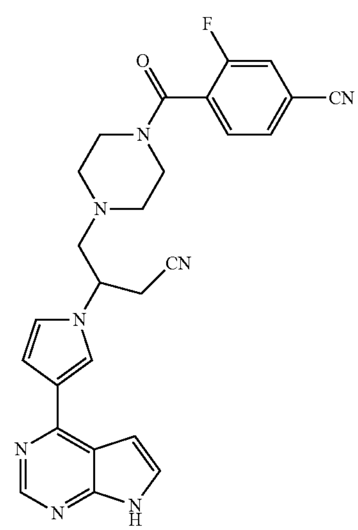 [SMILES: N#CCC(CN1CCN(C(=O)c2ccc(C#N)cc2F)CC1)n1ccc(-c2ncnc3[nH]ccc23)c1] |

TABLE A-continued

Examples of JAK inhibitors

| Comp. No. | Prep. | Name | Structure |
|---|---|---|---|
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 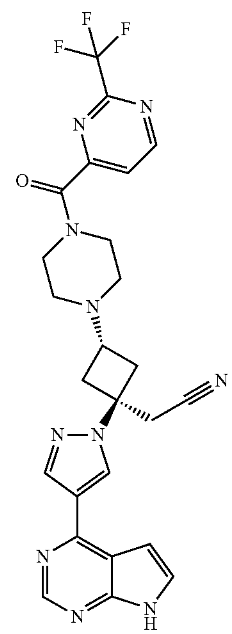 [SMILES: N#CC[C@]1(n2cc(-c3ncnc4[nH]ccc34)cn2)C[C@H](N2CCN(C(=O)c3ccnc(C(F)(F)F)n3)CC2)C1] |
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 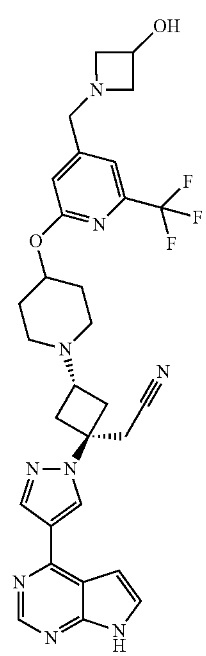 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] |

TABLE A-continued

Examples of JAK inhibitors

| Comp. No. | Prep. | Name | Structure |
|---|---|---|---|
| 12 | US 2012/ 0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 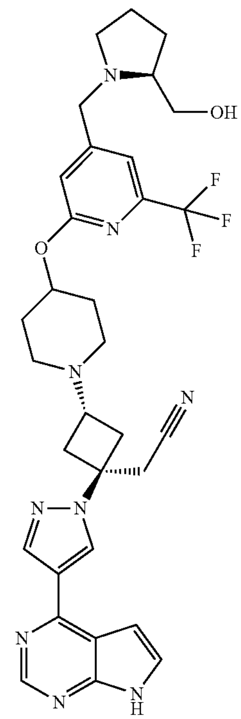 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] |
| 13 | US 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 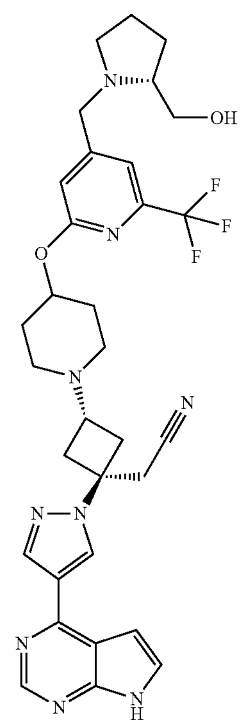 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] |

TABLE A-continued

Examples of JAK inhibitors

| Comp. No. | Prep. | Name | Structure |
|---|---|---|---|
| 14 | US 2012/ 0149682 (Example 20) | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 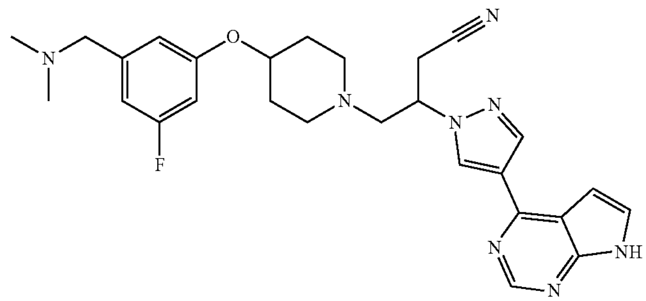 [SMILES: CN(C)Cc1cc(F)cc(OC2CCN(CC(CC#N)n3cc(-c4ncnc5[nH]ccc45)cn3)CC2)c1] |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 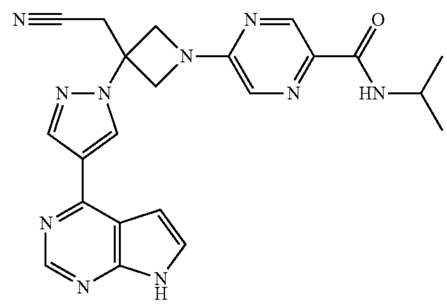 [SMILES: CC(C)NC(=O)c1cnc(N2CC(CC#N)(n3cc(-c4ncnc5[nH]ccc45)cn3)C2)cn1] |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 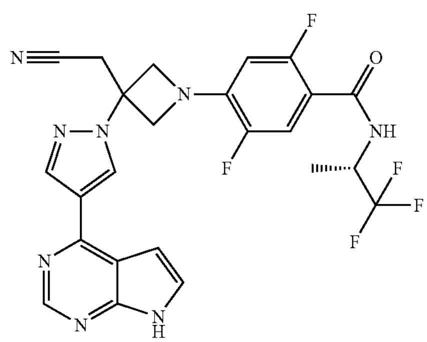 [SMILES: C[C@H](NC(=O)c1cc(F)c(N2CC(CC#N)(n3cc(-c4ncnc5[nH]ccc45)cn3)C2)cc1F)C(F)(F)F] |
| 17 | US 2013/ 0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 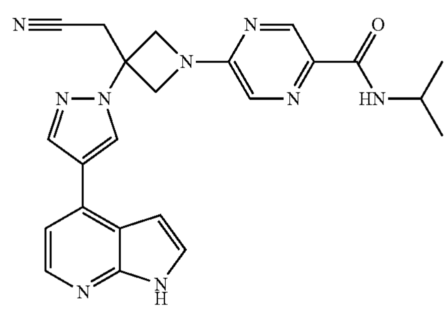 [SMILES: CC(C)NC(=O)c1cnc(N2CC(CC#N)(n3cc(-c4ccnc5[nH]ccc45)cn3)C2)cn1] |

TABLE A-continued

Examples of JAK inhibitors

| Comp. No. | Prep. | Name | Structure |
|---|---|---|---|
| 18 | US 2013/ 0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 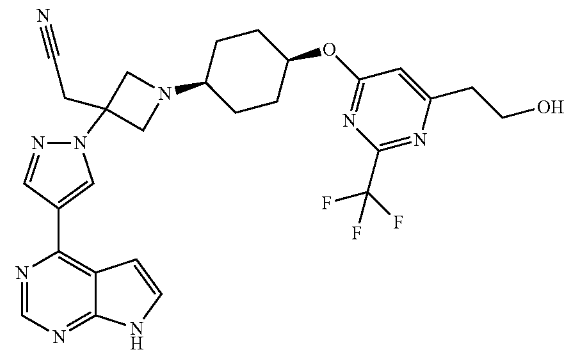 [SMILES: N#CCC1(n2cc(-c3ncnc4[nH]ccc34)cn2)CN([C@H]2CC[C@@H](Oc3cc(CCO)nc(C(F)(F)F)n3)CC2)C1] |
| 19 | US 2013/ 0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 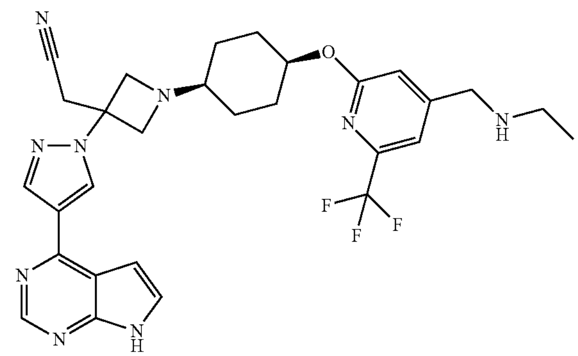 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] |
| 20 | US 2013/ 0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 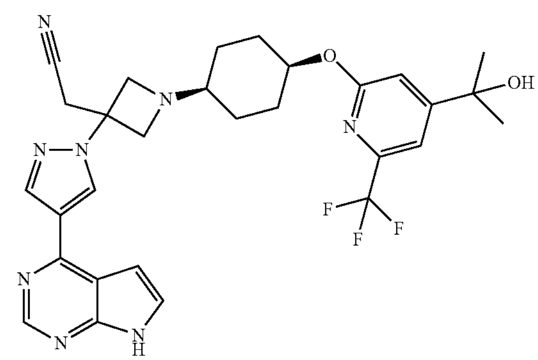 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] |
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 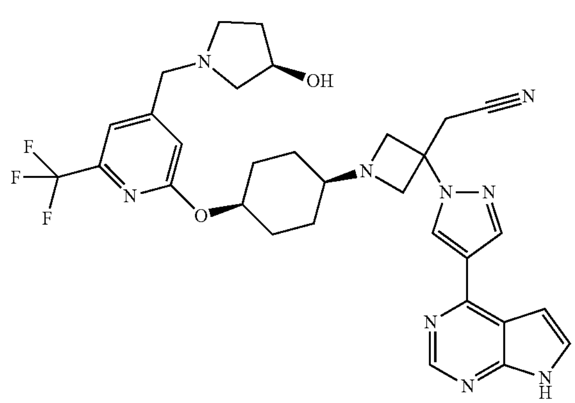 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] |

TABLE A-continued

Examples of JAK inhibitors

| Comp. No. | Prep. | Name | Structure |
|---|---|---|---|
| 22 | US 2013/0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 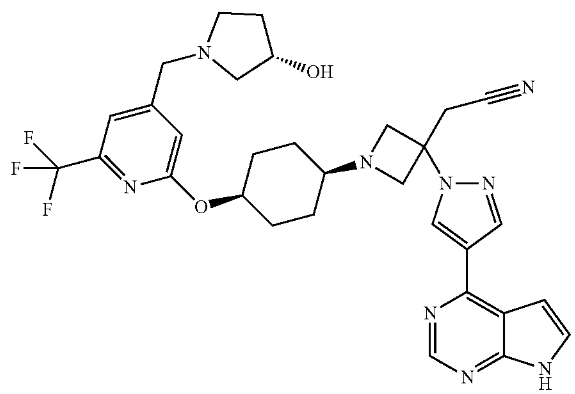 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] |
| 23 | US 2014/0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 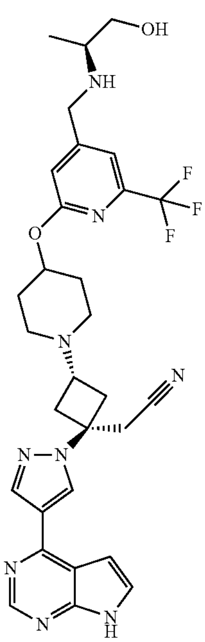 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] |

TABLE A-continued

Examples of JAK inhibitors

| Comp. No. | Prep. | Name | Structure |
|---|---|---|---|
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 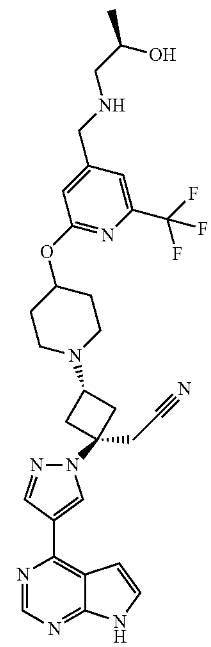 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] |
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 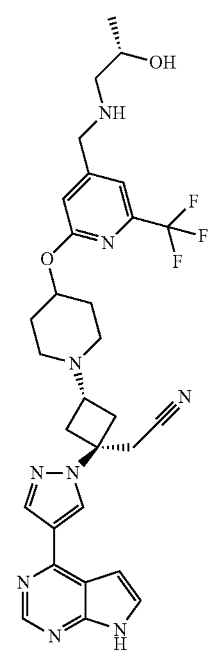 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] |

TABLE A-continued

Examples of JAK inhibitors

| Comp. No. | Prep. | Name | Structure |
|---|---|---|---|
| 26 | US 2014/0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 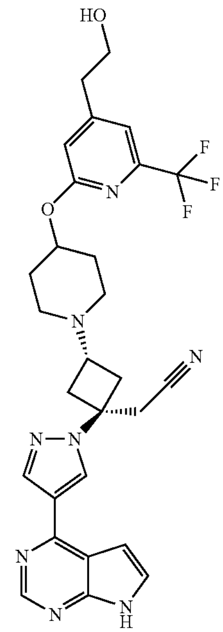 [SMILES: N#CC[C@]1(n2cc(-c3ncnc4[nH]ccc34)cn2)C[C@H](N2CCC(Oc3cc(CCO)cc(C(F)(F)F)n3)CC2)C1] |

In some embodiments, the JAK inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. US 2014/0343030, filed May 16, 2014, which is incorporated herein by reference in its entirety.

In some embodiments, the JAK inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table A are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, JAK inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

Methods of Treatment

The methods disclosed herein enable the assessment of whether or not a subject having, suspected of having or at risk of developing vitiligo is responding or is likely to respond (e.g., likely to have greater improvement in disease as evidenced by reduced disease severity and/or disease remission/resolution) to a JAK inhibitor. A subject having, suspected of having or at risk of developing vitiligo who is likely to respond to a JAK inhibitor can be administered a JAK inhibitor (e.g., ruxolitinib). Conversely, a subject having, suspected of having or at risk of developing vitiligo who is less likely to respond to a JAK inhibitor (e.g., ruxolitinib) can be administered an additional therapy that is suitable for treatment of vitiligo.

The methods of this disclosure also enable the stratification of subjects having, suspected of having or at risk of developing vitiligo into groups of subjects that are more likely to benefit, and groups of subjects that are less likely to benefit, from treatment comprising a JAK inhibitor. The ability to select such subjects from a pool of vitiligo subjects who are being considered for treatment with a JAK inhibitor is beneficial for administering an effective treatment to the subject.

In one embodiment, the subject to be treated with a JAK inhibitor (e.g., ruxolitinib) has, is suspected of having, or is likely to develop vitiligo. In certain embodiments, the subject to be treated with a JAK inhibitor (e.g., ruxolitinib) has, is suspected of having, or is likely to develop nonsegmental vitiligo. In other embodiments, the subject to be treated with a JAK inhibitor (e.g., ruxolitinib) has, is suspected of having, or is likely to develop segmental vitiligo.

If the subject having vitiligo is more likely to respond to a JAK inhibitor, the subject can then be administered an effective amount of the JAK inhibitor (e.g., ruxolitinib). An effective amount of the JAK inhibitor can suitably be determined by a health care practitioner taking into account, for example, the characteristics of the patient (age, sex, weight, race, etc.), the progression of the disease, and prior exposure to the drug. If the subject is less likely to respond to a JAK inhibitor, the subject can then be optionally administered a therapy that does not comprise a JAK inhibitor.

The methods can also be applied to individuals at risk of developing vitiligo.

After stratifying or selecting a subject based on whether the subject will be more likely or less likely to respond to a JAK inhibitor, a medical practitioner (e.g., a doctor) can administer the appropriate therapeutic modality to the subject. Methods of administering a JAK inhibitor are well known in the art.

In cases where the subject having vitiligo and predicted to respond to a JAK inhibitor has been previously administered one or more non-JAK inhibitor therapies, the JAK inhibitor can replace or augment a previously or currently administered therapy. For example, upon treating with the JAK inhibitor, administration of the one or more non-JAK inhibitor therapies can cease or diminish, e.g., be administered at lower levels. Administration of the previous therapy can be maintained while the JAK inhibitor is administered. In some embodiments, a previous therapy can be maintained until the level of the JAK inhibitor reaches a level sufficient to provide a therapeutic effect.

A subject treated with a JAK inhibitor (e.g., ruxolitinib) according to the methods described herein can be treated in combination with one or more additional compositions that are effective for treatment of vitiligo. Examples of compositions that can be used in such combination treatment include corticosteroids (e.g., methylprednisolone or prednisone), alcineurin inhibitors, vitamin D analogues, pseudocatalase, depigmenting agents, tacrolimus, pimecrolimus, oxsoralen, psoralen, khellin.

The following are examples of the practice of the invention. They are not to be construed as limiting the scope of the invention in any way.

EXAMPLES

Example 1: Human Serum CXCL9, CXCL10, and IFN-γ Levels in Subjects with Vitiligo Treated with Ruxolitinib Study subjects had a clinical diagnosis of vitiligo, with depigmented areas including at least 0.5% of the total body surface area on the face and at least 3% of the total body surface area on nonfacial areas affected using the palmar (or handprint) method (palm plus 5 digits).

CXCL9, CXCL10, and IFN-γ levels were evaluated in the sera of 134 vitiligo subjects at baseline (before treatment) and also at weeks 12 and 24 following topical treatment with one of the following five regimens: ruxolitinib cream 0.15% QD (once daily), ruxolitinib cream 0.5% QD (once daily), ruxolitinib cream 1.5% QD (once daily), ruxolitinib cream 1.5% BID (twice daily), and vehicle BID (twice daily). "%" in the various treatments refers to percent of total weight of the cream that is ruxolitinib.

Serum was collected from each subject in an 8.5 mL serum-separating tube (SST). Immediately following collection, the SST was inverted 5 times to mix clot activator with blood. Blood was allowed to clot for 30 minutes at room temperature in a vertical position. The SST was then centrifuged between 1100 and 1300×g for 10 minutes for swing-head units or 15 minutes for fixed angle units at room temperature (approximately 25° C.). The sera was collected from SST, aliquots were made then frozen and stored at −70° C. until tested.

CXCL9, CXCL10, and IFN-γ protein concentrations were measured in the sera of each subject using the Simple Plex cartridge kit (Catalog #SPCKC-PS-002038; Protein Simple-Biotechne, San Jose, Calif.) according to the manufacturer's guidelines. Samples were tested in duplicate and expressed as the mean of the duplicates for each subject. Statistical analysis was conducted using Graph Pad Prism (San Diego, Calif.). Data are presented as mean±standard error. Statistical differences between the vehicle and each treatment group were evaluated using a Mann-Whitney test. Specifically, baseline levels of CXCL9, CXCL10, and IFN-γ were calculated for individual subjects within each treatment group of the study and compared to the vehicle-treated subjects for statistical differences. The percent change from baseline in CXCL9, CXCL10, and IFN-γ levels was calculated for each individual and then averaged for each group. Statistical differences in the percent change from baseline were determined by comparing each treatment group with the vehicle using a nonparametric Mann-Whitney test.

The baseline CXCL9 concentrations of the 134 subjects tested in this study ranged from 151.7 to 13,016 pg/mL, with a median concentration of 479.3 pg/mL. No statistically significant differences in baseline CXCL9 concentrations were observed between the treatment groups.

Mean percent changes in CXCL9 levels from baseline to Week 24 for each treatment group are shown in FIG. 1.

0.15% QD-treated subjects, and 15 of 28 (54%) ruxolitinib cream 0.5% QD-treated subjects moved in a similar manner.

The changes in serum CXCL9 and CXCL10 levels, reflected in absolute values and percent change, from baseline to week 24 are depicted in Table B.

TABLE B

Change in serum CXCL9 and CXCL10 levels from baseline to week 24

| | Baseline | | | Week 24 | | | |
| --- | --- | --- | --- | --- | --- | --- | --- |
| Treatment Arm | Absolute Value Mean pg/mL ± SEM | Minimum (pg/mL) | Maximum (pg/mL) | Absolute Value Mean pg/mL ± SEM | Minimum (pg/mL) | Maximum (pg/mL) | % Change from Baseline Mean ± SEM |
| CXCL9 | | | | | | | |
| Vehicle | 633.7 ± 78.3 | 183.9 | 2034.7 | 655.8 ± 80.9 | 157.9 | 2093.9 | 6.12 ± 6.4 |
| 0.15% QD | 708.6 ± 210.7 | 249.2 | 5890.4 | 469.2 ± 33.4 | 160.9 | 904.6 | −5.80 ± 6.7 |
| 0.5% QD | 1009.7 ± 449.1 | 214.6 | 13016.0 | 760.5 ± 209.3 | 158.1 | 6070.5 | 12.44 ± 10.3 |
| 1.5% QD | 519.8 ± 84.1 | 151.7 | 2334.3 | 422.2 ± 44.0 | 125.3 | 1073.8 | −4.26 ± 10.6 |
| 1.5% BID | 767.0 ± 144.6 | 247.7 | 4616.8 | 655.4 ± 137.1 | 148.5 | 3443.9 | −18.17 ± 5.8 |
| CXCL10 | | | | | | | |
| Vehicle | 177.6 ± 15.1 | 80.9 | 408.2 | 177.4 ± 15.4 | 56.6 | 380.2 | 0.39 ± 3.6 |
| 0.15% QD | 152.0 ± 11.8 | 78.9 | 323.0 | 135.8 ± 9.1 | 56.2 | 232.3 | −5.64 ± 5.2 |
| 0.5% QD | 181.3 ± 18.0 | 79.0 | 507.3 | 162.4 ± 12.7 | 80.3 | 381.8 | −2.53 ± 5.6 |
| 1.5% QD | 149.4 ± 16.5 | 73.1 | 405.6 | 119.6 ± 15.7 | 49.5 | 446.1 | −15.49 ± 6.7 |
| 1.5% BID | 177.0 ± 12.7 | 56.5 | 361.3 | 138.3 ± 13.9 | 54.0 | 340.7 | −19.74 ± 6.6 |

Levels of CXCL9 for most subjects fell within a given range for each treatment group; however, there were outliers in the vehicle (n=1), 0.15% QD (n=1), 0.5% QD (n=1), 1.5% QD, and 1.5% BID (n=1) groups. Despite these outlying values, application of ruxolitinib cream 1.5% BID for 24 weeks significantly ($p<0.05$) reduced the CXCL9 levels in circulation as compared to vehicle (FIG. 1). Removal of the outliers did not result in any changes to the observed significance. Additionally, when comparing the directionality of the change in CXCL9 levels, 17 of 24 in the ruxolitinib cream 1.5% QD (71%) and 24 of 30 (80%) in the ruxolitinib cream 1.5% BID treatment groups saw reductions in circulating CXCL9 levels between the baseline and Week 24. As a comparison, only 13 of 26 (50%) vehicle-treated subjects, 15 of 26 (58%) ruxolitinib cream 0.15% QD-treated subjects, and 10 of 28 (36%) ruxolitinib cream 0.5% QD-treated subjects moved in a similar manner.

The baseline CXCL10 concentrations of the 134 subjects tested in this study ranged from 56.5 to 507.3 pg/mL, with a median concentration of 145.6 pg/mL. No statistically significant differences in baseline CXCL10 concentrations were observed between the treatment groups.

Figure 2:
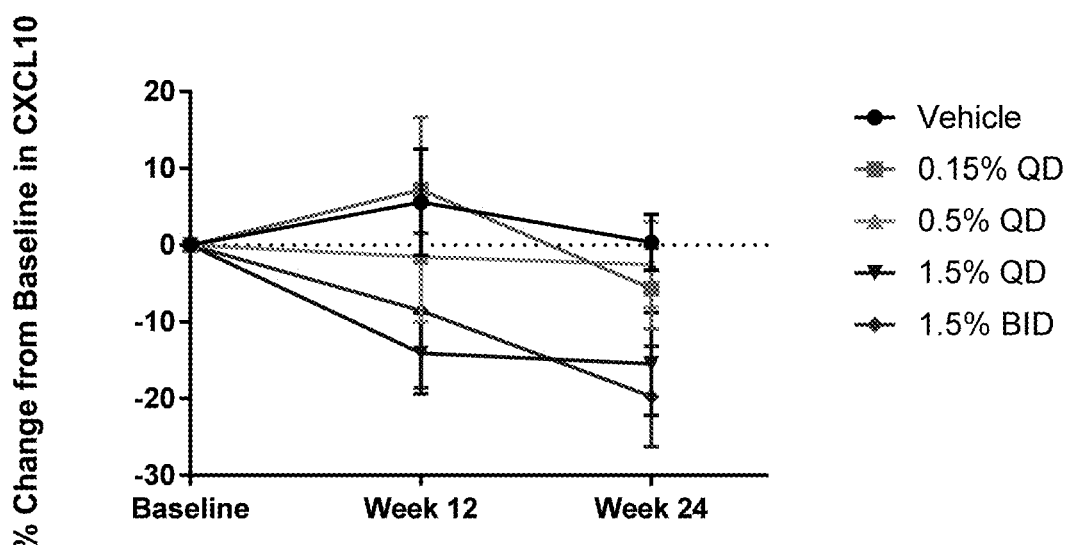
FIG. 2 is a graph depicting percent changes from baseline in CXCL10 levels at weeks 12 and 24 following treatment with a vehicle control or ruxolitinib-containing compositions.

Mean percent changes in CXCL10 levels from baseline to Week 24 for each treatment group are shown in FIG. 2. Levels of CXCL10 for most subjects fell within a given range for each treatment group; however, there were outliers in the ruxolitinib cream 1.5% QD (n=2) group. Despite these outlying values, application of ruxolitinib cream 1.5% QD or BID for 24 weeks significantly ($p<0.05$) reduced the CXCL10 levels in circulation as compared to vehicle (FIG. 2). Removal of the outliers did not result in any changes to the observed significance. Additionally, when comparing the directionality of the change in CXCL10 levels, 20 of 24 in the ruxolitinib cream 1.5% QD (83%) and 23 of 30 (77%) in the ruxolitinib cream 1.5% BID treatment groups saw reductions in circulating CXCL10 levels between the baseline and Week 24. As a comparison, only 13 of 26 (50%) vehicle-treated subjects, 15 of 26 (58%) ruxolitinib cream The baseline IFN-γ concentrations of 16 out of 137 subjects were above the lower limit of detection. The baseline levels of those 16 subjects ranged from 1.14 to 5.07 pg/mL, with a median concentration of 1.78 pg/mL. No statistically significant differences in baseline IFN-γ concentrations were observed between the treatment groups. Mean percent changes in IFN-γ levels from baseline to Weeks 12 and 24 for each treatment group are shown in Table C. No significant differences in the percent change of IFN-γ were observed between groups.

TABLE C

Mean percent change serum IFN-γ levels from baseline to weeks 12 and 24

| Treatment Group | Number of Subjects | % Change in Serum IFN-γ Levels from Baseline to Week 12[a] | % Change in Serum IFN-γ Levels from Baseline to Week 24[a] |
| --- | --- | --- | --- |
| Vehicle | 3 | −44.8 ± 22.8 | −35.2 ± 14.5 |
| 0.15% QD | 3 | 6.8 ± 17.4 | −8.6 ± 7.2 |
| 0.5% QD | 2 | −58.3 ± 41.7 | −44.9 ± 55.1 |
| 1.5% QD | 3 | −23.3 ± 31.7 | −49.9 ± 17.9 |
| 1.5% BID | 5 | −20.5 ± 20.5 | −10.7 ± 26.8 |

[a]Data presented as mean ± standard error

Example 2: Identification of Proteins Significantly Modulated in Vitiligo Patients Treated with Ruxolitinib Serum samples were collected from individuals enrolled in the study described in Example 1. Once collected, serum samples underwent broad proteomic profiling using OLINK™, which allows analysis of greater than 1000 proteins. Samples were separated into groups based on treatment group with topical ruxolitinib. Broad proteomic analysis of serum identified significantly modulated proteins from baseline to weeks 12 and/or 24 within each group. See Tables 1A through 7B. Down-regulated proteins are proteins whose expression decreased over time, while up-regulated proteins are proteins whose expression increased over time. Fold change in expression is shown for each protein, which is a ratio of protein expression level post-treatment (week 12 or week 24) to expression level pre-treatment (baseline). Values greater than 1 indicate an increase from baseline, whereas values less than 1 indicate a decrease from baseline.

TABLE 1A

Significantly modulated proteins in Vehicle at week 12

| Treatment | Week | Assay | p-value | Fold Change |
|---|---|---|---|---|
| Significantly down-regulated proteins at week 12 | | | | |
| Vehicle BID | 12 | GLB1 | 0.026 | 0.82 |
| Vehicle BID | 12 | CD63 | 0.007 | 0.87 |
| Vehicle BID | 12 | SERPINA12 | 0.044 | 0.87 |
| Vehicle BID | 12 | WISP-1 | 0.010 | 0.89 |
| Vehicle BID | 12 | CTSV | 0.011 | 0.90 |
| Vehicle BID | 12 | SERPINA5 | 0.038 | 0.92 |
| Vehicle BID | 12 | ITGAV | 0.026 | 0.92 |
| Vehicle BID | 12 | CRIM1 | 0.041 | 0.93 |
| Vehicle BID | 12 | HSD11B1 | 0.033 | 0.93 |
| Vehicle BID | 12 | FGF-BP1 | 0.020 | 0.93 |
| Vehicle BID | 12 | DPP10 | 0.049 | 0.94 |
| Vehicle BID | 12 | LEPR | 0.022 | 0.95 |
| Vehicle BID | 12 | Siglec-9 | 0.041 | 0.96 |
| Significantly up-regulated proteins at week 12 | | | | |
| Vehicle BID | 12 | TNFSF13B | 0.024 | 1.05 |
| Vehicle BID | 12 | RAGE | 0.041 | 1.06 |
| Vehicle BID | 12 | CDHR5 | 0.050 | 1.06 |
| Vehicle BID | 12 | Gal-9 | 0.014 | 1.07 |
| Vehicle BID | 12 | AMN | 0.034 | 1.07 |
| Vehicle BID | 12 | PDGFC | 0.019 | 1.07 |
| Vehicle BID | 12 | TRAIL | 0.034 | 1.09 |
| Vehicle BID | 12 | MAX | 0.011 | 1.09 |
| Vehicle BID | 12 | FAM19A5 | 0.024 | 1.09 |
| Vehicle BID | 12 | CST6 | 0.004 | 1.10 |
| Vehicle BID | 12 | IL18 | 0.035 | 1.10 |
| Vehicle BID | 12 | TYMP | 0.050 | 1.11 |
| Vehicle BID | 12 | CDSN | 0.013 | 1.13 |
| Vehicle BID | 12 | MMP-10 | 0.029 | 1.14 |
| Vehicle BID | 12 | CALCA | 0.020 | 1.16 |
| Vehicle BID | 12 | MB | 0.045 | 1.19 |

TABLE 1B

Significantly modulated proteins in Vehicle at week 24

| TRT01A | Week | Assay | wk24probt | Wk24FC |
|---|---|---|---|---|
| Proteins significantly down-regulated at week 24 | | | | |
| Vehicle BID | 24 | TANK | 0.005 | 0.74 |
| Vehicle BID | 24 | LAG3 | 0.025 | 0.93 |
| Vehicle BID | 24 | LEPR | 0.011 | 0.94 |
| Proteins significantly up-regulated at week 24 | | | | |
| Vehicle BID | 24 | MAX | 0.021 | 1.05 |
| Vehicle BID | 24 | CSF-1 | 0.024 | 1.05 |
| Vehicle BID | 24 | TRAIL | 0.013 | 1.06 |
| Vehicle BID | 24 | TNFRSF9 | 0.026 | 1.06 |
| Vehicle BID | 24 | CD5 | 0.024 | 1.06 |
| Vehicle BID | 24 | FSTL3 | 0.042 | 1.06 |
| Vehicle BID | 24 | MRC2 | 0.021 | 1.06 |
| Vehicle BID | 24 | TNFSF13B | 0.018 | 1.06 |
| Vehicle BID | 24 | PILRB | 0.049 | 1.06 |
| Vehicle BID | 24 | OPG | 0.042 | 1.07 |
| Vehicle BID | 24 | CD163 | 0.035 | 1.07 |
| Vehicle BID | 24 | LRP11 | 0.048 | 1.07 |
| Vehicle BID | 24 | CRHBP | 0.045 | 1.07 |
| Vehicle BID | 24 | LAIR1 | 0.016 | 1.07 |
| Vehicle BID | 24 | VEGFA | 0.027 | 1.07 |
| Vehicle BID | 24 | SIGLEC10 | 0.004 | 1.07 |
| Vehicle BID | 24 | TNF-R1 | 0.024 | 1.08 |
| Vehicle BID | 24 | PTN | 0.046 | 1.08 |
| Vehicle BID | 24 | IGSF3 | 0.020 | 1.08 |
| Vehicle BID | 24 | MFGE8 | 0.010 | 1.08 |
| Vehicle BID | 24 | MATN2 | 0.005 | 1.08 |
| Vehicle BID | 24 | CCL25 | 0.039 | 1.09 |
| Vehicle BID | 24 | TXNDC5 | 0.020 | 1.09 |
| Vehicle BID | 24 | CST6 | 0.029 | 1.09 |
| Vehicle BID | 24 | CLSTN2 | 0.020 | 1.09 |
| Vehicle BID | 24 | NECTIN2 | 0.009 | 1.10 |
| Vehicle BID | 24 | SCGB3A2 | 0.020 | 1.10 |
| Vehicle BID | 24 | IL18 | 0.016 | 1.10 |
| Vehicle BID | 24 | SEZ6L2 | 0.008 | 1.10 |
| Vehicle BID | 24 | FAM19A5 | 0.036 | 1.11 |
| Vehicle BID | 24 | MESDC2 | 0.044 | 1.11 |
| Vehicle BID | 24 | SUMF2 | 0.014 | 1.11 |
| Vehicle BID | 24 | IL10 | 0.013 | 1.12 |
| Vehicle BID | 24 | PPP1R2 | 0.045 | 1.12 |
| Vehicle BID | 24 | DAPP1 | 0.033 | 1.12 |
| Vehicle BID | 24 | DDAH1 | 0.025 | 1.12 |
| Vehicle BID | 24 | CDSN | 0.016 | 1.13 |
| Vehicle BID | 24 | FLI1 | 0.031 | 1.13 |
| Vehicle BID | 24 | REG4 | 0.026 | 1.14 |
| Vehicle BID | 24 | DDC | 0.006 | 1.15 |
| Vehicle BID | 24 | PARK7 | 0.040 | 1.15 |
| Vehicle BID | 24 | ICA1 | 0.024 | 1.17 |
| Vehicle BID | 24 | LEP | 0.006 | 1.17 |
| Vehicle BID | 24 | ERBB2IP | 0.047 | 1.18 |
| Vehicle BID | 24 | BCR | 0.008 | 1.19 |
| Vehicle BID | 24 | INPPL1 | 0.016 | 1.20 |
| Vehicle BID | 24 | AGR2 | 0.046 | 1.21 |
| Vehicle BID | 24 | PEBP1 | 0.030 | 1.21 |
| Vehicle BID | 24 | MAP4K5 | 0.037 | 1.23 |
| Vehicle BID | 24 | Ep-CAM | 0.031 | 1.27 |
| Vehicle BID | 24 | SIRT2 | 0.029 | 1.29 |
| Vehicle BID | 24 | GCG | 0.017 | 1.34 |
| Vehicle BID | 24 | TSHB | 0.031 | 1.42 |

TABLE 2A

Significantly modulated proteins in 0.15% ruxolitinib QD at week 12

| Treatment | Week | Assay | p-value | Fold Change |
|---|---|---|---|---|
| Significantly down-regulated proteins at week 12 | | | | |
| INCB018424 0.15% QD | 12 | BANK1 | 0.010 | 0.61 |
| INCB018424 0.15% QD | 12 | AXIN1 | 0.005 | 0.68 |
| INCB018424 0.15% QD | 12 | EREG | 0.046 | 0.69 |
| INCB018424 0.15% QD | 12 | ST1A1 | 0.034 | 0.70 |
| INCB018424 0.15% QD | 12 | FATCI | 0.022 | 0.72 |
| INCB018424 0.15% QD | 12 | INPPL1 | 0.019 | 0.75 |
| INCB018424 0.15% QD | 12 | NEMO | 0.047 | 0.76 |
| INCB018424 0.15% QD | 12 | TANK | 0.035 | 0.77 |
| INCB018424 0.15% QD | 12 | CDKN1A | 0.043 | 0.79 |
| INCB018424 0.15% QD | 12 | PPP1R9B | 0.015 | 0.79 |
| INCB018424 0.15% QD | 12 | ZBTB16 | 0.037 | 0.80 |
| INCB018424 0.15% QD | 12 | TXLNA | 0.030 | 0.81 |
| INCB018424 0.15% QD | 12 | MGMT | 0.022 | 0.82 |
| INCB018424 0.15% QD | 12 | BCR | 0.044 | 0.83 |
| INCB018424 0.15% QD | 12 | GRAP2 | 0.036 | 0.83 |
| INCB018424 0.15% QD | 12 | WWP2 | 0.030 | 0.85 |
| INCB018424 0.15% QD | 12 | G-CSF | 0.030 | 0.85 |
| INCB018424 0.15% QD | 12 | ANXA10 | 0.037 | 0.85 |
| INCB018424 0.15% QD | 12 | STX6 | 0.011 | 0.86 |
| INCB018424 0.15% QD | 12 | CRX | 0.044 | 0.86 |
| INCB018424 0.15% QD | 12 | IL-20 | 0.012 | 0.88 |
| INCB018424 0.15% QD | 12 | WASF1 | 0.016 | 0.89 |
| INCB018424 0.15% QD | 12 | NTF4 | 0.037 | 0.90 |
| INCB018424 0.15% QD | 12 | IL13 | 0.022 | 0.90 |
| INCB018424 0.15% QD | 12 | NCR1 | 0.025 | 0.91 |
| INCB018424 0.15% QD | 12 | IL-10RA | 0.014 | 0.91 |

TABLE 2A-continued

Significantly modulated proteins in
0.15% ruxolitinib QD at week 12

| Treatment | Week | Assay | p-value | Fold Change |
|---|---|---|---|---|
| INCB018424 0.15% QD | 12 | HTRA2 | 0.023 | 0.91 |
| INCB018424 0.15% QD | 12 | CTRC | 0.028 | 0.92 |
| INCB018424 0.15% QD | 12 | DDAH1 | 0.035 | 0.93 |
| INCB018424 0.15% QD | 12 | PLXNB2 | 0.016 | 0.94 |
| INCB018424 0.15% QD | 12 | IL1RL2 | 0.034 | 0.94 |
| INCB018424 0.15% QD | 12 | CLEC4G | 0.040 | 0.94 |
| INCB018424 0.15% QD | 12 | IL-17D | 0.013 | 0.94 |
| INCB018424 0.15% QD | 12 | CFC1 | 0.041 | 0.95 |
| INCB018424 0.15% QD | 12 | FKBP7 | 0.049 | 0.95 |
| INCB018424 0.15% QD | 12 | COL18A1 | 0.036 | 0.95 |
| INCB018424 0.15% QD | 12 | CCL14 | 0.040 | 0.95 |
| INCB018424 0.15% QD | 12 | LILRB1 | 0.029 | 0.95 |
| INCB018424 0.15% QD | 12 | OSMR | 0.044 | 0.96 |
| INCB018424 0.15% QD | 12 | AMBP | 0.049 | 0.97 |
| Significantly up-regulated proteins at week 12 | | | | |
| INCB018424 0.15% QD | 12 | Gal-1 | 0.037 | 1.05 |
| INCB018424 0.15% QD | 12 | CLSPN | 0.047 | 1.06 |
| INCB018424 0.15% QD | 12 | CPE | 0.049 | 1.06 |
| INCB018424 0.15% QD | 12 | PVRL4 | 0.018 | 1.06 |
| INCB018424 0.15% QD | 12 | ACP6 | 0.049 | 1.06 |
| INCB018424 0.15% QD | 12 | FR-alpha | 0.031 | 1.06 |
| INCB018424 0.15% QD | 12 | hK11 | 0.008 | 1.07 |
| INCB018424 0.15% QD | 12 | ITGB5 | 0.017 | 1.08 |
| INCB018424 0.15% QD | 12 | FURIN | 0.031 | 1.08 |
| INCB018424 0.15% QD | 12 | hK8 | 0.014 | 1.09 |
| INCB018424 0.15% QD | 12 | CLSTN2 | 0.023 | 1.10 |
| INCB018424 0.15% QD | 12 | hK14 | 0.011 | 1.10 |
| INCB018424 0.15% QD | 12 | CXL17 | 0.020 | 1.11 |
| INCB018424 0.15% QD | 12 | TFPI-2 | 0.019 | 1.11 |
| INCB018424 0.15% QD | 12 | TNFRSF12A | 0.019 | 1.13 |
| INCB018424 0.15% QD | 12 | MYOC | 0.028 | 1.13 |
| INCB018424 0.15% QD | 12 | ESM-1 | 0.008 | 1.13 |

TABLE 2B

Significantly modulated proteins in
0.15% ruxolitinib QD at week 24

| Treatment | Week | Assay | p-value | Fold Change |
|---|---|---|---|---|
| Proteins significantly down-regulated at week 24 | | | | |
| INCB018424 0.15% QD | 24 | PPY | 0.033 | 0.71 |
| INCB018424 0.15% QD | 24 | TANK | 0.043 | 0.76 |
| INCB018424 0.15% QD | 24 | ANXA10 | 0.029 | 0.82 |
| INCB018424 0.15% QD | 24 | PRTFDC1 | 0.021 | 0.90 |
| INCB018424 0.15% QD | 24 | CDH17 | 0.021 | 0.91 |
| INCB018424 0.15% QD | 24 | FKBP7 | 0.031 | 0.92 |
| INCB018424 0.15% QD | 24 | STXBP3 | 0.044 | 0.93 |
| INCB018424 0.15% QD | 24 | CFC1 | 0.016 | 0.93 |
| INCB018424 0.15% QD | 24 | SMOC1 | 0.045 | 0.94 |
| INCB018424 0.15% QD | 24 | PRDX3 | 0.037 | 0.95 |
| Proteins significantly up-regulated at week 24 | | | | |
| INCB018424 0.15% QD | 24 | ACP6 | 0.037 | 1.06 |
| INCB018424 0.15% QD | 24 | PRSS8 | 0.030 | 1.06 |
| INCB018424 0.15% QD | 24 | CDCP1 | 0.032 | 1.08 |
| INCB018424 0.15% QD | 24 | CSTB | 0.025 | 1.08 |
| INCB018424 0.15% QD | 24 | SH2D1A | 0.028 | 1.09 |
| INCB018424 0.15% QD | 24 | FGF-BP1 | 0.005 | 1.10 |
| INCB018424 0.15% QD | 24 | TFPI-2 | 0.026 | 1.10 |
| INCB018424 0.15% QD | 24 | HNMT | 0.008 | 1.11 |
| INCB018424 0.15% QD | 24 | MSLN | 0.015 | 1.12 |
| INCB018424 0.15% QD | 24 | SERPINA9 | 0.020 | 1.12 |
| INCB018424 0.15% QD | 24 | t-PA | 0.033 | 1.13 |
| INCB018424 0.15% QD | 24 | FABP4 | 0.028 | 1.13 |
| INCB018424 0.15% QD | 24 | PTN | 0.018 | 1.14 |
| INCB018424 0.15% QD | 24 | CGA | 0.045 | 1.19 |
| INCB018424 0.15% QD | 24 | MAGED1 | 0.014 | 1.24 |

TABLE 2B-continued

Significantly modulated proteins in
0.15% ruxolitinib QD at week 24

| Treatment | Week | Assay | p-value | Fold Change |
|---|---|---|---|---|
| INCB018424 0.15% QD | 24 | IGFBP-1 | 0.047 | 1.34 |
| INCB018424 0.15% QD | 24 | FGF-21 | 0.032 | 1.42 |
| INCB018424 0.15% QD | 24 | FGF-21 | 0.024 | 1.44 |

TABLE 3A

Significantly modulated proteins 0.5% ruxolitinib QD at week 12

| Treatment | Week | Assay | p-value | Fold Change |
|---|---|---|---|---|
| Significantly down-regulated proteins at week 12 | | | | |
| INCB018424 0.5% QD | 12 | CA2 | 0.043 | 0.78 |
| INCB018424 0.5% QD | 12 | GLO1 | 0.016 | 0.82 |
| INCB018424 0.5% QD | 12 | CASP-8 | 0.010 | 0.84 |
| INCB018424 0.5% QD | 12 | AARSD1 | 0.041 | 0.85 |
| INCB018424 0.5% QD | 12 | ATG4A | 0.041 | 0.85 |
| INCB018424 0.5% QD | 12 | MMP12 | 0.017 | 0.85 |
| INCB018424 0.5% QD | 12 | TRANCE | 0.038 | 0.87 |
| INCB018424 0.5% QD | 12 | FGF-23 | 0.019 | 0.88 |
| INCB018424 0.5% QD | 12 | DFFA | 0.040 | 0.88 |
| INCB018424 0.5% QD | 12 | KLRD1 | 0.003 | 0.88 |
| INCB018424 0.5% QD | 12 | BACH1 | 0.029 | 0.89 |
| INCB018424 0.5% QD | 12 | BLVRB | 0.028 | 0.89 |
| INCB018424 0.5% QD | 12 | IL2-RA | 0.003 | 0.89 |
| INCB018424 0.5% QD | 12 | PAPPA | 0.023 | 0.89 |
| INCB018424 0.5% QD | 12 | IL16 | 0.036 | 0.90 |
| INCB018424 0.5% QD | 12 | XCL1 | 0.020 | 0.90 |
| INCB018424 0.5% QD | 12 | DRAXIN | 0.035 | 0.90 |
| INCB018424 0.5% QD | 12 | DCTN2 | 0.023 | 0.90 |
| INCB018424 0.5% QD | 12 | MAEA | 0.008 | 0.90 |
| INCB018424 0.5% QD | 12 | FCRL6 | <<0.00011 | 0.91 |
| INCB018424 0.5% QD | 12 | FES | 0.045 | 0.91 |
| INCB018424 0.5% QD | 12 | NCR1 | 0.016 | 0.91 |
| INCB018424 0.5% QD | 12 | FASLG | 0.011 | 0.91 |
| INCB018424 0.5% QD | 12 | IL-18BP | 0.046 | 0.92 |
| INCB018424 0.5% QD | 12 | NFKBIE | 0.014 | 0.92 |
| INCB018424 0.5% QD | 12 | ZBTB17 | 0.050 | 0.92 |
| INCB018424 0.5% QD | 12 | SRPK2 | 0.033 | 0.93 |
| INCB018424 0.5% QD | 12 | IGFBP-2 | 0.037 | 0.93 |
| INCB018424 0.5% QD | 12 | GRN | 0.028 | 0.93 |
| INCB018424 0.5% QD | 12 | TNFSF13B | 0.038 | 0.93 |
| INCB018424 0.5% QD | 12 | BOC | 0.050 | 0.95 |
| Significantly up-regulated proteins at week 12 | | | | |
| INCB018424 0.5% QD | 12 | IL15 | 0.023 | 1.05 |
| INCB018424 0.5% QD | 12 | VAMP5 | 0.027 | 1.06 |
| INCB018424 0.5% QD | 12 | PRSS8 | 0.015 | 1.06 |
| INCB018424 0.5% QD | 12 | PCOLCE | 0.028 | 1.07 |
| INCB018424 0.5% QD | 12 | CD300LG | 0.038 | 1.07 |
| INCB018424 0.5% QD | 12 | SMOC1 | 0.027 | 1.08 |
| INCB018424 0.5% QD | 12 | CTSF | 0.049 | 1.09 |
| INCB018424 0.5% QD | 12 | PCSK9 | 0.040 | 1.09 |
| INCB018424 0.5% QD | 12 | LPL | 0.041 | 1.10 |
| INCB018424 0.5% QD | 12 | RSPO3 | 0.023 | 1.10 |
| INCB018424 0.5% QD | 12 | SUMF2 | 0.031 | 1.10 |
| INCB018424 0.5% QD | 12 | NT-3 | 0.006 | 1.11 |
| INCB018424 0.5% QD | 12 | CST6 | 0.010 | 1.12 |
| INCB018424 0.5% QD | 12 | PTN | 0.005 | 1.13 |
| INCB018424 0.5% QD | 12 | SERPINA9 | 0.002 | 1.13 |
| INCB018424 0.5% QD | 12 | IL6 | 0.025 | 1.14 |
| INCB018424 0.5% QD | 12 | CHI3L1 | 0.045 | 1.15 |
| INCB018424 0.5% QD | 12 | SFRP1 | 0.003 | 1.23 |
| INCB018424 0.5% QD | 12 | CES1 | 0.021 | 1.27 |

TABLE 3B

Significantly modulated proteins 0.5% ruxolitinib QD at week 24

| Treatment | Week | Assay | p-value | Fold Change |
|---|---|---|---|---|
| Proteins significantly down-regulated at week 24 | | | | |
| INCB018424 0.5% QD | 24 | BMP-6 | 0.009 | 0.80 |
| INCB018424 0.5% QD | 24 | GHRL | 0.024 | 0.80 |
| INCB018424 0.5% QD | 24 | TNFRSF6B | 0.007 | 0.81 |
| INCB018424 0.5% QD | 24 | DAPP1 | 0.006 | 0.82 |
| INCB018424 0.5% QD | 24 | BCL2L11 | 0.003 | 0.83 |
| INCB018424 0.5% QD | 24 | SPINT2 | 0.021 | 0.84 |
| INCB018424 0.5% QD | 24 | CRH | 0.027 | 0.87 |
| INCB018424 0.5% QD | 24 | DRAXIN | 0.026 | 0.88 |
| INCB018424 0.5% QD | 24 | OPN | 0.004 | 0.89 |
| INCB018424 0.5% QD | 24 | RASA1 | 0.013 | 0.89 |
| INCB018424 0.5% QD | 24 | MMP-3 | 0.044 | 0.90 |
| INCB018424 0.5% QD | 24 | CLSTN2 | 0.017 | 0.90 |
| INCB018424 0.5% QD | 24 | CD8A | 0.047 | 0.91 |
| INCB018424 0.5% QD | 24 | PDGFC | 0.011 | 0.91 |
| INCB018424 0.5% QD | 24 | IL2-RA | 0.017 | 0.92 |
| INCB018424 0.5% QD | 24 | NCR1 | 0.015 | 0.92 |
| INCB018424 0.5% QD | 24 | FLI1 | 0.046 | 0.93 |
| INCB018424 0.5% QD | 24 | FCRL6 | 0.042 | 0.93 |
| INCB018424 0.5% QD | 24 | BOC | 0.035 | 0.94 |
| INCB018424 0.5% QD | 24 | LYPD1 | 0.031 | 0.94 |
| Proteins significantly up-regulated at Week 24 | | | | |
| INCB018424 0.5% QD | 24 | QPCT | 0.027 | 1.04 |
| INCB018424 0.5% QD | 24 | ITGAV | 0.033 | 1.04 |
| INCB018424 0.5% QD | 24 | DPEP1 | 0.039 | 1.05 |
| INCB018424 0.5% QD | 24 | FGFR2 | 0.040 | 1.05 |
| INCB018424 0.5% QD | 24 | NCAM1 | 0.050 | 1.05 |
| INCB018424 0.5% QD | 24 | ERBB4 | 0.037 | 1.06 |
| INCB018424 0.5% QD | 24 | IGF1R | 0.045 | 1.06 |
| INCB018424 0.5% QD | 24 | DPP4 | 0.026 | 1.06 |
| INCB018424 0.5% QD | 24 | TRAIL-R2 | 0.030 | 1.06 |
| INCB018424 0.5% QD | 24 | PAM | 0.016 | 1.06 |
| INCB018424 0.5% QD | 24 | PEAR1 | 0.046 | 1.07 |
| INCB018424 0.5% QD | 24 | ITGB5 | 0.015 | 1.07 |
| INCB018424 0.5% QD | 24 | SIRPB1 | 0.034 | 1.07 |
| INCB018424 0.5% QD | 24 | CCL16 | 0.033 | 1.07 |
| INCB018424 0.5% QD | 24 | ASGR1 | 0.038 | 1.07 |
| INCB018424 0.5% QD | 24 | CR2 | 0.042 | 1.07 |
| INCB018424 0.5% QD | 24 | CCL14 | 0.016 | 1.07 |
| INCB018424 0.5% QD | 24 | ICOSLG | 0.044 | 1.07 |
| INCB018424 0.5% QD | 24 | TNFRSF19 | 0.042 | 1.08 |
| INCB018424 0.5% QD | 24 | Gal-4 | 0.042 | 1.08 |
| INCB018424 0.5% QD | 24 | PLC | 0.024 | 1.08 |
| INCB018424 0.5% QD | 24 | CRTAC1 | 0.015 | 1.09 |
| INCB018424 0.5% QD | 24 | RELT | 0.032 | 1.09 |
| INCB018424 0.5% QD | 24 | RNF31 | 0.038 | 1.09 |
| INCB018424 0.5% QD | 24 | CD59 | 0.035 | 1.09 |
| INCB018424 0.5% QD | 24 | VEGFA | 0.046 | 1.10 |
| INCB018424 0.5% QD | 24 | CTSF | 0.037 | 1.10 |
| INCB018424 0.5% QD | 24 | FCGR3B | 0.008 | 1.10 |
| INCB018424 0.5% QD | 24 | IGFBP6 | 0.013 | 1.10 |
| INCB018424 0.5% QD | 24 | TGFBI | 0.018 | 1.10 |
| INCB018424 0.5% QD | 24 | MMP7 | 0.001 | 1.11 |
| INCB018424 0.5% QD | 24 | CD300LG | 0.029 | 1.11 |
| INCB018424 0.5% QD | 24 | COCH | 0.037 | 1.11 |
| INCB018424 0.5% QD | 24 | SCGB1A1 | 0.005 | 1.12 |
| INCB018424 0.5% QD | 24 | SCGB3A2 | 0.018 | 1.12 |
| INCB018424 0.5% QD | 24 | SCGB3A1 | 0.001 | 1.12 |
| INCB018424 0.5% QD | 24 | EPHA10 | 0.037 | 1.12 |
| INCB018424 0.5% QD | 24 | TFPI-2 | 0.041 | 1.13 |
| INCB018424 0.5% QD | 24 | ECE1 | 0.014 | 1.13 |
| INCB018424 0.5% QD | 24 | MUC-16 | 0.031 | 1.14 |
| INCB018424 0.5% QD | 24 | SERPINA5 | <<0.00011 | 1.16 |
| INCB018424 0.5% QD | 24 | PTN | 0.043 | 1.16 |
| INCB018424 0.5% QD | 24 | TP53 | 0.029 | 1.17 |
| INCB018424 0.5% QD | 24 | CHI3L1 | 0.022 | 1.17 |
| INCB018424 0.5% QD | 24 | ITGAM | 0.014 | 1.17 |
| INCB018424 0.5% QD | 24 | NRP2 | 0.035 | 1.20 |
| INCB018424 0.5% QD | 24 | SNCG | 0.006 | 1.21 |
| INCB018424 0.5% QD | 24 | LEP | 0.040 | 1.24 |
| INCB018424 0.5% QD | 24 | FGF-21 | 0.003 | 1.31 |
| INCB018424 0.5% QD | 24 | FGF-21 | 0.004 | 1.33 |
| INCB018424 0.5% QD | 24 | FGF-21 | 0.002 | 1.40 |

TABLE 4A

Significantly modulated proteins 1.5% ruxolitinib QD at week 12

| Treatment | Week | Assay | p-value | Fold Change |
|---|---|---|---|---|
| Significantly down-regulated proteins at week 12 | | | | |
| INCB018424 1.5% QD | 12 | CCL19 | <.0001 | 0.73 |
| INCB018424 1.5% QD | 12 | NCR1 | <.0001 | 0.79 |
| INCB018424 1.5% QD | 12 | LAIR-2 | <.0001 | 0.79 |
| INCB018424 1.5% QD | 12 | FASLG | <.0001 | 0.83 |
| INCB018424 1.5% QD | 12 | TNFRSF9 | <.0001 | 0.84 |
| INCB018424 1.5% QD | 12 | CRTAM | <.0001 | 0.85 |
| INCB018424 1.5% QD | 12 | CD6 | <.0001 | 0.86 |
| INCB018424 1.5% QD | 12 | DEFB4A | 0.032 | 0.72 |
| INCB018424 1.5% QD | 12 | IGFBP-1 | 0.028 | 0.74 |
| INCB018424 1.5% QD | 12 | CXCL10 | <<0.00011 | 0.74 |
| INCB018424 1.5% QD | 12 | GZMH | 0.001 | 0.80 |
| INCB018424 1.5% QD | 12 | FS | 0.011 | 0.80 |
| INCB018424 1.5% QD | 12 | KIR2DL3 | 0.025 | 0.81 |
| INCB018424 1.5% QD | 12 | GZMB | 0.005 | 0.82 |
| INCB018424 1.5% QD | 12 | IFNL1 | 0.001 | 0.82 |
| INCB018424 1.5% QD | 12 | DRAXIN | 0.018 | 0.83 |
| INCB018424 1.5% QD | 12 | SH2D1A | 0.007 | 0.84 |
| INCB018424 1.5% QD | 12 | IL-12B | <0.0001 | 0.84 |
| INCB018424 1.5% QD | 12 | CXCL11 | 0.041 | 0.85 |
| INCB018424 1.5% QD | 12 | KLRD1 | <0.0001 | 0.85 |
| INCB018424 1.5% QD | 12 | CD160 | <0.0001 | 0.85 |
| INCB018424 1.5% QD | 12 | GZMA | <0.0001 | 0.86 |
| INCB018424 1.5% QD | 12 | FCRL6 | 0.001 | 0.86 |
| INCB018424 1.5% QD | 12 | MCP-4 | 0.027 | 0.86 |
| INCB018424 1.5% QD | 12 | IL12 | 0.001 | 0.87 |
| INCB018424 1.5% QD | 12 | XCL1 | 0.011 | 0.87 |
| INCB018424 1.5% QD | 12 | ANGPTL4 | 0.027 | 0.87 |
| INCB018424 1.5% QD | 12 | CCL21 | 0.001 | 0.87 |
| INCB018424 1.5% QD | 12 | IL6 | 0.026 | 0.87 |
| INCB018424 1.5% QD | 12 | MMP12 | 0.003 | 0.87 |
| INCB018424 1.5% QD | 12 | TYMP | 0.005 | 0.87 |
| INCB018424 1.5% QD | 12 | CD5 | <0.0001 | 0.88 |
| INCB018424 1.5% QD | 12 | CCL18 | 0.018 | 0.88 |
| INCB018424 1.5% QD | 12 | ITGB2 | <0.0001 | 0.88 |
| INCB018424 1.5% QD | 12 | TNFB | 0.008 | 0.89 |
| INCB018424 1.5% QD | 12 | CD8A | 0.018 | 0.89 |
| INCB018424 1.5% QD | 12 | ARTN | 0.015 | 0.89 |
| INCB018424 1.5% QD | 12 | SIGLEC1 | 0.004 | 0.90 |
| INCB018424 1.5% QD | 12 | IL-15RA | 0.034 | 0.90 |
| INCB018424 1.5% QD | 12 | CD163 | <0.0001 | 0.90 |
| INCB018424 1.5% QD | 12 | SLAMF1 | 0.049 | 0.90 |
| INCB018424 1.5% QD | 12 | REIN | 0.006 | 0.90 |
| INCB018424 1.5% QD | 12 | TNFSF13B | 0.005 | 0.91 |
| INCB018424 1.5% QD | 12 | CLEC6A | 0.036 | 0.91 |
| INCB018424 1.5% QD | 12 | PAPPA | 0.036 | 0.91 |
| INCB018424 1.5% QD | 12 | CLEC10A | 0.002 | 0.91 |
| INCB018424 1.5% QD | 12 | SELE | 0.017 | 0.92 |
| INCB018424 1.5% QD | 12 | ADAM 8 | 0.012 | 0.92 |
| INCB018424 1.5% QD | 12 | GDF-15 | 0.025 | 0.92 |
| INCB018424 1.5% QD | 12 | IL-1RT1 | 0.007 | 0.92 |
| INCB018424 1.5% QD | 12 | CD244 | 0.015 | 0.92 |
| INCB018424 1.5% QD | 12 | CLM-1 | 0.009 | 0.93 |
| INCB018424 1.5% QD | 12 | DSC2 | 0.006 | 0.93 |
| INCB018424 1.5% QD | 12 | FOLR2 | 0.001 | 0.93 |
| INCB018424 1.5% QD | 12 | TNF-R2 | 0.019 | 0.93 |
| INCB018424 1.5% QD | 12 | LIF-R | 0.014 | 0.93 |
| INCB018424 1.5% QD | 12 | IL12RB1 | 0.017 | 0.93 |
| INCB018424 1.5% QD | 12 | CDH3 | 0.032 | 0.93 |
| INCB018424 1.5% QD | 12 | CLEC4G | 0.020 | 0.93 |
| INCB018424 1.5% QD | 12 | CD79B | 0.037 | 0.93 |
| INCB018424 1.5% QD | 12 | IL-18BP | 0.028 | 0.93 |
| INCB018424 1.5% QD | 12 | GM-CSF-R-alpha | 0.026 | 0.94 |
| INCB018424 1.5% QD | 12 | CD1C | 0.005 | 0.94 |
| INCB018424 1.5% QD | 12 | ST2 | 0.034 | 0.94 |
| INCB018424 1.5% QD | 12 | MSR1 | 0.015 | 0.94 |
| INCB018424 1.5% QD | 12 | PDCD1 | 0.022 | 0.94 |
| INCB018424 1.5% QD | 12 | CSF-1 | 0.046 | 0.94 |
| INCB018424 1.5% QD | 12 | FcRL2 | 0.016 | 0.94 |
| INCB018424 1.5% QD | 12 | LY9 | 0.032 | 0.95 |
| INCB018424 1.5% QD | 12 | CD27 | 0.026 | 0.95 |
| INCB018424 1.5% QD | 12 | CD48 | 0.024 | 0.95 |
| INCB018424 1.5% QD | 12 | CD200R1 | 0.013 | 0.95 |
| INCB018424 1.5% QD | 12 | hOSCAR | 0.030 | 0.96 |

TABLE 4A-continued

Significantly modulated proteins 1.5% ruxolitinib QD at week 12

| Treatment | Week | Assay | p-value | Fold Change |
|---|---|---|---|---|
| Significantly up-regulated proteins at week 12 | | | | |
| INCB018424 1.5% QD | 12 | CD300LG | <.0001 | 1.10 |
| INCB018424 1.5% QD | 12 | hK11 | <.0001 | 1.11 |
| INCB018424 1.5% QD | 12 | IL15 | <.0001 | 1.12 |
| INCB018424 1.5% QD | 12 | KLK10 | <.0001 | 1.12 |
| INCB018424 1.5% QD | 12 | FGF-BP1 | <.0001 | 1.23 |
| INCB018424 1.5% QD | 12 | MYOC | <.0001 | 1.29 |
| INCB018424 1.5% QD | 12 | GPNMB | 0.035 | 1.04 |
| INCB018424 1.5% QD | 12 | CAMKK1 | 0.028 | 1.04 |
| INCB018424 1.5% QD | 12 | ITGB1 | 0.012 | 1.04 |
| INCB018424 1.5% QD | 12 | PDGFRB | 0.013 | 1.04 |
| INCB018424 1.5% QD | 12 | TYRO3 | 0.030 | 1.04 |
| INCB018424 1.5% QD | 12 | B4GAT1 | 0.035 | 1.05 |
| INCB018424 1.5% QD | 12 | CLEC4A | 0.017 | 1.05 |
| INCB018424 1.5% QD | 12 | GFRA2 | 0.026 | 1.05 |
| INCB018424 1.5% QD | 12 | ENTPD6 | 0.021 | 1.05 |
| INCB018424 1.5% QD | 12 | SPON2 | 0.005 | 1.05 |
| INCB018424 1.5% QD | 12 | TCL1B | 0.048 | 1.05 |
| INCB018424 1.5% QD | 12 | GALNT2 | 0.042 | 1.06 |
| INCB018424 1.5% QD | 12 | CRISP2 | 0.042 | 1.06 |
| INCB018424 1.5% QD | 12 | CA14 | 0.034 | 1.06 |
| INCB018424 1.5% QD | 12 | IGF2R | 0.038 | 1.06 |
| INCB018424 1.5% QD | 12 | MRC2 | 0.015 | 1.06 |
| INCB018424 1.5% QD | 12 | CD200 | 0.025 | 1.06 |
| INCB018424 1.5% QD | 12 | LRRN1 | 0.023 | 1.06 |
| INCB018424 1.5% QD | 12 | TCN2 | 0.034 | 1.06 |
| INCB018424 1.5% QD | 12 | DPP4 | 0.010 | 1.06 |
| INCB018424 1.5% QD | 12 | ESAM | 0.031 | 1.07 |
| INCB018424 1.5% QD | 12 | SCGB3A1 | 0.039 | 1.07 |
| INCB018424 1.5% QD | 12 | AOC3 | 0.016 | 1.07 |
| INCB018424 1.5% QD | 12 | BCAM | 0.003 | 1.07 |
| INCB018424 1.5% QD | 12 | WFIKKN2 | 0.003 | 1.07 |
| INCB018424 1.5% QD | 12 | IGSF3 | 0.029 | 1.07 |
| INCB018424 1.5% QD | 12 | ENTPD6 | 0.012 | 1.07 |
| INCB018424 1.5% QD | 12 | SMAD1 | 0.043 | 1.07 |
| INCB018424 1.5% QD | 12 | SAA4 | 0.027 | 1.07 |
| INCB018424 1.5% QD | 12 | ANG-1 | 0.027 | 1.07 |
| INCB018424 1.5% QD | 12 | SEZ6L2 | 0.024 | 1.07 |
| INCB018424 1.5% QD | 12 | APOM | 0.005 | 1.07 |
| INCB018424 1.5% QD | 12 | IGFBPL1 | 0.016 | 1.07 |
| INCB018424 1.5% QD | 12 | ITGB5 | 0.006 | 1.07 |
| INCB018424 1.5% QD | 12 | CPXM1 | 0.004 | 1.07 |
| INCB018424 1.5% QD | 12 | METRNL | 0.002 | 1.07 |
| INCB018424 1.5% QD | 12 | ENAH | 0.020 | 1.08 |
| INCB018424 1.5% QD | 12 | LRP11 | 0.017 | 1.08 |
| INCB018424 1.5% QD | 12 | SOD2 | 0.020 | 1.08 |
| INCB018424 1.5% QD | 12 | DCBLD2 | 0.049 | 1.08 |
| INCB018424 1.5% QD | 12 | VEGFA | 0.040 | 1.08 |
| INCB018424 1.5% QD | 12 | MFAP5 | 0.045 | 1.08 |
| INCB018424 1.5% QD | 12 | MCFD2 | 0.020 | 1.08 |
| INCB018424 1.5% QD | 12 | RAGE | 0.003 | 1.08 |
| INCB018424 1.5% QD | 12 | KLK6 | 0.033 | 1.08 |
| INCB018424 1.5% QD | 12 | SPINK5 | 0.002 | 1.08 |
| INCB018424 1.5% QD | 12 | NCAM1 | 0.003 | 1.08 |
| INCB018424 1.5% QD | 12 | FR-alpha | 0.008 | 1.08 |
| INCB018424 1.5% QD | 12 | CLUL1 | 0.006 | 1.08 |
| INCB018424 1.5% QD | 12 | CXCL16 | 0.011 | 1.08 |
| INCB018424 1.5% QD | 12 | TACSTD2 | <0.0001 | 1.08 |
| INCB018424 1.5% QD | 12 | ENTPD2 | 0.035 | 1.09 |
| INCB018424 1.5% QD | 12 | VEGFC | 0.005 | 1.09 |
| INCB018424 1.5% QD | 12 | CNTN2 | 0.022 | 1.09 |
| INCB018424 1.5% QD | 12 | PAI | 0.050 | 1.09 |
| INCB018424 1.5% QD | 12 | GPC1 | 0.005 | 1.09 |
| INCB018424 1.5% QD | 12 | Flt3L | 0.027 | 1.09 |
| INCB018424 1.5% QD | 12 | DKK3 | 0.002 | 1.09 |
| INCB018424 1.5% QD | 12 | VEGFD | 0.007 | 1.09 |
| INCB018424 1.5% QD | 12 | hK14 | 0.011 | 1.09 |
| INCB018424 1.5% QD | 12 | APP | 0.018 | 1.09 |
| INCB018424 1.5% QD | 12 | ISLR2 | 0.030 | 1.09 |
| INCB018424 1.5% QD | 12 | PVRL4 | 0.002 | 1.10 |
| INCB018424 1.5% QD | 12 | DDC | 0.039 | 1.10 |
| INCB018424 1.5% QD | 12 | SCGB3A2 | <0.0001 | 1.10 |
| INCB018424 1.5% QD | 12 | CLMP | 0.006 | 1.10 |
| INCB018424 1.5% QD | 12 | REG4 | 0.030 | 1.10 |
| INCB018424 1.5% QD | 12 | KAZALD1 | 0.003 | 1.10 |
| INCB018424 1.5% QD | 12 | DPP7 | 0.042 | 1.10 |
| INCB018424 1.5% QD | 12 | ANGPTL7 | 0.001 | 1.10 |
| INCB018424 1.5% QD | 12 | CD46 | 0.043 | 1.10 |
| INCB018424 1.5% QD | 12 | TIMP1 | 0.001 | 1.11 |
| INCB018424 1.5% QD | 12 | COCH | 0.015 | 1.11 |
| INCB018424 1.5% QD | 12 | ROR1 | 0.004 | 1.11 |
| INCB018424 1.5% QD | 12 | FAM3B | 0.020 | 1.11 |
| INCB018424 1.5% QD | 12 | IL7R | 0.042 | 1.11 |
| INCB018424 1.5% QD | 12 | CXCL5 | 0.048 | 1.11 |
| INCB018424 1.5% QD | 12 | PROC | <0.0001 | 1.11 |
| INCB018424 1.5% QD | 12 | IGFBP6 | 0.001 | 1.11 |
| INCB018424 1.5% QD | 12 | CYR61 | 0.021 | 1.11 |
| INCB018424 1.5% QD | 12 | PAM | <0.0001 | 1.11 |
| INCB018424 1.5% QD | 12 | MSLN | <0.0001 | 1.11 |
| INCB018424 1.5% QD | 12 | SYND1 | 0.038 | 1.11 |
| INCB018424 1.5% QD | 12 | CCL11 | 0.017 | 1.12 |
| INCB018424 1.5% QD | 12 | CA6 | 0.006 | 1.12 |
| INCB018424 1.5% QD | 12 | KLK13 | 0.012 | 1.12 |
| INCB018424 1.5% QD | 12 | CLSTN2 | 0.047 | 1.12 |
| INCB018424 1.5% QD | 12 | MMP-3 | 0.022 | 1.12 |
| INCB018424 1.5% QD | 12 | COMP | 0.006 | 1.12 |
| INCB018424 1.5% QD | 12 | DPP6 | 0.017 | 1.12 |
| INCB018424 1.5% QD | 12 | MMP-1 | 0.001 | 1.12 |
| INCB018424 1.5% QD | 12 | ST6GAL1 | 0.002 | 1.12 |
| INCB018424 1.5% QD | 12 | SOST | 0.002 | 1.12 |
| INCB018424 1.5% QD | 12 | ANGPTL3 | 0.001 | 1.12 |
| INCB018424 1.5% QD | 12 | CST6 | 0.038 | 1.13 |
| INCB018424 1.5% QD | 12 | DSG4 | <0.0001 | 1.13 |
| INCB018424 1.5% QD | 12 | CXCL1 | 0.013 | 1.13 |
| INCB018424 1.5% QD | 12 | FAM3C | 0.007 | 1.13 |
| INCB018424 1.5% QD | 12 | NID1 | 0.011 | 1.13 |
| INCB018424 1.5% QD | 12 | PLTP | 0.003 | 1.13 |
| INCB018424 1.5% QD | 12 | CPE | 0.007 | 1.13 |
| INCB018424 1.5% QD | 12 | MOG | 0.001 | 1.14 |
| INCB018424 1.5% QD | 12 | CA4 | 0.010 | 1.14 |
| INCB018424 1.5% QD | 12 | SERPINA9 | 0.003 | 1.15 |
| INCB018424 1.5% QD | 12 | LEP | 0.025 | 1.15 |
| INCB018424 1.5% QD | 12 | CRTAC1 | <0.0001 | 1.15 |
| INCB018424 1.5% QD | 12 | F11 | 0.029 | 1.17 |
| INCB018424 1.5% QD | 12 | APLP1 | 0.040 | 1.17 |
| INCB018424 1.5% QD | 12 | hK8 | <0.0001 | 1.18 |
| INCB018424 1.5% QD | 12 | MAP4K5 | 0.049 | 1.20 |
| INCB018424 1.5% QD | 12 | CES2 | 0.047 | 1.23 |
| INCB018424 1.5% QD | 12 | GAL | 0.001 | 1.24 |
| INCB018424 1.5% QD | 12 | CEACAM5 | 0.003 | 1.25 |
| INCB018424 1.5% QD | 12 | EPO | 0.021 | 1.25 |
| INCB018424 1.5% QD | 12 | CCL5 | 0.010 | 1.28 |
| INCB0 18424 1.5% QD | 12 | OMG | 0.010 | 1.28 |

TABLE 4B

Significantly modulated proteins 1.5% ruxolitinib QD at week 24

| Treatment | Week | Assay | p-value | Fold Change |
|---|---|---|---|---|
| Proteins significantly down-regulated at Week 24 | | | | |
| INCB018424 1.5% QD | 24 | CXCL10 | 0.002 | 0.70 |
| INCB018424 1.5% QD | 24 | CCL19 | <0.0001 | 0.70 |
| INCB018424 1.5% QD | 24 | DEFB4A | 0.008 | 0.74 |
| INCB018424 1.5% QD | 24 | CXCL11 | 0.005 | 0.76 |
| INCB018424 1.5% QD | 24 | DRAXIN | 0.011 | 0.76 |
| INCB018424 1.5% QD | 24 | XCL1 | 0.016 | 0.76 |
| INCB018424 1.5% QD | 24 | LAIR-2 | <0.0001 | 0.76 |
| INCB018424 1.5% QD | 24 | GZMH | 0.002 | 0.77 |
| INCB018424 1.5% QD | 24 | TRANCE | 0.013 | 0.78 |
| INCB018424 1.5% QD | 24 | CD8A | 0.005 | 0.78 |
| INCB018424 1.5% QD | 24 | CD160 | <0.0001 | 0.78 |
| INCB018424 1.5% QD | 24 | GZMB | 0.013 | 0.79 |
| INCB018424 1.5% QD | 24 | TNFRSF6B | 0.045 | 0.79 |
| INCB018424 1.5% QD | 24 | IL5 | 0.037 | 0.79 |
| INCB018424 1.5% QD | 24 | FASLG | <0.0001 | 0.79 |
| INCB018424 1.5% QD | 24 | TNFRSF9 | <0.0001 | 0.79 |

TABLE 4B-continued

Significantly modulated proteins 1.5% ruxolitinib QD at week 24

| Treatment | Week | Assay | p-value | Fold Change |
|---|---|---|---|---|
| INCB018424 1.5% QD | 24 | CRTAM | <.0001 | 0.80 |
| INCB018424 1.5% QD | 24 | IL12 | <0.0001 | 0.80 |
| INCB018424 1.5% QD | 24 | IL-12B | <.0001 | 0.81 |
| INCB018424 1.5% QD | 24 | KLRD1 | 0.001 | 0.81 |
| INCB018424 1.5% QD | 24 | NCR1 | <0.0001 | 0.81 |
| INCB018424 1.5% QD | 24 | FCRL6 | 0.001 | 0.81 |
| INCB018424 1.5% QD | 24 | GZMA | <0.0001 | 0.82 |
| INCB018424 1.5% QD | 24 | IL2-RA | 0.001 | 0.82 |
| INCB018424 1.5% QD | 24 | CD6 | 0.001 | 0.82 |
| INCB018424 1.5% QD | 24 | MCP-4 | 0.002 | 0.83 |
| INCB018424 1.5% QD | 24 | SH2D1A | 0.006 | 0.83 |
| INCB018424 1.5% QD | 24 | CRH | 0.046 | 0.84 |
| INCB018424 1.5% QD | 24 | CD5 | <0.0001 | 0.84 |
| INCB018424 1.5% QD | 24 | MBL2 | 0.040 | 0.84 |
| INCB018424 1.5% QD | 24 | TNFB | 0.001 | 0.85 |
| INCB018424 1.5% QD | 24 | IL10 | 0.027 | 0.85 |
| INCB018424 1.5% QD | 24 | CCL18 | 0.017 | 0.85 |
| INCB018424 1.5% QD | 24 | PTH1R | 0.029 | 0.86 |
| INCB018424 1.5% QD | 24 | IL6 | 0.044 | 0.86 |
| INCB018424 1.5% QD | 24 | MMP12 | 0.021 | 0.86 |
| INCB018424 1.5% QD | 24 | PTX3 | 0.041 | 0.87 |
| INCB018424 1.5% QD | 24 | PAPPA | 0.001 | 0.87 |
| INCB018424 1.5% QD | 24 | IL10 | 0.042 | 0.87 |
| INCB018424 1.5% QD | 24 | SIGLEC1 | 0.008 | 0.87 |
| INCB018424 1.5% QD | 24 | sFRP-3 | 0.024 | 0.88 |
| INCB018424 1.5% QD | 24 | IL-15RA | 0.045 | 0.88 |
| INCB018424 1.5% QD | 24 | CCL23 | 0.030 | 0.88 |
| INCB018424 1.5% QD | 24 | ADAM 8 | 0.001 | 0.88 |
| INCB018424 1.5% QD | 24 | SLAMF1 | 0.018 | 0.89 |
| INCB018424 1.5% QD | 24 | TNFRSF4 | 0.012 | 0.89 |
| INCB018424 1.5% QD | 24 | ESM-1 | 0.028 | 0.89 |
| INCB018424 1.5% QD | 24 | CLM-1 | 0.001 | 0.89 |
| INCB018424 1.5% QD | 24 | CDH3 | 0.002 | 0.89 |
| INCB018424 1.5% QD | 24 | CLEC4C | 0.004 | 0.89 |
| INCB018424 1.5% QD | 24 | CCL21 | 0.024 | 0.89 |
| INCB018424 1.5% QD | 24 | PON2 | 0.027 | 0.89 |
| INCB018424 1.5% QD | 24 | TNC | 0.036 | 0.89 |
| INCB018424 1.5% QD | 24 | IL12RB1 | 0.019 | 0.89 |
| INCB018424 1.5% QD | 24 | FcRL2 | 0.004 | 0.90 |
| INCB018424 1.5% QD | 24 | CD48 | <0.0001 | 0.90 |
| INCB018424 1.5% QD | 24 | COL4A3BP | 0.010 | 0.90 |
| INCB018424 1.5% QD | 24 | CD27 | 0.001 | 0.90 |
| INCB018424 1.5% QD | 24 | CD1C | 0.001 | 0.90 |
| INCB018424 1.5% QD | 24 | CD79B | 0.042 | 0.90 |
| INCB018424 1.5% QD | 24 | GM-CSF-R-alpha | 0.014 | 0.90 |
| INCB018424 1.5% QD | 24 | PDCD1 | 0.009 | 0.91 |
| INCB018424 1.5% QD | 24 | CD83 | 0.011 | 0.91 |
| INCB018424 1.5% QD | 24 | CLEC10A | 0.006 | 0.91 |
| INCB018424 1.5% QD | 24 | IL-1RT1 | 0.026 | 0.91 |
| INCB018424 1.5% QD | 24 | CD244 | 0.012 | 0.91 |
| INCB018424 1.5% QD | 24 | LY9 | <0.0001 | 0.91 |
| INCB018424 1.5% QD | 24 | FCRL1 | 0.042 | 0.92 |
| INCB018424 1.5% QD | 24 | PD-L1 | 0.022 | 0.92 |
| INCB018424 1.5% QD | 24 | IL17RB | 0.040 | 0.92 |
| INCB018424 1.5% QD | 24 | TNFRSF13B | 0.018 | 0.92 |
| INCB018424 1.5% QD | 24 | CLEC7A | 0.040 | 0.92 |
| INCB018424 1.5% QD | 24 | LIF-R | 0.031 | 0.92 |
| INCB018424 1.5% QD | 24 | SIRT5 | 0.029 | 0.93 |
| INCB018424 1.5% QD | 24 | IFNLR1 | 0.043 | 0.93 |
| INCB018424 1.5% QD | 24 | CD200R1 | 0.026 | 0.93 |
| INCB018424 1.5% QD | 24 | IL-5R-alpha | 0.015 | 0.93 |
| INCB018424 1.5% QD | 24 | PDGF-R-alpha | 0.009 | 0.93 |
| INCB018424 1.5% QD | 24 | TNF-R2 | 0.031 | 0.93 |
| INCB018424 1.5% QD | 24 | TM | 0.021 | 0.93 |
| INCB018424 1.5% QD | 24 | WFIKKN1 | 0.042 | 0.93 |
| INCB018424 1.5% QD | 24 | CSF-1 | 0.024 | 0.94 |
| INCB018424 1.5% QD | 24 | EFNA4 | 0.006 | 0.94 |
| INCB018424 1.5% QD | 24 | CLM-6 | 0.010 | 0.94 |
| INCB018424 1.5% QD | 24 | N2DL-2 | 0.038 | 0.94 |
| INCB018424 1.5% QD | 24 | GFR-alpha-1 | 0.033 | 0.95 |
| INCB018424 1.5% QD | 24 | THBS2 | 0.011 | 0.95 |
| INCB018424 1.5% QD | 24 | LY75 | 0.044 | 0.95 |
| INCB018424 1.5% QD | 24 | NBL1 | 0.040 | 0.97 |
| Proteins significantly up-regulated at week 24 | | | | |
| INCB018424 1.5% QD | 24 | TACSTD2 | 0.035 | 1.04 |
| INCB018424 1.5% QD | 24 | GALNT2 | 0.034 | 1.05 |
| INCB018424 1.5% QD | 24 | EGFR | 0.042 | 1.05 |
| INCB018424 1.5% QD | 24 | BAMBI | 0.040 | 1.05 |
| INCB018424 1.5% QD | 24 | AOC3 | 0.038 | 1.06 |
| INCB018424 1.5% QD | 24 | CNDP1 | 0.047 | 1.06 |
| INCB018424 1.5% QD | 24 | ITGB5 | 0.010 | 1.06 |
| INCB018424 1.5% QD | 24 | CLEC4A | 0.022 | 1.07 |
| INCB018424 1.5% QD | 24 | ST6GAL1 | 0.025 | 1.07 |
| INCB018424 1.5% QD | 24 | MEP1B | 0.002 | 1.07 |
| INCB018424 1.5% QD | 24 | CNTN1 | 0.032 | 1.07 |
| INCB018424 1.5% QD | 24 | B4GAT1 | 0.031 | 1.07 |
| INCB018424 1.5% QD | 24 | CA4 | 0.048 | 1.07 |
| INCB018424 1.5% QD | 24 | KIT | 0.008 | 1.07 |
| INCB018424 1.5% QD | 24 | TIMP1 | 0.028 | 1.08 |
| INCB018424 1.5% QD | 24 | DPP4 | 0.009 | 1.08 |
| INCB018424 1.5% QD | 24 | CD300LG | 0.016 | 1.08 |
| INCB018424 1.5% QD | 24 | Flt3L | 0.038 | 1.08 |
| INCB018424 1.5% QD | 24 | NCAM1 | 0.006 | 1.08 |
| INCB018424 1.5% QD | 24 | DPP6 | 0.031 | 1.08 |
| INCB018424 1.5% QD | 24 | ADGRG2 | 0.007 | 1.08 |
| INCB018424 1.5% QD | 24 | DKK3 | 0.028 | 1.09 |
| INCB018424 1.5% QD | 24 | SPINK5 | 0.002 | 1.09 |
| INCB018424 1.5% QD | 24 | TF | 0.040 | 1.09 |
| INCB018424 1.5% QD | 24 | BLM hydrolase | 0.047 | 1.09 |
| INCB018424 1.5% QD | 24 | VEGFD | 0.016 | 1.09 |
| INCB018424 1.5% QD | 24 | IGF2R | 0.006 | 1.09 |
| INCB018424 1.5% QD | 24 | ISLR2 | 0.041 | 1.09 |
| INCB018424 1.5% QD | 24 | WFIKKN2 | 0.019 | 1.09 |
| INCB018424 1.5% QD | 24 | KLK6 | 0.006 | 1.09 |
| INCB018424 1.5% QD | 24 | PAI | 0.006 | 1.10 |
| INCB018424 1.5% QD | 24 | CXCL5 | 0.021 | 1.10 |
| INCB018424 1.5% QD | 24 | PROC | 0.003 | 1.10 |
| INCB018424 1.5% QD | 24 | CLMP | 0.035 | 1.10 |
| INCB018424 1.5% QD | 24 | KLK10 | 0.007 | 1.10 |
| INCB018424 1.5% QD | 24 | ITGB1 | 0.036 | 1.10 |
| INCB018424 1.5% QD | 24 | TGFBI | 0.004 | 1.10 |
| INCB018424 1.5% QD | 24 | MOG | 0.024 | 1.10 |
| INCB018424 1.5% QD | 24 | PDGF subunit A | 0.017 | 1.11 |
| INCB018424 1.5% QD | 24 | hK8 | 0.031 | 1.11 |
| INCB018424 1.5% QD | 24 | EDIL3 | 0.036 | 1.11 |
| INCB018424 1.5% QD | 24 | CA6 | 0.020 | 1.11 |
| INCB018424 1.5% QD | 24 | BCAM | 0.048 | 1.11 |
| INCB018424 1.5% QD | 24 | KLK13 | 0.023 | 1.11 |
| INCB018424 1.5% QD | 24 | COCH | 0.010 | 1.11 |
| INCB018424 1.5% QD | 24 | CRTAC1 | 0.023 | 1.12 |
| INCB018424 1.5% QD | 24 | MMP-1 | 0.003 | 1.12 |
| INCB018424 1.5% QD | 24 | CA3 | 0.040 | 1.12 |
| INCB018424 1.5% QD | 24 | IGFBP6 | <0.0001 | 1.12 |
| INCB018424 1.5% QD | 24 | MB | 0.032 | 1.13 |
| INCB018424 1.5% QD | 24 | KYAT1 | 0.042 | 1.13 |
| INCB018424 1.5% QD | 24 | CXCL16 | <0.0001 | 1.13 |
| INCB018424 1.5% QD | 24 | SNCG | 0.034 | 1.13 |
| INCB018424 1.5% QD | 24 | SPINK1 | 0.006 | 1.14 |
| INCB018424 1.5% QD | 24 | SCGB3A2 | 0.010 | 1.14 |
| INCB018424 1.5% QD | 24 | IL15 | <0.0001 | 1.14 |
| INCB018424 1.5% QD | 24 | Gal-4 | 0.018 | 1.15 |
| INCB018424 1.5% QD | 24 | DDC | 0.009 | 1.16 |
| INCB018424 1.5% QD | 24 | MMP-3 | 0.015 | 1.16 |
| INCB018424 1.5% QD | 24 | LGALS7 | 0.006 | 1.16 |
| INCB018424 1.5% QD | 24 | PLIN1 | 0.018 | 1.17 |
| INCB018424 1.5% QD | 24 | TIMP4 | 0.023 | 1.17 |
| INCB018424 1.5% QD | 24 | PCSK9 | 0.001 | 1.17 |
| INCB018424 1.5% QD | 24 | F11 | 0.018 | 1.17 |
| INCB018424 1.5% QD | 24 | FAM3C | 0.001 | 1.18 |
| INCB018424 1.5% QD | 24 | FGF-BP1 | <0.0001 | 1.19 |
| INCB018424 1.5% QD | 24 | CES2 | 0.040 | 1.19 |
| INCB018424 1.5% QD | 24 | CES1 | 0.026 | 1.22 |
| INCB018424 1.5% QD | 24 | P4HB | 0.015 | 1.22 |
| INCB018424 1.5% QD | 24 | LEP | 0.014 | 1.23 |

TABLE 4B-continued

Significantly modulated proteins 1.5% ruxolitinib QD at week 24

| Treatment | Week | Assay | p-value | Fold Change |
|---|---|---|---|---|
| INCB018424 1.5% QD | 24 | TMPRSS15 | 0.025 | 1.24 |
| INCB018424 1.5% QD | 24 | Ep-CAM | 0.010 | 1.26 |
| INCB018424 1.5% QD | 24 | FABP4 | 0.001 | 1.28 |

TABLE 5A

Significantly modulated proteins 1.5% ruxolitinib BID at week 12

| Treatment | Week | Assay | p-value | Fold Change |
|---|---|---|---|---|
| Significantly down-regulated proteins at week 12 | | | | |
| INCB018424 1.5% BID | 12 | FASLG | <.0001 | 0.78 |
| INCB018424 1.5% BID | 12 | TRANCE | <.0001 | 0.78 |
| INCB018424 1.5% BID | 12 | CD160 | <.0001 | 0.79 |
| INCB018424 1.5% BID | 12 | FCRL6 | <.0001 | 0.79 |
| INCB018424 1.5% BID | 12 | TNFB | <.0001 | 0.82 |
| INCB018424 1.5% BID | 12 | TNFRSF9 | <.0001 | 0.84 |
| INCB018424 1.5% BID | 12 | ITGB2 | <.0001 | 0.85 |
| INCB018424 1.5% BID | 12 | TIMD4 | <.0001 | 0.86 |
| INCB018424 1.5% BID | 12 | CD5 | <.0001 | 0.88 |
| INCB018424 1.5% BID | 12 | RNASE3 | 0.024 | 0.73 |
| INCB018424 1.5% BID | 12 | CCL19 | <0.0001 | 0.75 |
| INCB018424 1.5% BID | 12 | MCP-4 | 0.002 | 0.78 |
| INCB018424 1.5% BID | 12 | CXCL9 | <0.0001 | 0.78 |
| INCB018424 1.5% BID | 12 | CCL18 | 0.002 | 0.79 |
| INCB018424 1.5% BID | 12 | CRH | 0.007 | 0.79 |
| INCB018424 1.5% BID | 12 | KLRD1 | <0.0001 | 0.81 |
| INCB018424 1.5% BID | 12 | CXCL10 | 0.044 | 0.82 |
| INCB018424 1.5% BID | 12 | LAIR-2 | <0.0001 | 0.83 |
| INCB018424 1.5% BID | 12 | NCR1 | <0.0001 | 0.84 |
| INCB018424 1.5% BID | 12 | IL2-RA | <0.0001 | 0.84 |
| INCB018424 1.5% BID | 12 | IL-12B | 0.001 | 0.85 |
| INCB018424 1.5% BID | 12 | XCL1 | <0.0001 | 0.85 |
| INCB018424 1.5% BID | 12 | TCL1B | 0.024 | 0.85 |
| INCB018424 1.5% BID | 12 | CA5A | 0.028 | 0.86 |
| INCB018424 1.5% BID | 12 | DRAXIN | 0.003 | 0.86 |
| INCB018424 1.5% BID | 12 | TNFRSF6B | 0.004 | 0.86 |
| INCB018424 1.5% BID | 12 | CHIT1 | 0.013 | 0.87 |
| INCB018424 1.5% BID | 12 | TGF-alpha | 0.025 | 0.87 |
| INCB018424 1.5% BID | 12 | CD6 | <0.0001 | 0.87 |
| INCB018424 1.5% BID | 12 | OSM | 0.043 | 0.87 |
| INCB018424 1.5% BID | 12 | CD1C | <0.001 | 0.87 |
| INCB018424 1.5% BID | 12 | CRTAM | 0.001 | 0.87 |
| INCB018424 1.5% BID | 12 | PRTN3 | 0.021 | 0.88 |
| INCB018424 1.5% BID | 12 | MBL2 | 0.002 | 0.88 |
| INCB018424 1.5% BID | 12 | KIR2DL3 | 0.001 | 0.88 |
| INCB018424 1.5% BID | 12 | IL5 | 0.006 | 0.88 |
| INCB018424 1.5% BID | 12 | TNFSF13B | <0.0001 | 0.88 |
| INCB018424 1.5% BID | 12 | ADAM 8 | <0.0001 | 0.88 |
| INCB018424 1.5% BID | 12 | GZMB | 0.045 | 0.89 |
| INCB018424 1.5% BID | 12 | CCL21 | 0.001 | 0.89 |
| INCB018424 1.5% BID | 12 | MMP12 | 0.041 | 0.89 |
| INCB018424 1.5% BID | 12 | PAPPA | 0.009 | 0.89 |
| INCB018424 1.5% BID | 12 | CLEC4D | 0.039 | 0.89 |
| INCB018424 1.5% BID | 12 | IFNL1 | 0.007 | 0.89 |
| INCB018424 1.5% BID | 12 | COL1A1 | 0.001 | 0.89 |
| INCB018424 1.5% BID | 12 | CLEC4C | 0.026 | 0.89 |
| INCB018424 1.5% BID | 12 | LIF | 0.020 | 0.90 |
| INCB018424 1.5% BID | 12 | IL-2RB | 0.033 | 0.90 |
| INCB018424 1.5% BID | 12 | NOV | 0.005 | 0.90 |
| INCB018424 1.5% BID | 12 | IL12 | 0.030 | 0.90 |
| INCB018424 1.5% BID | 12 | INC | 0.044 | 0.90 |
| INCB018424 1.5% BID | 12 | VSTM1 | 0.002 | 0.91 |
| INCB018424 1.5% BID | 12 | DSC2 | 0.002 | 0.91 |
| INCB018424 1.5% BID | 12 | WISP-1 | 0.002 | 0.91 |
| INCB018424 1.5% BID | 12 | TNFRSF10C | 0.015 | 0.91 |
| INCB018424 1.5% BID | 12 | CD163 | 0.003 | 0.92 |
| INCB018424 1.5% BID | 12 | IL3RA | 0.010 | 0.92 |
| INCB018424 1.5% BID | 12 | PGLYRP1 | 0.040 | 0.92 |
| INCB018424 1.5% BID | 12 | RETN | 0.021 | 0.92 |
| INCB018424 1.5% BID | 12 | ICAM3 | 0.001 | 0.92 |
| INCB018424 1.5% BID | 12 | ICAM1 | 0.003 | 0.92 |
| INCB018424 1.5% BID | 12 | FCRL5 | 0.005 | 0.92 |
| INCB018424 1.5% BID | 12 | IL-18BP | 0.008 | 0.92 |
| INCB018424 1.5% BID | 12 | IL-1RT1 | 0.004 | 0.92 |
| INCB018424 1.5% BID | 12 | CLEC7A | 0.004 | 0.92 |
| INCB018424 1.5% BID | 12 | VCAM1 | 0.002 | 0.92 |
| INCB018424 1.5% BID | 12 | SLAMF8 | 0.024 | 0.92 |
| INCB018424 1.5% BID | 12 | CDON | 0.011 | 0.92 |
| INCB018424 1.5% BID | 12 | FCER2 | 0.006 | 0.93 |
| INCB018424 1.5% BID | 12 | SELL | 0.013 | 0.93 |
| INCB018424 1.5% BID | 12 | PON2 | 0.029 | 0.93 |
| INCB018424 1.5% BID | 12 | CD244 | 0.006 | 0.93 |
| INCB018424 1.5% BID | 12 | CD48 | 0.003 | 0.93 |
| INCB018424 1.5% BID | 12 | TNF-R2 | 0.028 | 0.94 |
| INCB018424 1.5% BID | 12 | CD209 | 0.023 | 0.94 |
| INCB018424 1.5% BID | 12 | IL-10RB | 0.010 | 0.94 |
| INCB018424 1.5% BID | 12 | ARTN | 0.028 | 0.94 |
| INCB018424 1.5% BID | 12 | LAIR1 | 0.022 | 0.94 |
| INCB018424 1.5% BID | 12 | TNF-R1 | 0.037 | 0.94 |
| INCB018424 1.5% BID | 12 | KIRREL2 | 0.027 | 0.94 |
| INCB018424 1.5% BID | 12 | FCRL1 | 0.004 | 0.94 |
| INCB018424 1.5% BID | 12 | LY9 | 0.044 | 0.95 |
| INCB018424 1.5% BID | 12 | MILR1 | 0.049 | 0.95 |
| INCB018424 1.5% BID | 12 | CD79B | 0.015 | 0.95 |
| INCB018424 1.5% BID | 12 | CD27 | 0.034 | 0.95 |
| INCB018424 1.5% BID | 12 | hOSCAR | 0.006 | 0.96 |
| INCB018424 1.5% BID | 12 | HAVCR2 | 0.017 | 0.96 |
| INCB018424 1.5% BID | 12 | KPNA1 | 0.029 | 0.96 |
| INCB018424 1.5% BID | 12 | TGFR-2 | 0.036 | 0.96 |
| Significantly up-regulated proteins at week 12 | | | | |
| INCB018424 1.5% BID | 12 | NTRK3 | <.0001 | 1.10 |
| INCB018424 1.5% BID | 12 | TF | <.0001 | 1.12 |
| INCB018424 1.5% BID | 12 | KLK13 | <.0001 | 1.14 |
| INCB018424 1.5% BID | 12 | FGF-BP1 | <.0001 | 1.27 |
| INCB018424 1.5% BID | 12 | EPO | <.0001 | 1.59 |
| INCB018424 1.5% BID | 12 | Gal-1 | 0.012 | 1.04 |
| INCB018424 1.5% BID | 12 | ITGAV | 0.035 | 1.04 |
| INCB018424 1.5% BID | 12 | ERBB3 | 0.016 | 1.04 |
| INCB018424 1.5% BID | 12 | ITGB1 | 0.038 | 1.05 |
| INCB018424 1.5% BID | 12 | CLEC14A | 0.044 | 1.05 |
| INCB018424 1.5% BID | 12 | GALNT2 | 0.027 | 1.05 |
| INCB018424 1.5% BID | 12 | ERBB4 | 0.008 | 1.05 |
| INCB018424 1.5% BID | 12 | Nr-CAM | 0.005 | 1.05 |
| INCB018424 1.5% BID | 12 | CRISP2 | 0.048 | 1.05 |
| INCB018424 1.5% BID | 12 | ENTPD6 | 0.019 | 1.05 |
| INCB018424 1.5% BID | 12 | NTRK2 | 0.010 | 1.05 |
| INCB018424 1.5% BID | 12 | EDA2R | 0.028 | 1.05 |
| INCB018424 1.5% BID | 12 | LTBP2 | 0.045 | 1.05 |
| INCB018424 1.5% BID | 12 | CD300LG | 0.029 | 1.05 |
| INCB018424 1.5% BID | 12 | DKKL1 | 0.007 | 1.05 |
| INCB018424 1.5% BID | 12 | CD58 | 0.004 | 1.06 |
| INCB018424 1.5% BID | 12 | Gal-3 | 0.035 | 1.06 |
| INCB018424 1.5% BID | 12 | DPP4 | 0.022 | 1.06 |
| INCB018424 1.5% BID | 12 | AOC3 | 0.031 | 1.06 |
| INCB018424 1.5% BID | 12 | GDNFR-alpha-3 | 0.013 | 1.06 |
| INCB018424 1.5% BID | 12 | FABP9 | 0.029 | 1.06 |
| INCB018424 1.5% BID | 12 | Alpha-2-MRAP | 0.045 | 1.06 |
| INCB018424 1.5% BID | 12 | PRELP | 0.008 | 1.06 |
| INCB018424 1.5% BID | 12 | DPEP1 | 0.019 | 1.06 |
| INCB018424 1.5% BID | 12 | hK11 | 0.008 | 1.06 |
| INCB018424 1.5% BID | 12 | DCBLD2 | 0.042 | 1.06 |
| INCB018424 1.5% BID | 12 | ANGPTL7 | 0.035 | 1.06 |
| INCB018424 1.5% BID | 12 | MMP7 | 0.025 | 1.06 |
| INCB018424 1.5% BID | 12 | SCARB2 | 0.032 | 1.06 |
| INCB018424 1.5% BID | 12 | B4GAT1 | 0.011 | 1.06 |
| INCB018424 1.5% BID | 12 | ITGB5 | 0.010 | 1.06 |
| INCB018424 1.5% BID | 12 | BAMBI | 0.047 | 1.06 |
| INCB018424 1.5% BID | 12 | SPINK5 | 0.001 | 1.06 |
| INCB018424 1.5% BID | 12 | ACAN | 0.010 | 1.06 |
| INCB018424 1.5% BID | 12 | TACSTD2 | 0.002 | 1.06 |
| INCB018424 1.5% BID | 12 | DCN | 0.002 | 1.07 |
| INCB018424 1.5% BID | 12 | PEAR1 | 0.017 | 1.07 |
| INCB018424 1.5% BID | 12 | PODXL2 | 0.011 | 1.07 |
| INCB018424 1.5% BID | 12 | VWC2 | 0.025 | 1.07 |

TABLE 5A-continued

Significantly modulated proteins 1.5% ruxolitinib BID at week 12

| Treatment | Week | Assay | p-value | Fold Change |
|---|---|---|---|---|
| INCB018424 1.5% BID | 12 | BLM hydrolase | 0.008 | 1.07 |
| INCB018424 1.5% BID | 12 | CCL25 | 0.028 | 1.07 |
| INCB018424 1.5% BID | 12 | VEGFD | 0.029 | 1.07 |
| INCB018424 1.5% BID | 12 | FAM3C | 0.024 | 1.07 |
| INCB018424 1.5% BID | 12 | SCARF2 | 0.011 | 1.07 |
| INCB018424 1.5% BID | 12 | CLUL1 | 0.009 | 1.07 |
| INCB018424 1.5% BID | 12 | EZR | 0.008 | 1.07 |
| INCB018424 1.5% BID | 12 | OPTC | 0.007 | 1.07 |
| INCB018424 1.5% BID | 12 | SOD2 | 0.003 | 1.07 |
| INCB018424 1.5% BID | 12 | EPHB6 | 0.015 | 1.07 |
| INCB018424 1.5% BID | 12 | PVR | 0.002 | 1.07 |
| INCB018424 1.5% BID | 12 | DPP10 | 0.017 | 1.07 |
| INCB018424 1.5% BID | 12 | PRTG | 0.002 | 1.08 |
| INCB018424 1.5% BID | 12 | TMPRSS5 | 0.004 | 1.08 |
| INCB018424 1.5% BID | 12 | CPE | 0.012 | 1.08 |
| INCB018424 1.5% BID | 12 | CD70 | 0.035 | 1.08 |
| INCB018424 1.5% BID | 12 | hK8 | 0.023 | 1.08 |
| INCB018424 1.5% BID | 12 | CXCL16 | 0.004 | 1.08 |
| INCB018424 1.5% BID | 12 | THPO | 0.026 | 1.08 |
| INCB018424 1.5% BID | 12 | KIM1 | 0.038 | 1.08 |
| INCB018424 1.5% BID | 12 | GPC1 | 0.002 | 1.08 |
| INCB018424 1.5% BID | 12 | VEGFD | 0.003 | 1.08 |
| INCB018424 1.5% BID | 12 | ROBO2 | 0.003 | 1.08 |
| INCB018424 1.5% BID | 12 | DKK3 | 0.036 | 1.08 |
| INCB018424 1.5% BID | 12 | CLEC4A | 0.009 | 1.08 |
| INCB018424 1.5% BID | 12 | CDNF | 0.014 | 1.09 |
| INCB018424 1.5% BID | 12 | SPOCK1 | 0.012 | 1.09 |
| INCB018424 1.5% BID | 12 | ST3GAL1 | 0.022 | 1.09 |
| INCB018424 1.5% BID | 12 | CNTN5 | 0.001 | 1.09 |
| INCB018424 1.5% BID | 12 | GCP5 | 0.032 | 1.09 |
| INCB018424 1.5% BID | 12 | GP1BA | 0.032 | 1.09 |
| INCB018424 1.5% BID | 12 | KLK6 | 0.018 | 1.09 |
| INCB018424 1.5% BID | 12 | hK14 | 0.011 | 1.09 |
| INCB018424 1.5% BID | 12 | RGMB | 0.001 | 1.09 |
| INCB018424 1.5% BID | 12 | LGALS7 | 0.025 | 1.09 |
| INCB018424 1.5% BID | 12 | RAGE | 0.003 | 1.10 |
| INCB018424 1.5% BID | 12 | KLK10 | 0.003 | 1.10 |
| INCB018424 1.5% BID | 12 | FUT8 | 0.041 | 1.10 |
| INCB018424 1.5% BID | 12 | FAM3B | 0.011 | 1.10 |
| INCB018424 1.5% BID | 12 | CXADR | 0.038 | 1.10 |
| INCB018424 1.5% BID | 12 | CD200 | <0.0001 | 1.10 |
| INCB018424 1.5% BID | 12 | MATN3 | 0.013 | 1.10 |
| INCB018424 1.5% BID | 12 | SCF | 0.001 | 1.10 |
| INCB018424 1.5% BID | 12 | SCF | <0.0001 | 1.10 |
| INCB018424 1.5% BID | 12 | NCAN | <0.0001 | 1.10 |
| INCB018424 1.5% BID | 12 | GDF-2 | 0.016 | 1.10 |
| INCB018424 1.5% BID | 12 | TFPI-2 | 0.001 | 1.10 |
| INCB018424 1.5% BID | 12 | CAIX | 0.037 | 1.10 |
| INCB018424 1.5% BID | 12 | WFIKKN2 | <0.0001 | 1.10 |
| INCB018424 1.5% BID | 12 | RGMA | <0.0001 | 1.10 |
| INCB018424 1.5% BID | 12 | SFRP1 | 0.042 | 1.11 |
| INCB018424 1.5% BID | 12 | NPTXR | 0.001 | 1.11 |
| INCB018424 1.5% BID | 12 | PHOSPHO1 | 0.005 | 1.11 |
| INCB018424 1.5% BID | 12 | STX6 | 0.018 | 1.11 |
| INCB018424 1.5% BID | 12 | CA6 | 0.005 | 1.11 |
| INCB018424 1.5% BID | 12 | PON3 | 0.003 | 1.11 |
| INCB018424 1.5% BID | 12 | gal-8 | 0.003 | 1.11 |
| INCB018424 1.5% BID | 12 | NCAM1 | <0.0001 | 1.12 |
| INCB018424 1.5% BID | 12 | CADM3 | 0.001 | 1.12 |
| INCB018424 1.5% BID | 12 | CX3CL1 | 0.009 | 1.12 |
| INCB018424 1.5% BID | 12 | SCF | <0.0001 | 1.12 |
| INCB018424 1.5% BID | 12 | PADI2 | 0.025 | 1.12 |
| INCB018424 1.5% BID | 12 | PREB | 0.039 | 1.12 |
| INCB018424 1.5% BID | 12 | DDC | 0.004 | 1.12 |
| INCB018424 1.5% BID | 12 | MDGA1 | <0.0001 | 1.13 |
| INCB018424 1.5% BID | 12 | SCGB1A1 | 0.004 | 1.13 |
| INCB018424 1.5% BID | 12 | IL-17A | 0.035 | 1.13 |
| INCB018424 1.5% BID | 12 | SCGB3A2 | 0.037 | 1.13 |
| INCB018424 1.5% BID | 12 | NEFL | 0.005 | 1.13 |
| INCB018424 1.5% BID | 12 | GIF | 0.014 | 1.13 |
| INCB018424 1.5% BID | 12 | TN-R | 0.001 | 1.13 |
| INCB018424 1.5% BID | 12 | MOG | 0.001 | 1.14 |
| INCB018424 1.5% BID | 12 | CCL11 | 0.008 | 1.14 |
| INCB018424 1.5% BID | 12 | ITM2A | <0.0001 | 1.14 |
| INCB018424 1.5% BID | 12 | PLXNB3 | 0.016 | 1.14 |
| INCB018424 1.5% BID | 12 | CYR61 | <0.0001 | 1.14 |
| INCB018424 1.5% BID | 12 | SMOC2 | <0.0001 | 1.14 |
| INCB018424 1.5% BID | 12 | Dkk-4 | 0.002 | 1.14 |
| INCB018424 1.5% BID | 12 | IL15 | 0.006 | 1.14 |
| INCB018424 1.5% BID | 12 | BCAN | <0.0001 | 1.14 |
| INCB018424 1.5% BID | 12 | MFGE8 | 0.024 | 1.14 |
| INCB018424 1.5% BID | 12 | Flt3L | <0.0001 | 1.15 |
| INCB018424 1.5% BID | 12 | CEACAM5 | 0.049 | 1.16 |
| INCB018424 1.5% BID | 12 | G-CSF | 0.007 | 1.16 |
| INCB018424 1.5% BID | 12 | P4HB | 0.006 | 1.16 |
| INCB018424 1.5% BID | 12 | MMP-3 | 0.024 | 1.17 |
| INCB018424 1.5% BID | 12 | MYOC | 0.001 | 1.19 |
| INCB018424 1.5% BID | 12 | PLIN1 | 0.006 | 1.20 |
| INCB018424 1.5% BID | 12 | TNFRSF12A | 0.001 | 1.21 |
| INCB018424 1.5% BID | 12 | GAL | 0.002 | 1.22 |
| INCB018424 1.5% BID | 12 | APLP1 | 0.001 | 1.23 |
| INCB018424 1.5% BID | 12 | AGR3 | 0.025 | 1.23 |
| INCB018424 1.5% BID | 12 | Ep-CAM | 0.005 | 1.27 |
| INCB018424 1.5% BID | 12 | TSHB | 0.011 | 1.27 |
| INCB018424 1.5% BID | 12 | TNNI3 | 0.019 | 1.59 |

TABLE 5B

Significantly modulated proteins 1.5% ruxolitinib BID at week 24

| Treatment | Week | Assay | p-value | Fold Change |
|---|---|---|---|---|
| Proteins significantly down-regulated at Week 24 | | | | |
| INCB018424 1.5% BID | 24 | CXCL10 | <0.0001 | 0.68 |
| INCB018424 1.5% BID | 24 | CCL19 | <0.0001 | 0.71 |
| INCB018424 1.5% BID | 24 | CXCL9 | <.0001 | 0.73 |
| INCB018424 1.5% BID | 24 | TRANCE | <.0001 | 0.74 |
| INCB018424 1.5% BID | 24 | CCL18 | 0.001 | 0.76 |
| INCB018424 1.5% BID | 24 | IL2-RA | <0.0001 | 0.79 |
| INCB018424 1.5% BID | 24 | FCRL6 | <0.0001 | 0.79 |
| INCB018424 1.5% BID | 24 | TNFB | <0.0001 | 0.80 |
| INCB018424 1.5% BID | 24 | CRH | 0.001 | 0.80 |
| INCB018424 1.5% BID | 24 | GZMB | 0.002 | 0.80 |
| INCB018424 1.5% BID | 24 | TNFRSF9 | <0.0001 | 0.80 |
| INCB018424 1.5% BID | 24 | KLRD1 | <0.0001 | 0.81 |
| INCB018424 1.5% BID | 24 | IL-12B | <.0001 | 0.81 |
| INCB018424 1.5% BID | 24 | FASLG | <.0001 | 0.81 |
| INCB018424 1.5% BID | 24 | MMP12 | 0.001 | 0.81 |
| INCB018424 1.5% BID | 24 | CD160 | <.0001 | 0.82 |
| INCB018424 1.5% BID | 24 | XCL1 | <.0001 | 0.82 |
| INCB018424 1.5% BID | 24 | CXCL11 | 0.019 | 0.82 |
| INCB018424 1.5% BID | 24 | LAIR-2 | 0.003 | 0.82 |
| INCB018424 1.5% BID | 24 | MCP-4 | 0.010 | 0.84 |
| INCB018424 1.5% BID | 24 | NCR1 | <0.0001 | 0.84 |
| INCB018424 1.5% BID | 24 | IL-2RB | 0.003 | 0.84 |
| INCB018424 1.5% BID | 24 | DRAXIN | 0.008 | 0.85 |
| INCB018424 1.5% BID | 24 | IL12 | 0.001 | 0.85 |
| INCB018424 1.5% BID | 24 | TNFRSF6B | 0.001 | 0.85 |
| INCB018424 1.5% BID | 24 | COL1A1 | 0.001 | 0.86 |
| INCB018424 1.5% BID | 24 | CD8A | <0.0001 | 0.86 |
| INCB018424 1.5% BID | 24 | KIR2DL3 | 0.008 | 0.86 |
| INCB018424 1.5% BID | 24 | SIGLEC1 | <0.0001 | 0.86 |
| INCB018424 1.5% BID | 24 | LAP TGF-beta-1 | 0.018 | 0.86 |
| INCB018424 1.5% BID | 24 | CHIT1 | 0.016 | 0.86 |
| INCB018424 1.5% BID | 24 | OPN | 0.011 | 0.87 |
| INCB018424 1.5% BID | 24 | CD6 | <.0001 | 0.87 |
| INCB018424 1.5% BID | 24 | IFNL1 | 0.037 | 0.87 |
| INCB018424 1.5% BID | 24 | CLEC4C | 0.001 | 0.87 |
| INCB018424 1.5% BID | 24 | CD5 | <.0001 | 0.88 |
| INCB018424 1.5% BID | 24 | CRTAM | 0.015 | 0.88 |
| INCB018424 1.5% BID | 24 | CCL21 | 0.002 | 0.88 |
| INCB018424 1.5% BID | 24 | ITGB2 | <.0001 | 0.88 |
| INCB018424 1.5% BID | 24 | SLAMF8 | 0.001 | 0.88 |
| INCB018424 1.5% BID | 24 | ADAM 8 | 0.001 | 0.88 |
| INCB018424 1.5% BID | 24 | IL10 | 0.040 | 0.88 |
| INCB018424 1.5% BID | 24 | IL-18BP | 0.001 | 0.89 |

TABLE 5B-continued

Significantly modulated proteins 1.5% ruxolitinib BID at week 24

| Treatment | Week | Assay | p-value | Fold Change |
|---|---|---|---|---|
| INCB018424 1.5% BID | 24 | CLEC7A | <.0001 | 0.89 |
| INCB018424 1.5% BID | 24 | SLAMF1 | 0.003 | 0.90 |
| INCB018424 1.5% BID | 24 | TNFSF13B | 0.003 | 0.90 |
| INCB018424 1.5% BID | 24 | LILRB4 | 0.001 | 0.90 |
| INCB018424 1.5% BID | 24 | FCER2 | 0.001 | 0.90 |
| INCB018424 1.5% BID | 24 | CCL23 | 0.010 | 0.90 |
| INCB018424 1.5% BID | 24 | CD1C | <0.0001 | 0.90 |
| INCB018424 1.5% BID | 24 | TIMD4 | 0.008 | 0.91 |
| INCB018424 1.5% BID | 24 | MBL2 | 0.011 | 0.91 |
| INCB018424 1.5% BID | 24 | TNF-R2 | 0.001 | 0.91 |
| INCB018424 1.5% BID | 24 | IL12RB1 | 0.006 | 0.91 |
| INCB018424 1.5% BID | 24 | CD163 | 0.010 | 0.91 |
| INCB018424 1.5% BID | 24 | MILR1 | 0.002 | 0.91 |
| INCB018424 1.5% BID | 24 | NOV | 0.022 | 0.92 |
| INCB018424 1.5% BID | 24 | CD48 | 0.001 | 0.92 |
| INCB018424 1.5% BID | 24 | GZMA | 0.014 | 0.92 |
| INCB018424 1.5% BID | 24 | IL-18R1 | 0.012 | 0.92 |
| INCB018424 1.5% BID | 24 | IL-1RT1 | 0.010 | 0.92 |
| INCB018424 1.5% BID | 24 | TRAIL | 0.009 | 0.92 |
| INCB018424 1.5% BID | 24 | GM-CSF-R-alpha | 0.015 | 0.92 |
| INCB018424 1.5% BID | 24 | CDON | 0.006 | 0.92 |
| INCB018424 1.5% BID | 24 | PAPPA | 0.046 | 0.92 |
| INCB018424 1.5% BID | 24 | WISP-1 | 0.004 | 0.92 |
| INCB018424 1.5% BID | 24 | TNFRSF4 | 0.016 | 0.93 |
| INCB018424 1.5% BID | 24 | IFNLR1 | 0.011 | 0.93 |
| INCB018424 1.5% BID | 24 | CD244 | 0.018 | 0.93 |
| INCB018424 1.5% BID | 24 | PGF | 0.014 | 0.93 |
| INCB018424 1.5% BID | 24 | CLEC4G | 0.008 | 0.93 |
| INCB018424 1.5% BID | 24 | SELL | 0.006 | 0.93 |
| INCB018424 1.5% BID | 24 | CSF-1 | 0.003 | 0.93 |
| INCB018424 1.5% BID | 24 | ICAM1 | 0.022 | 0.93 |
| INCB018424 1.5% BID | 24 | VCAM1 | 0.014 | 0.94 |
| INCB018424 1.5% BID | 24 | IL32 | 0.048 | 0.94 |
| INCB018424 1.5% BID | 24 | CD27 | 0.006 | 0.94 |
| INCB018424 1.5% BID | 24 | CD83 | 0.008 | 0.94 |
| INCB018424 1.5% BID | 24 | PON2 | 0.050 | 0.94 |
| INCB018424 1.5% BID | 24 | LY9 | 0.014 | 0.94 |
| INCB018424 1.5% BID | 24 | PILRA | 0.004 | 0.94 |
| INCB018424 1.5% BID | 24 | DSC2 | 0.007 | 0.94 |
| INCB018424 1.5% BID | 24 | RELT | 0.021 | 0.94 |
| INCB018424 1.5% BID | 24 | KIRREL2 | 0.027 | 0.94 |
| INCB018424 1.5% BID | 24 | FcRL2 | 0.037 | 0.95 |
| INCB018424 1.5% BID | 24 | ICAM3 | 0.050 | 0.95 |
| INCB018424 1.5% BID | 24 | DLL1 | 0.012 | 0.95 |
| INCB018424 1.5% BID | 24 | Gal-9 | 0.017 | 0.95 |
| INCB018424 1.5% BID | 24 | CLEC10A | 0.043 | 0.95 |
| INCB018424 1.5% BID | 24 | TRAIL | 0.045 | 0.95 |
| INCB018424 1.5% BID | 24 | PDCD1 | 0.035 | 0.95 |
| INCB018424 1.5% BID | 24 | CLM-6 | 0.015 | 0.95 |
| INCB018424 1.5% BID | 24 | SIRPB1 | 0.042 | 0.95 |
| INCB018424 1.5% BID | 24 | SIGLEC10 | 0.018 | 0.95 |
| INCB018424 1.5% BID | 24 | SIGLEC6 | 0.030 | 0.95 |
| INCB018424 1.5% BID | 24 | hOSCAR | 0.020 | 0.96 |
| INCB018424 1.5% BID | 24 | SHPS-1 | 0.038 | 0.96 |
| Proteins Significantly Up-Regulated at Week 24 | | | | |
| INCB018424 1.5% BID | 24 | CLEC14A | 0.044 | 1.04 |
| INCB018424 1.5% BID | 24 | SPINT1 | 0.040 | 1.05 |
| INCB018424 1.5% BID | 24 | TACSTD2 | 0.026 | 1.05 |
| INCB018424 1.5% BID | 24 | ROBO1 | 0.035 | 1.05 |
| INCB018424 1.5% BID | 24 | DCN | 0.011 | 1.05 |
| INCB018424 1.5% BID | 24 | ITGB1 | 0.021 | 1.05 |
| INCB018424 1.5% BID | 24 | PRELP | 0.004 | 1.05 |
| INCB018424 1.5% BID | 24 | IGF2R | 0.027 | 1.05 |
| INCB018424 1.5% BID | 24 | MMP7 | 0.018 | 1.05 |
| INCB018424 1.5% BID | 24 | PVR | 0.026 | 1.05 |
| INCB018424 1.5% BID | 24 | CDH1 | 0.049 | 1.06 |
| INCB018424 1.5% BID | 24 | RGMA | 0.023 | 1.06 |
| INCB018424 1.5% BID | 24 | TMPRSS5 | 0.036 | 1.06 |
| INCB018424 1.5% BID | 24 | GDNFR-alpha-3 | 0.023 | 1.06 |
| INCB018424 1.5% BID | 24 | GPC1 | 0.039 | 1.06 |
| INCB018424 1.5% BID | 24 | LYPD3 | 0.039 | 1.06 |
| INCB018424 1.5% BID | 24 | ITM2A | 0.034 | 1.06 |
| INCB018424 1.5% BID | 24 | Notch 3 | 0.041 | 1.06 |
| INCB018424 1.5% BID | 24 | ACAN | 0.030 | 1.06 |
| INCB018424 1.5% BID | 24 | hK11 | 0.028 | 1.06 |
| INCB018424 1.5% BID | 24 | MSMB | 0.003 | 1.07 |
| INCB018424 1.5% BID | 24 | SCF | 0.013 | 1.07 |
| INCB018424 1.5% BID | 24 | CNTN1 | 0.023 | 1.07 |
| INCB018424 1.5% BID | 24 | RGMB | 0.045 | 1.07 |
| INCB018424 1.5% BID | 24 | AOC3 | 0.016 | 1.07 |
| INCB018424 1.5% BID | 24 | PRSS27 | 0.037 | 1.07 |
| INCB018424 1.5% BID | 24 | VEGFD | 0.004 | 1.07 |
| INCB018424 1.5% BID | 24 | DPP4 | 0.020 | 1.07 |
| INCB018424 1.5% BID | 24 | CLEC4A | 0.033 | 1.07 |
| INCB018424 1.5% BID | 24 | PEAR1 | 0.032 | 1.07 |
| INCB018424 1.5% BID | 24 | CRISP2 | 0.030 | 1.07 |
| INCB018424 1.5% BID | 24 | CD300LG | 0.005 | 1.07 |
| INCB018424 1.5% BID | 24 | DKK3 | 0.027 | 1.07 |
| INCB018424 1.5% BID | 24 | SPINK5 | 0.002 | 1.07 |
| INCB018424 1.5% BID | 24 | CNTN5 | 0.021 | 1.07 |
| INCB018424 1.5% BID | 24 | CXCL16 | 0.018 | 1.07 |
| INCB018424 1.5% BID | 24 | B4GAT1 | 0.004 | 1.07 |
| INCB018424 1.5% BID | 24 | PRTG | 0.007 | 1.07 |
| INCB018424 1.5% BID | 24 | FABP9 | 0.006 | 1.07 |
| INCB018424 1.5% BID | 24 | PAM | 0.011 | 1.07 |
| INCB018424 1.5% BID | 24 | BLM hydrolase | 0.012 | 1.07 |
| INCB018424 1.5% BID | 24 | RAGE | 0.027 | 1.08 |
| INCB018424 1.5% BID | 24 | IGFBP6 | 0.027 | 1.08 |
| INCB018424 1.5% BID | 24 | BCAM | <.0001 | 1.08 |
| INCB018424 1.5% BID | 24 | MFAP5 | 0.003 | 1.08 |
| INCB018424 1.5% BID | 24 | NTRK3 | 0.006 | 1.08 |
| INCB018424 1.5% BID | 24 | TGFBI | 0.041 | 1.08 |
| INCB018424 1.5% BID | 24 | PON3 | 0.043 | 1.08 |
| INCB018424 1.5% BID | 24 | ISLR2 | 0.039 | 1.08 |
| INCB018424 1.5% BID | 24 | SOST | 0.046 | 1.08 |
| INCB018424 1.5% BID | 24 | DPP10 | 0.008 | 1.08 |
| INCB018424 1.5% BID | 24 | SCF | <0.0001 | 1.08 |
| INCB018424 1.5% BID | 24 | CRIM1 | 0.035 | 1.08 |
| INCB018424 1.5% BID | 24 | ITGB5 | 0.010 | 1.09 |
| INCB018424 1.5% BID | 24 | TF | 0.014 | 1.09 |
| INCB018424 1.5% BID | 24 | CLUL1 | 0.001 | 1.09 |
| INCB018424 1.5% BID | 24 | CTSV | 0.020 | 1.09 |
| INCB018424 1.5% BID | 24 | KLK10 | 0.030 | 1.09 |
| INCB018424 1.5% BID | 24 | WFIKKN2 | 0.001 | 1.09 |
| INCB018424 1.5% BID | 24 | DPEP1 | 0.001 | 1.10 |
| INCB018424 1.5% BID | 24 | hK8 | 0.048 | 1.10 |
| INCB018424 1.5% BID | 24 | SCF | 0.001 | 1.10 |
| INCB018424 1.5% BID | 24 | hK14 | 0.002 | 1.10 |
| INCB018424 1.5% BID | 24 | COMP | 0.030 | 1.10 |
| INCB018424 1.5% BID | 24 | MDGA1 | 0.004 | 1.10 |
| INCB018424 1.5% BID | 24 | GDF-2 | 0.009 | 1.10 |
| INCB018424 1.5% BID | 24 | Gal-4 | 0.046 | 1.10 |
| INCB018424 1.5% BID | 24 | SMOC2 | 0.026 | 1.10 |
| INCB018424 1.5% BID | 24 | SNCG | 0.031 | 1.11 |
| INCB018424 1.5% BID | 24 | COCH | 0.018 | 1.11 |
| INCB018424 1.5% BID | 24 | F11 | 0.006 | 1.11 |
| INCB018424 1.5% BID | 24 | NPTXR | 0.007 | 1.11 |
| INCB018424 1.5% BID | 24 | PHOSPHO1 | 0.001 | 1.11 |
| INCB018424 1.5% BID | 24 | NCAM1 | 0.002 | 1.11 |
| INCB018424 1.5% BID | 24 | TNXB | 0.012 | 1.12 |
| INCB018424 1.5% BID | 24 | SCGB3A1 | 0.002 | 1.12 |
| INCB018424 1.5% BID | 24 | Flt3L | 0.015 | 1.12 |
| INCB018424 1.5% BID | 24 | MFGE8 | 0.048 | 1.12 |
| INCB018424 1.5% BID | 24 | IL15 | 0.009 | 1.12 |
| INCB018424 1.5% BID | 24 | CYR61 | 0.026 | 1.13 |
| INCB018424 1.5% BID | 24 | SCGB1A1 | 0.004 | 1.13 |
| INCB018424 1.5% BID | 24 | DDC | 0.042 | 1.13 |
| INCB018424 1.5% BID | 24 | TN-R | <0.0001 | 1.13 |
| INCB018424 1.5% BID | 24 | WASF1 | 0.042 | 1.13 |
| INCB018424 1.5% BID | 24 | CPA2 | 0.034 | 1.14 |
| INCB018424 1.5% BID | 24 | CRTAC1 | 0.001 | 1.14 |
| INCB018424 1.5% BID | 24 | P4HB | 0.009 | 1.14 |
| INCB018424 1.5% BID | 24 | PADI2 | 0.041 | 1.14 |
| INCB018424 1.5% BID | 24 | BAG6 | 0.016 | 1.14 |
| INCB018424 1.5% BID | 24 | PLIN1 | 0.002 | 1.15 |
| INCB018424 1.5% BID | 24 | CA6 | <0.0001 | 1.15 |
| INCB018424 1.5% BID | 24 | GAL | 0.005 | 1.15 |
| INCB018424 1.5% BID | 24 | NAAA | 0.013 | 1.15 |
| INCB018424 1.5% BID | 24 | KLK13 | <0.0001 | 1.16 |

TABLE 5B-continued

Significantly modulated proteins 1.5% ruxolitinib BID at week 24

| Treatment | Week | Assay | p-value | Fold Change |
|---|---|---|---|---|
| INCB018424 1.5% BID | 24 | REG4 | 0.002 | 1.16 |
| INCB018424 1.5% BID | 24 | GIF | 0.006 | 1.17 |
| INCB018424 1.5% BID | 24 | PTN | 0.026 | 1.17 |
| INCB018424 1.5% BID | 24 | NID2 | 0.026 | 1.17 |
| INCB018424 1.5% BID | 24 | GSAP | 0.014 | 1.17 |
| INCB018424 1.5% BID | 24 | TNFRSF12A | 0.001 | 1.19 |
| INCB018424 1.5% BID | 24 | SCGB3A2 | 0.007 | 1.19 |
| INCB018424 1.5% BID | 24 | Ep-CAM | 0.049 | 1.19 |
| INCB018424 1.5% BID | 24 | NEFL | 0.014 | 1.19 |
| INCB018424 1.5% BID | 24 | MYOC | <0.0001 | 1.21 |
| INCB018424 1.5% BID | 24 | CEACAM5 | 0.007 | 1.22 |
| INCB018424 1.5% BID | 24 | FGF-BP1 | <.0001 | 1.24 |
| INCB018424 1.5% BID | 24 | EPO | 0.003 | 1.41 |

TABLE 6A

Proteins down-regulated in 1.5% ruxolitinib QD and 1.5% ruxolitinib BID at week 12

| Unique to 1.5% QD | Both 1.5% QD and 1.5% BID | Unique to 1.5% BID |
|---|---|---|
| DEFB4A | CD160 | TIMD4 |
| IGFBP-1 | TNFB | RNASE3 |
| GZMH | TNFRSF9 | CXCL9 |
| FS | ITGB2 | CRH |
| SH2D1A | CD5 | TCL1B |
| CXCL11 | CCL19 | CA5A |
| GZMA | MCP-4 | TNFRSF6B |
| ANGPTL4 | CCL18 | CHIT1 |
| IL6 | CXCL10 | TGF-alpha |
| TYMP | LAIR-2 | OSM |
| CD8A | IL-12B | PRTN3 |
| SIGLEC1 | CD6 | MBL2 |
| IL-15RA | CD1C | IL5 |
| SLAMF1 | CRTAM | CLEC4D |
| CLEC6A | KIR2DL3 | COL1A1 |
| CLEC10A | ADAM 8 | CLEC4C |
| SELE | GZMB | LIF |
| GDF-15 | CCL21 | IL-2RB |
| CLM-1 | IFNL1 | NOV |
| FOLR2 | IL12 | TNC |
| LIF-R | DSC2 | VSTM1 |
| IL12RB1 | CD163 | WISP-1 |
| CDH3 | RETN | TNFRSF10C |
| GM-CSF-R-alpha | IL-1RT1 | IL3RA |
| ST2 | CD244 | PGLYRP1 |
| MSR1 | CD48 | ICAM3 |
| PDCD1 | TNF-R2 | ICAM1 |
| CSF-1 | ARTN | FCRL5 |
| FcRL2 | LY9 | CLEC7A |
| CD200R1 | CD79B | VCAM1 |
| | | SLAMF8 |
| | | CDON |
| | | FCER2 |
| | | SELL |
| | | PON2 |
| | | CD209 |
| | | IL-10RB |
| | | LAIR1 |
| | | TNF-R1 |
| | | KIRREL2 |
| | | FCRL1 |
| | | MILR1 |
| | | HAVCR2 |
| | | KPNA1 |
| | | TGFR-2 |

TABLE 6B

Proteins down-regulated in 1.5% ruxolitinib QD and 1.5% ruxolitinib BID at week 24

| Unique to 1.5% QD | Both 1.5% QD and 1.5% BID | Unique to 1.5% BID |
|---|---|---|
| DEFB4A | CXCL10 | CXCL9 |
| GZMH | CCL19 | IL-2RB |
| IL5 | TRANCE | COL1A1 |
| SH2D1A | CCL18 | KIR2DL3 |
| PTH1R | TNFB | LAP TGF-beta-1 |
| IL6 | GZMB | CHIT1 |
| PTX3 | TNFRSF9 | IFNL1 |
| sFRP-3 | KLRD1 | ITGB2 |
| IL-15RA | IL-12B | SLAMF8 |
| ESM-1 | FASLG | IL-18BP |
| CLM-1 | MMP12 | TNFSF13B |
| CDH3 | CD160 | LILRB4 |
| TNC | XCL1 | FCER2 |
| COL4A3BP | CXCL11 | TIMD4 |
| CD79B | LAIR-2 | CD163 |
| FCRL1 | MCP-4 | MILR1 |
| PD-L1 | IL12 | NOV |
| IL17RB | SIGLEC1 | IL-18R1 |
| TNFRSF13B | CD6 | TRAIL |
| LIF-R | CLEC4C | CDON |
| SIRT5 | CD5 | WISP-1 |
| CD200R1 | CRTAM | PGF |
| IL-5R-alpha | CCL21 | CLEC4G |
| PDGF-R-alpha | ADAM 8 | SELL |
| TM | IL10 | ICAM1 |
| WFIKKN1 | CLEC7A | VCAM1 |
| EFNA4 | SLAMF1 | IL32 |
| N2DL-2 | CCL23 | PILRA |
| GFR-alpha-1 | CD1C | DSC2 |
| THBS2 | MBL2 | RELT |
| LY75 | TNF-R2 | KIRREL2 |
| NBL1 | IL12RB1 | ICAM3 |
| | CD48 | DLL1 |
| | GZMA | Gal-9 |
| | IL-1RT1 | SIRPB1 |
| | GM-CSF-R-alpha | SIGLEC10 |
| | PAPPA | SIGLEC6 |
| | TNFRSF4 | hOSCAR |
| | IFNLR1 | SHPS-1 |
| | CD244 | |
| | CSF-1 | |
| | CD27 | |
| | CD83 | |
| | PON2 | |
| | LY9 | |
| | FcRL2 | |
| | CLEC10A | |
| | PDCD1 | |
| | CLM-6 | |

TABLE 7A

Proteins up-regulated in 1.5% ruxolitinib QD and 1.5% ruxolitinib BID at week 12

| Unique to 1.5% QD | Both 1.5% QD and 1.5% BID | Unique to 1.5% BID |
|---|---|---|
| GPNMB | KLK13 | NTRK3 |
| CAMKK1 | FGF-BP1 | TF |
| PDGFRB | EPO | ITGAV |
| TYRO3 | ITGB1 | ERBB3 |
| GFRA2 | GALNT2 | CLEC14A |
| SPON2 | CRISP2 | ERBB4 |
| TCL1B | ENTPD6 | Nr-CAM |
| CA14 | DPP4 | NTRK2 |
| IGF2R | AOC3 | EDA2R |
| MRC2 | DCBLD2 | LTBP2 |
| LRRN1 | ANGPTL7 | DKKL1 |
| TCN2 | B4GAT1 | CD58 |
| ESAM | SPINK5 | Gal-3 |

TABLE 7A-continued

Proteins up-regulated in 1.5% ruxolitinib QD and 1.5% ruxolitinib BID at week 12

| Unique to 1.5% QD | Both 1.5% QD and 1.5% BID | Unique to 1.5% BID |
|---|---|---|
| SCGB3A1 | TACSTD2 | GDNFR-alpha-3 |
| BCAM | VEGFD | FABP9 |
| IGSF3 | FAM3C | Alpha-2-MRAP |
| SMAD1 | CLUL1 | PRELP |
| SAA4 | SOD2 | DPEP1 |
| ANG-1 | CXCL16 | MMP7 |
| SEZ6L2 | GPC1 | SCARB2 |
| APOM | DKK3 | BAMBI |
| IGFBPL1 | CLEC4A | ACAN |
| CPXM1 | KLK6 | DCN |
| METRNL | RAGE | PEAR1 |
| ENAH | KLK10 | PODXL2 |
| LRP11 | FAM3B | VWC2 |
| VEGFA | CD200 | BLM hydrolase |
| MFAP5 | WFIKKN2 | CCL25 |
| MCFD2 | CA6 | SCARF2 |
| ENTPD2 | NCAM1 | EZR |
| VEGFC | DDC | OPTC |
| CNTN2 | SCGB3A2 | EPHB6 |
| PAI | MOG | PVR |
| APP | CCL11 | DPP10 |
| ISLR2 | CYR61 | PRTG |
| CLMP | Flt3L | TMPRSS5 |
| REG4 | CEACAM5 | CD70 |
| KAZALD1 | MMP-3 | THPO |
| DPP7 | GAL | KIM1 |
| CD46 | APLP1 | ROBO2 |
| TIMP1 | | CDNF |
| COCH | | SPOCK1 |
| ROR1 | | ST3GAL1 |
| IL7R | | CNTN5 |
| CXCL5 | | GCP5 |
| PROC | | GP1BA |
| IGFBP6 | | RGMB |
| PAM | | LGALS7 |
| MSLN | | FUT8 |
| SYND1 | | CXADR |
| COMP | | MATN3 |
| DPP6 | | SCF |
| MMP-1 | | NCAN |
| ST6GAL1 | | GDF-2 |
| SOST | | CAIX |
| ANGPTL3 | | RGMA |
| DSG4 | | NPTXR |
| CXCL1 | | PHOSPHO1 |
| NID1 | | STX6 |
| PLTP | | PON3 |
| CA4 | | gal-8 |
| LEP | | CADM3 |
| CRTAC1 | | CX3CL1 |
| F11 | | PADI2 |
| MAP4K5 | | PREB |
| CES2 | | MDGA1 |
| CCL5 | | SCGB1A1 |
| OMG | | IL-17A |
| | | NEFL |
| | | GIF |
| | | TN-R |
| | | ITM2A |
| | | PLXNB3 |
| | | SMOC2 |
| | | Dkk-4 |
| | | BCAN |
| | | MFGE8 |
| | | G-CSF |
| | | P4HB |
| | | PLIN1 |
| | | AGR3 |
| | | Ep-CAM |
| | | TSHB |
| | | TNNI3 |

TABLE 7B

Proteins up-regulated in 1.5% ruxolitinib QD and 1.5% ruxolitinib BID at week 24

| Unique to 1.5% QD | Both 1.5% QD and 1.5% BID | Unique to 1.5% BID |
|---|---|---|
| GALNT2 | TACSTD2 | CLEC14A |
| EGFR | ITGB1 | SPINT1 |
| BAMBI | IGF2R | ROBO1 |
| CNDP1 | CNTN1 | DCN |
| ST6GAL1 | AOC3 | PRELP |
| MEP1B | VEGFD | PVR |
| CA4 | CLEC4A | CDH1 |
| KIT | DKK3 | RGMA |
| TIMP1 | SPINK5 | TMPRSS5 |
| DPP6 | CXCL16 | GDNFR-alpha-3 |
| ADGRG2 | B4GAT1 | GPC1 |
| KLK6 | BLM hydrolase | LYPD3 |
| PAI | BCAM | ITM2A |
| CXCL5 | ISLR2 | Notch 3 |
| PROC | TF | ACAN |
| CLMP | KLK10 | hK11 |
| MOG | WFIKKN2 | MSMB |
| PDGF subunit A | hK8 | SCF |
| EDIL3 | F11 | RGMB |
| MMP-1 | Flt3L | PRSS27 |
| CA3 | IL15 | CRISP2 |
| MB | DDC | CNTN5 |
| KYAT1 | P4HB | PRTG |
| SPINK1 | PLIN1 | FABP9 |
| MMP-3 | CA6 | RAGE |
| LGALS7 | KLK13 | MFAP5 |
| TIMP4 | Ep-CAM | NTRK3 |
| PCSK9 | | PON3 |
| FAM3C | | SOST |
| CES2 | | DPP10 |
| CES1 | | CRIM1 |
| TMPRSS15 | | CLUL1 |
| | | CTSV |
| | | hK14 |
| | | COMP |
| | | MDGA1 |
| | | GDF-2 |
| | | SMOC2 |
| | | NPTXR |
| | | PHOSPHO1 |
| | | TNXB |
| | | MFGE8 |
| | | CYR61 |
| | | TN-R |
| | | WASF1 |
| | | CPA2 |
| | | PADI2 |
| | | BAG6 |
| | | GAL |
| | | NAAA |
| | | REG4 |
| | | GIF |
| | | NID2 |
| | | GSAP |
| | | TNFRSF12A |
| | | NEFL |
| | | MYOC |
| | | CEACAM5 |
| | | EPO |

The effects of topical treatment with ruxolitinib cream on inflammatory mediator expression in circulation was investigated. Sera from 130 participants (n=23 vehicle, n=26 0.15% once daily [QD], n=27 0.5% QD, n=24 1.5% QD, n=30 1.5% twice daily [BID]) with baseline and Week 24 samples were analyzed for broad proteomic changes. Paired t-tests established significant changes within treatment groups at a cutoff of p<0.05. Baseline biomarkers and facial Vitiligo Area Scoring Index (F-VASI) were assessed for significance using Spearman's correlation. Proteins in circulation that positively correlated with baseline F-VASI are depicted in FIG. 3. Fold change from baseline to week 24 in select inflammatory mediators is depicted in FIG. 4 (values greater than 1 indicate an increase, while values less than 1 indicate a decrease). Overall, topical treatment with ruxolitinib cream, and the associated skin improvement, corresponded with dose-dependent modulation of circulating inflammatory mediators. All inflammatory mediators stayed steady or increased slightly with vehicle BID treatment. Inflammatory mediators decreased more significantly with increasing doses of ruxolitinib cream.

Example 3: Correlations Between Percent Change in Facial Vitiligo Area Scoring Index and Proteins at Baseline, Fold Change from Baseline to Week 12, and Fold Change from Baseline to Week 24

Correlations between percent change in facial Vitiligo Area Scoring Index (VASI) and proteins at baseline, fold change from baseline to week 12, and fold change from baseline to week 24 were investigated. Spearman correlation values >|0.3| and p-values <0.05 indicated a moderate correlation. Correlations were completed for a) all patients, b) responders, and c) non-responders. All correlation calculations excluded the vehicle cohort. Proteins moderately correlated with percent change in facial VASI are presented.

The following tables describe associations of percent change in facial VASI with a) baseline protein levels; b) fold change in protein expression from baseline to week 12; and c) fold change in protein expression from baseline to week 24. The cut-off value for correlations was Spearman Correlation>|0.3| and p<0.05 to indicate a moderately significant correlation.

TABLE 8A

Association between percent change in facial VASI and Baseline protein levels

| Assay | Spearman Correlation | p-value |
|---|---|---|
| IL-20RA | 0.34 | <0.00013 |
| PON2 | 0.34 | <0.00013 |

TABLE 8B

Association between percent change in facial VASI and fold change in protein expression from baseline to week 12

| Assay | Spearman Correlation | p-value |
|---|---|---|
| DEFA1 | −0.30 | 0.002 |
| DKKL1 | −0.35 | <0.00012 |

TABLE 8C

Association between percent change in facial VASI and fold change in protein expression from baseline to week 24

| Assay | Spearman Correlation | p-value |
|---|---|---|
| GH | 0.33 | <0.00016 |

TABLE 9A

Association between percent change in facial VASI and Baseline protein levels in Responders

| Response | Assay | Spearman Correlation | p-value |
|---|---|---|---|
| Baseline proteins negativey correlated with Percent Change in Facial VASI in responders | | | |
| Responders | SCF | −0.35 | 0.017 |
| Responders | CPA2 | −0.34 | 0.019 |
| Responders | P4HB | −0.34 | 0.019 |
| Responders | SPARCL1 | −0.34 | 0.021 |
| Responders | ST2 | −0.34 | 0.021 |
| Responders | SCF | −0.33 | 0.023 |
| Responders | CNDP1 | −0.33 | 0.024 |
| Responders | TRAIL | −0.32 | 0.027 |
| Responders | KIRREL2 | −0.32 | 0.028 |
| Responders | SCF | −0.32 | 0.029 |
| Responders | EGFR | −0.32 | 0.030 |
| Responders | ISLR2 | −0.32 | 0.030 |
| Responders | PPP3R1 | −0.32 | 0.030 |
| Responders | FCGR3B | −0.31 | 0.031 |
| Responders | MMP-3 | −0.31 | 0.031 |
| Responders | IL-18BP | −0.31 | 0.033 |
| Responders | Flt3L | −0.31 | 0.035 |
| Responders | PPY | −0.31 | 0.036 |
| Responders | LTA4H | −0.31 | 0.036 |
| Responders | ITGB2 | −0.30 | 0.037 |
| Responders | PTN | −0.30 | 0.038 |
| Responders | GPNMB | −0.30 | 0.039 |
| Responders | SIRPB1 | −0.30 | 0.040 |
| Responders | PLTP | −0.35 | 0.017 |
| Responders | PSP-D | −0.34 | 0.019 |
| Responders | COMP | −0.34 | 0.019 |
| Responders | PAMR1 | −0.34 | 0.021 |
| Responders | VASN | −0.34 | 0.021 |
| Responders | F11 | −0.33 | 0.023 |
| Responders | IL10 | −0.33 | 0.024 |
| Responders | CA3 | −0.32 | 0.027 |
| Responders | CXCL10 | −0.32 | 0.028 |
| Responders | Notch 3 | −0.32 | 0.029 |
| Responders | NCAM1 | −0.32 | 0.030 |
| Responders | PROC | −0.32 | 0.030 |
| Responders | CLEC14A | −0.32 | 0.030 |
| Responders | IL-12B | −0.31 | 0.031 |
| Responders | IL10 | −0.31 | 0.031 |
| Responders | CD40 | −0.31 | 0.033 |
| Responders | IFN-gamma | −0.31 | 0.035 |
| Baseline proteins positively correlated with Percent Change in Facial VASI in responders | | | |
| Responders | SERPINA12 | 12 | 0.34 | 0.019 |
| Responders | GHRL | 12 | 0.34 | 0.019 |
| Responders | PREB | 12 | 0.31 | 0.036 |

TABLE 9B

Association between percent change in facial VASI and Baseline protein levels in Non-Responders

| Response | Assay | Spearman Correlation | p-value |
|---|---|---|---|
| Baseline proteins negatively correlated with Percent Change in Facial VASI in non-responders | | | |
| Non-Responders | EPHA10 | −0.46 | 0.001 |
| Non-Responders | GH2 | −0.36 | 0.005 |
| Non-Responders | PARP-1 | −0.35 | 0.005 |
| Non-Responders | GLRX | −0.32 | 0.012 |
| Non-Responders | ARSB | −0.31 | 0.013 |
| Non-Responders | SCAMP3 | −0.30 | 0.016 |

TABLE 9B-continued

Association between percent change in facial VASI
and Baseline protein levels in Non-Responders

| Response | Assay | Spearman Correlation | p-value |
|---|---|---|---|
| Baseline proteins positively correlated with Percent Change in Facial VASI in non-responders | | | |
| Non-Responders | t-PA | 0.48 | <0.0001 |
| Non-Responders | LDL receptor | 0.45 | <0.0001 |
| Non-Responders | DLK-1 | 0.44 | <0.0001 |
| Non-Responders | SELE | 0.40 | 0.001 |
| Non-Responders | EPHB4 | 0.39 | 0.002 |
| Non-Responders | GFRA2 | 0.38 | 0.002 |
| Non-Responders | PLC | 0.37 | 0.003 |
| Non-Responders | LTBR | 0.35 | 0.005 |
| Non-Responders | PAMR1 | 0.35 | 0.006 |
| Non-Responders | TACSTD2 | 0.35 | 0.006 |
| Non-Responders | FS | 0.34 | 0.006 |
| Non-Responders | ICAM-2 | 0.34 | 0.007 |
| Non-Responders | AXL | 0.34 | 0.007 |
| Non-Responders | PRSS8 | 0.33 | 0.009 |
| Non-Responders | SPINK5 | 0.32 | 0.010 |
| Non-Responders | AMN | 0.32 | 0.011 |
| Non-Responders | NOMO1 | 0.31 | 0.014 |
| Non-Responders | PAI | 0.31 | 0.015 |
| Non-Responders | CPM | 0.30 | 0.017 |

TABLE 10A

Association between percent change in facial VASI and
Fold Change in protein levels in Responders from either
baseline to week 12 or base ine to week 24

| Response | Assay | Week | Spearman Correlation | p-value |
|---|---|---|---|---|
| Fold Change proteins negatively correlated with Percent Change in Facial VASI in responders | | | | |
| Responders | FAP | 12 | −0.45 | 0.002 |
| Responders | RET | 12 | −0.44 | 0.002 |
| Responders | CNTN5 | 12 | −0.40 | 0.005 |
| Responders | FUCA1 | 12 | −0.40 | 0.006 |
| Responders | ITGAV | 12 | −0.39 | 0.007 |
| Responders | ITGB5 | 12 | −0.39 | 0.008 |
| Responders | THBS4 | 12 | −0.38 | 0.009 |
| Responders | CD207 | 12 | −0.36 | 0.013 |
| Responders | GDF-8 | 12 | −0.36 | 0.013 |
| Responders | CDH6 | 12 | −0.36 | 0.013 |
| Responders | MRC2 | 12 | −0.36 | 0.015 |
| Responders | ICOSLG | 12 | −0.36 | 0.015 |
| Responders | TNXB | 12 | −0.35 | 0.017 |
| Responders | EDIL3 | 12 | −0.35 | 0.018 |
| Responders | OSMR | 12 | −0.35 | 0.019 |
| Responders | GPC1 | 12 | −0.34 | 0.020 |
| Responders | MIC-A/B | 12 | −0.34 | 0.021 |
| Responders | TGFR-2 | 12 | −0.34 | 0.022 |
| Responders | LRRN1 | 12 | −0.34 | 0.022 |
| Responders | TLR3 | 12 | −0.33 | 0.024 |
| Responders | KIM1 | 12 | −0.32 | 0.029 |
| Responders | ROBO2 | 12 | −0.32 | 0.030 |
| Responders | CD70 | 12 | −0.32 | 0.032 |
| Responders | CLMP | 12 | −0.31 | 0.033 |
| Responders | N-CDase | 12 | −0.31 | 0.034 |
| Responders | FCRL5 | 12 | −0.31 | 0.035 |
| Responders | CTSV | 12 | −0.31 | 0.037 |
| Responders | SCARF2 | 12 | −0.31 | 0.037 |
| Responders | KIMI | 12 | −0.31 | 0.038 |
| Responders | PLXDC1 | 12 | −0.31 | 0.038 |
| Responders | PRTG | 12 | −0.31 | 0.039 |
| Responders | ERBB4 | 12 | −0.30 | 0.040 |
| Responders | MAGED1 | 12 | −0.30 | 0.040 |
| Responders | CEACAM1 | 12 | −0.30 | 0.042 |
| Responders | TSHB | 24 | −0.54 | <0.0001 |

TABLE 10A-continued

Association between percent change in facial VASI and
Fold Change in protein levels in Responders from either
baseline to week 12 or base ine to week 24

| Response | Assay | Week | Spearman Correlation | p-value |
|---|---|---|---|---|
| Responders | PTK7 | 24 | −0.46 | 0.001 |
| Responders | ICOSLG | 24 | −0.36 | 0.014 |
| Responders | TGFR-2 | 24 | −0.34 | 0.023 |
| Responders | RET | 24 | −0.33 | 0.027 |
| Responders | ADAM 22 | 24 | −0.32 | 0.030 |
| Responders | CTSC | 24 | −0.32 | 0.031 |
| Responders | DLK-1 | 24 | −0.32 | 0.032 |
| Responders | USP8 | 24 | −0.32 | 0.035 |
| Responders | SCARF2 | 24 | −0.31 | 0.037 |
| Responders | TNFRSF13B | 24 | −0.31 | 0.038 |
| Responders | MB | 24 | −0.31 | 0.038 |
| Responders | TMPRSS5 | 24 | −0.30 | 0.044 |
| Fold Change proteins positively correlated with Percent Change in Facial VASI in responders | | | | |
| Responders | NUDT5 | 12 | 0.38 | 0.010 |
| Responders | MMP-3 | 12 | 0.37 | 0.010 |
| Responders | MAEA | 12 | 0.36 | 0.013 |
| Responders | NEMO | 12 | 0.35 | 0.019 |
| Responders | IFN-gamma | 12 | 0.34 | 0.020 |
| Responders | IL18 | 12 | 0.33 | 0.024 |
| Responders | AKT1S1 | 12 | 0.33 | 0.025 |
| Responders | CASP-8 | 12 | 0.33 | 0.025 |
| Responders | PPP1R2 | 12 | 0.33 | 0.026 |
| Responders | ST2 | 12 | 0.33 | 0.027 |
| Responders | VSIG4 | 12 | 0.32 | 0.028 |
| Responders | SCGB3A2 | 12 | 0.32 | 0.028 |
| Responders | HDGF | 12 | 0.32 | 0.029 |
| Responders | ICA1 | 12 | 0.32 | 0.030 |
| Responders | IL13 | 12 | 0.32 | 0.032 |
| Responders | PEBP1 | 12 | 0.31 | 0.033 |
| Responders | PARK7 | 12 | 0.31 | 0.035 |
| Responders | MAP4K5 | 12 | 0.31 | 0.036 |
| Responders | FLI1 | 12 | 0.31 | 0.038 |
| Responders | MMP-3 | 24 | 0.45 | 0.002 |
| Responders | MMP-10 | 24 | 0.43 | 0.003 |
| Responders | ST2 | 24 | 0.43 | 0.003 |
| Responders | CCL24 | 24 | 0.42 | 0.004 |
| Responders | TIMP4 | 24 | 0.41 | 0.006 |
| Responders | MBL2 | 24 | 0.35 | 0.018 |
| Responders | FLI1 | 24 | 0.33 | 0.029 |
| Responders | IL18 | 24 | 0.32 | 0.030 |
| Responders | REG4 | 24 | 0.32 | 0.032 |
| Responders | IFN-gamma | 24 | 0.32 | 0.034 |
| Responders | CPA2 | 24 | 0.31 | 0.037 |

TABLE 10B

Association between percent change in facial VASI and
Fold Change in protein levels in Non-Responders from
either baseline to week 12 or baseline to week 24

| Response | Assay | Week | Spearman Correlation | p-value |
|---|---|---|---|---|
| Fold Change proteins negatively correlated with Percent Change in Facial VASI in non-responders | | | | |
| Non-Responders | DDR1 | 12 | −0.40 | 0.001 |
| Non-Responders | NTRK2 | 12 | −0.38 | 0.003 |
| Non-Responders | CES2 | 12 | −0.38 | 0.003 |
| Non-Responders | SCARA5 | 12 | −0.37 | 0.003 |
| Non-Responders | GDF-8 | 12 | −0.35 | 0.006 |
| Non-Responders | BOC | 12 | −0.35 | 0.007 |
| Non-Responders | PAEP | 12 | −0.35 | 0.007 |
| Non-Responders | ARTN | 12 | −0.35 | 0.007 |
| Non-Responders | CDNF | 12 | −0.34 | 0.008 |
| Non-Responders | TMPRSS5 | 12 | −0.34 | 0.008 |
| Non-Responders | FLRT2 | 12 | −0.34 | 0.009 |
| Non-Responders | ROBO2 | 12 | −0.33 | 0.011 |

TABLE 10B-continued

Association between percent change in facial VASI and Fold Change in protein levels in Non-Responders from either baseline to week 12 or baseline to week 24

| Response | Assay | Week | Spearman Correlation | p-value |
|---|---|---|---|---|
| Non-Responders | SIGLEC10 | 12 | −0.33 | 0.011 |
| Non-Responders | PRTG | 12 | −0.32 | 0.012 |
| Non-Responders | SCARF2 | 12 | −0.32 | 0.014 |
| Non-Responders | CDH3 | 12 | −0.32 | 0.014 |
| Non-Responders | GFR-alpha-1 | 12 | −0.31 | 0.015 |
| Non-Responders | TSHB | 12 | −0.31 | 0.015 |
| Non-Responders | CD200R1 | 12 | −0.31 | 0.017 |
| Non-Responders | RGMB | 12 | −0.31 | 0.017 |
| Non-Responders | KYNU | 12 | −0.30 | 0.018 |
| Non-Responders | HS3ST3B1 | 24 | −0.37 | 0.004 |
| Non-Responders | CHRDL2 | 24 | −0.33 | 0.010 |
| Non-Responders | CNTN1 | 24 | −0.30 | 0.019 |
| Fold Change proteins positively correlated with Percent Change in Facial VASI in non-responders | | | | |
| Non-Responders | VSIG4 | 12 | 0.38 | 0.002 |
| Non-Responders | ARHGAP1 | 12 | 0.38 | 0.003 |
| Non-Responders | B4GAT1 | 12 | 0.37 | 0.003 |
| Non-Responders | STX8 | 12 | 0.37 | 0.004 |
| Non-Responders | CRELD2 | 12 | 0.37 | 0.004 |
| Non-Responders | ARSA | 12 | 0.36 | 0.004 |
| Non-Responders | BCAM | 12 | 0.35 | 0.005 |
| Non-Responders | SCARF1 | 12 | 0.34 | 0.007 |
| Non-Responders | CA13 | 12 | 0.34 | 0.009 |
| Non-Responders | DAG1 | 12 | 0.34 | 0.009 |
| Non-Responders | LAIR1 | 12 | 0.33 | 0.009 |
| Non-Responders | GUSB | 12 | 0.33 | 0.009 |
| Non-Responders | PMVK | 12 | 0.33 | 0.009 |
| Non-Responders | PEAR1 | 12 | 0.33 | 0.010 |
| Non-Responders | GP1BA | 12 | 0.33 | 0.011 |
| Non-Responders | TACC3 | 12 | 0.32 | 0.013 |
| Non-Responders | PARK7 | 12 | 0.31 | 0.016 |
| Non-Responders | ARHGEF12 | 12 | 0.31 | 0.017 |
| Non-Responders | SEMA7A | 12 | 0.30 | 0.018 |
| Non-Responders | ESAM | 12 | 0.30 | 0.019 |
| Non-Responders | FKBP5 | 12 | 0.30 | 0.020 |
| Non-Responders | ARHGAP1 | 24 | 0.49 | <0.0001 |
| Non-Responders | SCAMP3 | 24 | 0.48 | <0.0001 |
| Non-Responders | ABL1 | 24 | 0.48 | <0.0001 |
| Non-Responders | EGF | 24 | 0.48 | <0.0001 |
| Non-Responders | TACC3 | 24 | 0.47 | <0.0001 |
| Non-Responders | FKBP5 | 24 | 0.47 | <0.0001 |
| Non-Responders | BID | 24 | 0.47 | <0.0001 |
| Non-Responders | PRDX5 | 24 | 0.47 | <0.0001 |
| Non-Responders | STX8 | 24 | 0.46 | <0.0001 |
| Non-Responders | CD63 | 24 | 0.46 | <0.0001 |
| Non-Responders | SCARF1 | 24 | 0.45 | <0.0001 |
| Non-Responders | PTPN1 | 24 | 0.45 | <0.0001 |
| Non-Responders | CLEC1B | 24 | 0.44 | <0.0001 |
| Non-Responders | ARSB | 24 | 0.44 | <0.0001 |
| Non-Responders | FKBP1B | 24 | 0.43 | 0.001 |
| Non-Responders | YES1 | 24 | 0.43 | 0.001 |
| Non-Responders | SRC | 24 | 0.43 | 0.001 |
| Non-Responders | TNFSF14 | 24 | 0.42 | 0.001 |
| Non-Responders | PLXNB3 | 24 | 0.42 | 0.001 |
| Non-Responders | LRMP | 24 | 0.42 | 0.001 |
| Non-Responders | CD164 | 24 | 0.42 | 0.001 |
| Non-Responders | DAG1 | 24 | 0.41 | 0.001 |
| Non-Responders | PVALB | 24 | 0.41 | 0.001 |
| Non-Responders | NAA10 | 24 | 0.41 | 0.001 |
| Non-Responders | TRIM5 | 24 | 0.41 | 0.001 |
| Non-Responders | ARHGEF12 | 24 | 0.41 | 0.001 |
| Non-Responders | HGF | 24 | 0.40 | 0.001 |
| Non-Responders | CA13 | 24 | 0.40 | 0.001 |
| Non-Responders | SNAP23 | 24 | 0.40 | 0.002 |
| Non-Responders | SORT1 | 24 | 0.40 | 0.002 |
| Non-Responders | GP6 | 24 | 0.39 | 0.002 |
| Non-Responders | CTSS | 24 | 0.39 | 0.002 |
| Non-Responders | PPIB | 24 | 0.39 | 0.002 |
| Non-Responders | CRKL | 24 | 0.38 | 0.003 |
| Non-Responders | MAP2K6 | 24 | 0.38 | 0.003 |
| Non-Responders | MANF | 24 | 0.38 | 0.003 |
| Non-Responders | PMVK | 24 | 0.38 | 0.003 |
| Non-Responders | ABHD14B | 24 | 0.38 | 0.003 |
| Non-Responders | GUSB | 24 | 0.38 | 0.003 |
| Non-Responders | FATC1 | 24 | 0.38 | 0.003 |
| Non-Responders | MAD1L1 | 24 | 0.37 | 0.003 |
| Non-Responders | EDAR | 24 | 0.37 | 0.004 |
| Non-Responders | CEACAM8 | 24 | 0.37 | 0.004 |
| Non-Responders | GLB1 | 24 | 0.36 | 0.004 |
| Non-Responders | ST3GAL1 | 24 | 0.36 | 0.004 |
| Non-Responders | ARSA | 24 | 0.36 | 0.005 |
| Non-Responders | ADAM 8 | 24 | 0.36 | 0.005 |
| Non-Responders | CD40 | 24 | 0.36 | 0.005 |
| Non-Responders | IFI30 | 24 | 0.36 | 0.005 |
| Non-Responders | ECE1 | 24 | 0.35 | 0.006 |
| Non-Responders | AXIN1 | 24 | 0.35 | 0.006 |
| Non-Responders | WFDC2 | 24 | 0.35 | 0.006 |
| Non-Responders | TBCB | 24 | 0.35 | 0.007 |
| Non-Responders | CXCL13 | 24 | 0.35 | 0.007 |
| Non-Responders | ST1A1 | 24 | 0.35 | 0.007 |
| Non-Responders | KIF1BP | 24 | 0.35 | 0.007 |
| Non-Responders | DPP7 | 24 | 0.34 | 0.007 |
| Non-Responders | VEGFA | 24 | 0.34 | 0.007 |
| Non-Responders | CETN2 | 24 | 0.34 | 0.007 |
| Non-Responders | TGF-alpha | 24 | 0.34 | 0.008 |
| Non-Responders | CD84 | 24 | 0.34 | 0.009 |
| Non-Responders | SNAP29 | 24 | 0.34 | 0.009 |
| Non-Responders | CASP-8 | 24 | 0.33 | 0.010 |
| Non-Responders | S100A11 | 24 | 0.33 | 0.010 |
| Non-Responders | GSTP1 | 24 | 0.33 | 0.010 |
| Non-Responders | CRADD | 24 | 0.33 | 0.010 |
| Non-Responders | PRKAB1 | 24 | 0.33 | 0.011 |
| Non-Responders | HGF | 24 | 0.33 | 0.011 |
| Non-Responders | STK4 | 24 | 0.33 | 0.011 |
| Non-Responders | RNASE3 | 24 | 0.33 | 0.011 |
| Non-Responders | SERPINB6 | 24 | 0.32 | 0.012 |
| Non-Responders | OSM | 24 | 0.32 | 0.012 |
| Non-Responders | MK | 24 | 0.32 | 0.012 |
| Non-Responders | FADD | 24 | 0.32 | 0.013 |
| Non-Responders | CLEC11A | 24 | 0.32 | 0.013 |
| Non-Responders | CD69 | 24 | 0.32 | 0.013 |
| Non-Responders | LOX-1 | 24 | 0.32 | 0.013 |
| Non-Responders | ITGA6 | 24 | 0.31 | 0.015 |
| Non-Responders | CLEC5A | 24 | 0.31 | 0.015 |
| Non-Responders | BCAM | 24 | 0.31 | 0.015 |
| Non-Responders | FES | 24 | 0.31 | 0.016 |
| Non-Responders | TXNDC5 | 24 | 0.31 | 0.016 |
| Non-Responders | LAT2 | 24 | 0.31 | 0.018 |
| Non-Responders | CXCL11 | 24 | 0.30 | 0.018 |
| Non-Responders | PARP-1 | 24 | 0.30 | 0.018 |
| Non-Responders | APBB1IP | 24 | 0.30 | 0.018 |
| Non-Responders | GZMB | 24 | 0.30 | 0.019 |
| Non-Responders | CRNN | 24 | 0.30 | 0.019 |

Example 4: Proteomic Changes from Baseline Between Responders and within Responders at Weeks 12 and 24

Proteomic changes from baseline were investigated between responders and within responders at week 12 and week 24. Paired t-tests were conducted and significance conferred at p<0.05. The tables below show the proteomic changes that differed significantly between responders and non-responders. Response was defined as percent change in facial VASI>50%.

TABLE 11A

Differences in proteomic changes between responders and non-responders (excluding vehicle) at week 12

| Assay | Week | p-value | Responder Fold Change | Non-Responder Fold Change |
|---|---|---|---|---|
| WAS | 12 | 0.001 | 1.26 | 0.90 |
| TRIM21 | 12 | 0.001 | 1.07 | 0.92 |
| DDAH1 | 12 | 0.002 | 1.11 | 0.97 |
| PSIP1 | 12 | 0.002 | 1.18 | 0.93 |
| IRF9 | 12 | 0.002 | 1.11 | 0.88 |
| FGF-BP1 | 12 | 0.002 | 1.19 | 1.06 |
| LGALS7 | 12 | 0.002 | 1.13 | 0.98 |
| TACSTD2 | 12 | 0.002 | 1.06 | 1.00 |
| CTSC | 12 | 0.003 | 1.08 | 0.93 |
| GDF-15 | 12 | 0.003 | 0.92 | 1.02 |
| GLB1 | 12 | 0.003 | 1.19 | 0.88 |
| HDGF | 12 | 0.003 | 1.13 | 0.92 |
| AMIGO2 | 12 | 0.003 | 1.05 | 0.97 |
| GSAP | 12 | 0.004 | 1.12 | 0.93 |
| CD1C | 12 | 0.004 | 0.90 | 0.98 |
| CCL11 | 12 | 0.004 | 1.12 | 1.00 |
| SIRT5 | 12 | 0.005 | 0.96 | 1.04 |
| APBB1IP | 12 | 0.005 | 1.09 | 0.91 |
| COL4A3BP | 12 | 0.006 | 1.04 | 0.93 |
| LRMP | 12 | 0.006 | 1.11 | 0.93 |
| ADAM-TS13 | 12 | 0.006 | 1.03 | 0.98 |
| DDX58 | 12 | 0.007 | 1.13 | 0.93 |
| PIK3AP1 | 12 | 0.007 | 1.09 | 0.87 |
| IL32 | 12 | 0.009 | 1.03 | 0.95 |
| DKKL1 | 12 | 0.009 | 1.05 | 0.99 |
| HS6ST1 | 12 | 0.010 | 1.07 | 0.97 |
| ILKAP | 12 | 0.010 | 1.17 | 0.93 |
| PRKRA | 12 | 0.010 | 1.06 | 0.95 |
| FES | 12 | 0.011 | 1.07 | 0.93 |
| VEGFD | 12 | 0.011 | 1.08 | 1.01 |
| CCL23 | 12 | 0.011 | 0.90 | 1.01 |
| CXCL1 | 12 | 0.011 | 1.12 | 1.00 |
| ARSB | 12 | 0.012 | 1.11 | 0.94 |
| TRIM5 | 12 | 0.013 | 1.13 | 0.90 |
| SPRY2 | 12 | 0.013 | 1.13 | 0.92 |
| ENTPD6 | 12 | 0.013 | 1.06 | 1.00 |
| CRISP2 | 12 | 0.013 | 1.06 | 0.99 |
| TOP2B | 12 | 0.014 | 1.15 | 0.84 |
| CASP-8 | 12 | 0.014 | 1.04 | 0.88 |
| CCL15 | 12 | 0.015 | 0.96 | 1.03 |
| CCL27 | 12 | 0.015 | 1.03 | 0.97 |
| IL15 | 12 | 0.016 | 1.12 | 1.04 |
| PRDX5 | 12 | 0.016 | 1.13 | 0.86 |
| SNCG | 12 | 0.016 | 1.08 | 0.98 |
| TNFRSF10C | 12 | 0.016 | 0.91 | 0.98 |
| DFFA | 12 | 0.017 | 1.04 | 0.90 |
| PLXNB3 | 12 | 0.017 | 1.13 | 0.97 |
| METRNL | 12 | 0.017 | 1.01 | 1.06 |
| NPM1 | 12 | 0.018 | 1.14 | 0.95 |
| PFKM | 12 | 0.019 | 1.17 | 0.97 |
| BST2 | 12 | 0.019 | 1.05 | 0.98 |
| CD160 | 12 | 0.020 | 0.85 | 0.93 |
| SERPINA5 | 12 | 0.020 | 1.05 | 0.97 |
| BNP | 12 | 0.021 | 1.06 | 0.98 |
| DPP7 | 12 | 0.021 | 1.10 | 0.98 |
| CXCL1 | 12 | 0.021 | 1.10 | 1.00 |
| SLITRK2 | 12 | 0.021 | 1.05 | 0.98 |
| CCL11 | 12 | 0.022 | 1.10 | 1.00 |
| LRRN1 | 12 | 0.022 | 1.08 | 1.01 |
| SIGLEC6 | 12 | 0.022 | 1.03 | 0.97 |
| FHIT | 12 | 0.022 | 1.05 | 0.95 |
| CBL | 12 | 0.022 | 1.06 | 0.88 |
| PHOSPHO1 | 12 | 0.023 | 1.08 | 1.00 |
| DCTN2 | 12 | 0.025 | 1.07 | 0.94 |
| GSTP1 | 12 | 0.025 | 1.06 | 0.97 |
| DSG3 | 12 | 0.025 | 1.03 | 0.96 |
| NMNAT1 | 12 | 0.026 | 1.14 | 0.89 |
| SRP14 | 12 | 0.026 | 1.15 | 0.90 |
| NAAA | 12 | 0.027 | 1.06 | 0.96 |
| DEFA1 | 12 | 0.027 | 1.26 | 0.96 |
| S100A4 | 12 | 0.027 | 1.08 | 0.94 |
| Siglec-9 | 12 | 0.028 | 1.02 | 0.98 |
| ARSA | 12 | 0.028 | 1.09 | 0.97 |
| CD46 | 12 | 0.030 | 1.06 | 0.99 |
| S100A11 | 12 | 0.030 | 1.05 | 0.96 |
| NPDC1 | 12 | 0.031 | 0.99 | 1.06 |
| FLI1 | 12 | 0.031 | 1.04 | 0.94 |
| CD79B | 12 | 0.032 | 0.95 | 1.00 |
| IGFBP-2 | 12 | 0.033 | 0.95 | 1.04 |
| IL5 | 12 | 0.033 | 0.88 | 1.02 |
| GCP5 | 12 | 0.033 | 1.07 | 0.98 |
| UMOD | 12 | 0.033 | 1.04 | 0.99 |
| SOD2 | 12 | 0.034 | 1.06 | 1.01 |
| gal-8 | 12 | 0.035 | 1.08 | 0.98 |
| HCLS1 | 12 | 0.035 | 1.07 | 0.85 |
| SORT1 | 12 | 0.036 | 1.05 | 0.98 |
| ATP6V1F | 12 | 0.036 | 1.06 | 0.96 |
| XCL1 | 12 | 0.036 | 0.86 | 0.94 |
| LIF | 12 | 0.036 | 0.92 | 1.01 |
| Flt3L | 12 | 0.037 | 1.12 | 1.04 |
| ABHD14B | 12 | 0.037 | 1.06 | 0.93 |
| PPP1R9B | 12 | 0.037 | 1.03 | 0.89 |
| MMP-1 | 12 | 0.039 | 1.11 | 1.00 |
| APOM | 12 | 0.039 | 1.05 | 1.00 |
| SCGB3A1 | 12 | 0.039 | 1.08 | 1.01 |
| IL-17D | 12 | 0.039 | 1.04 | 0.99 |
| HNMT | 12 | 0.039 | 1.05 | 0.98 |
| RBKS | 12 | 0.040 | 1.06 | 0.94 |
| MAD1L1 | 12 | 0.041 | 1.08 | 0.97 |
| PODXL2 | 12 | 0.041 | 1.05 | 1.00 |
| OPN | 12 | 0.042 | 0.90 | 0.99 |
| DPEP1 | 12 | 0.042 | 1.06 | 0.99 |
| FURIN | 12 | 0.044 | 1.07 | 0.99 |
| ANXA1 | 12 | 0.044 | 1.12 | 0.96 |
| NCAM1 | 12 | 0.045 | 1.08 | 1.02 |
| PADI2 | 12 | 0.046 | 1.09 | 1.00 |
| GFRA2 | 12 | 0.046 | 1.03 | 0.99 |
| IL2-RA | 12 | 0.046 | 0.86 | 0.95 |
| CEACAM5 | 12 | 0.048 | 1.19 | 1.03 |
| IRAK1 | 12 | 0.048 | 1.04 | 0.92 |
| BTC | 12 | 0.049 | 1.14 | 0.94 |
| ARHGAP1 | 12 | 0.050 | 1.18 | 0.82 |

TABLE 11B

Differences in proteomic changes between responders and non-responders (excluding vehicle) at week 24

| Assay | Visit | p-value | Responder Fold Change | Non-Responder Fold Change |
|---|---|---|---|---|
| WAS | 24 | 0.001 | 1.09 | 0.99 |
| TRIM21 | 24 | 0.001 | 1.05 | 0.97 |
| DDAH1 | 24 | 0.002 | 1.07 | 1.01 |
| PSIP1 | 24 | 0.002 | 1.21 | 0.98 |
| IRF9 | 24 | 0.002 | 1.02 | 0.93 |
| FGF-BP1 | 24 | 0.002 | 1.18 | 1.08 |
| LGALS7 | 24 | 0.002 | 1.11 | 1.04 |
| TACSTD2 | 24 | 0.002 | 1.05 | 1.00 |
| CTSC | 24 | 0.003 | 1.06 | 0.98 |
| GDF-15 | 24 | 0.003 | 0.98 | 1.06 |
| HDGF | 24 | 0.003 | 1.13 | 1.02 |
| GLB1 | 24 | 0.003 | 1.10 | 0.99 |
| AMIGO2 | 24 | 0.003 | 1.03 | 1.00 |
| GSAP | 24 | 0.004 | 1.14 | 0.95 |
| CD1C | 24 | 0.004 | 0.90 | 0.99 |
| CCL11 | 24 | 0.004 | 1.11 | 0.99 |
| SIRT5 | 24 | 0.005 | 0.98 | 1.01 |
| APBB1IP | 24 | 0.005 | 1.11 | 1.00 |

TABLE 11B-continued

Differences in proteomic changes between responders and non-responders (excluding vehicle) at week 24

| Assay | Visit | p-value | Responder Fold Change | Non-Responder Fold Change |
|---|---|---|---|---|
| COL4A3BP | 24 | 0.006 | 0.99 | 0.97 |
| LRMP | 24 | 0.006 | 1.04 | 0.99 |
| ADAM-TS13 | 24 | 0.006 | 1.01 | 1.01 |
| DDX58 | 24 | 0.007 | 1.09 | 0.98 |
| PIK3AP1 | 24 | 0.007 | 1.16 | 0.99 |
| IL32 | 24 | 0.009 | 1.01 | 0.96 |
| DKKL1 | 24 | 0.009 | 1.02 | 0.99 |
| HS6ST1 | 24 | 0.010 | 1.06 | 0.99 |
| ILKAP | 24 | 0.010 | 1.07 | 0.98 |
| PRKRA | 24 | 0.010 | 1.06 | 0.99 |
| FES | 24 | 0.011 | 1.04 | 1.00 |
| VEGFD | 24 | 0.011 | 1.08 | 1.04 |
| CCL23 | 24 | 0.011 | 0.89 | 0.99 |
| CXCL1 | 24 | 0.011 | 1.05 | 1.00 |
| ARSB | 24 | 0.012 | 1.08 | 1.01 |
| SPRY2 | 24 | 0.013 | 1.14 | 0.88 |
| TRIM5 | 24 | 0.013 | 1.12 | 0.95 |
| ENTPD6 | 24 | 0.013 | 1.03 | 0.99 |
| CRISP2 | 24 | 0.013 | 1.06 | 1.00 |
| TOP2B | 24 | 0.014 | 1.13 | 0.98 |
| CASP-8 | 24 | 0.014 | 1.08 | 0.99 |
| CCL15 | 24 | 0.015 | 0.99 | 1.04 |
| CCL27 | 24 | 0.015 | 1.02 | 0.99 |
| IL15 | 24 | 0.016 | 1.11 | 1.04 |
| PRDX5 | 24 | 0.016 | 1.13 | 0.96 |
| SNCG | 24 | 0.016 | 1.13 | 1.06 |
| TNFRSF10C | 24 | 0.016 | 0.97 | 1.02 |
| DFFA | 24 | 0.017 | 1.06 | 0.98 |
| PLXNB3 | 24 | 0.017 | 1.09 | 1.01 |
| METRNL | 24 | 0.017 | 1.02 | 1.04 |
| NPM1 | 24 | 0.018 | 1.16 | 1.04 |
| PFKM | 24 | 0.019 | 1.09 | 1.03 |
| BST2 | 24 | 0.019 | 1.05 | 0.99 |
| CD160 | 24 | 0.020 | 0.84 | 0.95 |
| SERPINA5 | 24 | 0.020 | 1.11 | 1.03 |
| BNP | 24 | 0.021 | 1.01 | 0.99 |
| DPP7 | 24 | 0.021 | 1.07 | 1.03 |
| CXCL1 | 24 | 0.021 | 1.05 | 0.99 |
| SLITRK2 | 24 | 0.021 | 1.01 | 1.01 |
| CCL11 | 24 | 0.022 | 1.11 | 1.00 |
| LRRN1 | 24 | 0.022 | 1.08 | 1.01 |
| SIGLEC6 | 24 | 0.022 | 0.99 | 0.98 |
| FHIT | 24 | 0.022 | 1.04 | 1.00 |
| CBL | 24 | 0.022 | 1.10 | 0.97 |
| PHOSPHO1 | 24 | 0.023 | 1.07 | 1.02 |
| DCTN2 | 24 | 0.025 | 1.11 | 1.01 |
| GSTP1 | 24 | 0.025 | 1.03 | 0.99 |
| DSG3 | 24 | 0.025 | 0.99 | 0.99 |
| NMNAT1 | 24 | 0.026 | 1.14 | 1.05 |
| SRP14 | 24 | 0.026 | 1.15 | 1.04 |
| NAAA | 24 | 0.027 | 1.09 | 1.02 |
| S100A4 | 24 | 0.027 | 1.09 | 1.04 |
| DEFA1 | 24 | 0.027 | 1.03 | 0.97 |
| Siglec-9 | 24 | 0.028 | 1.02 | 1.00 |
| ARSA | 24 | 0.028 | 1.06 | 1.02 |
| S100A11 | 24 | 0.030 | 1.07 | 0.99 |
| CD46 | 24 | 0.030 | 1.06 | 1.03 |
| NPDC1 | 24 | 0.031 | 1.00 | 1.07 |
| FLI1 | 24 | 0.031 | 1.05 | 0.98 |
| CD79B | 24 | 0.032 | 0.96 | 0.99 |
| IGFBP-2 | 24 | 0.033 | 0.94 | 1.04 |
| IL5 | 24 | 0.033 | 0.91 | 1.03 |
| GCP5 | 24 | 0.033 | 1.03 | 1.00 |
| UMOD | 24 | 0.033 | 1.04 | 1.01 |
| SOD2 | 24 | 0.034 | 1.05 | 1.02 |
| gal-8 | 24 | 0.035 | 1.07 | 1.02 |
| HCLS1 | 24 | 0.035 | 1.15 | 0.95 |
| SORT1 | 24 | 0.036 | 1.02 | 1.00 |
| ATP6V1F | 24 | 0.036 | 1.01 | 1.02 |
| XCL1 | 24 | 0.036 | 0.84 | 0.93 |
| LIF | 24 | 0.036 | 0.99 | 1.02 |
| Flt3L | 24 | 0.037 | 1.13 | 1.05 |
| ABHD14B | 24 | 0.037 | 1.05 | 1.02 |
| PPP1R9B | 24 | 0.037 | 1.01 | 0.96 |
| MMP-1 | 24 | 0.039 | 1.13 | 1.01 |
| APOM | 24 | 0.039 | 1.08 | 0.99 |
| SCGB3A1 | 24 | 0.039 | 1.07 | 1.08 |
| IL-17D | 24 | 0.039 | 1.02 | 0.98 |
| HNMT | 24 | 0.039 | 1.08 | 1.01 |
| RBKS | 24 | 0.040 | 1.11 | 1.02 |
| MAD1L1 | 24 | 0.041 | 1.03 | 1.03 |
| PODXL2 | 24 | 0.041 | 1.01 | 1.00 |
| OPN | 24 | 0.042 | 0.83 | 0.97 |
| DPEP1 | 24 | 0.042 | 1.04 | 1.01 |
| FURIN | 24 | 0.044 | 1.07 | 1.00 |
| ANXA1 | 24 | 0.044 | 1.12 | 1.01 |
| NCAM1 | 24 | 0.045 | 1.09 | 1.02 |
| PADI2 | 24 | 0.046 | 1.10 | 0.98 |
| GFRA2 | 24 | 0.046 | 1.01 | 0.99 |
| IL2-RA | 24 | 0.046 | 0.83 | 0.94 |
| CEACAM5 | 24 | 0.048 | 1.25 | 1.04 |
| IRAK1 | 24 | 0.048 | 1.02 | 0.99 |
| BTC | 24 | 0.049 | 1.09 | 0.97 |
| ARHGAP1 | 24 | 0.050 | 1.15 | 0.98 |

Example 5: Interferon-Gamma and Tumor Necrosis-Alpha Induced Janus Kinase Expression in Keratinocyte and Subsequent Production of Inflammatory Mediators Transformed human keratinocyte (HaCaT) cells were purchased from AddexBio (Catalog #T0020001) and cultured in Optimized Dulbecco's Modified Eagle's Medium (AddexBio, Catalog #C0003-02) supplemented with 10% Fetal Bovine Serum (Hyclone, Catalog #16140-071) and 1× Penicillin/Streptomycin (Gibco, Catalog #15140-122). When cells reached 80-90% confluency they were washed with 1×DPBS then detached from tissue culture flasks by incubation with 0.25% Trypsin (Gibco, Catalog #25200-056) for 3-5 minutes at 37° C./5% $CO_2$. Cell culture media was added to trypsinized cells then cell suspension was transferred to a sterile 15 mL centrifuge tube to be spun down for 10 minutes at 1300 rpms. Media containing trypsin was aspirated from the cell pellet and then the pellet was re-suspended in 10 mL of cell culture media. Cells were counted using a Countess II automated cell counter then seeded into tissue culture treated 24 well plates at a concentration of $4 \times 10^4$ cells/mL and incubated for 48 hours at 37° C./5% $CO_2$. After 48 hours media was removed and replaced with 500 uL of either cell culture media or a combinatory stimulation of Recombinant Human Interferon gamma (R&D Systems, Catalog #285-IF-100) and Recombinant Human Tumor Necrosis Factor alpha (R&D Systems, Catalog #210-TA-020). HaCaT cells treated with the combinatory cytokine stimulation were treated at final concentrations of 10 ng/mL, 25 ng/mL, 50 ng/mL, or 100 ng/mL of each cytokine. Treated plates were mixed by gentle agitation for 30 seconds then incubated for 24 hours at 37° C./5% $CO_2$. At the end of the 24 hour incubation, media was immediately removed from each plate.

RNA was isolated from HaCaT cells using the QuantiGene Plex Assay reagents and protocols (Affymetrix, Catalog #QGP-232-M18042302). Cells were washed with 1×DPBS then lysed by incubation with provided QuantiGene lysis buffer for 30 minutes at 50-55° C. Cell lysates were incubated for 18-24 hours at 55° C. with capture beads and probe set designed to specifically hybridize to mRNA from targets of interest. The panel of 32 targets of interest included housekeeping genes used for the normalization of the results. After the 18-24 hour incubation signal was amplified utilizing branched DNA methodologies, according to the manufacturer's procedures (Affymetrix, Catalog #QGP-232-M18042302). After hybridization and wash steps assay plate was read on the Luminex 200 and data were expressed as Net Median Fluorescence Intensity. Data was then normalized to the Net Median Fluorescence Intensity of the housekeeping gene HPRT1 (Table 12).

TABLE 12

Stimulation of Human Keratinocytes with TNFα and IFNγ Induces the JAK/STAT Pathway and Pro-Inflammatory Cytokines

| Gene | Treatment | MFI$^a$ | p-value |
|---|---|---|---|
| JAK1 | Vehicle | 126.7 ± 6.55 | — |
|  | 10 ng/ml TNFα/IFNγ | 178.19 ± 3.41 | <.0001 |
|  | 25 ng/ml TNFα/IFNγ | 195.02 ± 3.47 | <.0001 |
|  | 50 ng/ml TNFα/IFNγ | 198.23 ± 2.52 | <.0001 |
|  | 100 ng/ml TNFα/IFNγ | 207.34 ± 3.91 | <.0001 |
| JAK2 | Vehicle | 21.7 ± 0.53 | — |
|  | 10 ng/ml TNFα/IFNγ | 154.13 ± 11.65 | <.0001 |
|  | 25 ng/ml TNFα/IFNγ | 174.07 ± 12.34 | <.0001 |
|  | 50 ng/ml TNFα/IFNγ | 180.71 ± 13.63 | <.0001 |
|  | 100 ng/ml TNFα/IFNγ | 187.94 ± 13.12 | <.0001 |
| JAK3 | Vehicle | 0.1 ± 0.02 | — |
|  | 10 ng/ml TNFα/IFNγ | 0.16 ± 0.05 | 0.8111 |
|  | 25 ng/ml TNFα/IFNγ | 0.18 ± 0.05 | 0.596 |
|  | 50 ng/ml TNFα/IFNγ | 0.33 ± 0.06 | 0.0082 |
|  | 100 ng/ml TNFα/IFNγ | 0.28 ± 0.06 | 0.0532 |
| TYK2 | Vehicle | 167.84 ± 2.25 | — |
|  | 10 ng/ml TNFα/IFNγ | 240.49 ± 4.4 | <.0001 |
|  | 25 ng/ml TNFα/IFNγ | 250.15 ± 3.41 | <.0001 |
|  | 50 ng/ml TNFα/IFNγ | 257.24 ± 3.55 | <.0001 |
|  | 100 ng/ml TNFα/IFNγ | 265.37 ± 3.1 | <.0001 |
| STAT1 | Vehicle | 484.33 ± 4.52 | — |
|  | 10 ng/ml TNFα/IFNγ | 3834.09 ± 65.62 | <.0001 |
|  | 25 ng/ml TNFα/IFNγ | 3935.51 ± 66.15 | <.0001 |
|  | 50 ng/ml TNFα/IFNγ | 3943.03 ± 63.05 | <.0001 |
|  | 100 ng/ml TNFα/IFNγ | 4136.09 ± 67.06 | <.0001 |
| STAT3 | Vehicle | 606.76 ± 11.51 | — |
|  | 10 ng/ml TNFα/IFNγ | 1561.14 ± 40.35 | <.0001 |
|  | 25 ng/ml TNFα/IFNγ | 1652.97 ± 39.53 | <.0001 |
|  | 50 ng/ml TNFα/IFNγ | 1666.52 ± 52.15 | <.0001 |
|  | 100 ng/ml TNFα/IFNγ | 1742.81 ± 38.26 | <.0001 |
| STAT4 | Vehicle | 2.27 ± 0.12 | — |
|  | 10 ng/ml TNFα/IFNγ | 3.78 ± 0.22 | <.0001 |
|  | 25 ng/ml TNFα/IFNγ | 3.84 ± 0.23 | <.0001 |
|  | 50 ng/ml TNFα/IFNγ | 3.72 ± 0.25 | <.0001 |
|  | 100 ng/ml TNFα/IFNγ | 3.61 ± 0.28 | 0.0003 |
| STAT5A | Vehicle | 1.03 ± 0.1 | — |
|  | 10 ng/ml TNFα/IFNγ | 26.06 ± 3.1 | <.0001 |
|  | 25 ng/ml TNFα/IFNγ | 28.58 ± 3.23 | <.0001 |
|  | 50 ng/ml TNFα/IFNγ | 31.01 ± 3.37 | <.0001 |
|  | 100 ng/ml TNFα/IFNγ | 29.61 ± 2.91 | <.0001 |
| STAT5B | Vehicle | 37.04 ± 1.85 | — |
|  | 10 ng/ml TNFα/IFNγ | 28.06 ± 0.7 | 0.0002 |
|  | 25 ng/ml TNFα/IFNγ | 31.37 ± 1.24 | 0.0288 |
|  | 50 ng/ml TNFα/IFNγ | 34.89 ± 0.88 | 0.693 |
|  | 100 ng/ml TNFα/IFNγ | 41.66 ± 2.17 | 0.0978 |
| STAT6 | Vehicle | 626.95 ± 22 | — |
|  | 10 ng/ml TNFα/IFNγ | 1010.38 ± 14.28 | <.0001 |
|  | 25 ng/ml TNFα/IFNγ | 1044.97 ± 12.71 | <.0001 |
|  | 50 ng/ml TNFα/IFNγ | 1039.59 ± 10.5 | <.0001 |
|  | 100 ng/ml TNFα/IFNγ | 1059.01 ± 13.45 | <.0001 |
| IL1A | Vehicle | 156.9 ± 1.89 | — |
|  | 10 ng/ml TNFα/IFNγ | 1786.44 ± 31.13 | <.0001 |
|  | 25 ng/ml TNFα/IFNγ | 2135.03 ± 66.58 | <.0001 |
|  | 50 ng/ml TNFα/IFNγ | 2256.89 ± 90.79 | <.0001 |
|  | 100 ng/ml TNFα/IFNγ | 2459.6 ± 106.2 | <.0001 |
| IL6 | Vehicle | 5.89 ± 0.19 | — |
|  | 10 ng/ml TNFα/IFNγ | 311.31 ± 38.81 | 0.0002 |
|  | 25 ng/ml TNFα/IFNγ | 410.93 ± 52.93 | <.0001 |
|  | 50 ng/ml TNFα/IFNγ | 464.27 ± 61.46 | <.0001 |
|  | 100 ng/ml TNFα/IFNγ | 519.31 ± 68.04 | <.0001 |
| AREG | Vehicle | 400.84 ± 7.25 | — |
|  | 10 ng/ml TNFα/IFNγ | 1265.9 ± 28.84 | <.0001 |
|  | 25 ng/ml TNFα/IFNγ | 1336.82 ± 61.28 | <.0001 |
|  | 50 ng/ml TNFα/IFNγ | 1403.44 ± 80.21 | <.0001 |
|  | 100 ng/ml TNFα/IFNγ | 1644.4 ± 105.83 | <.0001 |
| CCL17 | Vehicle | 400.84 ± 7.25 | — |
|  | 10 ng/ml TNFα/IFNγ | 1265.9 ± 28.84 | <.0001 |
|  | 25 ng/ml TNFα/IFNγ | 1336.82 ± 61.28 | <.0001 |
|  | 50 ng/ml TNFα/IFNγ | 1403.44 ± 80.21 | <.0001 |
|  | 100 ng/ml TNFα/IFNγ | 1644.4 ± 105.83 | <.0001 |
| CCL18 | Vehicle | 400.84 ± 7.25 | — |
|  | 10 ng/ml TNFα/IFNγ | 1265.9 ± 28.84 | <.0001 |
|  | 25 ng/ml TNFα/IFNγ | 1336.82 ± 61.28 | <.0001 |
|  | 50 ng/ml TNFα/IFNγ | 1403.44 ± 80.21 | <.0001 |
|  | 100 ng/ml TNFα/IFNγ | 1644.4 ± 105.83 | <.0001 |
| FLG | Vehicle | 400.84 ± 7.25 | — |
|  | 10 ng/ml TNFα/IFNγ | 1265.9 ± 28.84 | <.0001 |
|  | 25 ng/ml TNFα/IFNγ | 1336.82 ± 61.28 | <.0001 |
|  | 50 ng/ml TNFα/IFNγ | 1403.44 ± 80.21 | <.0001 |
|  | 100 ng/ml TNFα/IFNγ | 1644.4 ± 105.83 | <.0001 |
| IL-17A | Vehicle | 0.15 ± 0.02 | — |
|  | 10 ng/ml TNFα/IFNγ | 0.44 ± 0.07 | 0.0957 |
|  | 25 ng/ml TNFα/IFNγ | 0.49 ± 0.07 | 0.0367 |
|  | 50 ng/ml TNFα/IFNγ | 0.6 ± 0.1 | 0.0032 |
|  | 100 ng/ml TNFα/IFNγ | 0.71 ± 0.15 | 0.0002 |
| IL-1A | Vehicle | 156.9 ± 1.89 | — |
|  | 10 ng/ml TNFα/IFNγ | 1786.44 ± 31.13 | <.0001 |
|  | 25 ng/ml TNFα/IFNγ | 2135.03 ± 66.58 | <.0001 |
|  | 50 ng/ml TNFα/IFNγ | 2256.89 ± 90.79 | <.0001 |
|  | 100 ng/ml TNFα/IFNγ | 2459.6 ± 106.2 | <.0001 |
| IL-22 | Vehicle | 0.23 ± 0.03 | — |
|  | 10 ng/ml TNFα/IFNγ | 0.41 ± 0.09 | 0.388 |
|  | 25 ng/ml TNFα/IFNγ | 0.47 ± 0.09 | 0.1539 |
|  | 50 ng/ml TNFα/IFNγ | 0.48 ± 0.11 | 0.1227 |
|  | 100 ng/ml TNFα/IFNγ | 0.67 ± 0.09 | 0.0015 |
| IL-23A | Vehicle | 12.76 ± 0.37 | — |
|  | 10 ng/ml TNFα/IFNγ | 38.09 ± 2.39 | <.0001 |
|  | 25 ng/ml TNFα/IFNγ | 39.07 ± 2.15 | <.0001 |
|  | 50 ng/ml TNFα/IFNγ | 42.28 ± 1.89 | <.0001 |
|  | 100 ng/ml TNFα/IFNγ | 47.07 ± 1.65 | <.0001 |
| IL-31 | Vehicle | 0.04 ± 0.01 | — |
|  | 10 ng/ml TNFα/IFNγ | 0.22 ± 0.07 | 0.3665 |
|  | 25 ng/ml TNFα/IFNγ | 0.11 ± 0.04 | 0.9472 |
|  | 50 ng/ml TNFα/IFNγ | 0.32 ± 0.09 | 0.0847 |
|  | 100 ng/ml TNFα/IFNγ | 0.86 ± 0.15 | <.0001 |
| IL-8 | Vehicle | 74.64 ± 3.13 | — |
|  | 10 ng/ml TNFα/IFNγ | 617.68 ± 42.23 | <.0001 |
|  | 25 ng/ml TNFα/IFNγ | 728.81 ± 54.99 | <.0001 |
|  | 50 ng/ml TNFα/IFNγ | 802.14 ± 74.58 | <.0001 |
|  | 100 ng/ml TNFα/IFNγ | 911.16 ± 81.8 | <.0001 |
| LOR | Vehicle | 0.04 ± 0.01 | — |
|  | 10 ng/ml TNFα/IFNγ | 0.22 ± 0.07 | 0.3665 |
|  | 25 ng/ml TNFα/IFNγ | 0.11 ± 0.04 | 0.9472 |
|  | 50 ng/ml TNFα/IFNγ | 0.32 ± 0.09 | 0.0847 |
|  | 100 ng/ml TNFα/IFNγ | 0.86 ± 0.15 | <.0001 |
| S100A12 | Vehicle | 0.04 ± 0.01 | — |
|  | 10 ng/ml TNFα/IFNγ | 0.22 ± 0.07 | 0.3665 |
|  | 25 ng/ml TNFα/IFNγ | 0.11 ± 0.04 | 0.9472 |
|  | 50 ng/ml TNFα/IFNγ | 0.32 ± 0.09 | 0.0847 |
|  | 100 ng/ml TNFα/IFNγ | 0.86 ± 0.15 | <.0001 |
| S100A7 | Vehicle | 0.04 ± 0.01 | — |
|  | 10 ng/ml TNFα/IFNγ | 0.22 ± 0.07 | 0.3665 |
|  | 25 ng/ml TNFα/IFNγ | 0.11 ± 0.04 | 0.9472 |
|  | 50 ng/ml TNFα/IFNγ | 0.32 ± 0.09 | 0.0847 |
|  | 100 ng/ml TNFα/IFNγ | 0.86 ± 0.15 | <.0001 |
| SERPINB3 | Vehicle | 0.04 ± 0.01 | — |
|  | 10 ng/ml TNFα/IFNγ | 0.22 ± 0.07 | 0.3665 |
|  | 25 ng/ml TNFα/IFNγ | 0.11 ± 0.04 | 0.9472 |
|  | 50 ng/ml TNFα/IFNγ | 0.32 ± 0.09 | 0.0847 |
|  | 100 ng/ml TNFα/IFNγ | 0.86 ± 0.15 | <.0001 |

TABLE 12-continued

Stimulation of Human Keratinocytes with TNFα and IFNγ Induces the JAK/STAT Pathway and Pro-Inflammatory Cytokines

| Gene | Treatment | MFI[a] | p-value |
|---|---|---|---|
| SERPINB4 | Vehicle | 0.04 ± 0.01 | — |
| | 10 ng/ml TNFα/IFNγ | 0.22 ± 0.07 | 0.3665 |
| | 25 ng/ml TNFα/IFNγ | 0.11 ± 0.04 | 0.9472 |
| | 50 ng/ml TNFα/IFNγ | 0.32 ± 0.09 | 0.0847 |
| | 100 ng/ml TNFα/IFNγ | 0.86 ± 0.15 | <.0001 |
| TNF-α | Vehicle | 2.18 ± 0.17 | — |
| | 10 ng/ml TNFα/IFNγ | 41.6 ± 4.36 | <.0001 |
| | 25 ng/ml TNFα/IFNγ | 47.25 ± 4.66 | <.0001 |
| | 50 ng/ml TNFα/IFNγ | 49.39 ± 5.12 | <.0001 |
| | 100 ng/ml TNFα/IFNγ | 46.97 ± 3.58 | <.0001 |
| VEGFA | Vehicle | 280 ± 5.86 | — |
| | 10 ng/ml TNFα/IFNγ | 777.83 ± 43.18 | <.0001 |
| | 25 ng/ml TNFα/IFNγ | 828.3 ± 42.48 | <.0001 |
| | 50 ng/ml TNFα/IFNγ | 874.08 ± 47.85 | <.0001 |
| | 100 ng/ml TNFα/IFNγ | 941.78 ± 48.85 | <.0001 |

[a] Data are presented as the mean ± standard error (SEM)

Target proteins of interest in the media were detected and quantified using the ProCarta Multiplex Immunoassay reagents and protocols (Invitrogen, Catalog #EPX450-12171-901). Media was incubated with antibody conjugated beads designed to bind to the epitopes of specific target proteins and identify the bound protein through the bead's distinctive spectral pattern. Biotinylated detection antibodies, designed to bind to different epitopes of the same target proteins, and Streptavidin-PE are added to assay plates to quantify the amount of the target protein. Assay plates were read on the Luminex 200 and data were expressed as Net Median Fluorescence Intensity. The Net Median Fluorescence Intensity values for the antigen standard curve, prepared according to the manufacturer's procedures (Invitrogen, Catalog #EPX450-12171-901) were plotted against the expected concentrations for each standard. The concentration of each protein was extrapolated from the antigen standard curve and concentrations were expressed as pg/mL (Table 13).

TABLE 13

Stimulation of Human Keratinocytes with TNFα and IFNγ Induces the Pro-Inflammatory Cytokine Production

| Protein | Treatment | pg/mL[a] | p-value |
|---|---|---|---|
| BDNF | Vehicle | 4.15 ± 0.08 | — |
| | 10 ng/ml TNF/IFN | 4.15 ± 0.19 | >0.9999 |
| | 25 ng/ml TNF/IFN | 4.09 ± 0.16 | 0.9977 |
| | 50 ng/ml TNF/IFN | 3.84 ± 0.17 | 0.4162 |
| | 100 ng/ml TNF/IFN | 3.68 ± 0.14 | 0.1121 |
| EGF | Vehicle | 0.83 ± 0.13 | — |
| | 10 ng/ml TNF/IFN | 0.9 ± 0.08 | 0.9983 |
| | 25 ng/ml TNF/IFN | 1.44 ± 0.16 | 0.1401 |
| | 50 ng/ml TNF/IFN | 2.55 ± 0.22 | <.0001 |
| | 100 ng/ml TNF/IFN | 5.49 ± 0.35 | <.0001 |
| Eotaxin | Vehicle | 2.95 ± 0.33 | — |
| | 10 ng/ml TNF/IFN | 9.46 ± 0.33 | <.0001 |
| | 25 ng/ml TNF/IFN | 9.67 ± 0.34 | <.0001 |
| | 50 ng/ml TNF/IFN | 9.49 ± 0.39 | <.0001 |
| | 100 ng/ml TNF/IFN | 9.83 ± 0.37 | <.0001 |
| FGF-2 | Vehicle | 20.84 ± 1.64 | — |
| | 10 ng/ml TNF/IFN | 40.98 ± 3.26 | <.0001 |
| | 25 ng/ml TNF/IFN | 40.02 ± 3.17 | <.0001 |
| | 50 ng/ml TNF/IFN | 39.86 ± 3.16 | <.0001 |
| | 100 ng/ml TNF/IFN | 38.08 ± 2.95 | 0.0003 |
| GM-CSF | Vehicle | 25.71 ± 2.38 | — |
| | 10 ng/ml TNF/IFN | 134.07 ± 3.66 | <.0001 |
| | 25 ng/ml TNF/IFN | 141.84 ± 4.48 | <.0001 |
| | 50 ng/ml TNF/IFN | 142.45 ± 5.69 | <.0001 |
| | 100 ng/ml TNF/IFN | 140.49 ± 4.62 | <.0001 |
| GRO alpha | Vehicle | 305.38 ± 40.82 | — |
| | 10 ng/ml TNF/IFN | 688.25 ± 83.68 | 0.0009 |
| | 25 ng/ml TNF/IFN | 698.98 ± 81.47 | 0.0006 |
| | 50 ng/ml TNF/IFN | 610.81 ± 69.54 | 0.0103 |
| | 100 ng/ml TNF/IFN | 548.83 ± 66.13 | 0.0546 |
| HGF | Vehicle | 7.57 ± 0.65 | — |
| | 10 ng/ml TNF/IFN | 14.55 ± 1.05 | 0.0006 |
| | 25 ng/ml TNF/IFN | 16.49 ± 1.01 | <.0001 |
| | 50 ng/ml TNF/IFN | 19.3 ± 1.44 | <.0001 |
| | 100 ng/ml TNF/IFN | 27.71 ± 1.76 | <.0001 |
| IFN alpha | Vehicle | 0.21 ± 0.02 | — |
| | 10 ng/ml TNF/IFN | 0.26 ± 0 | 0.0144 |
| | 25 ng/ml TNF/IFN | 0.26 ± 0 | 0.0144 |
| | 50 ng/ml TNF/IFN | 0.26 ± 0 | 0.0144 |
| | 100 ng/ml TNF/IFN | 0.25 ± 0.01 | 0.1082 |
| IFN gamma | Vehicle | 6.79 ± 0.41 | — |
| | 10 ng/ml TNF/IFN | 15919.19 ± 802.52 | <.0001 |
| | 25 ng/ml TNF/IFN | 23228.32 ± 780.43 | <.0001 |
| | 50 ng/ml TNF/IFN | 22666.44 ± 788.93 | <.0001 |
| | 100 ng/ml TNF/IFN | 19582.48 ± 496.94 | <.0001 |
| IL1 alpha | Vehicle | 0.37 ± 0.05 | — |
| | 10 ng/ml TNF/IFN | 13.22 ± 1.24 | <.0001 |
| | 25 ng/ml TNF/IFN | 15.12 ± 1.48 | <.0001 |
| | 50 ng/ml TNF/IFN | 14.74 ± 1.45 | <.0001 |
| | 100 ng/ml TNF/IFN | 13.64 ± 1.29 | <.0001 |
| IL1 beta | Vehicle | 0.69 ± 0.09 | — |
| | 10 ng/ml TNF/IFN | 9.79 ± 0.64 | <.0001 |
| | 25 ng/ml TNF/IFN | 11.45 ± 0.8 | <.0001 |
| | 50 ng/ml TNF/IFN | 14.14 ± 0.98 | <.0001 |
| | 100 ng/ml TNF/IFN | 23.46 ± 1.72 | <.0001 |
| IL10 | Vehicle | 0.28 ± 0.07 | — |
| | 10 ng/ml TNF/IFN | 0.37 ± 0.03 | 0.9194 |
| | 25 ng/ml TNF/IFN | 0.47 ± 0.04 | 0.4732 |
| | 50 ng/ml TNF/IFN | 0.95 ± 0.06 | <.0001 |
| | 100 ng/ml TNF/IFN | 2.4 ± 0.2 | <.0001 |
| IL12p70 | Vehicle | 0.59 ± 0.04 | — |
| | 10 ng/ml TNF/IFN | 1.07 ± 0.03 | <.0001 |
| | 25 ng/ml TNF/IFN | 1.18 ± 0.04 | <.0001 |
| | 50 ng/ml TNF/IFN | 1.37 ± 0.04 | <.0001 |
| | 100 ng/ml TNF/IFN | 1.55 ± 0.04 | <.0001 |
| IL13 | Vehicle | 1.28 ± 0.05 | — |
| | 10 ng/ml TNF/IFN | 1.41 ± 0.19 | 0.9825 |
| | 25 ng/ml TNF/IFN | 2.3 ± 0.23 | 0.0052 |
| | 50 ng/ml TNF/IFN | 2.79 ± 0.3 | <.0001 |
| | 100 ng/ml TNF/IFN | 2.98 ± 0.23 | <.0001 |
| IL15 | Vehicle | 1.39 ± 0 | — |
| | 10 ng/ml TNF/IFN | 1.43 ± 0.14 | 0.9999 |
| | 25 ng/ml TNF/IFN | 1.62 ± 0.18 | 0.9145 |
| | 50 ng/ml TNF/IFN | 1.79 ± 0.35 | 0.6378 |
| | 100 ng/ml TNF/IFN | 3.16 ± 0.39 | <.0001 |
| IL17A | Vehicle | 1.21 ± 0.13 | — |
| | 10 ng/ml TNF/IFN | 2.14 ± 0.15 | 0.7274 |
| | 25 ng/ml TNF/IFN | 3.27 ± 0.34 | 0.104 |
| | 50 ng/ml TNF/IFN | 6.05 ± 0.65 | <.0001 |
| | 100 ng/ml TNF/IFN | 14.95 ± 1.29 | <.0001 |
| IL18 | Vehicle | 4.38 ± 0.69 | — |
| | 10 ng/ml TNF/IFN | 110.9 ± 2.53 | <.0001 |
| | 25 ng/ml TNF/IFN | 122.55 ± 1.91 | <.0001 |
| | 50 ng/ml TNF/IFN | 120.77 ± 1.51 | <.0001 |
| | 100 ng/ml TNF/IFN | 118.99 ± 1.8 | <.0001 |
| IL1RA | Vehicle | 585.47 ± 72.44 | — |
| | 10 ng/ml TNF/IFN | 7383.84 ± 804.86 | <.0001 |
| | 25 ng/ml TNF/IFN | 7420.07 ± 815.17 | <.0001 |
| | 50 ng/ml TNF/IFN | 7311.36 ± 802.4 | <.0001 |
| | 100 ng/ml TNF/IFN | 7548.02 ± 827.05 | <.0001 |
| IL2 | Vehicle | 3.54 ± 0.43 | — |
| | 10 ng/ml TNF/IFN | 16.3 ± 1.24 | 0.0082 |
| | 25 ng/ml TNF/IFN | 23.72 ± 1.43 | <.0001 |
| | 50 ng/ml TNF/IFN | 37.7 ± 2.7 | <.0001 |
| | 100 ng/ml TNF/IFN | 70.58 ± 5.44 | <.0001 |
| IL21 | Vehicle | 2.62 ± 0.18 | — |
| | 10 ng/ml TNF/IFN | 2.88 ± 0 | 0.0911 |
| | 25 ng/ml TNF/IFN | 2.88 ± 0 | 0.0911 |
| | 50 ng/ml TNF/IFN | 2.88 ± 0 | 0.0911 |
| | 100 ng/ml TNF/IFN | 2.88 ± 0 | 0.0911 |

TABLE 13-continued

Stimulation of Human Keratinocytes with TNFα and IFNγ Induces the Pro-Inflammatory Cytokine Production

| Protein | Treatment | pg/mL[a] | p-value |
|---|---|---|---|
| IL22 | Vehicle | 8.41 ± 0.71 | — |
| | 10 ng/ml TNF/IFN | 8.68 ± 0.22 | 0.9808 |
| | 25 ng/ml TNF/IFN | 8.9 ± 0 | 0.8618 |
| | 50 ng/ml TNF/IFN | 8.21 ± 0.47 | 0.994 |
| | 100 ng/ml TNF/IFN | 8.24 ± 0.52 | 0.997 |
| IL23 | Vehicle | 5.68 ± 0.71 | — |
| | 10 ng/ml TNF/IFN | 6.64 ± 0.55 | 0.413 |
| | 25 ng/ml TNF/IFN | 7.07 ± 0.36 | 0.1265 |
| | 50 ng/ml TNF/IFN | 7.43 ± 0 | 0.036 |
| | 100 ng/ml TNF/IFN | 7 ± 0.44 | 0.1598 |
| IL27 | Vehicle | 8.55 ± 1.54 | — |
| | 10 ng/ml TNF/IFN | 6.61 ± 0.18 | 0.946 |
| | 25 ng/ml TNF/IFN | 6.59 ± 0.81 | 0.9441 |
| | 50 ng/ml TNF/IFN | 10.05 ± 2.65 | 0.9777 |
| | 100 ng/ml TNF/IFN | 19.3 ± 4.41 | 0.009 |
| IL31 | Vehicle | 2.99 ± 0.4 | — |
| | 10 ng/ml TNF/IFN | 4.34 ± 0.81 | 0.2722 |
| | 25 ng/ml TNF/IFN | 4.52 ± 0.56 | 0.1789 |
| | 50 ng/ml TNF/IFN | 3.55 ± 0.39 | 0.8899 |
| | 100 ng/ml TNF/IFN | 4.06 ± 0.55 | 0.4739 |
| IL4 | Vehicle | 5.48 ± 0.44 | — |
| | 10 ng/ml TNF/IFN | 4.99 ± 0.68 | 0.9822 |
| | 25 ng/ml TNF/IFN | 6.4 ± 0.7 | 0.8529 |
| | 50 ng/ml TNF/IFN | 7.24 ± 1 | 0.3834 |
| | 100 ng/ml TNF/IFN | 8.75 ± 1.18 | 0.0261 |
| IL5 | Vehicle | 3.72 ± 0 | — |
| | 10 ng/ml TNF/IFN | 26.46 ± 1.88 | <.0001 |
| | 25 ng/ml TNF/IFN | 29.73 ± 1.67 | <.0001 |
| | 50 ng/ml TNF/IFN | 33.05 ± 2.37 | <.0001 |
| | 100 ng/ml TNF/IFN | 47.28 ± 3.85 | <.0001 |
| IL6 | Vehicle | 72.86 ± 9.77 | — |
| | 10 ng/ml TNF/IFN | 2012.1 ± 337.23 | 0.0001 |
| | 25 ng/ml TNF/IFN | 2329.01 ± 384.78 | <.0001 |
| | 50 ng/ml TNF/IFN | 2208.6 ± 370.81 | <.0001 |
| | 100 ng/ml TNF/IFN | 1889.75 ± 298.39 | 0.0004 |
| IL7 | Vehicle | 2.55 ± 0.19 | — |
| | 10 ng/ml TNF/IFN | 2.12 ± 0.14 | 0.1103 |
| | 25 ng/ml TNF/IFN | 2.06 ± 0.1 | 0.0537 |
| | 50 ng/ml TNF/IFN | 2.03 ± 0.12 | 0.0378 |
| | 100 ng/ml TNF/IFN | 2.14 ± 0.14 | 0.137 |
| IL8 | Vehicle | 659.4 ± 97.41 | — |
| | 10 ng/ml TNF/IFN | 3799.39 ± 339.11 | <.0001 |
| | 25 ng/ml TNF/IFN | 3995.6 ± 356.89 | <.0001 |
| | 50 ng/ml TNF/IFN | 3698.94 ± 353.51 | <.0001 |
| | 100 ng/ml TNF/IFN | 3292.06 ± 314.73 | <.0001 |
| IL9 | Vehicle | 6.01 ± 1.19 | — |
| | 10 ng/ml TNF/IFN | 3.99 ± 0.48 | 0.2022 |
| | 25 ng/ml TNF/IFN | 3.91 ± 0.4 | 0.1747 |
| | 50 ng/ml TNF/IFN | 5.08 ± 0.69 | 0.8074 |
| | 100 ng/ml TNF/IFN | 5.47 ± 0.82 | 0.9645 |
| IP-10/CXCL10 | Vehicle | 16.61 ± 1.6 | — |
| | 10 ng/ml TNF/IFN | 3275.51 ± 174.48 | <.0001 |
| | 25 ng/ml TNF/IFN | 3243.28 ± 178.41 | <.0001 |
| | 50 ng/ml TNF/IFN | 3209.56 ± 211.43 | <.0001 |
| | 100 ng/ml TNF/IFN | 2978.45 ± 167.27 | <.0001 |
| LIF | Vehicle | 60.23 ± 7 | — |
| | 10 ng/ml TNF/IFN | 121.31 ± 11.64 | 0.0002 |
| | 25 ng/ml TNF/IFN | 120.23 ± 11.48 | 0.0002 |
| | 50 ng/ml TNF/IFN | 112.18 ± 10.84 | 0.0017 |
| | 100 ng/ml TNF/IFN | 100.63 ± 8.12 | 0.0195 |
| MCP1 | Vehicle | 575.07 ± 57.34 | — |
| | 10 ng/ml TNF/IFN | 99191.31 ± 42809.9 | >0.9999 |
| | 25 ng/ml TNF/IFN | 711985.75 ± 650934.52 | 0.9442 |
| | 50 ng/ml TNF/IFN | 43521.49 ± 10251.23 | >0.9999 |
| | 100 ng/ml TNF/IFN | 1906255.02 ± 1861136.23 | 0.3587 |
| MIP1 alpha | Vehicle | 7.47 ± 1.13 | — |
| | 10 ng/ml TNF/IFN | 525.75 ± 87.5 | <.0001 |
| | 25 ng/ml TNF/IFN | 546.69 ± 92.35 | <.0001 |
| | 50 ng/ml TNF/IFN | 531.55 ± 91.88 | <.0001 |
| | 100 ng/ml TNF/IFN | 409.14 ± 60.62 | 0.0012 |
| MIP1 beta | Vehicle | 133.69 ± 15.91 | — |
| | 10 ng/ml TNF/IFN | 312.85 ± 20.44 | <.0001 |
| | 25 ng/ml TNF/IFN | 319.91 ± 20.09 | <.0001 |
| | 50 ng/ml TNF/IFN | 305.48 ± 20.78 | <.0001 |
| | 100 ng/ml TNF/IFN | 281.82 ± 17.93 | <.0001 |
| PDGF-BB | Vehicle | 3.88 ± 0.47 | — |
| | 10 ng/ml TNF/IFN | 7.89 ± 0.95 | 0.0039 |
| | 25 ng/ml TNF/IFN | 8.11 ± 0.99 | 0.0022 |
| | 50 ng/ml TNF/IFN | 7.52 ± 0.92 | 0.01 |
| | 100 ng/ml TNF/IFN | 6.52 ± 0.72 | 0.0902 |
| PlGF-1 | Vehicle | 43.42 ± 4.08 | — |
| | 10 ng/ml TNF/IFN | 81.42 ± 4.94 | <.0001 |
| | 25 ng/ml TNF/IFN | 79.48 ± 4.09 | <.0001 |
| | 50 ng/ml TNF/IFN | 73.14 ± 4.31 | <.0001 |
| | 100 ng/ml TNF/IFN | 61.36 ± 3.52 | 0.0127 |
| RANTES | Vehicle | 11.78 ± 1.41 | — |
| | 10 ng/ml TNF/IFN | 126.13 ± 5.15 | <.0001 |
| | 25 ng/ml TNF/IFN | 127.73 ± 2.8 | <.0001 |
| | 50 ng/ml TNF/IFN | 119.95 ± 4.67 | <.0001 |
| | 100 ng/ml TNF/IFN | 103.48 ± 7.09 | <.0001 |
| SCF | Vehicle | 1.94 ± 0.06 | — |
| | 10 ng/ml TNF/IFN | 3.14 ± 0.05 | <.0001 |
| | 25 ng/ml TNF/IFN | 3.13 ± 0.05 | <.0001 |
| | 50 ng/ml TNF/IFN | 2.95 ± 0.06 | <.0001 |
| | 100 ng/ml TNF/IFN | 2.89 ± 0.07 | <.0001 |
| SDF-1 alpha | Vehicle | 1118.99 ± 135.41 | — |
| | 10 ng/ml TNF/IFN | 3192.57 ± 228.82 | <.0001 |
| | 25 ng/ml TNF/IFN | 3205.2 ± 218.97 | <.0001 |
| | 50 ng/ml TNF/IFN | 3032.51 ± 212.4 | <.0001 |
| | 100 ng/ml TNF/IFN | 2658.04 ± 190.6 | <.0001 |
| TNF alpha | Vehicle | 2.91 ± 0.61 | — |
| | 10 ng/ml TNF/IFN | 3939.26 ± 53.96 | 0.9636 |
| | 25 ng/ml TNF/IFN | 17995.73 ± 1620.77 | 0.0793 |
| | 50 ng/ml TNF/IFN | 57409.04 ± 12245.5 | <.0001 |
| | 100 ng/ml TNF/IFN | 41410 ± 610 | <.0001 |
| TNF beta | Vehicle | 4.34 ± 0.38 | — |
| | 10 ng/ml TNF/IFN | 4.9 ± 0.45 | 0.8774 |
| | 25 ng/ml TNF/IFN | 4.55 ± 0.29 | 0.9964 |
| | 50 ng/ml TNF/IFN | 5.6 ± 0.97 | 0.3051 |
| | 100 ng/ml TNF/IFN | 4.2 ± 0.38 | 0.9994 |
| VEGF-A | Vehicle | 1293.03 ± 126.33 | — |
| | 10 ng/ml TNF/IFN | 2226.76 ± 233.38 | 0.0016 |
| | 25 ng/ml TNF/IFN | 2066.69 ± 194.45 | 0.0113 |
| | 50 ng/ml TNF/IFN | 1829.38 ± 195.87 | 0.1193 |
| | 100 ng/ml TNF/IFN | 1372.76 ± 118.46 | 0.9935 |
| VEGF-D | Vehicle | 7.77 ± 0.61 | — |
| | 10 ng/ml TNF/IFN | 11.87 ± 0.67 | <.0001 |
| | 25 ng/ml TNF/IFN | 12.02 ± 0.45 | <.0001 |
| | 50 ng/ml TNF/IFN | 11.83 ± 0.67 | <.0001 |
| | 100 ng/ml TNF/IFN | 10.98 ± 0.5 | 0.0009 |
| bNGF | Vehicle | 7.59 ± 1.1 | — |
| | 10 ng/ml TNF/IFN | 11.65 ± 0.89 | 0.03 |
| | 25 ng/ml TNF/IFN | 10.97 ± 1.04 | 0.0893 |
| | 50 ng/ml TNF/IFN | 10.01 ± 1.32 | 0.3156 |
| | 100 ng/ml TNF/IFN | 8.2 ± 0.92 | 0.9829 |

[a]Data are presented as the mean ± standard error (SEM)

Example 6: Janus Kinase Inhibitors Interfere with Interferon-Gamma and Tumor Necrosis-Alpha Mediated Inflammation in Keratinocytes Transformed Human Keratinocyte (HaCaT) Cells were Purchased from AddexBio (Catalog #T0020001) and cultured as outlined in Example 5. Four compounds A-D (Cpd A: ruxolitinib, Cpd B: itacitinib ({1-{1-[3-fluoro-2-(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile), Cpd C: 4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, Cpd D: ((2R,5S)-5-{2-[(1R)-1-Hydroxyethyl]-1H-imidazo[4,5-d]thieno[3,2-b]pyridin-1-yl}tetrahydro-2H-pyran-2-yl)acetonitrile) were reconstituted in DMSO then each compound was serial diluted with cell culture media to 400 nM, 200 nM, 100 nM, and 50 nM concentrations. After 48 hours, cell culture media was removed from 24 well plates and replaced with 250 uL of media containing serial diluted drug, then incubated for 15 minutes at 37° C./5% $CO_2$. After drug incubation, 250 uL of combinatory stimulation containing Recombinant Human Interferon gamma (R&D Systems, Catalog #285-IF-100) and Recombinant Human Tumor Necrosis Factor alpha (R&D Systems, Catalog #210-TA-020) was added to plates. The final concentration of Recombinant Human Interferon gamma and Recombinant Human Tumor Necrosis Factor alpha was 25 ng/mL of each cytokine. Cytokine stimulation added to wells containing drug brought the final concentrations for each drug treatment to 25 nM, 50 nM, 100 nM, and 200 nM. Treated plates were mixed by gentle agitation for 30 seconds then incubated for 24 hours at 37° C./5% $CO_2$. At the end of the 24 hour incubation media was immediately removed from each plate.

RNA was isolated from HaCaT cells using the QuantiGene Plex Assay reagents and protocols (Affymetrix, Catalog #QGP-232-M18042302) according to the manufacturer's guidelines. Cells were washed with 1×DPBS then lysed by incubation with provided QuantiGene lysis buffer for 30 minutes at 50-55° C. Cell lysates were incubated for 18-24 hours at 55° C. with capture beads and probe set designed to specifically hybridize to mRNA from targets of interest. Genes included housekeeping genes (e.g., HPRT1 and GAPDH) used for the normalization of the results. After the 18-24 hour incubation signal was amplified utilizing branched DNA methodologies, according to the manufacturer's procedures (Affymetrix, Catalog #QGP-232-M18042302). After hybridization and wash steps assay plate was read on the Luminex 200 and data were expressed as Net Median Fluorescence Intensity. Data was then normalized to the Net Median Fluorescence Intensity of the housekeeping gene HPRT1 (Table 14).

TABLE 14

Normalized Expression of Target Genes in Human Keratinocyte cells Stimulated with TNFα and IFNγ in the Presence/Absence of JAK Inhibitors

| Gene | Stimulation[a] | Drug Conc | Cpd A MFI[b] | Cpd A p-value[c] | Cpd B MFI[b] |
|---|---|---|---|---|---|
| AREG | — | — | | 280.78 ± 16.51 | |
| | 25 ng/mL | — | | 751.69 ± 31.99[¥] | |
| | — | 200 nM | 260.77 ± 22.45 | 0.9518 | 260.61 ± 14.67 |
| | 25 ng/mL | 25 nM | 760.69 ± 22.09 | 0.9975 | 737.85 ± 22.1 |
| | 25 ng/mL | 50 nM | 777.53 ± 28.12 | 0.8906 | 701.57 ± 12.75 |
| | 25 ng/mL | 100 nM | 729.54 ± 20.47 | 0.933 | 731.24 ± 25.4 |
| | 25 ng/mL | 200 nM | 699.96 ± 26.4 | 0.4532 | 730.41 ± 24.58 |
| CCL17 | — | — | | 1.24 ± 0.32 | |
| | 25 ng/mL | — | | 2.58 ± 0.39[ϵ] | |
| | — | 200 nM | 1.91 ± 0.63 | 0.6035 | 1.56 ± 0.38 |
| | 25 ng/mL | 25 nM | 3.2 ± 0.5 | 0.7354 | 3.37 ± 0.54 |
| | 25 ng/mL | 50 nM | 2.5 ± 0.39 | 0.9999 | 3.06 ± 0.34 |
| | 25 ng/mL | 100 nM | 2.99 ± 0.35 | 0.9168 | 2.87 ± 0.33 |
| | 25 ng/mL | 200 nM | 3.86 ± 0.64 | 0.1754 | 3.13 ± 0.48 |
| CCL18 | — | — | | 1.7 ± 0.53 | |
| | 25 ng/mL | — | | 1.86 ± 0.21 | |
| | — | 200 nM | 1.17 ± 0.27 | 0.8529 | 1.49 ± 0.37 |
| | 25 ng/mL | 25 nM | 1.92 ± 0.33 | 0.9997 | 2.12 ± 0.32 |
| | 25 ng/mL | 50 nM | 1.89 ± 0.37 | 1 | 2.2 ± 0.35 |
| | 25 ng/mL | 100 nM | 1.7 ± 0.37 | 0.9909 | 2.01 ± 0.44 |
| | 25 ng/mL | 200 nM | 1.52 ± 0.37 | 0.8881 | 1.68 ± 0.32 |
| FLG | — | — | | 258.99 ± 34.78 | |
| | 25 ng/mL | — | | 66.67 ± 9.89 | |
| | — | 200 nM | 251.29 ± 35.44 | 0.9999 | 256.93 ± 36.45 |
| | 25 ng/mL | 25 nM | 100.31 ± 13.92 | 0.4228 | 71.57 ± 9.14 |
| | 25 ng/mL | 50 nM | 119.05 ± 15.88 | 0.0981 | 74.31 ± 8.77 |
| | 25 ng/mL | 100 nM | 142.19 ± 17.68 | 0.0083 | 74.99 ± 8.16 |
| | 25 ng/mL | 200 nM | 182.45 ± 24.67 | <.0001 | 87.37 ± 10.99 |
| IL17A | — | — | | 0.62 ± 0.14 | |
| | 25 ng/mL | — | | 0.73 ± 0.15 | |
| | — | 200 nM | 0.47 ± 0.11 | 0.8112 | 0.46 ± 0.1 |
| | 25 ng/mL | 25 nM | 0.86 ± 0.17 | 0.8935 | 0.88 ± 0.13 |
| | 25 ng/mL | 50 nM | 0.73 ± 0.11 | 1 | 0.92 ± 0.14 |
| | 25 ng/mL | 100 nM | 0.66 ± 0.11 | 0.9916 | 0.85 ± 0.15 |
| | 25 ng/mL | 200 nM | 0.55 ± 0.12 | 0.7651 | 0.91 ± 0.17 |
| IL1A | — | — | | 95.72 ± 5.84 | |
| | 25 ng/mL | — | | 1405.01 ± 27.93[¥] | |
| | — | 200 nM | 85.16 ± 6.5 | 0.9724 | 92.67 ± 5.54 |
| | 25 ng/mL | 25 nM | 1115.1 ± 18.96 | <.0001 | 1288.02 ± 20 |
| | 25 ng/mL | 50 nM | 962.51 ± 23 | <.0001 | 1258.76 ± 23.63 |
| | 25 ng/mL | 100 nM | 839.16 ± 21.04 | <.0001 | 1162.35 ± 23.34 |
| | 25 ng/mL | 200 nM | 755.65 ± 16.88 | <.0001 | 1126.94 ± 26.22 |
| IL22 | — | — | | 0.66 ± 0.15 | |
| | 25 ng/mL | — | | 0.92 ± 0.27 | |
| | — | 200 nM | 0.7 ± 0.11 | 0.9999 | 0.61 ± 0.13 |
| | 25 ng/mL | 25 nM | 1.07 ± 0.18 | 0.953 | 1.21 ± 0.24 |
| | 25 ng/mL | 50 nM | 1.03 ± 0.14 | 0.9841 | 1.15 ± 0.18 |
| | 25 ng/mL | 100 nM | 0.85 ± 0.18 | 0.9975 | 1 ± 0.17 |
| | 25 ng/mL | 200 nM | 0.9 ± 0.19 | 1 | 1.01 ± 0.19 |

TABLE 14-continued

Normalized Expression of Target Genes in Human Keratinocyte cells Stimulated
with TNFα and IFNγ in the Presence/Absence of JAK Inhibitors

| Gene | TNFα | Inhibitor | Value 1 | p-value | Value 2 |
|---|---|---|---|---|---|
| IL23A | — | — | | 12.36 ± 1.2 | |
| | 25 ng/mL | | | 36.02 ± 2.45¥ | |
| | — | 200 nM | 10.88 ± 1.35 | 0.939 | 11.41 ± 1.43 |
| | 25 ng/mL | 25 nM | 60.64 ± 3.34 | 0.0006 | 43.92 ± 1.89 |
| | 25 ng/mL | 50 nM | 75.92 ± 4.61 | <.0001 | 45.85 ± 2.3 |
| | 25 ng/mL | 100 nM | 89.83 ± 5.03 | <.0001 | 53.05 ± 3.22 |
| | 25 ng/mL | 200 nM | 104.5 ± 5.55 | <.0001 | 59.53 ± 3.83 |
| IL31 | — | — | | 0.61 ± 0.16 | |
| | 25 ng/mL | | | 1.08 ± 0.38 | |
| | — | 200 nM | 0.65 ± 0.18 | >0.999 | 0.72 ± 0.18 |
| | 25 ng/mL | 25 nM | 1.19 ± 0.32 | 0.9975 | 1.33 ± 0.33 |
| | 25 ng/mL | 50 nM | 1.27 ± 0.3 | 0.9833 | 1.22 ± 0.29 |
| | 25 ng/mL | 100 nM | 1.02 ± 0.31 | 0.9997 | 1.04 ± 0.31 |
| | 25 ng/mL | 200 nM | 0.95 ± 0.29 | 0.9948 | 1.14 ± 0.32 |
| IL6 | — | — | | 5.86 ± 0.38 | |
| | 25 ng/mL | | | 170.83 ± 5.28¥ | |
| | — | 200 nM | 4.98 ± 0.28 | 0.999 | 4.7 ± 0.32 |
| | 25 ng/mL | 25 nM | 93.79 ± 4.03 | <.0001 | 130.24 ± 3.84 |
| | 25 ng/mL | 50 nM | 69.7 ± 2.81 | <.0001 | 122.69 ± 4.36 |
| | 25 ng/mL | 100 nM | 51.01 ± 1.57 | <.0001 | 111.07 ± 4.74 |
| | 25 ng/mL | 200 nM | 40.39 ± 2.19 | <.0001 | 93.03 ± 3.25 |
| IL8 | — | — | | 69.62 ± 3.87 | |
| | 25 ng/mL | | | 361.15 ± 12.15¥ | |
| | — | 200 nM | 57.85 ± 4.65 | 0.6023 | 61.71 ± 4.86 |
| | 25 ng/mL | 25 nM | 420.45 ± 10.71 | 0.0534 | 381.74 ± 10.25 |
| | 25 ng/mL | 50 nM | 475.48 ± 17.32 | <.0001 | 376.41 ± 13.16 |
| | 25 ng/mL | 100 nM | 559.43 ± 18.52 | <.0001 | 387.33 ± 19.5 |
| | 25 ng/mL | 200 nM | 650.22 ± 24.17 | <.0001 | 377.69 ± 20.45 |
| JAK1 | — | — | | 183.21 ± 7.55 | |
| | 25 ng/mL | | | 213.93 ± 5.55€ | |
| | — | 200 nM | 177.67 ± 11.84 | 0.9936 | 177.97 ± 14.91 |
| | 25 ng/mL | 25 nM | 206.18 ± 7.99 | 0.894 | 216.23 ± 6.41 |
| | 25 ng/mL | 50 nM | 195.48 ± 9.54 | 0.2925 | 210.42 ± 10.89 |
| | 25 ng/mL | 100 nM | 186.97 ± 7.49 | 0.0621 | 205.03 ± 11.49 |
| | 25 ng/mL | 200 nM | 180.99 ± 8.58 | 0.0191 | 195.97 ± 10.45 |
| JAK2 | — | — | | 25.35 ± 0.95 | |
| | 25 ng/mL | | | 126.63 ± 4.89¥ | |
| | — | 200 nM | 25.67 ± 1.03 | >0.999 | 25.21 ± 1.12 |
| | 25 ng/mL | 25 nM | 89.4 ± 2.21 | <.0001 | 109.39 ± 2.8 |
| | 25 ng/mL | 50 nM | 69.7 ± 1.78 | <.0001 | 101 ± 2.26 |
| | 25 ng/mL | 100 nM | 54.4 ± 1.8 | <.0001 | 94.5 ± 2.65 |
| | 25 ng/mL | 200 nM | 40.25 ± 1.3 | <.0001 | 89.16 ± 3.43 |
| JAK3 | — | — | | 0.66 ± 0.14 | |
| | 25 ng/mL | | | 0.52 ± 0.16 | |
| | — | 200 nM | 0.71 ± 0.15 | 0.9996 | 0.68 ± 0.17 |
| | 25 ng/mL | 25 nM | 0.81 ± 0.15 | 0.5284 | 0.84 ± 0.12 |
| | 25 ng/mL | 50 nM | 1.01 ± 0.23 | 0.1284 | 0.83 ± 0.15 |
| | 25 ng/mL | 100 nM | 0.84 ± 0.13 | 0.4473 | 0.92 ± 0.13 |
| | 25 ng/mL | 200 nM | 0.68 ± 0.13 | 0.9133 | 0.79 ± 0.15 |
| LOR | — | — | | 27.47 ± 9.25 | |
| | 25 ng/mL | | | 31.02 ± 9.83 | |
| | — | 200 nM | 24.61 ± 7.5 | 0.9994 | 23.78 ± 7.16 |
| | 25 ng/mL | 25 nM | 40.79 ± 15.11 | 0.9505 | 43.2 ± 14.11 |
| | 25 ng/mL | 50 nM | 42.06 ± 14.64 | 0.9258 | 43.96 ± 15.87 |
| | 25 ng/mL | 100 nM | 33.46 ± 10.9 | 0.9997 | 31.4 ± 10.44 |
| | 25 ng/mL | 200 nM | 29.98 ± 11.67 | 1 | 38.46 ± 14.1 |
| S100A12 | — | — | | 1.00 ± 0.31 | |
| | 25 ng/mL | | | 1.13 ± 0.12 | |
| | — | 200 nM | 0.81 ± 0.22 | 0.9379 | 0.8 ± 0.13 |
| | 25 ng/mL | 25 nM | 1.16 ± 0.18 | 0.9997 | 1.21 ± 0.16 |
| | 25 ng/mL | 50 nM | 1.11 ± 0.18 | 1 | 1.04 ± 0.15 |
| | 25 ng/mL | 100 nM | 1.02 ± 0.12 | 0.969 | 1 ± 0.17 |
| | 25 ng/mL | 200 nM | 0.98 ± 0.2 | 0.9219 | 1.14 ± 0.16 |
| S100A7 | — | — | | 5.2 ± 1.46 | |
| | 25 ng/mL | | | 6.28 ± 1.61 | |
| | — | 200 nM | 4.4 ± 1.41 | 0.9928 | 4.94 ± 1.59 |
| | 25 ng/mL | 25 nM | 6.28 ± 1.42 | 1 | 5.45 ± 1.02 |
| | 25 ng/mL | 50 nM | 6.12 ± 1.82 | 1 | 7.08 ± 1.99 |
| | 25 ng/mL | 100 nM | 4 ± 0.77 | 0.6092 | 3.83 ± 1.02 |
| | 25 ng/mL | 200 nM | 3.91 ± 1.18 | 0.5945 | 5.73 ± 1.59 |
| SERPINB3 | — | — | | 2.66 ± 0.74 | |
| | 25 ng/mL | | | 2.65 ± 0.39 | |
| | — | 200 nM | 2.86 ± 0.72 | 0.9995 | 2.25 ± 0.49 |
| | 25 ng/mL | 25 nM | 2.53 ± 0.36 | 0.9984 | 3.16 ± 0.43 |
| | 25 ng/mL | 50 nM | 2.32 ± 0.44 | 0.9304 | 2.3 ± 0.34 |
| | 25 ng/mL | 100 nM | 2.23 ± 0.39 | 0.8555 | 2.2 ± 0.35 |
| | 25 ng/mL | 200 nM | 1.97 ± 0.32 | 0.552 | 2.21 ± 0.44 |

TABLE 14-continued

Normalized Expression of Target Genes in Human Keratinocyte cells Stimulated with TNFα and IFNγ in the Presence/Absence of JAK Inhibitors

| Gene | | | | | |
|---|---|---|---|---|---|
| SERPINB4 | — | — | | 4.45 ± 1.4 | |
| | 25 ng/mL | | | 3.72 ± 0.37 | |
| | — | 200 nM | 3.6 ± 0.97 | 0.9677 | 3.39 ± 0.89 |
| | 25 ng/mL | 25 nM | 3.39 ± 0.81 | 0.9939 | 4.23 ± 0.7 |
| | 25 ng/mL | 50 nM | 4.07 ± 1.17 | 0.9925 | 3.76 ± 0.66 |
| | 25 ng/mL | 100 nM | 3.02 ± 0.7 | 0.9158 | 2.87 ± 0.48 |
| | 25 ng/mL | 200 nM | 2.84 ± 0.5 | 0.8419 | 3.19 ± 0.7 |
| STAT1 | — | — | | 538.44 ± 16.19 | |
| | 25 ng/mL | | | 3092.83 ± 221.46[¥] | |
| | — | 200 nM | 548.21 ± 11.82 | >0.999 | 529.16 ± 21.86 |
| | 25 ng/mL | 25 nM | 2899.48 ± 209.59 | 0.8799 | 2861.37 ± 204.56 |
| | 25 ng/mL | 50 nM | 2896.02 ± 176.39 | 0.8733 | 2855.28 ± 166.89 |
| | 25 ng/mL | 100 nM | 2705.87 ± 184.25 | 0.406 | 2783.68 ± 179.19 |
| | 25 ng/mL | 200 nM | 2468.6 ± 137.34 | 0.0837 | 2850.04 ± 177.51 |
| STAT3 | — | — | | 751.2 ± 14.97 | |
| | 25 ng/mL | | 1608.39 ± 70.09[¥] | | |
| | — | 200 nM | 746.17 ± 16.73 | >0.999 | 732.19 ± 23.03 |
| | 25 ng/mL | 25 nM | 1434.08 ± 43.26 | 0.074 | 1466.73 ± 66.75 |
| | 25 ng/mL | 50 nM | 1301.55 ± 51.7 | 0.0005 | 1437.28 ± 60.69 |
| | 25 ng/mL | 100 nM | 1150.46 ± 52.66 | <.0001 | 1373.34 ± 55.51 |
| | 25 ng/mL | 200 nM | 1082.84 ± 39.32 | <.0001 | 1400.77 ± 58.44 |
| STAT4 | — | — | | 4.52 ± 0.64 | |
| | 25 ng/mL | | | 6.19 ± 0.53[€] | |
| | — | 200 nM | 4.32 ± 0.53 | 0.999 | 4.28 ± 0.61 |
| | 25 ng/mL | 25 nM | 6.15 ± 0.47 | 1 | 6 ± 0.46 |
| | 25 ng/mL | 50 nM | 5.57 ± 0.53 | 0.7712 | 6.22 ± 0.42 |
| | 25 ng/mL | 100 nM | 5.63 ± 0.39 | 0.8269 | 6.21 ± 0.48 |
| | 25 ng/mL | 200 nM | 5.25 ± 0.45 | 0.4653 | 6.27 ± 0.56 |
| STAT5A | — | — | | 2.17 ± 0.54 | |
| | 25 ng/mL | | | 26.41 ± 2.26[¥] | |
| | — | 200 nM | 1.99 ± 0.51 | >0.999 | 1.75 ± 0.44 |
| | 25 ng/mL | 25 nM | 19.04 ± 1.94 | 0.0111 | 23.69 ± 1.63 |
| | 25 ng/mL | 50 nM | 16.18 ± 1.66 | 0.0003 | 22.32 ± 2.16 |
| | 25 ng/mL | 100 nM | 12.94 ± 1.27 | <.0001 | 20.87 ± 2.1 |
| | 25 ng/mL | 200 nM | 9.48 ± 0.86 | <.0001 | 19.2 ± 1.94 |
| STAT5B | — | — | | 58.77 ± 4.23 | |
| | 25 ng/mL | | | 41.69 ± 2.3[€] | |
| | — | 200 nM | 57.17 ± 5.38 | 0.9994 | 58.85 ± 6.21 |
| | 25 ng/mL | 25 nM | 42.26 ± 2.35 | 0.9997 | 40.74 ± 2.3 |
| | 25 ng/mL | 50 nM | 43.63 ± 3.24 | 0.9665 | 42.9 ± 2.44 |
| | 25 ng/mL | 100 nM | 41.63 ± 2.76 | 1 | 40.75 ± 2.41 |
| | 25 ng/mL | 200 nM | 44.1 ± 3.37 | 0.9356 | 41 ± 3.46 |
| STAT6 | — | — | | 749.34 ± 20.85 | |
| | 25 ng/mL | | | 1045.99 ± 26.73[¥] | |
| | — | 200 nM | 777.03 ± 29.31 | 0.8981 | 740.11 ± 34.98 |
| | 25 ng/mL | 25 nM | 1043.96 ± 20.37 | 1 | 1004.82 ± 23.76 |
| | 25 ng/mL | 50 nM | 1016.85 ± 25.68 | 0.8028 | 990.05 ± 21.06 |
| | 25 ng/mL | 100 nM | 966.76 ± 28.58 | 0.0739 | 987.64 ± 15.75 |
| | 25 ng/mL | 200 nM | 976.22 ± 14.93 | 0.1487 | 985.17 ± 29.31 |
| TNF | — | — | | 3.3 ± 1 | |
| | 25 ng/mL | | | 26.79 ± 1.26[¥] | |
| | — | 200 nM | 2.39 ± 0.5 | 0.8882 | 2.58 ± 0.57 |
| | 25 ng/mL | 25 nM | 27.95 ± 2.01 | 0.9797 | 28.04 ± 1.24 |
| | 25 ng/mL | 50 nM | 26.21 ± 2.55 | 0.9986 | 28.66 ± 2.58 |
| | 25 ng/mL | 100 nM | 24.59 ± 1.6 | 0.8367 | 29.5 ± 2.82 |
| | 25 ng/mL | 200 nM | 24.02 ± 2.04 | 0.7181 | 28.31 ± 2.97 |
| TYK2 | — | — | | 217.4 ± 8.13 | |
| | 25 ng/mL | | | 296.98 ± 6.92 | |
| | — | 200 nM | 220.78 ± 12.01 | 0.9996 | 217.28 ± 14.28 |
| | 25 ng/mL | 25 nM | 298.27 ± 10.83 | 1 | 292.92 ± 7.99 |
| | 25 ng/mL | 50 nM | 287.93 ± 16.28 | 0.9305 | 287.31 ± 11.08 |
| | 25 ng/mL | 100 nM | 260.21 ± 7.05 | 0.0546 | 284.15 ± 9.62 |
| | 25 ng/mL | 200 nM | 264.75 ± 8.44 | 0.1204 | 277.52 ± 8.67 |
| VEGFA | — | — | | 214.26 ± 7.51 | |
| | 25 ng/mL | | | 614.31 ± 19.03[¥] | |
| | — | 200 nM | 200.65 ± 9.3 | 0.8794 | 211.13 ± 12.18 |
| | 25 ng/mL | 25 nM | 538.79 ± 9.54 | 0.0006 | 553.23 ± 11.38 |
| | 25 ng/mL | 50 nM | 479.91 ± 16.23 | <.0001 | 545.93 ± 9.71 |
| | 25 ng/mL | 100 nM | 415.36 ± 8.5 | <.0001 | 524.82 ± 13.65 |
| | 25 ng/mL | 200 nM | 398.41 ± 8.58 | <.0001 | 516.11 ± 14.7 |

TABLE 14-continued

Normalized Expression of Target Genes in Human Keratinocyte cells Stimulated with TNFα and IFNγ in the Presence/Absence of JAK Inhibitors

| Gene | Cpd B p-value[c] | Cpd C MFI[b] | Cpd C p-value[c] | Cpd D MFI[b] | Cpd D p-value[c] |
|---|---|---|---|---|---|
| AREG | | 280.78 ± 16.51 | | | |
| | | 751.69 ± 31.99[¥] | | | |
| | 0.9502 | 242.5 ± 16.14 | 0.6149 | 251.8 ± 23.68 | 0.8192 |
| | 0.9832 | 703.71 ± 20.69 | 0.5239 | 725.6 ± 33.78 | 0.9652 |
| | 0.3979 | 719.73 ± 30.82 | 0.8126 | 778.42 ± 44.28 | 0.9621 |
| | 0.9345 | 669.44 ± 30.13 | 0.1075 | 703.3 ± 37.3 | 0.7655 |
| | 0.9254 | 681.68 ± 16.1 | 0.206 | 713.33 ± 37.27 | 0.8774 |
| CCL17 | | 1.24 ± 0.32 | | | |
| | | 2.58 ± 0.39[€] | | | |
| | 0.9645 | 0.99 ± 0.28 | 0.9885 | 0.94 ± 0.14 | 0.9724 |
| | 0.487 | 2.63 ± 0.4 | 0.9999 | 3.08 ± 0.64 | 0.8407 |
| | 0.8373 | 2.94 ± 0.35 | 0.9148 | 2.71 ± 0.41 | 0.9987 |
| | 0.9682 | 3.06 ± 0.47 | 0.8012 | 2.86 ± 0.3 | 0.9756 |
| | 0.7611 | 2.59 ± 0.34 | 1 | 2.34 ± 0.4 | 0.9873 |
| CCL18 | | 1.7 ± 0.53 | | | |
| | | 1.86 ± 0.21 | | | |
| | 0.997 | 1.56 ± 0.73 | 0.9995 | 0.95 ± 0.19 | 0.6111 |
| | 0.949 | 2.11 ± 0.28 | 0.9923 | 1.89 ± 0.28 | 0.9999 |
| | 0.8808 | 2.13 ± 0.46 | 0.9891 | 2.16 ± 0.22 | 0.8129 |
| | 0.9932 | 2.55 ± 0.87 | 0.775 | 1.74 ± 0.26 | 0.9928 |
| | 0.9872 | 1.74 ± 0.62 | 0.9996 | 1.57 ± 0.3 | 0.847 |
| FLG | | 258.99 ± 34.78 | | | |
| | | 66.67 ± 9.89 | | | |
| | >0.999 | 211.48 ± 29.55 | 0.7251 | 219.44 ± 34.83 | 0.8406 |
| | 0.9882 | 62.5 ± 8.63 | 0.9921 | 71.27 ± 11.09 | 0.994 |
| | 0.9434 | 59.01 ± 8.69 | 0.9315 | 78.47 ± 10.63 | 0.8468 |
| | 0.925 | 65.04 ± 9.31 | 0.9998 | 69.64 ± 9.33 | 0.9989 |
| | 0.3487 | 68.26 ± 8.04 | 0.9998 | 72.06 ± 11.85 | 0.9891 |
| IL17A | | 0.62 ± 0.14 | | | |
| | | 0.73 ± 0.15 | | | |
| | 0.7849 | 0.51 ± 0.1 | 0.9335 | 0.43 ± 0.08 | 0.6608 |
| | 0.8705 | 0.87 ± 0.14 | 0.8988 | 1.05 ± 0.18 | 0.4119 |
| | 0.7718 | 1.07 ± 0.16 | 0.3001 | 1.06 ± 0.15 | 0.3772 |
| | 0.9406 | 0.89 ± 0.16 | 0.8425 | 0.84 ± 0.16 | 0.9649 |
| | 0.7898 | 0.87 ± 0.13 | 0.8859 | 0.82 ± 0.13 | 0.9778 |
| IL1A | | 95.72 ± 5.84 | | | |
| | | 1405.01 ± 27.93[¥] | | | |
| | 0.9999 | 88.72 ± 5.9 | 0.9955 | 84.51 ± 7.04 | 0.9647 |
| | 0.0047 | 1370.52 ± 35.28 | 0.8379 | 1269.66 ± 50.59 | 0.0744 |
| | 0.0003 | 1308.7 ± 45.12 | 0.0933 | 1336.95 ± 50.97 | 0.5871 |
| | <.0001 | 1194.29 ± 12.27 | <.0001 | 1244.96 ± 41.03 | 0.0264 |
| | <.0001 | 1151.31 ± 20.01 | <.0001 | 1163.14 ± 26.71 | 0.0004 |
| IL22 | | 0.66 ± 0.15 | | | |
| | | 0.92 ± 0.27 | | | |
| | 0.9997 | 0.71 ± 0.11 | 0.9996 | 0.62 ± 0.11 | 0.9999 |
| | 0.7351 | 1.23 ± 0.21 | 0.729 | 1.39 ± 0.23 | 0.4163 |
| | 0.8649 | 1.4 ± 0.19 | 0.3761 | 1.4 ± 0.21 | 0.392 |
| | 0.9963 | 1.19 ± 0.2 | 0.8132 | 1.24 ± 0.22 | 0.7256 |
| | 0.9936 | 1.14 ± 0.25 | 0.8924 | 1.28 ± 0.2 | 0.628 |
| IL23A | | 12.36 ± 1.2 | | | |
| | | 36.02 ± 2.45[¥] | | | |
| | 0.9902 | 9.42 ± 0.97 | 0.5247 | 9.55 ± 1.15 | 0.5682 |
| | 0.1624 | 42.15 ± 1.61 | 0.2312 | 48.01 ± 2.69 | 0.0213 |
| | 0.0568 | 45.16 ± 2.92 | 0.0339 | 56.64 ± 3.44 | <.0001 |
| | 0.0003 | 48.11 ± 1.85 | 0.0031 | 51.42 ± 2.55 | 0.0021 |
| | <.0001 | 51.86 ± 2.95 | <.0001 | 53.83 ± 3.54 | 0.0003 |
| IL31 | | 0.61 ± 0.16 | | | |
| | | 1.08 ± 0.38 | | | |
| | 0.997 | 0.79 ± 0.2 | 0.977 | 0.91 ± 0.23 | 0.8412 |
| | 0.9546 | 1.52 ± 0.37 | 0.7954 | 1.99 ± 0.4 | 0.2952 |
| | 0.9951 | 1.59 ± 0.33 | 0.6922 | 1.82 ± 0.44 | 0.4719 |
| | 0.9999 | 1.49 ± 0.35 | 0.8327 | 1.61 ± 0.35 | 0.7377 |
| | 0.9999 | 1.32 ± 0.34 | 0.9697 | 1.51 ± 0.36 | 0.8459 |

TABLE 14-continued

Normalized Expression of Target Genes in Human Keratinocyte cells Stimulated with TNFα and IFNγ in the Presence/Absence of JAK Inhibitors

| Gene | | | | | |
|---|---|---|---|---|---|
| IL6 | | 5.86 ± 0.38 | | | |
| | | 170.83 ± 5.28¥ | | | |
| | 0.9964 | 4.97 ± 0.36 | 0.999 | 5.15 ± 0.31 | 0.9997 |
| | <.0001 | 135.32 ± 3.36 | <.0001 | 132.28 ± 7.41 | <.0001 |
| | <.0001 | 128.14 ± 6.83 | <.0001 | 137.61 ± 5.87 | 0.0006 |
| | <.0001 | 112.13 ± 3.37 | <.0001 | 122.46 ± 5.35 | <.0001 |
| | <.0001 | 101.17 ± 2.91 | <.0001 | 119.49 ± 4.42 | <.0001 |
| IL8 | | 69.62 ± 3.87 | | | |
| | | 361.15 ± 12.15¥ | | | |
| | 0.8713 | 55.48 ± 3.11 | 0.4288 | 58.9 ± 5.89 | 0.6821 |
| | 0.759 | 387.86 ± 17.53 | 0.5469 | 398.64 ± 22.41 | 0.5547 |
| | 0.8968 | 369.89 ± 17.71 | 0.9832 | 417.47 ± 21.97 | 0.2108 |
| | 0.584 | 361.05 ± 16.02 | 1 | 410.72 ± 29.84 | 0.3111 |
| | 0.8684 | 350.6 ± 11.85 | 0.967 | 367.56 ± 17.81 | 0.9986 |
| JAK1 | | 183.21 ± 7.55 | | | |
| | | 213.93 ± 5.55ϵ | | | |
| | 0.995 | 159.13 ± 7.08 | 0.2871 | 171.53 ± 9.49 | 0.8675 |
| | 0.9993 | 206.29 ± 6.84 | 0.7834 | 200.4 ± 9.84 | 0.5654 |
| | 0.9965 | 194.2 ± 8.24 | 0.0808 | 210.52 ± 7.73 | 0.9942 |
| | 0.9026 | 193.28 ± 4.55 | 0.0631 | 200.25 ± 8.15 | 0.5562 |
| | 0.4597 | 182.86 ± 4.07 | 0.0023 | 190.53 ± 7.68 | 0.1286 |
| JAK2 | | 25.35 ± 0.95 | | | |
| | | 126.63 ± 4.89¥ | | | |
| | >0.999 | 23.67 ± 0.92 | 0.9806 | 25.25 ± 1.04 | >0.999 |
| | 0.0021 | 114.94 ± 2.16 | 0.0419 | 108.89 ± 3.25 | 0.0165 |
| | <.0001 | 107.16 ± 2.86 | 0.0003 | 106.83 ± 5.94 | 0.0063 |
| | <.0001 | 95.51 ± 3.13 | <.0001 | 102.64 ± 3.52 | 0.0007 |
| | <.0001 | 91.17 ± 2.15 | <.0001 | 92.21 ± 2.9 | <.0001 |
| JAK3 | | 0.66 ± 0.14 | | | |
| | | 0.52 ± 0.16 | | | |
| | >0.999 | 0.63 ± 0.1 | 0.9998 | 0.53 ± 0.09 | 0.9429 |
| | 0.3247 | 1.02 ± 0.19 | 0.1022 | 0.97 ± 0.18 | 0.2187 |
| | 0.3497 | 0.99 ± 0.16 | 0.1451 | 0.99 ± 0.2 | 0.1854 |
| | 0.1608 | 0.99 ± 0.15 | 0.1449 | 1.01 ± 0.17 | 0.1531 |
| | 0.4876 | 0.85 ± 0.15 | 0.425 | 0.86 ± 0.16 | 0.4442 |
| LOR | | 27.47 ± 9.25 | | | |
| | | 31.02 ± 9.83 | | | |
| | 0.998 | 19.48 ± 9.66 | 0.9402 | 12.79 ± 4.84 | 0.6024 |
| | 0.9107 | 23.22 ± 10.14 | 0.9976 | 23 ± 9.47 | 0.9343 |
| | 0.892 | 32.81 ± 17.47 | 1 | 28.28 ± 10.86 | 0.9987 |
| | 1 | 65.94 ± 37.89 | 0.6538 | 21.29 ± 9.59 | 0.8792 |
| | 0.9836 | 37.49 ± 25.57 | 0.9988 | 17 ± 7.28 | 0.6804 |
| S100A12 | | 1.00 ± 0.31 | | | |
| | | 1.13 ± 0.12 | | | |
| | 0.9172 | 0.72 ± 0.18 | 0.7495 | 0.61 ± 0.11 | 0.4876 |
| | 0.9829 | 1.31 ± 0.16 | 0.9298 | 1.31 ± 0.18 | 0.8142 |
| | 0.983 | 1.18 ± 0.18 | 0.9991 | 1.11 ± 0.18 | 1 |
| | 0.942 | 1.48 ± 0.32 | 0.5855 | 1.12 ± 0.15 | 1 |
| | 1 | 1.06 ± 0.2 | 0.9978 | 0.91 ± 0.14 | 0.7081 |
| S100A7 | | 5.2 ± 1.46 | | | |
| | | 6.28 ± 1.61 | | | |
| | >0.999 | 4.38 ± 1.15 | 0.992 | 3.69 ± 0.84 | 0.9024 |
| | 0.9847 | 5.33 ± 1.21 | 0.948 | 5.37 ± 1.3 | 0.9715 |
| | 0.987 | 3.62 ± 0.78 | 0.3469 | 5.94 ± 1.23 | 0.9993 |
| | 0.6011 | 4.3 ± 1.17 | 0.6007 | 4.6 ± 1.68 | 0.8016 |
| | 0.9968 | 3.95 ± 1.14 | 0.4638 | 3.77 ± 0.91 | 0.5084 |
| SERPINB3 | | 2.66 ± 0.74 | | | |
| | | 2.65 ± 0.39 | | | |
| | 0.9843 | 2.31 ± 0.77 | 0.9925 | 1.5 ± 0.27 | 0.5042 |
| | 0.7675 | 2.58 ± 0.41 | 1 | 2 ± 0.3 | 0.4027 |
| | 0.9228 | 2.6 ± 0.69 | 1 | 2.54 ± 0.33 | 0.9973 |
| | 0.8326 | 3.63 ± 1.32 | 0.7776 | 2 ± 0.26 | 0.4053 |
| | 0.8518 | 2.14 ± 0.67 | 0.9734 | 1.69 ± 0.29 | 0.1148 |
| SERPINB4 | | 4.45 ± 1.4 | | | |
| | | 3.72 ± 0.37 | | | |
| | 0.9238 | 3.37 ± 1.57 | 0.918 | 1.84 ± 0.42 | 0.2699 |
| | 0.9325 | 3.53 ± 0.5 | 1 | 2.78 ± 0.31 | 0.2638 |
| | 1 | 4.24 ± 1.6 | 0.9991 | 3.2 ± 0.53 | 0.7515 |
| | 0.7071 | 7.56 ± 3.67 | 0.4349 | 2.64 ± 0.3 | 0.1667 |
| | 0.9217 | 3.54 ± 1.5 | 1 | 2.33 ± 0.38 | 0.0489 |

TABLE 14-continued

Normalized Expression of Target Genes in Human Keratinocyte cells Stimulated with TNFα and IFNγ in the Presence/Absence of JAK Inhibitors

| Gene | | | | | |
|---|---|---|---|---|---|
| STAT1 | | 538.44 ± 16.19 | | | |
| | | 3092.83 ± 221.46[¥] | | | |
| | >0.999 | 522.12 ± 14.19 | >0.999 | 549.79 ± 12.18 | >0.999 |
| | 0.8059 | 3103.89 ± 185.88 | 1 | 3156.82 ± 244.78 | 0.9981 |
| | 0.7919 | 3049.62 ± 159.5 | 0.9993 | 3009.6 ± 169.64 | 0.9948 |
| | 0.6111 | 3028.93 ± 125.19 | 0.9969 | 2991.9 ± 200.56 | 0.9892 |
| | 0.7796 | 2977.26 ± 166.85 | 0.9717 | 3154.11 ± 139.56 | 0.9984 |
| STAT3 | | 751.2 ± 14.97 | | | |
| | 0.9952 | 728.97 ± 20.48 | 0.9903 | 750.9 ± 27.68 | >0.999 |
| | 0.3206 | 1557.84 ± 58.15 | 0.9399 | 1572.76 ± 65.5 | 0.988 |
| | 0.1762 | 1519.61 ± 69.92 | 0.6963 | 1543.4 ± 58.65 | 0.9042 |
| | 0.0352 | 1457.24 ± 54.48 | 0.2524 | 1549.17 ± 89.41 | 0.9288 |
| | 0.0738 | 1483.1 ± 51.73 | 0.4109 | 1570.19 ± 51.51 | 0.9845 |
| STAT4 | | 4.52 ± 0.64 | | | |
| | | 6.19 ± 0.53[€] | | | |
| | 0.9975 | 4.01 ± 0.45 | 0.9392 | 3.75 ± 0.33 | 0.7552 |
| | 0.9967 | 5.65 ± 0.44 | 0.7981 | 5.4 ± 0.45 | 0.5462 |
| | 1 | 5.41 ± 0.33 | 0.5294 | 6.1 ± 0.36 | 0.9997 |
| | 1 | 5.32 ± 0.46 | 0.4306 | 5.83 ± 0.34 | 0.9448 |
| | 0.9999 | 5.04 ± 0.36 | 0.1955 | 5.42 ± 0.52 | 0.5691 |
| STAT5A | | 2.17 ± 0.54 | | | |
| | | 26.41 ± 2.26[¥] | | | |
| | 0.9988 | 1.44 ± 0.41 | 0.9839 | 1.12 ± 0.19 | 0.9305 |
| | 0.7471 | 22.82 ± 1.77 | 0.452 | 20.12 ± 1.29 | 0.0428 |
| | 0.4225 | 20.71 ± 1.77 | 0.1041 | 22.69 ± 1.71 | 0.3629 |
| | 0.1784 | 18.44 ± 1.85 | 0.0122 | 19.54 ± 1.34 | 0.0233 |
| | 0.0505 | 17.64 ± 1.46 | 0.0051 | 18.33 ± 1.83 | 0.0059 |
| STAT5B | | 58.77 ± 4.23 | | | |
| | | 41.69 ± 2.3[€] | | | |
| | >0.999 | 50.91 ± 4.38 | 0.6377 | 54.64 ± 4.79 | 0.9556 |
| | 0.997 | 40.13 ± 1.97 | 0.9485 | 38.56 ± 2.02 | 0.6509 |
| | 0.9923 | 38.42 ± 2.28 | 0.5958 | 40.76 ± 1.91 | 0.9926 |
| | 0.9971 | 36.56 ± 1.18 | 0.2154 | 40.91 ± 2.17 | 0.9963 |
| | 0.9991 | 36.34 ± 1.97 | 0.1863 | 36.62 ± 1.7 | 0.2421 |
| STAT6 | | 749.34 ± 20.85 | | | |
| | | 1045.99 ± 26.73[¥] | | | |
| | 0.9991 | 723.56 ± 20.76 | 0.9214 | 762.04 ± 9.44 | 0.9961 |
| | 0.5557 | 1020.89 ± 23.57 | 0.8238 | 1042.76 ± 29.23 | 1 |
| | 0.2895 | 982.62 ± 14.34 | 0.1296 | 1046.46 ± 29.12 | 1 |
| | 0.2557 | 943.66 ± 25.99 | 0.005 | 985.1 ± 39.79 | 0.3955 |
| | 0.224 | 966.51 ± 12.3 | 0.0388 | 1013.25 ± 17.15 | 0.8453 |
| TNF | | 3.3 ± 1 | | | |
| | | 26.79 ± 1.26[¥] | | | |
| | 0.9528 | 2.19 ± 0.56 | 0.7829 | 1.59 ± 0.22 | 0.417 |
| | 0.9859 | 24.07 ± 1.43 | 0.5138 | 26.07 ± 1.13 | 0.9962 |
| | 0.9421 | 26.51 ± 1.84 | 0.9998 | 29.31 ± 2.52 | 0.7374 |
| | 0.8206 | 25.93 ± 1.59 | 0.9829 | 27.59 ± 1.64 | 0.994 |
| | 0.9717 | 24.73 ± 1.29 | 0.733 | 27.63 ± 2.3 | 0.9928 |
| IYK2 | | 217.4 ± 8.13 | | | |
| | | 296.98 ± 6.92 | | | |
| | >0.999 | 205.57 ± 10.87 | 0.8924 | 217.28 ± 10.09 | >0.999 |
| | 0.9929 | 283.97 ± 8.59 | 0.5015 | 283.93 ± 8.16 | 0.7981 |
| | 0.8603 | 273.68 ± 7.44 | 0.076 | 307.36 ± 14.87 | 0.8958 |
| | 0.7043 | 266 ± 6.82 | 0.0108 | 280.63 ± 10.46 | 0.65 |
| | 0.3578 | 263.49 ± 5.05 | 0.0053 | 283.28 ± 10.88 | 0.7707 |
| VEGFA | | 214.26 ± 7.51 | | | |
| | | 614.31 ± 19.03[¥] | | | |
| | 0.9998 | 199.88 ± 6.52 | 0.8548 | 210.34 ± 9.72 | 0.9995 |
| | 0.0119 | 570.27 ± 10.88 | 0.0433 | 600.98 ± 13.99 | 0.9438 |
| | 0.0041 | 531.53 ± 11.24 | <.0001 | 582.24 ± 17.89 | 0.4554 |
| | 0.0001 | 514.04 ± 7.46 | <.0001 | 572.2 ± 19.67 | 0.2261 |
| | <.0001 | 492.12 ± 8.32 | <.0001 | 541.01 ± 9.94 | 0.0098 |

[a]Stimulation with TNFα (25 ng/mL) and IFNγ (25 ng/mL)
[b]Data is presented as mean ± standard error
[c]Significant differences compared back to stimulation with TNFα and IFNγ alone
[¥]Indicates significant difference of p < 0.0001 from vehicle (no stimulation and no drug concentration) alone
[€]Indicates significant difference of p < 0.1 from vehicle Target proteins of interest in the media were detected and quantified using the ProCarta Multiplex Immunoassay reagents and protocols (Invitrogen, Catalog #EPX450-12171-901). Media was incubated with antibody conjugated beads designed to bind to the epitopes of specific target proteins and identify the bound protein through the bead's distinctive spectral pattern. Biotinylated detection antibodies, designed to bind to different epitopes of the same target proteins, and Streptavidin-PE are added to assay plates to quantify the amount of the target proteins. Assay plates were read on the Luminex 200 and data were expressed as Net Median Fluorescence Intensity. The net median florescence values for the antigen standard curve, prepared according to the manufacturer's procedures (Invitrogen, Catalog

EPX450-12171-901) was plotted against the expected concentrations for each standard. The concentration of each protein was extrapolated from the antigen standard curve and concentrations were expressed as pg/mL (Table 15).

TABLE 15

Concentrations of Inflammatory Mediators Produced by Human Keratinocyte cells Stimulated with TNFα and IFNγ in the Presence/Absence of JAK Inhibitors

| Protein | Stimulation[a] | Drug Concentration | Cpd A pg/mL[b] | Cpd A p-value[c] | Cpc B pg/mL[b] |
|---|---|---|---|---|---|
| BDNF | | | | 5.91 ± 0.28 | |
| | 25 ng/ml | | | 4.11 ± 0.15[¥] | |
| | 25 ng/ml | 200 nM | 5.59 ± 0.34 | 0.9116 | 5.35 ± 0.34 |
| | 25 ng/ml | 25 nM | 4.13 ± 0.18 | >0.999 | 4.05 ± 0.19 |
| | 25 ng/ml | 50 nM | 4.16 ± 0.29 | 0.9996 | 4.04 ± 0.24 |
| | 25 ng/ml | 100 nM | 4.22 ± 0.24 | 0.9928 | 4.06 ± 0.26 |
| | 25 ng/ml | 200 nM | 4.3 ± 0.26 | 0.9394 | 4.1 ± 0.24 |
| bNGF | | | | 2.13 ± 0.39 | |
| | 25 ng/ml | | | 6.86 ± 0.53[¥] | |
| | | 200 nM | 3.81 ± 0.48 | 0.1269 | 3.84 ± 0.71 |
| | 25 ng/ml | 25 nM | 7.4 ± 0.5 | 0.9486 | 7.7 ± 0.55 |
| | 25 ng/ml | 50 nM | 6.73 ± 0.69 | 0.9998 | 7.09 ± 0.71 |
| | 25 ng/ml | 100 nM | 6.54 ± 0.88 | 0.993 | 7.04 ± 0.59 |
| | 25 ng/ml | 200 nM | 7.72 ± 0.76 | 0.7846 | 6.52 ± 0.69 |
| EGF | | | | 1.2 ± 0.13 | |
| | 25 ng/ml | | | 1.33 ± 0.08 | |
| | | 200 nM | 0.97 ± 0.18 | 0.6107 | 1.06 ± 0.14 |
| | 25 ng/ml | 25 nM | 1.87 ± 0.17 | 0.1339 | 1.76 ± 0.17 |
| | 25 ng/ml | 50 nM | 1.57 ± 0.24 | 0.7734 | 1.67 ± 0.15 |
| | 25 ng/ml | 100 nM | 1.75 ± 0.22 | 0.3094 | 1.56 ± 0.2 |
| | 25 ng/ml | 200 nM | 1.82 ± 0.16 | 0.1796 | 1.52 ± 0.1 |
| Eotaxin | | | | 2.16 ± 0.08 | |
| | 25 ng/ml | | | 9.63 ± 0.17[¥] | |
| | | 200 nM | 2.28 ± 0.07 | 0.8577 | 2.22 ± 0.09 |
| | 25 ng/ml | 25 nM | 10.33 ± 0.15 | 0.0307 | 10.22 ± 0.15 |
| | 25 ng/ml | 50 nM | 10.2 ± 0.26 | 0.1019 | 9.92 ± 0.2 |
| | 25 ng/ml | 100 nM | 10.67 ± 0.11 | 0.0007 | 10.09 ± 0.19 |
| | 25 ng/ml | 200 nM | 11.02 ± 0.17 | <.0001 | 10.05 ± 0.19 |
| FGF-2 | | | | 9.44 ± 1.18 | |
| | 25 ng/ml | | | 22.39 ± 0.9[¥] | |
| | | 200 nM | 9.44 ± 0.62 | >0.999 | 8.5 ± 0.95 |
| | 25 ng/ml | 25 nM | 21.29 ± 1.39 | 0.9364 | 20.63 ± 1.49 |
| | 25 ng/ml | 50 nM | 20.92 ± 1.66 | 0.8456 | 19.94 ± 1.49 |
| | 25 ng/ml | 100 nM | 20.8 ± 1.16 | 0.8096 | 20.42 ± 1.5 |
| | 25 ng/ml | 200 nM | 20.13 ± 1.33 | 0.5458 | 21.39 ± 1.61 |
| GM-CSF | | | | 7.58 ± 1.05 | |
| | 25 ng/ml | | | 122.09 ± 2.57[¥] | |
| | | 200 nM | 11.32 ± 1.46 | 0.3826 | 8.69 ± 1.22 |
| | 25 ng/ml | 25 nM | 136.85 ± 3 | 0.0058 | 130.13 ± 2.13 |
| | 25 ng/ml | 50 nM | 137.01 ± 3.11 | 0.0052 | 128.05 ± 2.9 |
| | 25 ng/ml | 100 nM | 138.7 ± 3.64 | 0.0017 | 133.06 ± 4.24 |
| | 25 ng/ml | 200 nM | 136.87 ± 2.98 | 0.0045 | 134.13 ± 3.74 |
| GRO alpha | | | 244.73 ± 8.14 | | |
| | 25 ng/ml | | 529.34 ± 24.39 | | |
| | | 200 nM | 245.8 ± 12.99 | >0.999 | 228.97 ± 14.45 |
| | 25 ng/ml | 25 nM | 592.61 ± 42.91 | 0.8763 | 547.38 ± 31.41 |
| | 25 ng/ml | 50 nM | 650.74 ± 57.35 | 0.4383 | 544.63 ± 38.3 |
| | 25 ng/ml | 100 nM | 784.21 ± 70.75 | 0.018 | 568.49 ± 35.18 |
| | 25 ng/ml | 200 nM | 879.13 ± 83.38 | 0.0006 | 563.61 ± 42.17 |
| HGF | | | | 4.37 ± 0.38 | |
| | 25 ng/ml | | | 13.82 ± 0.29[¥] | |
| | | 200 nM | 4.54 ± 0.39 | 0.998 | 4.44 ± 0.32 |
| | 25 ng/ml | 25 nM | 14.89 ± 0.34 | 0.3296 | 14.15 ± 0.3 |
| | 25 ng/ml | 50 nM | 15.05 ± 0.56 | 0.2218 | 13.65 ± 0.53 |
| | 25 ng/ml | 100 nM | 15.5 ± 0.43 | 0.0549 | 14.41 ± 0.55 |
| | 25 ng/ml | 200 nM | 15.62 ± 0.61 | 0.0302 | 13.5 ± 0.57 |
| IFN alpha | | | | 0.24 ± 0.03 | |
| | 25 ng/ml | | | 0.26 ± 0 | |
| | | 200 nM | 0.22 ± 0.03 | 0.983 | 0.23 ± 0.02 |
| | 25 ng/ml | 25 nM | 0.24 ± 0.02 | 0.3231 | 0.24 ± 0.02 |
| | 25 ng/ml | 50 nM | 0.26 ± 0 | >0.999 | 0.26 ± 0 |
| | 25 ng/ml | 100 nM | 0.26 ± 0 | >0.999 | 0.26 ± 0 |
| | 25 ng/ml | 200 nM | 0.26 ± 0 | >0.999 | 0.26 ± 0 |

TABLE 15-continued

Concentrations of Inflammatory Mediators Produced by Human Keratinocyte cells
Stimulated with TNFα and IFNγ in the Presence/Absence of JAK Inhibitors

| | | | | | |
|---|---|---|---|---|---|
| IFN gamma | | | | 4.81 ± 0.71 | |
| | 25 ng/ml | | | 25004.72 ± 3327.44[¥] | |
| | | 200 nM | 3.02 ± 0.54 | >0.999 | 3.39 ± 0.69 |
| | 25 ng/ml | 25 nM | 24518.59 ± 2794.62 | 0.9999 | 35023.68 ± 10759.49 |
| | 25 ng/ml | 50 nM | 24118.43 ± 3991.24 | 0.9993 | 28977.92 ± 7400.61 |
| | 25 ng/ml | 100 nM | 27210.77 ± 4144.05 | 0.9787 | 29276.66 ± 7697.74 |
| | 25 ng/ml | 200 nM | 24961.65 ± 3542.59 | >0.999 | 25272.53 ± 3796.83 |
| IL1 alpha | | | | 0.29 ± 0.03 | |
| | 25 ng/ml | | | 7.82 ± 0.18[¥] | |
| | | 200 nM | 0.31 ± 0.04 | >0.999 | 0.29 ± 0.03 |
| | 25 ng/ml | 25 nM | 5.93 ± 0.29 | <.0001 | 7.34 ± 0.31 |
| | 25 ng/ml | 50 nM | 4.9 ± 0.3 | <.0001 | 7.06 ± 0.37 |
| | 25 ng/ml | 100 nM | 4.12 ± 0.26 | <.0001 | 7 ± 0.41 |
| | 25 ng/ml | 200 nM | 3.45 ± 0.23 | <.0001 | 6.16 ± 0.35 |
| IL1 beta | | | | 0.94 ± 0.1 | |
| | 25 ng/ml | | | 8.29 ± 0.44[¥] | |
| | | 200 nM | 0.7 ± 0.13 | 0.8893 | 0.98 ± 0.14 |
| | 25 ng/ml | 25 nM | 9.68 ± 0.61 | 0.1181 | 9.53 ± 0.3 |
| | 25 ng/ml | 50 nM | 8.96 ± 0.56 | 0.6835 | 8.96 ± 0.43 |
| | 25 ng/ml | 100 nM | 8.21 ± 0.33 | 0.9999 | 8.66 ± 0.41 |
| | 25 ng/ml | 200 nM | 8.04 ± 0.27 | 0.9851 | 8.43 ± 0.29 |
| IL10 | | | | 0.38 ± 0.08 | |
| | 25 ng/ml | | | 0.84 ± 0.08[¥] | |
| | | 200 nM | 0.3 ± 0.08 | 0.9638 | 0.32 ± 0.07 |
| | 25 ng/ml | 25 nM | 0.96 ± 0.06 | 0.5558 | 0.87 ± 0.06 |
| | 25 ng/ml | 50 nM | 0.95 ± 0.06 | 0.6701 | 0.85 ± 0.05 |
| | 25 ng/ml | 100 nM | 0.87 ± 0.06 | 0.9985 | 0.88 ± 0.06 |
| | 25 ng/ml | 200 nM | 0.91 ± 0.06 | 0.8842 | 0.84 ± 0.06 |
| IL12p70 | | | | 2.34 ± 0.27 | |
| | 25 ng/ml | | | 1.75 ± 0.23 | |
| | | 200 nM | 2.17 ± 0.25 | 0.9859 | 1.55 ± 0.29 |
| | 25 ng/ml | 25 nM | 1.91 ± 0.2 | 0.9534 | 2.01 ± 0.21 |
| | 25 ng/ml | 50 nM | 1.71 ± 0.23 | 0.9999 | 1.68 ± 0.21 |
| | 25 ng/ml | 100 nM | 1.76 ± 0.21 | >0.999 | 1.77 ± 0.18 |
| | 25 ng/ml | 200 nM | 1.82 ± 0.2 | 0.9966 | 1.87 ± 0.16 |
| IL13 | | | | 1.2 ± 0.13 | |
| | 25 ng/ml | | | 2.19 ± 0.42[¥] | |
| | | 200 nM | 1.22 ± 0.11 | >0.999 | 1.14 ± 0.13 |
| | 25 ng/ml | 25 nM | 3.12 ± 0.27 | 0.1649 | 2.79 ± 0.33 |
| | 25 ng/ml | 50 nM | 2.46 ± 0.31 | 0.9449 | 2.73 ± 0.23 |
| | 25 ng/ml | 100 nM | 2.16 ± 0.27 | >0.999 | 2.55 ± 0.33 |
| | 25 ng/ml | 200 nM | 2.44 ± 0.35 | 0.9547 | 2.52 ± 0.3 |
| IL15 | | | | 1.84 ± 0.29 | |
| | 25 ng/ml | | | 2.75 ± 0.78 | |
| | | 200 nM | 1.64 ± 0.22 | 0.999 | 2.22 ± 0.42 |
| | 25 ng/ml | 25 nM | 2.95 ± 0.78 | 0.9977 | 3.3 ± 0.93 |
| | 25 ng/ml | 50 nM | 2.36 ± 0.41 | 0.9731 | 2.71 ± 0.65 |
| | 25 ng/ml | 100 nM | 2.31 ± 0.39 | 0.9576 | 2.58 ± 0.68 |
| | 25 ng/ml | 200 nM | 2.88 ± 0.46 | 0.9994 | 2.57 ± 0.54 |
| IL17A | | | | 1.03 ± 0.09 | |
| | 25 ng/ml | | | 3.91 ± 0.36[¥] | |
| | | 200 nM | 1.26 ± 0.22 | 0.9429 | 1.2 ± 0.29 |
| | 25 ng/ml | 25 nM | 4.97 ± 0.36 | 0.1478 | 4.6 ± 0.5 |
| | 25 ng/ml | 50 nM | 4.7 ± 0.5 | 0.3725 | 4.09 ± 0.43 |
| | 25 ng/ml | 100 nM | 5.05 ± 0.15 | 0.1065 | 4.84 ± 0.34 |
| | 25 ng/ml | 200 nM | 4.91 ± 0.36 | 0.1703 | 4.43 ± 0.26 |
| IL18 | | | | 6.51 ± 0.55 | |
| | 25 ng/ml | | | 155.14 ± 2.91[¥] | |
| | | 200 nM | 7.11 ± 0.21 | 0.997 | 6.04 ± 0.5 |
| | 25 ng/ml | 25 nM | 159.94 ± 3.38 | 0.7069 | 162.16 ± 4.98 |
| | 25 ng/ml | 50 nM | 151.44 ± 4.51 | 0.851 | 153.4 ± 3.46 |
| | 25 ng/ml | 100 nM | 151.88 ± 3.38 | 0.8983 | 156.06 ± 3.24 |
| | 25 ng/ml | 200 nM | 150.47 ± 2.29 | 0.7082 | 159.36 ± 4.73 |
| IL1RA | | | | 513.38 ± 56.01 | |
| | 25 ng/ml | | | 6231.09 ± 271.61[¥] | |
| | | 200 nM | 559.82 ± 69.13 | 0.999 | 502.58 ± 57.22 |
| | 25 ng/ml | 25 nM | 5863.67 ± 328.02 | 0.8215 | 5944.59 ± 264.97 |
| | 25 ng/ml | 50 nM | 5640.46 ± 363 | 0.4817 | 5840.44 ± 314.35 |
| | 25 ng/ml | 100 nM | 5417.9 ± 272.66 | 0.2149 | 5953.24 ± 309.78 |
| | 25 ng/ml | 200 nM | 5320 ± 306.58 | 0.1274 | 5710.44 ± 269.38 |
| IL2 | | | | 2.99 ± 0.33 | |
| | 25 ng/ml | | | 29 ± 1.27[¥] | |
| | | 200 nM | 3.57 ± 0.62 | 0.955 | 3.32 ± 0.6 |
| | 25 ng/ml | 25 nM | 35.39 ± 2.01 | 0.0508 | 33.62 ± 1.88 |
| | 25 ng/ml | 50 nM | 34.31 ± 2.49 | 0.1292 | 31.96 ± 1.47 |
| | 25 ng/ml | 100 nM | 35.16 ± 1.54 | 0.0629 | 31.33 ± 1.43 |
| | 25 ng/ml | 200 nM | 34.65 ± 1.35 | 0.0871 | 31.86 ± 1.25 |

TABLE 15-continued

Concentrations of Inflammatory Mediators Produced by Human Keratinocyte cells
Stimulated with TNFα and IFNγ in the Presence/Absence of JAK Inhibitors

| | | | | | |
|---|---|---|---|---|---|
| IL21 | | | | 2.88 ± 0 | |
| | 25 ng/ml | | | 2.88 ± 0 | |
| | | 200 nM | 2.63 ± 0.24 | 0.9101 | 2.43 ± 0.31 |
| | 25 ng/ml | 25 nM | 2.55 ± 0.26 | 0.6216 | 2.66 ± 0.22 |
| | 25 ng/ml | 50 nM | 2.77 ± 0.11 | 0.9855 | 2.45 ± 0.29 |
| | 25 ng/ml | 100 nM | 2.33 ± 0.31 | 0.1873 | 2.36 ± 0.35 |
| | 25 ng/ml | 200 nM | 2.68 ± 0.18 | 0.883 | 2.47 ± 0.28 |
| IL22 | | | | 8.9 ± 0 | |
| | 25 ng/ml | | | 7.92 ± 0.65 | |
| | | 200 nM | 7.74 ± 0.8 | 0.74 | 8.13 ± 0.77 |
| | 25 ng/ml | 25 nM | 8.69 ± 0.42 | 0.7682 | 8.69 ± 0.42 |
| | 25 ng/ml | 50 nM | 8.24 ± 0.66 | 0.9868 | 8.9 ± 0 |
| | 25 ng/ml | 100 nM | 8.9 ± 0 | 0.596 | 8.03 ± 0.87 |
| | 25 ng/ml | 200 nM | 7.48 ± 0.79 | 0.9547 | 7.74 ± 0.78 |
| IL23 | | | | 7.35 ± 0.54 | |
| | 25 ng/ml | | | 5.56 ± 0.97 | |
| | | 200 nM | 6.18 ± 0.76 | 0.8627 | 5.8 ± 1.11 |
| | 25 ng/ml | 25 nM | 7.43 ± 0 | 0.0716 | 7.28 ± 0.16 |
| | 25 ng/ml | 50 nM | 6.82 ± 0.61 | 0.3244 | 7.43 ± 0 |
| | 25 ng/ml | 100 nM | 6.9 ± 0.53 | 0.2733 | 6.44 ± 0.69 |
| | 25 ng/ml | 200 nM | 7.5 ± 0.06 | 0.0525 | 7.41 ± 0.5 |
| IL27 | | | | 6.93 ± 0.9 | |
| | 25 ng/ml | | | 6.23 ± 0.97 | |
| | | 200 nM | 8.91 ± 2.62 | 0.9348 | 7.57 ± 2.22 |
| | 25 ng/ml | 25 nM | 6.59 ± 1.92 | 0.9997 | 8.03 ± 1.71 |
| | 25 ng/ml | 50 nM | 7.67 ± 1.39 | 0.9418 | 6.95 ± 0.83 |
| | 25 ng/ml | 100 nM | 7.11 ± 1.17 | 0.9899 | 5.36 ± 0.73 |
| | 25 ng/ml | 200 nM | 11.45 ± 2.57 | 0.1198 | 8.04 ± 1.65 |
| IL31 | | | | 3.67 ± 0 | |
| | 25 ng/ml | | | 2.6 ± 0.63 | |
| | | 200 nM | 3.32 ± 0.35 | 0.9393 | 3.01 ± 0.44 |
| | 25 ng/ml | 25 nM | 3.33 ± 0.36 | 0.5388 | 3.6 ± 0.28 |
| | 25 ng/ml | 50 nM | 3.32 ± 0.35 | 0.5468 | 3.22 ± 0.38 |
| | 25 ng/ml | 100 nM | 3.19 ± 0.34 | 0.7047 | 3.35 ± 0.44 |
| | 25 ng/ml | 200 nM | 3.2 ± 0.29 | 0.6722 | 3.93 ± 0.4 |
| IL4 | | | | 4.72 ± 0.44 | |
| | 25 ng/ml | | | 6.73 ± 1.28 | |
| | | 200 nM | 3.6 ± 0.51 | 0.8423 | 4.61 ± 0.7 |
| | 25 ng/ml | 25 nM | 8.29 ± 1.89 | 0.771 | 6.74 ± 1.65 |
| | 25 ng/ml | 50 nM | 3.75 ± 0.54 | 0.2516 | 5.74 ± 1.1 |
| | 25 ng/ml | 100 nM | 3.94 ± 0.7 | 0.304 | 5.78 ± 0.72 |
| | 25 ng/ml | 200 nM | 6.49 ± 1.1 | 0.9997 | 6.42 ± 1.24 |
| IL5 | | | | 2.7 ± 0.43 | |
| | 25 ng/ml | | | 28.59 ± 1.29[¥] | |
| | | 200 nM | 2.42 ± 0.45 | 0.9981 | 2.84 ± 0.38 |
| | 25 ng/ml | 25 nM | 25.21 ± 1.58 | 0.4178 | 27.31 ± 1.32 |
| | 25 ng/ml | 50 nM | 26.88 ± 2.14 | 0.8782 | 25.5 ± 1.65 |
| | 25 ng/ml | 100 nM | 26.65 ± 1.6 | 0.8262 | 26.52 ± 1.54 |
| | 25 ng/ml | 200 nM | 25.3 ± 1.55 | 0.4226 | 25.88 ± 1.37 |
| IL6 | | | | 30.57 ± 2.89 | |
| | 25 ng/ml | | | 862.33 ± 17.95[¥] | |
| | | 200 nM | 28.79 ± 2.91 | 0.9999 | 26.86 ± 2.62 |
| | 25 ng/ml | 25 nM | 594.5 ± 25.17 | <.0001 | 749.64 ± 32.94 |
| | 25 ng/ml | 50 nM | 446.35 ± 19.73 | <.0001 | 674.21 ± 27.15 |
| | 25 ng/ml | 100 nM | 362.14 ± 18.73 | <.0001 | 643.8 ± 27.14 |
| | 25 ng/ml | 200 nM | 295.21 ± 15.22 | <.0001 | 568.73 ± 24.74 |
| IL7 | | | | 3.22 ± 0.12 | |
| | 25 ng/ml | | | 2.26 ± 0.09[¥] | |
| | | 200 nM | 3.29 ± 0.21 | 0.9973 | 3.03 ± 0.2 |
| | 25 ng/ml | 25 nM | 2.1 ± 0.15 | 0.8024 | 2.14 ± 0.12 |
| | 25 ng/ml | 50 nM | 1.96 ± 0.11 | 0.2854 | 1.9 ± 0.12 |
| | 25 ng/ml | 100 nM | 2.05 ± 0.11 | 0.5818 | 2.12 ± 0.14 |
| | 25 ng/ml | 200 nM | 2.18 ± 0.14 | 0.9803 | 2.09 ± 0.14 |
| IL8 | | | | 271.75 ± 7.98 | |
| | 25 ng/ml | | | 2577.97 ± 63.03[¥] | |
| | | 200 nM | 273.06 ± 11.28 | >0.999 | 261.92 ± 12.12 |
| | 25 ng/ml | 25 nM | 3240.19 ± 156.41 | 0.5347 | 2837.03 ± 135.03 |
| | 25 ng/ml | 50 nM | 3611.64 ± 221.79 | 0.1708 | 2862.21 ± 240.57 |
| | 25 ng/ml | 100 nM | 4865.79 ± 574.48 | 0.0003 | 2980.9 ± 173.36 |
| | 25 ng/ml | 200 nM | 5827.91 ± 500.48 | <.0001 | 3023.88 ± 193.36 |
| IL9 | | | | 3.33 ± 0.37 | |
| | 25 ng/ml | | | 3.7 ± 0 | |
| | | 200 nM | 3.93 ± 0.33 | 0.5698 | 3.91 ± 0.48 |
| | 25 ng/ml | 25 nM | 3.7 ± 0 | >0.999 | 4.55 ± 0.85 |
| | 25 ng/ml | 50 nM | 3.27 ± 0.32 | 0.3649 | 4.13 ± 0.43 |
| | 25 ng/ml | 100 nM | 4.02 ± 0.31 | 0.6282 | 4.13 ± 0.43 |
| | 25 ng/ml | 200 nM | 3.62 ± 0.08 | 0.9958 | 3.28 ± 0.35 |

TABLE 15-continued

Concentrations of Inflammatory Mediators Produced by Human Keratinocyte cells
Stimulated with TNFα and IFNγ in the Presence/Absence of JAK Inhibitors

| Mediator | | | | | |
|---|---|---|---|---|---|
| IP-10/ | | | | 20.14 ± 0.36 | |
| CXCL10 | 25 ng/ml | | | 3935.46 ± 375.68¥ | |
| | | 200 nM | 20.39 ± 0.57 | >0.999 | 19.75 ± 0.42 |
| | 25 ng/ml | 25 nM | 3497.56 ± 194.81 | 0.6232 | 4068.98 ± 507.12 |
| | 25 ng/ml | 50 nM | 3599.04 ± 402.58 | 0.7995 | 3872.74 ± 295.01 |
| | 25 ng/ml | 100 nM | 3158.24 ± 189.25 | 0.1574 | 4050.7 ± 471.31 |
| | 25 ng/ml | 200 nM | 2662.18 ± 89.27 | 0.0059 | 4071.78 ± 411.22 |
| LIF | | | | 23.57 ± 0.93 | |
| | 25 ng/ml | | | 63.3 ± 2.1¥ | |
| | | 200 nM | 24.61 ± 0.9 | 0.9625 | 23.25 ± 0.99 |
| | 25 ng/ml | 25 nM | 74.41 ± 2.51 | 0.0243 | 68.82 ± 2.51 |
| | 25 ng/ml | 50 nM | 74.64 ± 3.23 | 0.0209 | 67.89 ± 3.08 |
| | 25 ng/ml | 100 nM | 80.58 ± 2.89 | 0.0003 | 70.3 ± 3.65 |
| | 25 ng/ml | 200 nM | 86.79 ± 2.87 | <.0001 | 71.92 ± 2.82 |
| MCP1 | | | | 1288.79 ± 44.4 | |
| | 25 ng/ml | | | 15200 ± 0¥ | |
| | | 200 nM | 1231.38 ± 54.82 | 0.8558 | 1125.31 ± 55.12 |
| | 25 ng/ml | 25 nM | 31401.9 ± 12245.69 | 0.6168 | 29762.04 ± 13226.23 |
| | 25 ng/ml | 50 nM | 21656.92 ± 6456.92 | 0.9745 | 27471.13 ± 12271.13 |
| | 25 ng/ml | 100 nM | 32481.08 ± 17281.08 | 0.564 | 15200 ± 0 |
| | 25 ng/ml | 200 nM | 20201.73 ± 5001.73 | 0.989 | 17302.89 ± 2102.89 |
| MIP1 | | | | 3.14 ± 0.24 | |
| alpha | 25 ng/ml | | | 105.63 ± 3.74¥ | |
| | | 200 nM | 3.11 ± 0.28 | >0.999 | 2.63 ± 0.35 |
| | 25 ng/ml | 25 nM | 82.56 ± 3.1 | <.0001 | 103.81 ± 3.29 |
| | 25 ng/ml | 50 nM | 70.57 ± 3.32 | <.0001 | 100.64 ± 4.66 |
| | 25 ng/ml | 100 nM | 50.91 ± 1.6 | <.0001 | 91.52 ± 5.05 |
| | 25 ng/ml | 200 nM | 40.36 ± 0.88 | <.0001 | 83.1 ± 2.77 |
| MIP1 | | | | 122.07 ± 4.05 | |
| beta | 25 ng/ml | | | 313.11 ± 5.46¥ | |
| | | 200 nM | 116.79 ± 5.02 | 0.8764 | 113.94 ± 3.76 |
| | 25 ng/ml | 25 nM | 328.74 ± 7.75 | 0.4072 | 319.77 ± 6.92 |
| | 25 ng/ml | 50 nM | 335.46 ± 9.56 | 0.1354 | 318.84 ± 8.17 |
| | 25 ng/ml | 100 nM | 348.55 ± 7.71 | 0.007 | 323.13 ± 6.82 |
| | 25 ng/ml | 200 nM | 361.86 ± 6.8 | 0.0001 | 318.83 ± 8.71 |
| PDGF-BB | | | | 2.13 ± 0.17 | |
| | 25 ng/ml | | | 4.27 ± 0.22¥ | |
| | | 200 nM | 1.95 ± 0.21 | 0.936 | 2.15 ± 0.13 |
| | 25 ng/ml | 25 nM | 5.15 ± 0.21 | 0.0234 | 5.19 ± 0.15 |
| | 25 ng/ml | 50 nM | 5.09 ± 0.22 | 0.0366 | 5.28 ± 0.18 |
| | 25 ng/ml | 100 nM | 5.09 ± 0.22 | 0.0373 | 5.4 ± 0.16 |
| | 25 ng/ml | 200 nM | 5.18 ± 0.22 | 0.0154 | 5.28 ± 0.15 |
| PlGF-1 | | | | 20.75 ± 0.87 | |
| | 25 ng/ml | | | 55.66 ± 1.47¥ | |
| | | 200 nM | 21.21 ± 1.23 | 0.9989 | 20.17 ± 1.26 |
| | 25 ng/ml | 25 nM | 59.03 ± 2.6 | 0.7932 | 56.69 ± 2.37 |
| | 25 ng/ml | 50 nM | 56.18 ± 3.04 | 0.9997 | 53.92 ± 2.81 |
| | 25 ng/ml | 100 nM | 57.5 ± 3.14 | 0.9689 | 54.67 ± 3.27 |
| | 25 ng/ml | 200 nM | 58.88 ± 2.87 | 0.8058 | 54.61 ± 2.69 |
| RANTES | | | | 9.56 ± 0.42 | |
| | 25 ng/ml | | | 230.17 ± 9.43¥ | |
| | | 200 nM | 9.51 ± 0.56 | >0.999 | 8.42 ± 0.51 |
| | 25 ng/ml | 25 nM | 192 ± 12.74 | 0.0311 | 203.77 ± 12.55 |
| | 25 ng/ml | 50 nM | 165.12 ± 11.76 | 0.0001 | 198.35 ± 15.1 |
| | 25 ng/ml | 100 nM | 136.24 ± 7.8 | <.0001 | 194.21 ± 12.67 |
| | 25 ng/ml | 200 nM | 111.94 ± 6.48 | <.0001 | 183.18 ± 13.92 |
| SCF | | | | 2.01 ± 0.08 | |
| | 25 ng/ml | | | 4.16 ± 0.08¥ | |
| | | 200 nM | 1.99 ± 0.14 | >0.999 | 1.93 ± 0.13 |
| | 25 ng/ml | 25 nM | 4.41 ± 0.13 | 0.6315 | 4.33 ± 0.18 |
| | 25 ng/ml | 50 nM | 4.41 ± 0.22 | 0.6213 | 4.16 ± 0.18 |
| | 25 ng/ml | 100 nM | 4.58 ± 0.16 | 0.203 | 4.26 ± 0.17 |
| | 25 ng/ml | 200 nM | 4.49 ± 0.16 | 0.3684 | 4.2 ± 0.17 |
| SDF-1 | | | | 1075.14 ± 36.63 | |
| alpha | 25 ng/ml | | | 3307.18 ± 98.57¥ | |
| | | 200 nM | 1050.43 ± 48.77 | 0.9981 | 1003.25 ± 40.97 |
| | 25 ng/ml | 25 nM | 3610.22 ± 119.33 | 0.2517 | 3430.87 ± 111.52 |
| | 25 ng/ml | 50 nM | 3666.62 ± 135.83 | 0.1361 | 3356.32 ± 136.22 |
| | 25 ng/ml | 100 nM | 3794.59 ± 134.61 | 0.0252 | 3471.01 ± 111.77 |
| | 25 ng/ml | 200 nM | 3962.77 ± 116.03 | 0.0013 | 3481.04 ± 134.24 |
| TNF | | | | 1.49 ± 0.59 | |
| alpha | 25 ng/ml | | | 9159.41 ± 1060.96¥ | |
| | | 200 nM | 2.61 ± 0.65 | >0.999 | 2.4 ± 0.71 |
| | 25 ng/ml | 25 nM | 10472.77 ± 779.28 | 0.9989 | 10574.99 ± 753.02 |
| | 25 ng/ml | 50 nM | 10873.61 ± 631.64 | 0.9969 | 11776.9 ± 1658.47 |
| | 25 ng/ml | 100 nM | 21115.64 ± 10093.98 | 0.2343 | 11722.68 ± 1259.67 |
| | 25 ng/ml | 200 nM | 13938.92 ± 2924.27 | 0.8755 | 11233.91 ± 945.2 |

TABLE 15-continued

Concentrations of Inflammatory Mediators Produced by Human Keratinocyte cells
Stimulated with TNFα and IFNγ in the Presence/Absence of JAK Inhibitors

| | | | | | |
|---|---|---|---|---|---|
| TNF beta | | | | 4.5 ± 0.48 | |
| | 25 ng/ml | | | 4.86 ± 0.09 | |
| | | 200 nM | 3.53 ± 0.62 | 0.4426 | 4.7 ± 0.28 |
| | 25 ng/ml | 25 nM | 3.85 ± 0.63 | 0.4631 | 4.91 ± 0.79 |
| | 25 ng/ml | 50 nM | 4.6 ± 0.68 | 0.9896 | 4.13 ± 0.5 |
| | 25 ng/ml | 100 nM | 4.31 ± 0.56 | 0.8742 | 4 ± 0.51 |
| | 25 ng/ml | 200 nM | 4.48 ± 0.44 | 0.9598 | 4.42 ± 0.45 |
| VEGF-A | | | | 633.68 ± 16.37 | |
| | 25 ng/ml | | | 1322.08 ± 42.07¥ | |
| | | 200 nM | 610.03 ± 18.16 | 0.9435 | 554.18 ± 29.76 |
| | 25 ng/ml | 25 nM | 1285.27 ± 48.3 | 0.9508 | 1249.75 ± 44.89 |
| | 25 ng/ml | 50 nM | 1251.08 ± 47.7 | 0.6733 | 1242.76 ± 50.39 |
| | 25 ng/ml | 100 nM | 1270.06 ± 51.71 | 0.8536 | 1262.01 ± 46.28 |
| | 25 ng/ml | 200 nM | 1206.81 ± 45.57 | 0.2491 | 1232.36 ± 49.33 |
| VEGF-D | | | | 3.63 ± 0.39 | |
| | 25 ng/ml | | | 8.37 ± 0.77¥ | |
| | | 200 nM | 2.98 ± 0.51 | 0.9007 | 3.19 ± 0.57 |
| | 25 ng/ml | 25 nM | 8.47 ± 0.59 | 0.9999 | 9.22 ± 0.87 |
| | 25 ng/ml | 50 nM | 8.05 ± 0.73 | 0.9939 | 9.72 ± 0.75 |
| | 25 ng/ml | 100 nM | 8.13 ± 0.8 | 0.9979 | 8.71 ± 0.65 |
| | 25 ng/ml | 200 nM | 7.76 ± 0.75 | 0.9332 | 9.12 ± 0.78 |

| | Cpc B | Cpc C | | Cpc D | |
|---|---|---|---|---|---|
| Protein | p-value$^c$ | pg/mL$^b$ | p-value$^c$ | pg/mL$^b$ | p-value$^c$ |
| BDNF | | 5.91 ± 0.28 | | | |
| | | 4.11 ± 0.15¥ | | | |
| | 0.5647 | 5.7 ± 0.31 | 0.9821 | 5.66 ± 0.38 | 0.9648 |
| | 0.9989 | 4.01 ± 0.19 | 0.9922 | 4.08 ± 0.26 | >0.999 |
| | 0.9972 | 4 ± 0.23 | 0.9887 | 3.97 ± 0.25 | 0.9848 |
| | 0.9993 | 4.24 ± 0.26 | 0.9819 | 4.18 ± 0.28 | 0.9989 |
| | >0.999 | 3.97 ± 0.22 | 0.9709 | 4.03 ± 0.28 | 0.9972 |
| bNGF | | 2.13 ± 0.39 | | | |
| | | 6.86 ± 0.53¥ | | | |
| | 0.1179 | 3.73 ± 0.63 | 0.1582 | 3.47 ± 0.48 | 0.2975 |
| | 0.743 | 7.86 ± 0.56 | 0.7301 | 7.44 ± 0.63 | 0.9268 |
| | 0.9968 | 6.86 ± 0.6 | >0.999 | 6.17 ± 0.74 | 0.8786 |
| | 0.9987 | 6.93 ± 1.04 | >0.999 | 7.12 ± 0.8 | 0.9962 |
| | 0.9855 | 5.7 ± 0.76 | 0.6114 | 6.73 ± 0.61 | 0.9997 |
| EGF | | 1.2 ± 0.13 | | | |
| | | 1.33 ± 0.08 | | | |
| | 0.8987 | 1.12 ± 0.14 | 0.9912 | 1.24 ± 0.09 | 0.9998 |
| | 0.1475 | 1.54 ± 0.13 | 0.7273 | 1.49 ± 0.14 | 0.8865 |
| | 0.3115 | 1.14 ± 0.17 | 0.7846 | 1.31 ± 0.19 | 0.9999 |
| | 0.6457 | 1.35 ± 0.18 | 0.9999 | 1.23 ± 0.16 | 0.9666 |
| | 0.7548 | 1.46 ± 0.17 | 0.9337 | 1.45 ± 0.17 | 0.9445 |
| Eotaxin | | 2.16 ± 0.08 | | | |
| | | 9.63 ± 0.17¥ | | | |
| | 0.9939 | 2.28 ± 0.07 | 0.853 | 2.08 ± 0.07 | 0.9688 |
| | 0.093 | 10.08 ± 0.15 | 0.353 | 9.82 ± 0.2 | 0.8778 |
| | 0.6424 | 9.84 ± 0.25 | 0.8797 | 9.58 ± 0.21 | 0.9991 |
| | 0.2456 | 9.89 ± 0.22 | 0.7879 | 10.02 ± 0.19 | 0.3925 |
| | 0.2976 | 9.89 ± 0.21 | 0.7655 | 9.85 ± 0.17 | 0.8038 |
| FGF-2 | | 9.44 ± 1.18 | | | |
| | | 22.39 ± 0.9¥ | | | |
| | 0.9283 | 8.77 ± 0.79 | 0.9818 | 8.19 ± 1.07 | 0.8096 |
| | 0.802 | 21.41 ± 1.39 | 0.9536 | 22.89 ± 1.39 | 0.9968 |
| | 0.571 | 20.77 ± 1.37 | 0.7882 | 20.96 ± 1.43 | 0.8636 |
| | 0.735 | 20.84 ± 1.31 | 0.8113 | 21.77 ± 1.51 | 0.9924 |
| | 0.9627 | 20.93 ± 1.37 | 0.8282 | 20.96 ± 1.34 | 0.8551 |
| GM-CSF | | 7.58 ± 1.05 | | | |
| | | 122.09 ± 2.57¥ | | | |
| | 0.9865 | 9.48 ± 1.48 | 0.8873 | 8.49 ± 1.84 | 0.9945 |
| | 0.2541 | 130 ± 3.15 | 0.3521 | 126.24 ± 3.53 | 0.8083 |
| | 0.5101 | 126.18 ± 3.4 | 0.8392 | 124.89 ± 3.37 | 0.9418 |
| | 0.0714 | 134.94 ± 4.45 | 0.052 | 133.19 ± 3.97 | 0.0881 |
| | 0.0359 | 132.6 ± 3.95 | 0.1275 | 130.42 ± 3.44 | 0.2505 |
| GRO alpha | — | | | | |
| | | <.0001 | | | |
| | 0.9163 | 236.87 ± 11.04 | 0.9955 | 234.42 ± 14.21 | 0.985 |
| | 0.989 | 548.93 ± 27.91 | 0.987 | 539.42 ± 38.03 | 0.9995 |
| | 0.9941 | 544.74 ± 37.71 | 0.9947 | 555.54 ± 44.74 | 0.9797 |
| | 0.8502 | 575.98 ± 43.22 | 0.7813 | 578.28 ± 48.32 | 0.842 |
| | 0.8918 | 560.99 ± 43.32 | 0.925 | 564.53 ± 52.35 | 0.9386 |

TABLE 15-continued

Concentrations of Inflammatory Mediators Produced by Human Keratinocyte cells Stimulated with TNFα and IFNγ in the Presence/Absence of JAK Inhibitors

| Analyte | | | | | |
|---|---|---|---|---|---|
| HGF | | | 4.37 ± 0.38 | | |
| | | | 13.82 ± 0.29[¥] | | |
| | >0.999 | 4.74 ± 0.47 | 0.9368 | 3.68 ± 0.39 | 0.5616 |
| | 0.9692 | 13.66 ± 0.51 | 0.9966 | 13.47 ± 0.45 | 0.9402 |
| | 0.9972 | 13.04 ± 0.28 | 0.5379 | 13.27 ± 0.45 | 0.7642 |
| | 0.7955 | 13.53 ± 0.5 | 0.9722 | 13.75 ± 0.4 | 0.9998 |
| | 0.9669 | 13.6 ± 0.53 | 0.9881 | 13.8 ± 0.48 | >0.999 |
| IFN alpha | | | 0.24 ± 0.03 | | |
| | | | 0.26 ± 0 | | |
| | >0.999 | 0.2 ± 0.03 | 0.7279 | 0.22 ± 0.03 | 0.986 |
| | 0.3231 | 0.25 ± 0.01 | 0.3231 | 0.26 ± 0.01 | 0.9405 |
| | >0.999 | 0.26 ± 0 | >0.999 | 0.26 ± 0 | >0.999 |
| | >0.999 | 0.26 ± 0 | >0.999 | 0.26 ± 0 | >0.999 |
| | >0.999 | 0.26 ± 0 | >0.999 | 0.25 ± 0.02 | 0.4509 |
| IFN gamma | | | 4.81 ± 0.71 | | |
| | | | 25004.72 ± 3327.44[¥] | | |
| | >0.999 | 3.81 ± 0.74 | >0.999 | 4.52 ± 0.68 | >0.999 |
| | 0.7134 | 27765.18 ± 4653.71 | 0.9432 | 24180.78 ± 2901.94 | 0.9996 |
| | 0.9843 | 23531.94 ± 2644.35 | 0.9941 | 25506.14 ± 3960.86 | >0.999 |
| | 0.9796 | 23113.79 ± 2086.62 | 0.985 | 29392.77 ± 4832.25 | 0.8463 |
| | >0.999 | 25179.01 ± 3591.71 | >0.999 | 26972.77 ± 4164.13 | 0.9888 |
| IL1 alpha | | | 0.29 ± 0.03 | | |
| | | | 7.82 ± 0.18[¥] | | |
| | >0.999 | 0.3 ± 0.05 | >0.999 | 0.26 ± 0.05 | 0.9989 |
| | 0.7043 | 7.74 ± 0.36 | 0.9994 | 6.8 ± 0.39 | 0.1498 |
| | 0.3281 | 7.01 ± 0.39 | 0.3537 | 6.76 ± 0.4 | 0.1249 |
| | 0.2631 | 7.27 ± 0.47 | 0.6747 | 6.92 ± 0.4 | 0.2281 |
| | 0.0034 | 6.45 ± 0.38 | 0.0358 | 6.3 ± 0.35 | 0.0121 |
| IL1 beta | | | 0.94 ± 0.1 | | |
| | | | 8.29 ± 0.44[¥] | | |
| | >0.999 | 0.93 ± 0.17 | >0.999 | 0.98 ± 0.12 | >0.999 |
| | 0.0812 | 8.88 ± 0.35 | 0.7302 | 8.92 ± 0.42 | 0.64 |
| | 0.5388 | 8.72 ± 0.47 | 0.8871 | 8.82 ± 0.46 | 0.7601 |
| | 0.8899 | 8.55 ± 0.34 | 0.9788 | 8.63 ± 0.36 | 0.9366 |
| | 0.9966 | 8.71 ± 0.5 | 0.8878 | 8.81 ± 0.35 | 0.759 |
| IL10 | | | 0.38 ± 0.08 | | |
| | | | 0.84 ± 0.08[¥] | | |
| | 0.9855 | 0.4 ± 0.11 | 0.9998 | 0.43 ± 0.11 | 0.993 |
| | 0.9913 | 0.75 ± 0.05 | 0.729 | 0.76 ± 0.08 | 0.8444 |
| | >0.999 | 0.74 ± 0.06 | 0.667 | 0.67 ± 0.07 | 0.3152 |
| | 0.9871 | 0.75 ± 0.07 | 0.7279 | 0.81 ± 0.07 | 0.9892 |
| | >0.999 | 0.84 ± 0.08 | >0.999 | 0.84 ± 0.08 | >0.999 |
| IL12p70 | | | 2.34 ± 0.27 | | |
| | | | 1.75 ± 0.23 | | |
| | 0.1466 | 1.52 ± 0.29 | 0.1263 | 2.15 ± 0.26 | 0.9799 |
| | 0.7679 | 1.97 ± 0.22 | 0.8905 | 1.88 ± 0.19 | 0.9744 |
| | 0.9979 | 1.72 ± 0.2 | >0.999 | 1.69 ± 0.19 | 0.9988 |
| | 0.9999 | 1.75 ± 0.23 | >0.999 | 1.75 ± 0.22 | >0.999 |
| | 0.9787 | 1.79 ± 0.23 | 0.9997 | 1.7 ± 0.2 | 0.9996 |
| IL13 | | | | | |
| | 0.9998 | 1.08 ± 0.13 | 0.9929 | 1.26 ± 0.15 | 0.9996 |
| | 0.5041 | 2.93 ± 0.41 | 0.402 | 2.67 ± 0.24 | 0.7568 |
| | 0.5946 | 2.24 ± 0.28 | 0.9999 | 2.21 ± 0.27 | >0.999 |
| | 0.8523 | 2.58 ± 0.36 | 0.8525 | 2.98 ± 0.4 | 0.363 |
| | 0.8751 | 2.12 ± 0.3 | 0.9996 | 2.52 ± 0.42 | 0.9127 |
| IL15 | | | 1.84 ± 0.29 | | |
| | | | 2.75 ± 0.78 | | |
| | 0.9814 | 1.98 ± 0.49 | 0.9999 | 3.2 ± 0.71 | 0.2474 |
| | 0.9541 | 3.97 ± 0.71 | 0.4062 | 4.2 ± 0.86 | 0.5333 |
| | >0.999 | 2.29 ± 0.44 | 0.9517 | 2.82 ± 0.72 | >0.999 |
| | 0.9995 | 2.42 ± 0.54 | 0.9859 | 3.29 ± 0.9 | 0.972 |
| | 0.9994 | 2.32 ± 0.44 | 0.959 | 3.37 ± 0.8 | 0.9493 |
| IL17A | | | 1.03 ± 0.09 | | |
| | | | 3.91 ± 0.36[¥] | | |
| | 0.9838 | 1.39 ± 0.22 | 0.7488 | 1.22 ± 0.2 | 0.9738 |
| | 0.5215 | 4.27 ± 0.42 | 0.9116 | 3.84 ± 0.3 | 0.9999 |
| | 0.991 | 3.48 ± 0.39 | 0.8568 | 4.15 ± 0.57 | 0.986 |
| | 0.2722 | 3.77 ± 0.42 | 0.9974 | 3.57 ± 0.45 | 0.9569 |
| | 0.729 | 4 ± 0.34 | 0.9993 | 4.04 ± 0.49 | 0.9984 |
| IL18 | | | 6.51 ± 0.55 | | |
| | | | 155.14 ± 2.91[¥] | | |
| | 0.9991 | 5.89 ± 0.58 | 0.9968 | 6.54 ± 0.37 | >0.9 |
| | 0.5501 | 163.63 ± 3.29 | 0.4124 | 159.38 ± 4.31 | 0.8787 |
| | 0.994 | 156.41 ± 4.19 | 0.9984 | 156.12 ± 3.47 | 0.9994 |
| | 0.9995 | 162.12 ± 5.14 | 0.5817 | 156.97 ± 5.2 | 0.9934 |
| | 0.8617 | 157.36 ± 4.56 | 0.9856 | 155.77 ± 4.15 | 0.9999 |

TABLE 15-continued

Concentrations of Inflammatory Mediators Produced by Human Keratinocyte cells Stimulated with TNFα and IFNγ in the Presence/Absence of JAK Inhibitors

| | | | | | |
|---|---|---|---|---|---|
| IL1RA | | 513.38 ± 56.01 | | | |
| | | 6231.09 ± 271.61[¥] | | | |
| | >0.999 | 488.84 ± 49.85 | >0.999 | 461.3 1 ± 30.68 | 0.9982 |
| | 0.8905 | 6175.66 ± 277.7 | 0.9998 | 5760.33 ± 367.09 | 0.7833 |
| | 0.7411 | 6065 ± 325.72 | 0.9881 | 5709.52 ± 391.3 | 0.7198 |
| | 0.9003 | 6167.55 ± 367.54 | 0.9997 | 5879.83 ± 410.09 | 0.9069 |
| | 0.501 | 5756.59 ± 328.24 | 0.6603 | 5450.17 ± 388.11 | 0.3705 |
| IL2 | | 2.99 ± 0.33 | | | |
| | | 29 ± 1.27[¥] | | | |
| | 0.9961 | 2.65 ± 0.28 | 0.9954 | 2.4 ± 0.09 | 0.9515 |
| | 0.1037 | 31.39 ± 1.44 | 0.578 | 31.46 ± 1.56 | 0.6728 |
| | 0.4299 | 29.87 ± 1.38 | 0.9779 | 29.16 ± 2.01 | >0.999 |
| | 0.6329 | 30.51 ± 1.23 | 0.8659 | 29.23 ± 1.62 | 0.9999 |
| | 0.4421 | 30.68 ± 1.62 | 0.8062 | 31.88 ± 1.61 | 0.5284 |
| IL21 | | 2.88 ± 0 | | | |
| | | 2.88 ± 0 | | | |
| | 0.5085 | 2.33 ± 0.29 | 0.3239 | 2.5 ± 0.3 | 0.6612 |
| | 0.9387 | 2.71 ± 0.18 | 0.9285 | 2.71 ± 0.18 | 0.942 |
| | 0.5954 | 2.88 ± 0 | >0.999 | 2.13 ± 0.39 | 0.0587 |
| | 0.4301 | 2.6 ± 0.28 | 0.733 | 2.64 ± 0.24 | 0.8512 |
| | 0.6156 | 2.45 ± 0.29 | 0.3546 | 2.84 ± 0.04 | 0.9996 |
| IL22 | | 8.9 ± 0 | | | |
| | | 7.92 ± 0.65 | | | |
| | 0.9345 | 7.16 ± 1.16 | 0.3838 | 8.08 ± 0.82 | 0.9165 |
| | 0.8119 | 7.15 ± 1.16 | 0.9285 | 7.83 ± 0.75 | 0.9999 |
| | 0.6582 | 8.03 ± 0.87 | >0.999 | 8.9 ± 0 | 0.5913 |
| | 0.9999 | 7.31 ± 1.07 | 0.9662 | 8.21 ± 0.69 | 0.9909 |
| | 0.9988 | 8.24 ± 0.53 | 0.9966 | 8.39 ± 0.51 | 0.94 |
| IL23 | | 7.35 ± 0.54 | | | |
| | | 5.56 ± 0.97 | | | |
| | 0.6828 | 6.54 ± 1 | 0.9642 | 6.43 ± 1.28 | 0.9407 |
| | 0.1332 | 7.43 ± 0 | 0.0906 | 7.43 ± 0 | 0.0117 |
| | 0.089 | 7.43 ± 0 | 0.0906 | 7.43 ± 0 | 0.0117 |
| | 0.667 | 6.7 ± 0.73 | 0.4485 | 7.43 ± 0 | 0.0117 |
| | 0.084 | 6.95 ± 0.48 | 0.2634 | 7.43 ± 0 | 0.0096 |
| IL27 | | 6.93 ± 0.9 | | | |
| | | 6.23 ± 0.97 | | | |
| | 0.9996 | 9.17 ± 2.36 | 0.8968 | 11.9 ± 2.31 | 0.2941 |
| | 0.7164 | 8.88 ± 1.64 | 0.3282 | 7.42 ± 0.9 | 0.8475 |
| | 0.9844 | 5.98 ± 1.08 | 0.9996 | 5.51 ± 1.25 | 0.9695 |
| | 0.9686 | 5.7 ± 1.04 | 0.993 | 5.92 ± 0.88 | 0.9988 |
| | 0.6958 | 6.59 ± 0.99 | 0.9982 | 8.3 ± 1.2 | 0.4393 |
| IL31 | | 3.67 ± 0 | | | |
| | | 2.6 ± 0.63 | | | |
| | 0.5865 | 3.28 ± 0.31 | 0.9074 | 3.7 ± 0.06 | >0.999 |
| | 0.3255 | 3.52 ± 0.53 | 0.559 | 2.97 ± 0.37 | 0.9353 |
| | 0.722 | 3.36 ± 0.27 | 0.7072 | 3.43 ± 0.31 | 0.4939 |
| | 0.5741 | 2.95 ± 0.38 | 0.9708 | 4.14 ± 0.48 | 0.0632 |
| | 0.1137 | 3.34 ± 0.69 | 0.7103 | 3.05 ± 0.38 | 0.875 |
| IL4 | | 4.72 ± 0.44 | | | |
| | | 6.73 ± 1.28 | | | |
| | >0.999 | 4.89 ± 1.18 | >0.999 | 5.34 ± 0.89 | 0.9842 |
| | >0.999 | 8.31 ± 2.19 | 0.8432 | 7.2 ± 1.25 | 0.9963 |
| | 0.9463 | 5.24 ± 0.99 | 0.8657 | 5.9 ± 1.18 | 0.968 |
| | 0.9522 | 6.26 ± 1.35 | 0.9978 | 5.13 ± 0.78 | 0.7576 |
| | 0.9992 | 7.07 ± 0.88 | 0.9994 | 8.19 ± 1.39 | 0.8006 |
| IL5 | | 2.7 ± 0.43 | | | |
| | | 28.59 ± 1.29[¥] | | | |
| | 0.9999 | 3.04 ± 0.41 | 0.9956 | 2.88 ± 0.36 | 0.9998 |
| | 0.9256 | 27.03 ± 1.35 | 0.8768 | 26.66 ± 1.72 | 0.8703 |
| | 0.3753 | 26.49 ± 1.58 | 0.7237 | 28.49 ± 1.85 | >0.999 |
| | 0.7073 | 28.64 ± 1.4 | >0.999 | 27.43 ± 2.11 | 0.9759 |
| | 0.472 | 27.1 ± 1.76 | 0.886 | 25.61 ± 1.98 | 0.59 |
| IL6 | | 30.57 ± 2.89 | | | |
| | | 862.33 ± 17.95[¥] | | | |
| | 0.997 | 28.49 ± 2.89 | 0.9998 | 28.84 ± 1.89 | 0.9999 |
| | 0.0158 | 774.87 ± 31.09 | 0.1794 | 743.07 ± 36.3 | 0.0476 |
| | <.0001 | 710.89 ± 36.7 | 0.006 | 698.04 ± 29.79 | 0.0037 |
| | <.0001 | 690.4 ± 35.25 | 0.0016 | 703.99 ± 42.22 | 0.0054 |
| | <.0001 | 621.7 9 ± 33.44 | <.0001 | 646.2 ± 32.46 | <.0001 |
| IL7 | | 3.22 ± 0.12 | | | |
| | | 2.26 ± 0.09[¥] | | | |
| | 0.8957 | 3.35 ± 0.18 | 0.9726 | 3.44 ± 0.16 | 0.7986 |
| | 0.9135 | 2.18 ± 0.15 | 0.9587 | 2.16 ± 0.11 | 0.9291 |
| | 0.1612 | 2.02 ± 0.07 | 0.3795 | 2.14 ± 0.07 | 0.8446 |
| | 0.8633 | 2.04 ± 0.11 | 0.4449 | 2.15 ± 0.14 | 0.8923 |
| | 0.7513 | 1.91 ± 0.11 | 0.0979 | 2.14 ± 0.12 | 0.8584 |

TABLE 15-continued

Concentrations of Inflammatory Mediators Produced by Human Keratinocyte cells
Stimulated with TNFα and IFNγ in the Presence/Absence of JAK Inhibitors

| | | | | | |
|---|---|---|---|---|---|
| IL8 | | 271.75 ± 7.98 | | | |
| | | 2577.97 ± 63.03¥ | | | |
| | 0.9992 | 269.53 ± 10.35 | >0.999 | 257.62 ± 7.07 | 0.9957 |
| | 0.6768 | 2879.27 ± 117.07 | 0.4575 | 2820.21 ± 159.05 | 0.7286 |
| | 0.6054 | 2869.74 ± 167.65 | 0.4857 | 2907.08 ± 193.16 | 0.4877 |
| | 0.306 | 3035.52 ± 206.85 | 0.1337 | 3061.2 ± 217.26 | 0.1753 |
| | 0.2093 | 2874.26 ± 169.59 | 0.4518 | 2893.51 ± 190.51 | 0.5041 |
| IL9 | | 3.33 ± 0.37 | | | |
| | | 3.7 ± 0 | | | |
| | 0.5942 | 3.65 ± 0.2 | 0.9404 | 3.98 ± 0.36 | 0.4998 |
| | 0.5554 | 3.37 ± 0.33 | 0.7599 | 3.7 ± 0 | >0.999 |
| | 0.9285 | 3.7 ± 0 | >0.999 | 3.37 ± 0.33 | 0.8739 |
| | 0.9285 | 4.16 ± 0.46 | 0.5047 | 3.58 ± 0.24 | 0.9965 |
| | 0.9249 | 3.66 ± 0.04 | 0.9999 | 4.44 ± 0.54 | 0.2822 |
| IP-10/ | | 20.14 ± 0.36 | | | |
| CXCL10 | | 3935.46 ± 375.68¥ | | | |
| | >0.999 | 19.83 ± 0.4 | >0.999 | 20.23 ± 0.48 | >0.999 |
| | 0.9982 | 3999.9 ± 370.53 | 0.9998 | 3903.67 ± 366.97 | >0.999 |
| | 0.9999 | 3665.2 ± 277.11 | 0.9431 | 3998.62 ± 456.34 | 0.9999 |
| | 0.999 | 3860.41 ± 323.05 | 0.9995 | 4100.26 ± 502.48 | 0.9978 |
| | 0.9979 | 3835.78 ± 304.58 | 0.9984 | 4407.56 ± 645.63 | 0.8945 |
| LIF | | 23.57 ± 0.93 | | | |
| | | 63.3 ± 2.1¥ | | | |
| | 0.9998 | 24.24 ± 1.14 | 0.9947 | 22.66 ± 0.82 | 0.9784 |
| | 0.4762 | 67.72 ± 2.04 | 0.6687 | 65.71 ± 2.6 | 0.9551 |
| | 0.6301 | 67.64 ± 3.17 | 0.6825 | 66.01 ± 3.21 | 0.9336 |
| | 0.2723 | 73.12 ± 3.62 | 0.0743 | 70.02 ± 3.89 | 0.3858 |
| | 0.117 | 70.66 ± 3.22 | 0.2261 | 67.62 ± 3.58 | 0.7257 |
| MCP1 | | 1288.79 ± 44.4 | | | |
| | | 15200 ± 0¥ | | | |
| | 0.0677 | 1158.23 ± 47.13 | 0.1939 | 1306.83 ± 54.65 | 0.9989 |
| | 0.5166 | 15200 ± 0 | >0.999 | 21968.74 ± 4662.32 | 0.7846 |
| | 0.6564 | 33175.72 ± 17975.72 | 0.4889 | 25836.84 ± 10636.84 | 0.4403 |
| | >0.999 | 26334.64 ± 11134.64 | 0.8276 | 15200 ± 0 | >0.999 |
| | 0.9991 | 19811.45 ± 4611.45 | 0.9903 | 18512.1 ± 3312.1 | 0.9759 |
| MIP1 | | 3.14 ± 0.24 | | | |
| alpha | | 105.63 ± 3.74¥ | | | |
| | 0.9995 | 2.9 ± 0.21 | >0.999 | 2.75 ± 0.26 | 0.9999 |
| | 0.9925 | 101.71 ± 3.84 | 0.931 | 102.06 ± 4.18 | 0.9303 |
| | 0.7866 | 104.54 ± 6.56 | 0.9994 | 96.35 ± 3.57 | 0.3335 |
| | 0.0532 | 96.4 ± 4.18 | 0.4229 | 96.22 ± 3.58 | 0.3215 |
| | 0.0007 | 98.72 ± 3.87 | 0.6469 | 88.49 ± 5.06 | 0.016 |
| MIP1 | | 122.07 ± 4.05 | | | |
| beta | | 313.11 ± 5.46¥ | | | |
| | 0.5849 | 117.97 ± 3.75 | 0.9512 | 113.08 ± 4.82 | 0.4912 |
| | 0.9203 | 318.92 ± 6.03 | 0.9606 | 313.64 ± 8.9 | >0.999 |
| | 0.9516 | 318.37 ± 9.88 | 0.9722 | 316.87 ± 10.18 | 0.9939 |
| | 0.7439 | 324.42 ± 8.52 | 0.7136 | 317.95 ± 8.1 | 0.9843 |
| | 0.9479 | 318.74 ± 8.72 | 0.9617 | 316.74 ± 9.29 | 0.9942 |
| PDGF-BB | | 2.13 ± 0.17 | | | |
| | | 4.27 ± 0.22¥ | | | |
| | >0.999 | 2.19 ± 0.17 | 0.9993 | 1.93 ± 0.18 | 0.8993 |
| | 0.002 | 4.93 ± 0.21 | 0.1721 | 4.23 ± 0.18 | 0.9995 |
| | 0.0007 | 5.22 ± 0.25 | 0.0254 | 4.36 ± 0.18 | 0.9926 |
| | 0.0001 | 5.57 ± 0.23 | 0.0015 | 4.71 ± 0.23 | 0.329 |
| | 0.0005 | 5.52 ± 0.27 | 0.0017 | 4.75 ± 0.16 | 0.2397 |
| PlGF-1 | | 20.75 ± 0.87 | | | |
| | | 55.66 ± 1.47¥ | | | |
| | 0.9968 | 21.19 ± 1.05 | 0.9991 | 20.55 ± 1.16 | >0.999 |
| | 0.9958 | 58.04 ± 2.17 | 0.9291 | 59.56 ± 3.2 | 0.7867 |
| | 0.9714 | 55.59 ± 2.74 | >0.999 | 56.72 ± 3.48 | 0.9975 |
| | 0.9965 | 58.69 ± 3.37 | 0.8506 | 59.49 ± 3.52 | 0.7971 |
| | 0.9951 | 55.71 ± 3.28 | >0.999 | 55.63 ± 3.23 | >0.999 |
| RANTES | | 9.56 ± 0.42 | | | |
| | | 230.17 ± 9.43¥ | | | |
| | 0.9997 | 8.61 ± 0.52 | 0.9999 | 10.17 ± 0.54 | >0.999 |
| | 0.4195 | 216.88 ± 13.45 | 0.9096 | 237.57 ± 17.46 | 0.9967 |
| | 0.262 | 201.93 ± 15.44 | 0.439 | 237.55 ± 21.78 | 0.9967 |
| | 0.1736 | 207.79 ± 17.38 | 0.6354 | 241.39 ± 22.79 | 0.9841 |
| | 0.0416 | 189.62 ± 13.78 | 0.1403 | 238.51 ± 23.12 | 0.9942 |

TABLE 15-continued

Concentrations of Inflammatory Mediators Produced by Human Keratinocyte cells Stimulated with TNFα and IFNγ in the Presence/Absence of JAK Inhibitors

| | | | | | |
|---|---|---|---|---|---|
| SCF | | | 2.01 ± 0.08 | | |
| | | | 4.16 ± 0.08¥ | | |
| | 0.9847 | 2 ± 0.1 | >0.999 | 1.91 ± 0.15 | 0.9538 |
| | 0.8691 | 4.34 ± 0.19 | 0.9047 | 4.18 ± 0.24 | >0.999 |
| | >0.999 | 4.25 ± 0.22 | 0.9888 | 4.1 ± 0.21 | 0.9989 |
| | 0.9739 | 4.59 ± 0.25 | 0.3051 | 4.29 ± 0.29 | 0.9805 |
| | 0.9988 | 4.23 ± 0.15 | 0.9962 | 4.07 ± 0.21 | 0.9952 |
| SDF-1 | | | 1075.14 ± 36.63 | | |
| alpha | | | 3307.18 ± 98.57¥ | | |
| | 0.8391 | 1028.82 ± 43.21 | 0.9683 | 990.69 ± 48.87 | 0.7402 |
| | 0.8805 | 3503.89 ± 90.15 | 0.6507 | 3456.41 ± 158.06 | 0.8874 |
| | 0.9953 | 3471.01 ± 141.19 | 0.7742 | 3450.69 ± 158.13 | 0.9001 |
| | 0.7414 | 3521.98 ± 154.06 | 0.5807 | 3563.68 ± 157.35 | 0.5609 |
| | 0.6851 | 3436.48 ± 134.91 | 0.8755 | 3464.97 ± 155.2 | 0.8577 |
| TNF | | | 1.49 ± 0.59 | | |
| alpha | | | 9159.41 ± 1060.96¥ | | |
| | >0.999 | 2.82 ± 0.72 | >0.999 | 2.41 ± 0.7 | >0.999 |
| | 0.8099 | 11212.78 ± 1168.53 | 0.4872 | 8951.15 ± 870.67 | 0.9997 |
| | 0.3395 | 10367.04 ± 1016.28 | 0.8503 | 9862.6 ± 1041 | 0.9662 |
| | 0.3574 | 10632.61 ± 795.65 | 0.7448 | 10525.46 ± 1077.11 | 0.7438 |
| | 0.5219 | 10619.05 ± 1276.72 | 0.7358 | 9777.73 ± 966.87 | 0.9767 |
| TNF | | | 4.5 ± 0.48 | | |
| beta | | | 4.86 ± 0.09 | | |
| | 0.9978 | 4.5 ± 0.5 | >0.999 | 4.42 ± 0.57 | >0.999 |
| | 1 | 5.68 ± 1.4 | 0.8542 | 4.62 ± 0.49 | 0.9848 |
| | 0.7159 | 5.54 ± 0.56 | 0.9179 | 5.03 ± 0.38 | 0.9959 |
| | 0.5971 | 4.6 ± 0.46 | 0.9976 | 4.47 ± 0.37 | 0.915 |
| | 0.9271 | 3.78 ± 0.57 | 0.686 | 4.96 ± 0.56 | 0.9994 |
| VEGF-A | | | 633.68 ± 16.37 | | |
| | | | 1322.08 ± 42.07¥ | | |
| | 0.1114 | 609.51 ± 15.83 | 0.9386 | 598.11 ± 16.67 | 0.7728 |
| | 0.6545 | 1261.47 ± 37.95 | 0.8399 | 1303.84 ± 56.86 | 0.9983 |
| | 0.5813 | 1268.91 ± 59.05 | 0.8911 | 1286.84 ± 61.29 | 0.9801 |
| | 0.7787 | 1335.99 ± 63.65 | 0.9992 | 1346.72 ± 67.56 | 0.9947 |
| | 0.4555 | 1262.36 ± 57.42 | 0.836 | 1256.89 ± 60.57 | 0.8386 |
| VEGF-D | | | 3.63 ± 0.39 | | |
| | | | 8.37 ± 0.77¥ | | |
| | 0.9787 | 3.63 ± 0.6 | >0.999 | 3.55 ± 0.66 | >0.999 |
| | 0.8543 | 8.6 ± 0.74 | 0.9982 | 8.7 ± 0.52 | 0.9949 |
| | 0.5549 | 8.44 ± 0.66 | >0.999 | 8.49 ± 0.72 | 0.9999 |
| | 0.9936 | 9.25 ± 0.7 | 0.8045 | 9.64 ± 0.91 | 0.6256 |
| | 0.8932 | 8.82 ± 0.7 | 0.9752 | 8.03 ± 0.93 | 0.9933 |

[a]Stimulation with TNFα (25 ng/mL) and IFNγ (25 ng/mL)
[b]Data is presented as mean ± standard error
[c]Significant differences compared back to stimulation with TNFα and IFNγ alone
¥Indicates significant difference of $p < 0.01$ from vehicle (no stimulation and no drug concentration) alone

Example 7: Identification of Genes Differentially Expressed in Patients with Vitiligo that are Complete Responders to Treatment with Ruxolitinib Cream Using non-invasive skin tape, skin tissue was collected from each subject with vitiligo enrolled in a study of ruxolitinib cream (INCB018424) for the treatment of subjects with a clinical diagnosis of vitiligo, depigmented areas including at least 0.5% of the total body surface area on the face, and at least 3% of the total body surface area on nonfacial areas affected using the palmar (or handprint) method (palm plus 5 digits). All subjects consented to the skin tissue collection and met the inclusion and exclusion criteria outlined in the clinical protocol. Once collected, skin tissue was processed from the non-invasive skin tape into ribonucleic acid (RNA) for further analysis and subsequently analyzed using RNA sequencing. Samples were separated into to two groups based on clinical response to treatment with topical INCB018424. Specifically, samples were classified as "responder" or "non-responder" based on their therapeutic response at Week 24 of treatment ("F-VASI" refers to facial-vitiligo area and severity index). Individuals were topically applied INCB018424 either once or twice daily at dose strengths of 0.15%, 0.5%, or 1.5%. Twice daily applications were at least 10 hours apart in a cream formulation.

RNA-sequencing was conducted on all biopsy samples by Beijing Genomics Institute using the Illumina HiSeq 4000 system. Data was then aligned and quality controlled in OmicSoft Array Studio using the Human Genome B38 library. The Fragments Per Kilobase of transcript per Million (FPKM) mapped reads (the relative expression of a transcript) were generated and used in all downstream analysis. Significant differences in differentially expressed genes between groups were identified using ANOVA tests. RNA-sequencing identified differentially expressed genes between the responder and non-responder groups at baseline (with raw p-value<0.05). Three hundred sixty-nine genes were increased and 339 genes were decreased in responders compared to non-responders (Table 16).

TABLE 16

Differentially Expressed Genes in the Skin Biopsies
of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| TBC1D3 | 68.0367 | 0.0006 | RARRES3 | −153.032 | 0.0012 |
| MT1E | 53.8104 | 0.0182 | CXCL10 | −62.5312 | 0.0345 |
| RBPMS2 | 37.1356 | 0.0044 | ABLIM2 | −62.3872 | 2.79E−07 |
| HIST1H2AK | 29.0245 | 0.038 | FMO4 | −61.6695 | 0.0002 |
| ARHGAP19-SLIT1 | 27.4855 | 0.003 | ZSCAN31 | −57.6809 | 0.0003 |
| DRC3 | 23.4005 | 0.0236 | FAM153C | −45.9711 | 0.0102 |
| OVCH2 | 21.9183 | 0.0201 | VCAM1 | −43.9304 | 0.0137 |
| CCDC78 | 20.8539 | 0.0031 | CDC42EP5 | −41.845 | 0.0002 |
| UGT1A6 | 19.6003 | 0.0445 | KCNRG | −41.3377 | 0.0023 |
| CCDC105 | 18.5561 | 0.0098 | PRR5 | −40.7814 | 0.0003 |
| KCNAB3 | 16.7528 | 0.019 | HIST1H2AB | −40.7575 | 0.0413 |
| ECE2 | 16.4402 | 0.0264 | GOLGA8Q | −38.142 | 0.0103 |
| ANKRD2 | 15.9273 | 0.0213 | PRR7 | −37.6323 | 0.0002 |
| ACVR1C | 15.3089 | 0.0301 | C10orf128 | −37.3554 | 0.002 |
| B3GNT4 | 14.755 | 0.0352 | CXCL11 | −36.054 | 0.0286 |
| IYD | 14.1814 | 0.0484 | NUDT6 | −34.7085 | 0.0029 |
| TWIST2 | 13.314 | 0.0346 | CD3E | −32.0222 | 0.0272 |
| DERL3 | 13.0597 | 0.0178 | LDHD | −31.0204 | 0.0024 |
| KCNJ1 | 12.9249 | 0.013 | CTAGE15 | −30.8756 | 0.0263 |
| SYT12 | 12.6703 | 0.0193 | SLFN12 | −30.8518 | 0.0104 |
| GPR61 | 12.3318 | 0.0089 | GGACT | −29.4351 | 0.0041 |
| KRT71 | 12.0543 | 0.0346 | APOL3 | −28.8838 | 0.0248 |
| CCDC153 | 11.7483 | 0.0213 | DLEU1 | −27.6186 | 0.0178 |
| ZNF764 | 11.7269 | 0.0293 | FAM231D | −27.6104 | 0.0043 |
| TCEB3B | 11.6698 | 0.0124 | C1orf233 | −27.2263 | 0.0003 |
| FEZ1 | 11.6487 | 0.0325 | SPRR3 | −26.4914 | 0.0291 |
| C3orf49 | 11.6458 | 0.0428 | KCNIP4 | −26.065 | 0.0108 |
| VEPH1 | 11.5131 | 0.0442 | TBX19 | −26.0579 | 0.002 |
| PDE9A | 11.2422 | 0.0133 | HLA-DMA | −24.1058 | 0.0485 |
| GAGE2E | 10.6926 | 0.0309 | IL2RB | −23.2681 | 0.0065 |
| POU5F1B | 9.2163 | 0.0141 | GPR27 | −23.088 | 0.0068 |
| COL11A1 | 8.9606 | 0.0219 | IL1RL1 | −22.1689 | 0.0304 |
| HBZ | 8.9457 | 0.0418 | AGTRAP | −21.8711 | 0.0407 |
| CCNI2 | 8.8795 | 0.0336 | EDARADD | −21.2019 | 0.0173 |
| ADAMTS13 | 8.8091 | 0.0337 | SH3BGR | −21.0306 | 0.0263 |
| CNDP1 | 8.5325 | 0.0328 | IGFN1 | −20.7897 | 0.0013 |
| CILP | 8.2659 | 0.0326 | GOLGA8R | −20.0035 | 0.0361 |
| ZYG11A | 7.8521 | 0.0282 | OCEL1 | −19.5751 | 0.0078 |
| GEMIN6 | 7.5022 | 0.0424 | MLKL | −19.533 | 0.0114 |
| PSD2 | 7.4261 | 0.0035 | JPH3 | −19.5114 | 0.0044 |
| C10orf62 | 7.1923 | 0.0382 | APOBEC3G | −19.371 | 0.0498 |
| TAS1R3 | 7.0305 | 0.0281 | TRPM2 | −19.3403 | 0.0116 |
| TMEM170B | 6.8909 | 0.019 | KLHDC7B | −19.2599 | 0.0288 |
| APLN | 6.8326 | 0.0141 | GAS2L3 | −19.2454 | 0.0293 |
| ETNPPL | 6.094 | 0.0309 | CYP27B1 | −19.1669 | 0.0005 |
| WBSCR17 | 5.8639 | 0.0307 | LRRC70 | −19.1541 | 0.012 |
| PPIAL4G | 5.8596 | 0.0254 | MMP25 | −18.8131 | 0.0152 |
| ZNF77 | 5.7936 | 0.035 | SYNE4 | −18.7815 | 0.0088 |
| VWA5B2 | 5.5818 | 0.0325 | KBTBD8 | −18.5263 | 0.0145 |
| SLC2A10 | 5.3839 | 0.0367 | FAM124A | −18.2655 | 0.0016 |
| PTGER1 | 5.3803 | 0.0305 | TVP23C-CDRT4 | −18.1156 | 0.0453 |
| NPR3 | 5.1731 | 0.0153 | CD3G | −17.8975 | 0.032 |
| ZSCAN1 | 5.0883 | 0.03 | GSTT2B | −17.5226 | 0.01 |
| EFR3B | 4.8859 | 0.0379 | CYP4V2 | −17.304 | 0.0292 |
| TFR2 | 4.7716 | 0.0294 | H3F3C | −17.2902 | 0.0113 |
| FAM13C | 4.5878 | 0.0335 | RNF148 | −17.2129 | 0.0324 |
| CLEC4E | 4.5778 | 0.0393 | TICAM2 | −17.0725 | 0.0315 |
| GRM3 | 4.5593 | 0.0177 | KLB | −17.041 | 0.0008 |
| CACNA1F | 4.5255 | 0.046 | RGS9 | −17.0012 | 0.0093 |
| IL17B | 4.5105 | 0.0334 | BTN3A3 | −16.4997 | 0.0129 |
| METTL20 | 4.4939 | 0.0038 | MTRNR2L3 | −16.4822 | 0.0099 |
| C1QL1 | 4.1931 | 0.0314 | HIST4H4 | −16.3414 | 0.016 |
| NID2 | 4.1828 | 0.0344 | ZNF597 | −16.2528 | 0.0094 |
| FCER2 | 4.121 | 0.0427 | RCBTB2 | −15.9872 | 0.0413 |
| OR10A4 | 3.9713 | 0.0337 | HMMR | −15.6366 | 0.0345 |
| CLMN | 3.9588 | 0.024 | MYCL | −14.709 | 0.0196 |
| PDGFRL | 3.8707 | 0.0374 | C15orf65 | −14.6809 | 0.0435 |
| MRAP2 | 3.8395 | 0.0207 | RARB | −14.6653 | 0.0069 |
| OR7G1 | 3.7882 | 0.0319 | KLHDC1 | −14.5112 | 0.0068 |
| LIN52 | 3.7792 | 0.0347 | TMEM8A | −14.3754 | 0.0124 |

TABLE 16-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| TAF1L | 3.7768 | 0.0211 | SKA1 | −14.2437 | 0.0386 |
| GOLGA6D | 3.7667 | 0.03 | SERINC4 | −14.1611 | 0.032 |
| SIRT3 | 3.5852 | 0.0104 | AHRR | −14.1386 | 0.0113 |
| SEMA4G | 3.4866 | 0.0182 | C1QTNF6 | −14.0618 | 0.0401 |
| IFT43 | 3.3886 | 0.0406 | C4orf27 | −13.9415 | 0.0386 |
| STK16 | 3.3738 | 0.0102 | FUT2 | −13.8461 | 0.0133 |
| ARMC7 | 3.3542 | 0.0291 | PAEP | −13.7052 | 0.0318 |
| RFNG | 3.3135 | 0.0482 | TDRKH | −13.6903 | 0.0359 |
| CSAG1 | 3.2459 | 0.0299 | C9orf172 | −13.5475 | 0.0065 |
| HRNR | 3.1974 | 0.0406 | AIMP2 | −13.4501 | 0.0049 |
| RAB30 | 3.1613 | 0.0366 | LZTS1 | −13.3286 | 0.0122 |
| TMEM174 | 3.1396 | 0.0293 | NEK3 | −13.2495 | 0.0103 |
| CCDC77 | 3.034 | 0.0054 | ADAM21 | −13.0459 | 0.027 |
| PRR21 | 3.0038 | 0.0298 | FAM216A | −13.0367 | 0.0188 |
| NHSL2 | 2.9573 | 0.0367 | PIK3CG | −12.9166 | 0.0341 |
| C1orf123 | 2.9328 | 0.0095 | SDF2L1 | −12.8938 | 0.0335 |
| ZNF787 | 2.9154 | 0.0486 | LAIR1 | −12.8913 | 0.0079 |
| RUNX2 | 2.854 | 0.0347 | ANGPTL3 | −12.8408 | 0.0323 |
| ZNRF1 | 2.846 | 0.018 | TTYH2 | −12.6181 | 0.0382 |
| ASB1 | 2.8451 | 0.0073 | BEST1 | −12.5347 | 0.0434 |
| BRINP2 | 2.8274 | 0.0325 | SELPLG | −12.4437 | 0.0426 |
| PUSL1 | 2.8167 | 0.0119 | PRKAR2B | −12.4218 | 0.0276 |
| TMEM108 | 2.7928 | 0.0414 | NKX3-2 | −12.41 | 0.0215 |
| AP3M1 | 2.759 | 0.0024 | SCO2 | −12.3332 | 0.0427 |
| PALD1 | 2.738 | 0.0142 | C20orf27 | −12.1621 | 0.0076 |
| BMF | 2.7127 | 0.0084 | RGS16 | −11.9215 | 0.0266 |
| UTP23 | 2.6966 | 0.0084 | COQ6 | −11.8346 | 0.0084 |
| GTF2H3 | 2.6344 | 0.0211 | TMEM158 | −11.8129 | 0.0111 |
| GLRX5 | 2.632 | 0.0211 | PCDHB5 | −11.6183 | 0.0119 |
| PEPD | 2.6262 | 0.0246 | WNT5A | −11.6009 | 0.0168 |
| DUSP23 | 2.5657 | 0.0093 | PRR15 | −11.4573 | 0.0264 |
| EVA1B | 2.5237 | 0.0254 | ERAP2 | −11.3813 | 0.0071 |
| ZNF444 | 2.4989 | 0.0432 | LDHAL6A | −11.3778 | 0.0299 |
| FAM219A | 2.4931 | 0.0252 | MRPS28 | −11.3045 | 0.022 |
| HAUS4 | 2.4771 | 0.0144 | PSG1 | −11.2907 | 0.0327 |
| VBP1 | 2.4476 | 0.018 | GNB5 | −11.2064 | 0.0374 |
| TMEM208 | 2.4346 | 0.0459 | PILRB | −11.1383 | 0.0126 |
| NMRK1 | 2.4342 | 0.0178 | SHCBP1 | −11.0917 | 0.0348 |
| ARID3B | 2.4294 | 0.044 | MROH7 | −11.0736 | 0.0466 |
| MPLKIP | 2.4118 | 0.0249 | GBP3 | −11.0394 | 0.0402 |
| CAB39L | 2.3956 | 0.0034 | RFC4 | −10.9808 | 0.0101 |
| ALKBH3 | 2.3941 | 0.0014 | NHLH1 | −10.9216 | 0.0478 |
| RNF113A | 2.3587 | 0.045 | CTF1 | −10.7115 | 0.0433 |
| LAMTOR5 | 2.3182 | 0.0433 | BIN2 | −10.651 | 0.0464 |
| CHRNB1 | 2.3101 | 0.0383 | ANKRD13B | −10.6479 | 0.0091 |
| PLCE1 | 2.304 | 0.0074 | MAP1A | −10.6232 | 0.0292 |
| NDUFB6 | 2.302 | 0.0393 | PRMT6 | −10.6027 | 0.0239 |
| DDX55 | 2.2971 | 0.0036 | WSCD2 | −10.4554 | 0.0099 |
| TMEM14A | 2.2938 | 0.008 | KCNMB1 | −10.2631 | 0.0151 |
| C12orf29 | 2.2891 | 0.0062 | PLIN1 | −9.9343 | 0.0335 |
| NUDT9 | 2.2659 | 0.0058 | ARHGAP15 | −9.9233 | 0.0439 |
| THG1L | 2.2594 | 0.0387 | KIF18A | −9.8102 | 0.0353 |
| SERTAD1 | 2.2401 | 0.0403 | RAD51B | −9.7928 | 0.0259 |
| LSAMP | 2.2351 | 0.0474 | DNAJB5 | −9.7628 | 0.0177 |
| CHST15 | 2.2172 | 0.0329 | LRRC8C | −9.7212 | 0.0448 |
| VARS2 | 2.2089 | 0.0391 | CUZD1 | −9.7111 | 0.0312 |
| SMIM5 | 2.2004 | 0.0331 | DISC1 | −9.6567 | 0.031 |
| CUEDC1 | 2.1963 | 0.0305 | ADCY7 | −9.6462 | 0.0295 |
| ZNF619 | 2.1826 | 0.0295 | WAS | −9.5953 | 0.0418 |
| FAM89B | 2.1601 | 0.0223 | CCBL1 | −9.4587 | 0.028 |
| MRPL14 | 2.154 | 0.0372 | ZNF286B | −9.3988 | 0.011 |
| RPL36A | 2.1513 | 0.0466 | SLA2 | −9.3314 | 0.0432 |
| UQCC2 | 2.1142 | 0.0357 | PLA2G4C | −9.2972 | 0.0301 |
| ORAOV1 | 2.1074 | 0.0264 | MAP1LC3C | −9.2483 | 0.0288 |
| FAM96B | 2.1 | 0.0496 | DNAH9 | −9.0277 | 0.026 |
| GID4 | 2.0867 | 0.0078 | MUC1 | −9.0163 | 0.0362 |
| LMLN | 2.0845 | 0.0414 | PROX1 | −8.9899 | 0.0084 |
| AKAP10 | 2.0712 | 0.0017 | SSC4D | −8.7828 | 0.0307 |
| RNF166 | 2.0613 | 0.0301 | SLC9A4 | −8.6475 | 0.0245 |
| HMGCL | 2.0551 | 0.0228 | ARHGEF39 | −8.5813 | 0.0453 |
| C11orf49 | 2.0425 | 0.0107 | RAB3IL1 | −8.5209 | 0.0338 |

TABLE 16-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| TSHZ1 | 2.0399 | 0.0324 | TNFRSF8 | −8.4521 | 0.0311 |
| ERMARD | 2.0267 | 0.0112 | GINS1 | −8.2901 | 0.0339 |
| TATDN2 | 2.0046 | 0.0258 | P3H3 | −8.2773 | 0.0311 |
| GTF2H5 | 1.9878 | 0.0448 | CD5 | −8.1417 | 0.0371 |
| REXO2 | 1.9865 | 0.0162 | GPR34 | −8.1372 | 0.0496 |
| PCCA | 1.9856 | 0.035 | HHIPL2 | −8.1104 | 0.0338 |
| ZNF780A | 1.9837 | 0.036 | NEFH | −8.0898 | 0.0309 |
| ZNF133 | 1.982 | 0.0114 | PADI3 | −8.0437 | 0.0436 |
| RWDD4 | 1.9749 | 0.0011 | NUGGC | −8.02 | 0.0304 |
| MAPK3 | 1.9741 | 0.0429 | SEZ6L2 | −8.016 | 0.0399 |
| CRY2 | 1.9599 | 0.0196 | ETS1 | −8.0143 | 0.0015 |
| ZNF397 | 1.9584 | 0.044 | CSF1R | −8.0002 | 0.0498 |
| TMEM68 | 1.949 | 0.0442 | GPR89B | −7.9587 | 0.0288 |
| HLCS | 1.945 | 0.0079 | MRPL24 | −7.9498 | 0.0431 |
| MRPL33 | 1.9409 | 0.0019 | SLC25A25 | −7.8202 | 0.0167 |
| RAB3B | 1.9339 | 0.05 | LRRC37A3 | −7.6832 | 0.0282 |
| CSTF2 | 1.9291 | 0.0213 | C1orf109 | −7.5885 | 0.0312 |
| SMPD2 | 1.9171 | 0.0348 | FBXO4 | −7.5231 | 0.0207 |
| DNAJA3 | 1.9077 | 0.0256 | SGIP1 | −7.4578 | 0.0426 |
| BTF3L4 | 1.9049 | 0.0464 | PRKG1 | −7.455 | 0.0108 |
| RANBP9 | 1.9028 | 0.0221 | TMC8 | −7.4527 | 0.0388 |
| MCFD2 | 1.9021 | 0.0091 | SRSF12 | −7.3006 | 0.0399 |
| CSNK1G3 | 1.8954 | 0.0037 | GJA3 | −7.2952 | 0.0494 |
| SEPSECS | 1.8912 | 0.0246 | LMAN2L | −7.2387 | 0.021 |
| TEX264 | 1.8749 | 0.0302 | GALNT16 | −7.2288 | 0.0388 |
| AMOTL2 | 1.8745 | 0.0254 | EN1 | −7.2271 | 0.0387 |
| ASAH1 | 1.8711 | 0.0255 | FAXC | −7.2246 | 0.0365 |
| PMF1 | 1.8691 | 0.0335 | MUC4 | −7.0712 | 0.0231 |
| ZNF865 | 1.8645 | 0.0376 | CUX2 | −7.0366 | 0.0244 |
| RARS2 | 1.8549 | 0.0027 | NDOR1 | −7.0359 | 0.0256 |
| LYPLA2 | 1.8525 | 0.0495 | TEX14 | −7.0294 | 0.0352 |
| MRPS10 | 1.8459 | 0.0267 | PDIA5 | −7.0173 | 0.0134 |
| MOAP1 | 1.8357 | 0.0331 | FOSL1 | −6.9778 | 0.0278 |
| TFAM | 1.8176 | 0.0399 | FBXO2 | −6.9416 | 0.0381 |
| LIPH | 1.8045 | 0.0359 | TGIF2 | −6.9025 | 0.0367 |
| RDH11 | 1.8019 | 0.0418 | EED | −6.8688 | 0.0318 |
| RNF41 | 1.801 | 0.0135 | WNT4 | −6.8002 | 0.0287 |
| HAUS5 | 1.8 | 0.0223 | IFT88 | −6.6886 | 0.0348 |
| FBXO8 | 1.7986 | 0.0334 | GORAB | −6.5339 | 0.0256 |
| SUMF1 | 1.79 | 0.0494 | ESRRG | −6.5206 | 0.0362 |
| CNNM3 | 1.7821 | 0.0452 | NPAS3 | −6.4759 | 0.0474 |
| MRPL50 | 1.7811 | 0.0038 | DNAJC25 | −6.4515 | 0.0255 |
| DCAF17 | 1.7746 | 0.0223 | CNGB1 | −6.4413 | 0.0364 |
| DCXR | 1.7739 | 0.0098 | AVPR1A | −6.4102 | 0.0057 |
| RPS6KB1 | 1.7721 | 0.0073 | QTRTD1 | −6.4086 | 0.0089 |
| RAB11FIP2 | 1.7699 | 0.0432 | C9orf64 | −6.324 | 0.0389 |
| SFMBT1 | 1.7681 | 0.028 | NANOS1 | −6.2575 | 0.0281 |
| MANEA | 1.766 | 0.0307 | GTF2H2C | −6.2444 | 0.0113 |
| ZNF266 | 1.7643 | 0.0306 | ARMC9 | −6.2366 | 0.0254 |
| IKZF5 | 1.7618 | 0.004 | PLSCR1 | −6.1774 | 0.0038 |
| EIF2AK4 | 1.7598 | 0.0298 | PHTF1 | −6.081 | 0.0316 |
| CHMP6 | 1.7493 | 0.0065 | EEF1E1 | −6.0239 | 0.025 |
| ZNF525 | 1.7492 | 0.0203 | APOLD1 | −5.9596 | 0.024 |
| VPS33A | 1.7483 | 0.0123 | ZBTB46 | −5.9247 | 0.0184 |
| MIDN | 1.7458 | 0.0243 | SLC22A18 | −5.8962 | 0.0417 |
| CMTM4 | 1.7449 | 0.044 | SS18L2 | −5.7458 | 0.0484 |
| POLR1B | 1.743 | 0.0122 | SLC41A2 | −5.7433 | 0.0427 |
| TRIM11 | 1.736 | 0.0453 | C3 | −5.4761 | 0.0447 |
| COX7A2 | 1.7329 | 0.029 | FGFRL1 | −5.4726 | 0.0499 |
| PRPF40B | 1.7259 | 0.0039 | DENND1C | −5.3414 | 0.0459 |
| SUPV3L1 | 1.7245 | 0.0369 | TNFAIP8L1 | −5.2489 | 0.033 |
| CCP110 | 1.7177 | 0.0195 | CILP2 | −5.0874 | 0.028 |
| PGRMC1 | 1.7171 | 0.0285 | DUSP28 | −4.9879 | 0.0366 |
| PCDHGB7 | 1.7097 | 0.0003 | S1PR2 | −4.8478 | 0.0438 |
| PEX26 | 1.708 | 0.0374 | C1orf74 | −4.8217 | 0.0335 |
| POLR2E | 1.6977 | 0.0057 | IMPG2 | −4.7994 | 0.0155 |
| FHL2 | 1.6965 | 0.023 | ACAN | −4.6964 | 0.0344 |
| MCPH1 | 1.6935 | 0.0248 | TARSL2 | −4.6505 | 0.0001 |
| RNASEH1 | 1.6927 | 0.0101 | SARM1 | −4.4398 | 0.0485 |
| TMEM70 | 1.6875 | 0.0425 | ALPK3 | −4.3531 | 0.007 |
| CNOT7 | 1.6848 | 0.0393 | SYCP2 | −4.3321 | 0.0427 |

TABLE 16-continued

Differentially Expressed Genes in the Skin Biopsies of Responders Compared to Non-Responders

| Up-regulated in Responders vs. Non-Responders | | | Down-regulated in Responders vs. Non-Responders | | |
| --- | --- | --- | --- | --- | --- |
| Gene Symbol | Fold Change | Raw P-value | Gene Symbol | Fold Change | Raw P-value |
| PPP1R37 | 1.681 | 0.0427 | ZNF555 | −4.2258 | 0.035 |
| PPP1R14B | 1.6793 | 0.0471 | NLRP2 | −4.0548 | 0.0392 |
| MAK16 | 1.6778 | 0.0286 | ZNF34 | −4.0366 | 0.0336 |
| TANK | 1.6768 | 0.0342 | GPRC5A | −4.027 | 0.0387 |
| APLF | 1.6766 | 0.0132 | CECR5 | −3.8695 | 0.0009 |
| MAGEF1 | 1.6717 | 0.0382 | JMJD6 | −3.8462 | 0.0024 |
| RUFY1 | 1.6712 | 0.0486 | SPATA5L1 | −3.8252 | 0.0241 |
| CDK4 | 1.6694 | 0.046 | MSRB2 | −3.8049 | 0.0441 |
| SNRK | 1.6669 | 0.0362 | ZNF469 | −3.6847 | 0.0105 |
| GLOD4 | 1.6615 | 0.0101 | SLC35E3 | −3.677 | 0.0032 |
| PHLPP1 | 1.6594 | 0.0478 | FECH | −3.5554 | 0.0407 |
| DCAF15 | 1.6546 | 0.0174 | NOP16 | −3.4316 | 0.0125 |
| PSMB3 | 1.6539 | 0.0357 | PTRHD1 | −3.3579 | 0.0037 |
| ZNF467 | 1.6474 | 0.0454 | SLC5A6 | −3.276 | 0.0048 |
| PIGV | 1.6448 | 0.0392 | SCARB1 | −3.1716 | 0.0072 |
| HCFC2 | 1.6409 | 0.0284 | MSANTD4 | −3.1499 | 0.0224 |
| C11orf57 | 1.6332 | 0.0143 | HCN4 | −3.0177 | 0.0496 |
| PCNXL4 | 1.628 | 0.0195 | RNF180 | −2.9924 | 0.0132 |
| SLC25A44 | 1.627 | 0.0327 | BCL2L12 | −2.9658 | 0.0487 |
| LRIG3 | 1.6263 | 0.0102 | MRPL27 | −2.8904 | 0.0058 |
| HSPA4L | 1.625 | 0.0216 | XK | −2.8026 | 0.0072 |
| PTK2B | 1.6221 | 0.0409 | CYB5R4 | −2.7853 | 0.0352 |
| DNAJC4 | 1.619 | 0.0326 | VOPP1 | −2.7641 | 0.0074 |
| CCDC117 | 1.6127 | 0.0216 | PDLIM7 | −2.7221 | 0.0116 |
| CAPG | 1.6117 | 0.0371 | PAAF1 | −2.7215 | 0.0266 |
| ARHGEF5 | 1.6091 | 0.0483 | INTS2 | −2.663 | 0.0081 |
| ENOSF1 | 1.6084 | 0.0226 | CTGF | −2.6517 | 0.0391 |
| MAST2 | 1.6068 | 0.0397 | ABCA7 | −2.6328 | 0.048 |
| ST6GALNAC6 | 1.6038 | 0.0293 | TRUB2 | −2.5715 | 0.034 |
| NFYB | 1.6025 | 0.0409 | NAV1 | −2.5603 | 0.0495 |
| TMED7 | 1.5976 | 0.01 | NPIPB4 | −2.5301 | 0.0001 |
| SLIT3 | 1.5936 | 0.0152 | IQCG | −2.5235 | 0.0287 |
| GLCCI1 | 1.5838 | 0.0275 | ZNF124 | −2.5084 | 0.0229 |
| ZNF765 | 1.5737 | 0.0229 | GRIP1 | −2.457 | 0.0246 |
| BLOC1S1 | 1.5718 | 0.0327 | NDC1 | −2.4318 | 0.0449 |
| NDFIP2 | 1.5714 | 0.0352 | HSF4 | −2.4304 | 0.0246 |
| PSME3 | 1.5708 | 0.0139 | BACE1 | −2.4226 | 0.0322 |
| MED1 | 1.5663 | 0.017 | EOGT | −2.3483 | 0.0282 |
| FAM60A | 1.5652 | 0.037 | NAF1 | −2.3137 | 0.0291 |
| CAMK2D | 1.5631 | 0.0411 | BHLHE41 | −2.303 | 0.0448 |
| DVL1 | 1.5627 | 0.0346 | ESD | −2.2919 | 0.0149 |
| BIRC2 | 1.5623 | 0.0269 | USP28 | −2.2862 | 0.001 |
| PRPF4 | 1.5571 | 0.0306 | PLXND1 | −2.2778 | 0.0364 |
| DOCK6 | 1.556 | 0.0497 | CKS1B | −2.2471 | 0.0149 |
| SPTLC1 | 1.5552 | 0.0179 | PPT2 | −2.2363 | 0.0313 |
| ACAD11 | 1.5517 | 0.0057 | KATNAL2 | −2.2113 | 0.0465 |
| H2AFV | 1.5491 | 0.0471 | PRKAA1 | −2.1788 | 0.0108 |
| SWAP70 | 1.5477 | 0.0129 | FTSJ1 | −2.1679 | 0.0383 |
| MTCH1 | 1.5441 | 0.0494 | RNF2 | −2.1655 | 0.0306 |
| RNF167 | 1.5393 | 0.0489 | SPRY4 | −2.1628 | 0.0463 |
| CD2BP2 | 1.5368 | 0.0199 | PDE5A | −2.1518 | 0.042 |
| PHF8 | 1.5358 | 0.0185 | CARD16 | −2.1372 | 0.0404 |
| SKAP2 | 1.5355 | 0.0458 | TAF6 | −2.1197 | 0.0401 |
| TSPAN6 | 1.535 | 0.0218 | FBXL4 | −2.1123 | 0.0008 |
| DCTN4 | 1.5348 | 0.0393 | EGLN2 | −2.0977 | 0.0151 |
| FBXO42 | 1.5336 | 0.0356 | SLC39A14 | −2.0906 | 0.0054 |
| TOB2 | 1.5327 | 0.0261 | ASPSCR1 | −2.0848 | 0.0392 |
| SCAF1 | 1.5323 | 0.0107 | DENND6A | −2.0844 | 0.0439 |
| KDM6A | 1.5295 | 0.0406 | HEXA | −2.0705 | 0.0379 |
| PHF1 | 1.528 | 0.0499 | DHFR | −2.0671 | 0.0452 |
| RNPC3 | 1.5275 | 0.0134 | ZNF43 | −2.0455 | 0.0028 |
| UBE2K | 1.5234 | 0.0174 | HEATR5A | −2.0294 | 0.0497 |
| ZNF91 | 1.5229 | 0.0369 | SCFD2 | −2.0009 | 0.0374 |
| FOXO1 | 1.5207 | 0.0376 | MLH1 | −1.9963 | 0.0116 |
| STX7 | 1.5195 | 0.0324 | GAA | −1.9848 | 0.0214 |
| CDC27 | 1.5186 | 0.0107 | FLOT2 | −1.9772 | 0.0249 |
| CGGBP1 | 1.5159 | 0.0362 | TNPO1 | −1.9693 | 0.023 |
| CASC4 | 1.5117 | 0.0265 | RNF8 | −1.9597 | 0.0334 |
| FBXO25 | 1.5103 | 0.0375 | SHMT2 | −1.9187 | 0.0211 |
| CDK16 | 1.5005 | 0.0125 | TAPT1 | −1.9096 | 0.0401 |
| MAPK7 | 1.4978 | 0.0237 | FBXO48 | −1.9025 | 0.0471 |

TABLE 16-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| XPO4 | 1.4976 | 0.0197 | STARD9 | −1.9024 | 0.0071 |
| MAN2C1 | 1.4976 | 0.0354 | ARL13B | −1.8733 | 0.0425 |
| MZF1 | 1.4936 | 0.0406 | CNTN4 | −1.8547 | 0.0318 |
| EDC4 | 1.4913 | 0.0272 | ZSCAN16 | −1.8429 | 0.0495 |
| RNF34 | 1.4882 | 0.0302 | CTPS1 | −1.8415 | 0.0071 |
| DCAF4 | 1.488 | 0.0472 | HNRNPLL | −1.8397 | 0.0417 |
| LRP11 | 1.4853 | 0.0407 | MRPL30 | −1.8365 | 0.0311 |
| WTAP | 1.4772 | 0.0131 | EXOC5 | −1.82 | 0.0067 |
| RBM23 | 1.4763 | 0.0487 | PDCD7 | −1.8129 | 0.0284 |
| ZNF224 | 1.47 | 0.0286 | ARHGAP30 | −1.8009 | 0.0447 |
| ATP11A | 1.4699 | 0.0275 | MTHFD1 | −1.757 | 0.0318 |
| CLASRP | 1.4674 | 0.0108 | RINT1 | −1.7568 | 0.0087 |
| CPSF2 | 1.4594 | 0.0498 | DNMT3A | −1.7456 | 0.0053 |
| FAM50A | 1.4579 | 0.0154 | NAA10 | −1.7147 | 0.034 |
| PHF10 | 1.4546 | 0.011 | RFX7 | −1.7118 | 0.0084 |
| CDK2 | 1.454 | 0.0365 | SDCCAG8 | −1.7004 | 0.0196 |
| EFR3A | 1.4466 | 0.0044 | TMX3 | −1.6894 | 0.0168 |
| SAR1A | 1.4465 | 0.0258 | NUP107 | −1.6884 | 0.0315 |
| BUB3 | 1.4456 | 0.0398 | DENND1A | −1.6801 | 0.017 |
| ATP5E | 1.4441 | 0.0493 | DAXX | −1.6753 | 0.0009 |
| MEA1 | 1.4435 | 0.0427 | ACBD6 | −1.6687 | 0.0051 |
| TARDBP | 1.4379 | 0.0185 | WSB2 | −1.6676 | 0.0268 |
| LZTS2 | 1.4358 | 0.0223 | KLHL9 | −1.6617 | 0.0083 |
| ATP11B | 1.4202 | 0.038 | ABCA2 | −1.6526 | 0.0369 |
| ANKHD1 | 1.4186 | 0.0196 | CHTF8 | −1.6523 | 0.0105 |
| ANKS1A | 1.4176 | 0.0489 | TRIM66 | −1.6518 | 0.0071 |
| CD2AP | 1.4174 | 0.0329 | ARNTL | −1.6485 | 0.0297 |
| AGFG1 | 1.4156 | 0.0481 | PLD2 | −1.6456 | 0.0112 |
| EIF2A | 1.4149 | 0.0096 | IL6ST | −1.6403 | 0.0389 |
| METTL7A | 1.4107 | 0.0426 | ZNF551 | −1.6251 | 0.0289 |
| HINT1 | 1.4073 | 0.0469 | LIMA1 | −1.6226 | 0.0124 |
| REXO1 | 1.4069 | 0.0184 | SYNJ1 | −1.6023 | 0.0393 |
| TBC1D22A | 1.4003 | 0.0409 | SRC | −1.5899 | 0.0462 |
| ARHGAP5 | 1.4002 | 0.0338 | MDM4 | −1.5825 | 0.0135 |
| CCDC174 | 1.3992 | 0.035 | INTS3 | −1.5722 | 0.0436 |
| SERINC1 | 1.3973 | 0.0367 | HIVEP1 | −1.559 | 0.0097 |
| SAP18 | 1.3949 | 0.0338 | DNHD1 | −1.5442 | 0.0493 |
| SEC16A | 1.3849 | 0.0471 | MEF2A | −1.5306 | 0.0277 |
| RALBP1 | 1.3837 | 0.0264 | TMSB10 | −1.5295 | 0.0499 |
| PRPF18 | 1.3802 | 0.0334 | ARFRP1 | −1.5238 | 0.0468 |
| STK24 | 1.3751 | 0.0431 | MCC | −1.5213 | 0.009 |
| MPHOSPH10 | 1.3743 | 0.0484 | POLR3GL | −1.5197 | 0.0308 |
| AVL9 | 1.3659 | 0.0376 | CABIN1 | −1.5105 | 0.0072 |
| TRIM28 | 1.356 | 0.0239 | BBS9 | −1.4879 | 0.0404 |
| UBTF | 1.3536 | 0.0324 | RAB2B | −1.4817 | 0.0346 |
| PAFAH1B2 | 1.352 | 0.024 | BRAT1 | −1.4566 | 0.0458 |
| CDC5L | 1.3516 | 0.0171 | TM7SF3 | −1.4542 | 0.046 |
| PAF1 | 1.3435 | 0.0396 | WDR33 | −1.4522 | 0.0167 |
| SLMAP | 1.3356 | 0.003 | WDR46 | −1.4522 | 0.0116 |
| IPO8 | 1.3307 | 0.0345 | PLXNA3 | −1.4331 | 0.0403 |
| CALU | 1.3268 | 0.0306 | PAPD4 | −1.4057 | 0.0355 |
| KDM5A | 1.3258 | 0.0157 | ATP2B4 | −1.3949 | 0.0275 |
| TRA2A | 1.3241 | 0.003 | OXSR1 | −1.3411 | 0.0235 |
| WNK1 | 1.3218 | 0.0276 | TBC1D8B | −1.3347 | 0.0297 |
| NBAS | 1.3148 | 0.0167 | FBRSL1 | −1.2975 | 0.0479 |
| KAT6B | 1.3111 | 0.0182 | IMMT | −1.2443 | 0.0452 |
| TAOK3 | 1.2979 | 0.0453 | | | |
| ITGB1 | 1.2977 | 0.0489 | | | |
| PPP1R12A | 1.2976 | 0.0249 | | | |
| RNF20 | 1.295 | 0.0097 | | | |
| SMC1A | 1.2917 | 0.0156 | | | |
| ZC3H11A | 1.2916 | 0.0229 | | | |
| DNAJC8 | 1.2892 | 0.02 | | | |
| RAB22A | 1.2886 | 0.0406 | | | |
| SPEN | 1.2812 | 0.006 | | | |
| HNRNPD | 1.2737 | 0.0326 | | | |
| YWHAZ | 1.2704 | 0.0471 | | | |
| DNAJC13 | 1.2687 | 0.0317 | | | |
| IFNAR1 | 1.2677 | 0.0437 | | | |
| INO80D | 1.2663 | 0.0096 | | | |
| TRIP11 | 1.2661 | 0.0404 | | | |

TABLE 16-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| ARID2 | 1.2649 | 0.0377 | | | |
| DDB1 | 1.2649 | 0.0221 | | | |
| TGOLN2 | 1.2605 | 0.0444 | | | |
| C3orf58 | 1.2578 | 0.03 | | | |
| IARS2 | 1.2553 | 0.0436 | | | |
| PMPCB | 1.2502 | 0.0285 | | | |
| USP47 | 1.2426 | 0.0201 | | | |
| PHIP | 1.2382 | 0.0118 | | | |
| IQGAP1 | 1.2353 | 0.043 | | | |
| HNRNPK | 1.2227 | 0.0282 | | | |
| NUMA1 | 1.2168 | 0.021 | | | |
| VPS36 | 1.2153 | 0.0257 | | | |
| FUBP1 | 1.1848 | 0.0447 | | | |
| ZNF638 | 1.1446 | 0.0493 | | | |
| KMT2C | 1.1063 | 0.0278 | | | |

Example 8: Characterization of Gene Expression During the Course of Treatment Skin tissue and corresponding RNA samples were collected from individuals enrolled in the clinical study of Example 7 at baseline and at Week 24. Table 17 and Table 18 list genes that were significantly modulated (P<0.05) in responders and non-responders, respectively, by treatment between baseline and week 24. These genes represent biomarkers which potentially correlate with therapeutic response.

TABLE 17

Genes Significantly Modulated Between Baseline and Week 24 in Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| OCEL1 | 98.7285 | 0.0205 | HIST1H1B | −359.79 | 0.0152 |
| FMO4 | 90.1456 | 0.0179 | HLA-DPA1 | −276.107 | 0.0071 |
| DPF1 | 87.0034 | 0.0042 | C3orf14 | −217.796 | 0.0158 |
| TNNC2 | 63.2953 | 0.0223 | HIST1H3D | −200.86 | 0.0256 |
| TMEM217 | 54.4275 | 0.0189 | IFI6 | −193.193 | 0.0044 |
| FAM131C | 48.5846 | 0.017 | PXMP2 | −156.391 | 0.0107 |
| RSG1 | 44.7652 | 0.032 | HLA-DQB2 | −150.163 | 0.0201 |
| ADAM21 | 41.0881 | 0.0176 | IL32 | −137.196 | 0.0231 |
| FANK1 | 40.7236 | 0.0416 | FUOM | −131.679 | 0.017 |
| PCDHB8 | 37.0503 | 0.0472 | GKAP1 | −119.173 | 0.0059 |
| CORO7-PAM16 | 31.3983 | 0.0399 | RANGRF | −118.714 | 0.0139 |
| CORO6 | 30.762 | 0.0361 | DCTPP1 | −115.051 | 0.0166 |
| FSCN2 | 23.8405 | 0.0425 | MT1E | −93.8553 | 0.0438 |
| VRTN | 23.787 | 0.029 | RGS14 | −87.6162 | 0.0125 |
| ARHGEF39 | 22.5721 | 0.0222 | GMNN | −83.8834 | 0.0204 |
| CNGA3 | 21.5758 | 0.025 | THOC3 | −77.7502 | 0.0434 |
| ALPK3 | 20.8473 | 0.0354 | SNRNP25 | −76.015 | 0.0248 |
| PCDHB5 | 20.4521 | 0.0445 | PARP8 | −75.5333 | 0.0062 |
| FKBP10 | 17.8669 | 0.0426 | PLXNC1 | −74.1112 | 0.005 |
| IMPG1 | 16.6877 | 0.0428 | GPX7 | −72.2 | 0.0167 |
| ISCA2 | 14.3856 | 0.0448 | HEY1 | −72.0076 | 0.0212 |
| LMAN2L | 12.2518 | 0.0458 | TBC1D3 | −71.9042 | 0.016 |
| ETS1 | 11.5607 | 0.0096 | APOBEC3A | −70.5453 | 0.0174 |
| RYR2 | 11.5153 | 0.03 | CCDC121 | −67.9646 | 0.0193 |
| HSPA1L | 11.2961 | 0.0162 | HLA-DPB1 | −67.536 | 0.0315 |
| AK1 | 8.8674 | 0.0244 | GK | −66.7528 | 0.0263 |
| SLC35C1 | 6.2951 | 0.0025 | GAMT | −65.346 | 0.0418 |
| SLC9A3R2 | 5.8779 | 0.007 | TAS2R4 | −64.2421 | 0.0193 |
| ZNF675 | 5.6136 | 0.0343 | ZNF467 | −61.8768 | 0.0421 |
| MINPP1 | 5.1774 | 0.04 | FOXM1 | −60.8531 | 0.0133 |
| SLC38A7 | 5.0401 | 0.0489 | FABP7 | −58.5431 | 0.0323 |
| QPCT | 5.0112 | 0.0401 | NRM | −58.1637 | 0.036 |
| NCBP1 | 4.902 | 0.0367 | RAB15 | −57.8193 | 0.0066 |
| SLC22A15 | 4.8508 | 0.0409 | TGFBI | −57.5202 | 0.0386 |
| DIRAS1 | 4.4943 | 0.0133 | CXCR4 | −54.4873 | 0.0208 |

TABLE 17-continued

Genes Significantly Modulated Between Baseline and Week 24 in Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| EEF1E1 | 4.4432 | 0.0188 | TMEM97 | −52.6704 | 0.0122 |
| TRPV1 | 4.3896 | 0.0349 | PSMB9 | −51.5829 | 0.0487 |
| FTSJ1 | 4.1583 | 0.0256 | XRCC6BP1 | −51.511 | 0.0118 |
| C5orf63 | 4.0234 | 0.044 | ABCC4 | −51.222 | 0.0244 |
| DCTN5 | 4.0233 | 0.0115 | CENPK | −51.0641 | 0.0128 |
| C15orf41 | 4.0134 | 0.0132 | NEIL3 | −50.7632 | 0.0149 |
| PSCA | 3.9162 | 0.0086 | IL4I1 | −49.4381 | 0.0349 |
| SNX21 | 3.7733 | 0.0494 | ZDHHC11B | −47.5953 | 0.0232 |
| GRB7 | 3.7309 | 0.0326 | TMC4 | −47.4074 | 0.0162 |
| NAA38 | 3.666 | 0.0376 | TMEM263 | −47.1555 | 0.0321 |
| NUBP2 | 3.6297 | 0.0419 | CASS4 | −46.9763 | 0.0019 |
| PTGER4 | 3.5756 | 0.0172 | CEP57L1 | −45.4386 | 0.0262 |
| ALG14 | 3.5539 | 0.0073 | HIST1H2BO | −43.9862 | 0.0191 |
| PPT2 | 3.5499 | 0.0105 | AKAP7 | −43.364 | 0.0314 |
| FIS1 | 3.4167 | 0.0271 | PKIB | −42.739 | 0.0093 |
| USP3 | 3.379 | 0.0407 | DLK2 | −41.1394 | 0.0393 |
| KCTD10 | 3.3438 | 0.046 | DZIP1L | −41.1156 | 0.0486 |
| PGBD2 | 3.279 | 0.0332 | HIST1H3H | −40.6258 | 0.0382 |
| GATSL2 | 3.2773 | 0.0456 | PDPN | −40.5786 | 0.0437 |
| SOCS5 | 3.2578 | 0.0187 | KREMEN2 | −39.3427 | 0.0378 |
| EHD4 | 3.2433 | 0.0438 | CLSPN | −39.1791 | 0.0211 |
| ROBO4 | 3.2411 | 0.0113 | GPR137C | −39.0863 | 0.0252 |
| IQCD | 3.1765 | 0.0319 | ZNF311 | −37.7704 | 0.0275 |
| MARS | 3.1429 | 0.0258 | CDCA5 | −37.6608 | 0.0466 |
| BCL7B | 3.1189 | 0.0456 | TRO | −37.2777 | 0.0314 |
| MGLL | 3.0578 | 0.015 | ENO2 | −35.1392 | 0.0479 |
| ARHGAP10 | 3.0277 | 0.0172 | THEM6 | −34.6052 | 0.0429 |
| GLB1L | 3.0025 | 0.0284 | KLHL31 | −34.4252 | 0.0433 |
| PAQR7 | 2.9935 | 0.0459 | LUZP2 | −33.8607 | 0.0235 |
| PTRHD1 | 2.9473 | 0.0093 | AARD | −33.5312 | 0.031 |
| C6orf47 | 2.9414 | 0.0121 | AK8 | −33.4846 | 0.0125 |
| KSR1 | 2.9244 | 0.0335 | CXCL8 | −33.4768 | 0.0323 |
| CANT1 | 2.8911 | 0.0328 | ENTPD6 | −32.7907 | 0.0471 |
| FAM73B | 2.8863 | 0.0435 | TRIM6-TRIM34 | −32.6836 | 0.0241 |
| SUCLA2 | 2.8802 | 0.0496 | ZEB2 | −32.4325 | 0.0233 |
| C1orf210 | 2.8715 | 0.0193 | LAPTM5 | −32.2047 | 0.0494 |
| ZNF782 | 2.8504 | 0.024 | CD40 | −31.8683 | 0.0481 |
| KCNK1 | 2.8137 | 0.0373 | RILP | −31.6352 | 0.0131 |
| WSB2 | 2.8047 | 0.0417 | G0S2 | −31.2738 | 0.0428 |
| ARL2 | 2.7965 | 0.0378 | MSTO1 | −30.8368 | 0.0464 |
| ANKRD42 | 2.7657 | 0.0482 | SCN3B | −30.7775 | 0.0159 |
| GTPBP1 | 2.7639 | 0.0485 | ZC3HAV1L | −30.4503 | 0.0473 |
| NFATC2IP | 2.7612 | 0.0103 | ANKRD23 | −30.2129 | 0.0236 |
| TMEM253 | 2.7155 | 0.028 | TMEM173 | −29.9866 | 0.0222 |
| COMMD5 | 2.6792 | 0.0082 | L3MBTL3 | −29.8492 | 0.0486 |
| FAM83G | 2.6336 | 0.0216 | LRP5L | −29.4901 | 0.0424 |
| IFT122 | 2.6166 | 0.004 | CCNI2 | −29.2839 | 0.0151 |
| NLK | 2.5961 | 0.0162 | HES5 | −29.2459 | 0.0207 |
| PLA2G12A | 2.5949 | 0.0431 | FSTL4 | −28.8924 | 0.0349 |
| PPM1F | 2.594 | 0.0339 | EGF | −28.8183 | 0.0221 |
| SLC52A2 | 2.5563 | 0.041 | CCDC150 | −28.7454 | 0.0365 |
| HAGH | 2.5495 | 0.0117 | TRIQK | −28.5707 | 0.0286 |
| FBXO28 | 2.4864 | 0.0405 | MAD2L2 | −28.5107 | 0.0497 |
| SELO | 2.4697 | 0.0255 | ADAMTSL3 | −28.4729 | 0.0201 |
| STAMBP | 2.4509 | 0.0206 | NUSAP1 | −28.1331 | 0.0256 |
| ASPSCR1 | 2.4269 | 0.0054 | GRB10 | −27.4522 | 0.0421 |
| NAA30 | 2.4218 | 0.0474 | PLS1 | −27.2378 | 0.0454 |
| MRPL4 | 2.4063 | 0.0259 | GPR61 | −26.9031 | 0.0135 |
| MTF1 | 2.4043 | 0.0388 | EFCAB11 | −26.8626 | 0.0487 |
| COX6A1 | 2.3921 | 0.0239 | GBP4 | −26.5841 | 0.0375 |
| FRAT2 | 2.3902 | 0.0095 | SLC29A2 | −26.498 | 0.0277 |
| RUVBL2 | 2.3867 | 0.0463 | CDPF1 | −26.3582 | 0.0401 |
| TSG101 | 2.378 | 0.0282 | ITGA4 | −25.7113 | 0.0416 |
| DVL3 | 2.3747 | 0.0498 | XRRA1 | −25.6188 | 0.0375 |
| HINFP | 2.3697 | 0.0419 | AURKA | −25.5369 | 0.0379 |
| ZNF662 | 2.3487 | 0.0398 | SRRM5 | −25.4946 | 0.0467 |
| COPE | 2.3467 | 0.0345 | SPARC | −24.7261 | 0.0459 |
| GPATCH2L | 2.3286 | 0.0373 | LUM | −24.2772 | 0.0348 |
| ENTPD7 | 2.3284 | 0.0064 | ZXDA | −24.0619 | 0.0376 |
| SEMA3F | 2.3238 | 0.0191 | ENTPD1 | −23.4596 | 0.0498 |
| EMD | 2.3123 | 0.0004 | STK32C | −22.7667 | 0.0425 |
| TRIM23 | 2.2968 | 0.0071 | SERPINI1 | −22.7181 | 0.0432 |

TABLE 17-continued

Genes Significantly Modulated Between Baseline and Week 24 in Responders

| Increased Expression from Baseline to Week 24 ||| Decreased Expression from Baseline to Week 24 |||
|---|---|---|---|---|---|
| Gene Symbol | Fold Change | Raw P Value | Gene Symbol | Fold Change | Raw P Value |
| TMUB2 | 2.2907 | 0.0187 | FAM107A | −22.6607 | 0.0464 |
| TMEM9B | 2.2768 | 0.0362 | C9orf40 | −22.4845 | 0.0491 |
| EPHA2 | 2.263 | 0.0353 | CAP2 | −22.2152 | 0.0386 |
| DDX52 | 2.2627 | 0.0483 | ZFP2 | −21.7457 | 0.0045 |
| REEP3 | 2.2441 | 0.0449 | IPMK | −21.6486 | 0.0373 |
| CEBPA | 2.2405 | 0.0112 | MFSD2A | −21.5646 | 0.0363 |
| EVC2 | 2.2375 | 0.0369 | VAV2 | −21.1989 | 0.0355 |
| EGLN2 | 2.2283 | 0.0317 | ZMAT1 | −21.0583 | 0.0478 |
| HCAR2 | 2.2214 | 0.0193 | CORO7 | −20.9029 | 0.0203 |
| PAPD5 | 2.2071 | 0.0327 | LSP1 | −20.0737 | 0.0067 |
| PDK2 | 2.1998 | 0.0296 | TSC22D3 | −18.9586 | 0.0457 |
| RNASEH2C | 2.1987 | 0.0095 | TYROBP | −18.9243 | 0.0416 |
| ST3GAL4 | 2.1983 | 0.0398 | SRGN | −18.9043 | 0.0443 |
| CXCR6 | 2.1791 | 0.0068 | MAATS1 | −18.3625 | 0.0396 |
| RPP14 | 2.1707 | 0.0185 | IL17RB | −17.4369 | 0.0484 |
| WDR81 | 2.1629 | 0.0205 | PRRG3 | −17.1027 | 0.0306 |
| SPAST | 2.1592 | 0.009 | SLC9C1 | −16.544 | 0.0495 |
| NAA16 | 2.1378 | 0.0301 | GPN3 | −15.3097 | 0.0391 |
| ATP5D | 2.1311 | 0.0476 | CNR1 | −15.2997 | 0.0457 |
| SUPT4H1 | 2.1272 | 0.0193 | ADAMTS13 | −14.1636 | 0.0472 |
| SETD8 | 2.1254 | 0.039 | METTL12 | −14.087 | 0.0349 |
| SLC9A3R1 | 2.1031 | 0.049 | SLC25A2 | −13.1634 | 0.0494 |
| CCDC134 | 2.0952 | 0.0213 | ZNF367 | −13.0319 | 0.0373 |
| CHURC1 | 2.0922 | 0.0215 | PCDH9 | −12.9108 | 0.0143 |
| TRMT44 | 2.0917 | 0.0174 | CASC10 | −12.8107 | 0.0219 |
| PCDHGA11 | 2.078 | 0.0385 | PPP1R36 | −12.6748 | 0.0398 |
| SDHC | 2.0768 | 0.0403 | IGFBP2 | −12.6237 | 0.049 |
| ERVK3-1 | 2.0744 | 0.0483 | ANPEP | −12.549 | 0.0425 |
| GATS | 2.0689 | 0.0486 | ARSK | −12.4404 | 0.0344 |
| OCLN | 2.0494 | 0.0078 | POSTN | −12.3583 | 0.0333 |
| CWC25 | 2.0441 | 0.0384 | FBXL13 | −11.8859 | 0.0247 |
| APBB1 | 2.0432 | 0.0457 | CLVS2 | −11.6619 | 0.0472 |
| SIL1 | 2.0414 | 0.0157 | DGKD | −11.6574 | 0.0365 |
| RPS19BP1 | 2.0293 | 0.0166 | LDLRAD4 | −11.5383 | 0.0411 |
| TLE3 | 2.0263 | 0.0074 | MTL5 | −11.153 | 0.0382 |
| ATP13A1 | 2.0239 | 0.0365 | LYRM9 | −10.6131 | 0.0494 |
| TMEM183A | 2.0144 | 0.0325 | UAP1L1 | −9.4021 | 0.0247 |
| LLGL2 | 2.0135 | 0.0266 | TFEC | −8.9599 | 0.0356 |
| MOSPD1 | 2.0108 | 0.0312 | CEP85L | −8.7638 | 0.0349 |
| DCTD | 2.0049 | 0.0357 | RALYL | −8.212 | 0.0266 |
| CPT1A | 1.9939 | 0.0377 | ZNF850 | −7.7793 | 0.034 |
| FAM104B | 1.9774 | 0.0319 | NOVA1 | −7.6282 | 0.0354 |
| SHROOM3 | 1.9663 | 0.0218 | LRFN1 | −7.1462 | 0.0363 |
| TRAPPC3 | 1.9631 | 0.0475 | XRCC3 | −7.0565 | 0.0167 |
| MKRN1 | 1.9569 | 0.0426 | CSF3R | −6.426 | 0.041 |
| SMCR8 | 1.9398 | 0.0455 | CCND2 | −5.3947 | 0.0485 |
| PLCG1 | 1.9253 | 0.0281 | LY75 | −5.1311 | 0.0378 |
| RINT1 | 1.9171 | 0.048 | CLMN | −5.1058 | 0.032 |
| CHTF8 | 1.9151 | 0.0364 | PRKAA2 | −4.4212 | 0.0248 |
| NFATC1 | 1.8755 | 0.0219 | LYRM7 | −4.0258 | 0.0474 |
| USP10 | 1.8733 | 0.0224 | TTC22 | −3.9781 | 0.0267 |
| UQCRC1 | 1.8623 | 0.0135 | PTRF | −3.1496 | 0.0381 |
| ZNF768 | 1.858 | 0.0348 | RWDD4 | −3.1078 | 0.0381 |
| ARHGEF4 | 1.8392 | 0.039 | HAUS4 | −2.5437 | 0.0062 |
| RGL2 | 1.8375 | 0.0331 | GPRIN2 | −2.4111 | 0.0117 |
| KMT2E | 1.8351 | 0.0111 | RANBP1 | −2.3475 | 0.0498 |
| ATG16L1 | 1.8253 | 0.0482 | TSHZ1 | −2.2857 | 0.0482 |
| MORC4 | 1.8195 | 0.0296 | LETMD1 | −2.241 | 0.0113 |
| CNKSR1 | 1.8089 | 0.0318 | MYD88 | −2.1916 | 0.0221 |
| IL1RL2 | 1.8089 | 0.0482 | THUMPD3 | −2.1272 | 0.01 |
| CEBPD | 1.8067 | 0.0328 | TNFRSF14 | −2.0876 | 0.0409 |
| NIN | 1.8008 | 0.0165 | G3BP1 | −2.0353 | 0.0221 |
| JARID2 | 1.8001 | 0.0468 | NDUFS7 | −1.9952 | 0.045 |
| TNPO3 | 1.7989 | 0.0025 | PCBP4 | −1.979 | 0.0419 |
| ZNF846 | 1.7963 | 0.0271 | ESF1 | −1.9593 | 0.041 |
| SLC35A4 | 1.796 | 0.0261 | ASPH | −1.9536 | 0.0392 |
| COL16A1 | 1.795 | 0.0188 | TXK | −1.9424 | 0.02 |
| HMCES | 1.7861 | 0.0455 | PMM2 | −1.8767 | 0.0496 |
| POLG | 1.7796 | 0.0087 | LMNB2 | −1.8177 | 0.0464 |
| PPP1R2 | 1.7717 | 0.0359 | TBC1D5 | −1.8149 | 0.0495 |
| KDELR2 | 1.7572 | 0.046 | TSR1 | −1.7509 | 0.0274 |
| ANKRD27 | 1.7494 | 0.0096 | PODXL2 | −1.7508 | 0.0276 |
| MXD4 | 1.7397 | 0.0476 | SPG20 | −1.7498 | 0.0493 |

TABLE 17-continued

Genes Significantly Modulated Between Baseline and Week 24 in Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| NOMO2 | 1.7386 | 0.0434 | TEF | −1.6918 | 0.0026 |
| HES4 | 1.7374 | 0.0348 | PPT1 | −1.6881 | 0.0025 |
| NRIP1 | 1.737 | 0.0433 | PCDHGB7 | −1.6049 | 0.0305 |
| STIM1 | 1.7304 | 0.0311 | ESYT1 | −1.5984 | 0.032 |
| CNOT3 | 1.7217 | 0.0154 | AK2 | −1.5761 | 0.0429 |
| LYSMD4 | 1.7216 | 0.0257 | TIMM13 | −1.5672 | 0.0493 |
| TBK1 | 1.7158 | 0.0454 | ZNF362 | −1.5589 | 0.0076 |
| TCTN3 | 1.7114 | 0.0256 | ZNF587B | −1.5566 | 0.0358 |
| ABL2 | 1.7085 | 0.0454 | TANC1 | −1.4725 | 0.0328 |
| KIFC2 | 1.7082 | 0.0109 | MAP1B | −1.4626 | 0.0344 |
| ANAPC15 | 1.7032 | 0.0215 | DARS | −1.4286 | 0.0186 |
| MAP2K4 | 1.7031 | 0.0194 | GSTM4 | −1.3866 | 0.0182 |
| PPP6R2 | 1.7008 | 0.0182 | MAGED1 | −1.3738 | 0.0231 |
| GTF2F1 | 1.6812 | 0.0024 | RPS21 | −1.3622 | 0.0291 |
| C1orf198 | 1.6782 | 0.03 | AARS2 | −1.3422 | 0.0156 |
| C7orf60 | 1.6728 | 0.0347 | BCL6 | −1.2351 | 0.0254 |
| UBA2 | 1.671 | 0.0366 | CDK3 | −1.0356 | 0.0343 |
| SLC25A23 | 1.6698 | 0.0444 | | | |
| VEZT | 1.6693 | 0.0199 | | | |
| LRRC8A | 1.6682 | 0.0107 | | | |
| MFF | 1.668 | 0.0175 | | | |
| PLEKHF1 | 1.663 | 0.0362 | | | |
| SS18L1 | 1.6622 | 0.0051 | | | |
| AP1G1 | 1.6422 | 0.0372 | | | |
| ZNF384 | 1.6237 | 0.001 | | | |
| TECR | 1.6232 | 0.016 | | | |
| ESRP2 | 1.6132 | 0.0294 | | | |
| NDUFA10 | 1.6132 | 0.0032 | | | |
| STOML2 | 1.6124 | 0.0395 | | | |
| NIPAL1 | 1.6016 | 0.0363 | | | |
| HM13 | 1.5968 | 0.0147 | | | |
| FUS | 1.5949 | 0.0207 | | | |
| DUSP22 | 1.5812 | 0.0095 | | | |
| RNPEPL1 | 1.5778 | 0.0145 | | | |
| SMURF1 | 1.5754 | 0.0378 | | | |
| PREP | 1.5686 | 0.003 | | | |
| RNF14 | 1.5649 | 0.0473 | | | |
| BLZF1 | 1.5621 | 0.0443 | | | |
| DNAJB2 | 1.5493 | 0.0241 | | | |
| FBXO18 | 1.5407 | 0.0438 | | | |
| EIF2AK1 | 1.5379 | 0.0193 | | | |
| C9orf69 | 1.5376 | 0.0281 | | | |
| PIGO | 1.5337 | 0.0334 | | | |
| VDAC2 | 1.5215 | 0.0234 | | | |
| OTUD7B | 1.5126 | 0.0025 | | | |
| FAM129B | 1.5108 | 0.0435 | | | |
| PAPOLA | 1.4963 | 0.0227 | | | |
| RNF146 | 1.4909 | 0.0188 | | | |
| AGAP3 | 1.4896 | 0.0474 | | | |
| SSR3 | 1.4876 | 0.041 | | | |
| DDX27 | 1.4851 | 0.0137 | | | |
| MOGS | 1.4775 | 0.0039 | | | |
| ZBTB11 | 1.477 | 0.0067 | | | |
| CKAP4 | 1.4755 | 0.037 | | | |
| CHMP4B | 1.4663 | 0.0441 | | | |
| ANKRD12 | 1.4549 | 0.0016 | | | |
| AHDC1 | 1.4542 | 0.0145 | | | |
| WDR46 | 1.4483 | 0.0317 | | | |
| PRDM2 | 1.4319 | 0.0069 | | | |
| C19orf43 | 1.4275 | 0.0378 | | | |
| SLC4A2 | 1.4219 | 0.0387 | | | |
| TTYH3 | 1.421 | 0.0163 | | | |
| PPP4R2 | 1.4207 | 0.0192 | | | |
| RBM19 | 1.4204 | 0.0241 | | | |
| ACSL1 | 1.405 | 0.033 | | | |
| KAT7 | 1.4016 | 0.0307 | | | |
| SPTAN1 | 1.4 | 0.0331 | | | |
| ZNF654 | 1.3982 | 0.0419 | | | |
| KDM6B | 1.3947 | 0.0467 | | | |
| CDC42SE1 | 1.3932 | 0.044 | | | |
| CABIN1 | 1.3875 | 0.0067 | | | |
| TNFAIP2 | 1.3847 | 0.0109 | | | |
| UBE2Q1 | 1.382 | 0.0403 | | | |

TABLE 17-continued

Genes Significantly Modulated Between Baseline and Week 24 in Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| SON | 1.3584 | 0.0484 | | | |
| TXNDC16 | 1.3542 | 0.0441 | | | |
| NCOR1 | 1.3492 | 0.0045 | | | |
| FAM102A | 1.3319 | 0.003 | | | |
| IPP | 1.3303 | 0.008 | | | |
| NARFL | 1.3288 | 0.0272 | | | |
| SUGP1 | 1.3045 | 0.0112 | | | |
| KLHL24 | 1.2912 | 0.0131 | | | |
| PLCH2 | 1.285 | 0.0126 | | | |
| NPIPB5 | 1.2724 | 0.0315 | | | |
| NUPR1 | 1.2695 | 0.0036 | | | |
| RBM18 | 1.2591 | 0.0292 | | | |
| ATP2B4 | 1.2529 | 0.0208 | | | |
| AACS | 1.2472 | 0.0375 | | | |
| COX5A | 1.2307 | 0.0428 | | | |
| CUL2 | 1.2095 | 0.0484 | | | |

TABLE 18

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| MADCAM1 | 27.6015 | 0.0007 | GMFG | −22.3167 | 0.0097 |
| EVI2A | 25.3613 | 0.0015 | IL1RL1 | −22.1689 | 0.0074 |
| S100A5 | 21.2684 | 0.0021 | NIPSNAP3B | −21.7911 | 0.0031 |
| HIST2H4B | 16.2558 | 0.0112 | FMO2 | −19.3532 | 0.0037 |
| BCO1 | 15.2064 | 0.0035 | LUZP6 | −18.3831 | 0.0373 |
| GPR52 | 14.5969 | 0.0262 | TICAM2 | −17.0725 | 0.0078 |
| USP17L2 | 14.3178 | 0.0038 | RNF148 | −16.9574 | 0.0293 |
| THBS4 | 13.9528 | 0.0008 | ABHD14A | −16.9299 | 0.0072 |
| BIK | 13.8984 | 0.0169 | SIGLEC10 | −16.0127 | 0.0072 |
| ZYG11A | 11.6203 | 0.0016 | DEFB103B | −14.7613 | 0.0041 |
| RASGRP4 | 11.6041 | 0.003 | RHOF | −14.111 | 0.0338 |
| CRYGS | 11.5803 | 0.0283 | RHCG | −13.9626 | 0.0246 |
| ENTPD8 | 11.3311 | 0.0386 | CCL20 | −13.8396 | 0.0339 |
| THAP10 | 11.1195 | 0.0101 | LCE5A | −13.4353 | 0.0063 |
| MEP1B | 10.2003 | 0.0314 | C10orf128 | −13.3022 | 0.0129 |
| RAB3A | 10.1306 | 0.0064 | IL37 | −13.122 | 0.0158 |
| UBE2Q2L | 10.1167 | 0.0407 | CYP27B1 | −12.6505 | 0.0006 |
| MLXIPL | 9.975 | 0.0153 | SH3BGR | −12.366 | 0.0197 |
| MAPK12 | 9.6678 | 0.013 | VNN3 | −11.7831 | 0.0073 |
| WBP2NL | 9.3408 | 0.0155 | PRR7 | −11.7235 | 0.0434 |
| MROH7-TTC4 | 8.9094 | 0.0279 | ADCY2 | −11.6259 | 0.0144 |
| ASIC1 | 8.8674 | 0.0041 | KBTBD8 | −10.5372 | 0.0222 |
| MYEF2 | 8.7777 | 0.027 | CD28 | −10.3214 | 0.0352 |
| TSLP | 8.6794 | 0.004 | SOX10 | −10.3179 | 0.001 |
| CHRNA7 | 8.5419 | 0.006 | CD36 | −10.1313 | 0.0169 |
| PSORS1C1 | 8.2205 | 0.0498 | KRT3 | −9.945 | 0.0064 |
| ANKDD1A | 8.1112 | 0.0214 | TRIM36 | −9.6633 | 0.0104 |
| FBXO5 | 8.0028 | 0.0386 | ARL4D | −9.5441 | 0.0273 |
| BSCL2 | 7.7117 | 0.0307 | IGFN1 | −9.3742 | 0.0091 |
| AS3MT | 7.5298 | 0.0256 | S100A12 | −9.2963 | 0.0413 |
| DERL3 | 7.4784 | 0.0187 | PROX1 | −8.9646 | 0.0106 |
| UFSP1 | 7.3488 | 0.0393 | FAM19A5 | −8.8138 | 0.0147 |
| AGBL3 | 7.2792 | 0.0181 | C19orf80 | −8.659 | 0.0157 |
| AGBL4 | 7.2768 | 0.0176 | APOBEC3A | −8.5652 | 0.0249 |
| RAB42 | 7.2584 | 0.0255 | DLEU1 | −8.5213 | 0.0357 |
| YPEL1 | 7.223 | 0.0121 | PARVG | −8.4144 | 0.0464 |
| TPO | 7.1394 | 0.0135 | GSTT2B | −8.3303 | 0.0329 |
| PYROXD2 | 7.0715 | 0.0268 | SLCO4C1 | −8.0891 | 0.0272 |
| ASPDH | 7.0177 | 0.0177 | ENG | −7.819 | 0.0225 |
| UTS2 | 6.6584 | 0.0276 | RCBTB2 | −7.7833 | 0.0232 |
| GRM3 | 6.5925 | 0.0324 | GZMB | −7.7809 | 0.0456 |
| MPP3 | 6.5563 | 0.0365 | OASL | −7.7308 | 0.0217 |
| TSPYL6 | 6.5459 | 0.0399 | LY6K | −7.6642 | 0.0325 |
| NAGLU | 6.5148 | 0.0428 | VMO1 | −7.5022 | 0.0422 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| ARHGAP19-SLIT1 | 6.41 | 0.0434 | LZTS1 | −7.4675 | 0.0335 |
| FAM69B | 6.234 | 0.0474 | TF | −7.3803 | 0.0431 |
| RNASE2 | 6.2032 | 0.0428 | AMDHD1 | −7.38 | 0.0478 |
| ACKR3 | 6.2027 | 0.0272 | SLFN12 | −7.303 | 0.0095 |
| COLGALT2 | 6.2027 | 0.0218 | PPP1R14A | −7.2477 | 0.0419 |
| UGT1A4 | 6.1468 | 0.0348 | MYPN | −7.1862 | 0.0238 |
| TEKT2 | 6.0415 | 0.024 | JAKMIP1 | −7.0395 | 0.0191 |
| TMEM121 | 6.0361 | 0.0165 | AHRR | −6.9435 | 0.0297 |
| SULT1A1 | 5.8246 | 0.0382 | LGALS2 | −6.8965 | 0.0396 |
| CYP4A11 | 5.8074 | 0.0283 | TIGD3 | −6.7542 | 0.0288 |
| PRB3 | 5.797 | 0.0347 | GPRIN1 | −6.7215 | 0.0187 |
| NPIPA3 | 5.7805 | 0.0361 | CHKB-CPT1B | −6.6251 | 0.039 |
| STK31 | 5.757 | 0.0349 | NRN1 | −6.6135 | 0.0139 |
| GRID1 | 5.75 | 0.0068 | PIK3R5 | −6.6118 | 0.0383 |
| ZNF773 | 5.729 | 0.0488 | SLAMF7 | −6.5562 | 0.0484 |
| TMEM35 | 5.6621 | 0.0182 | SRGN | −6.5542 | 0.0169 |
| SYCP2L | 5.642 | 0.026 | RNF113B | −6.434 | 0.0392 |
| TMEM143 | 5.5559 | 0.0418 | TRPV2 | −6.4053 | 0.0239 |
| PDE9A | 5.5511 | 0.0287 | KRTAP5-1 | −6.2339 | 0.0342 |
| CNTN2 | 5.5263 | 0.022 | TRAF5 | −6.1305 | 0.0317 |
| RMDN2 | 5.505 | 0.0356 | PDE6A | −6.0672 | 0.0328 |
| SV2A | 5.3862 | 0.0348 | CD244 | −6.0509 | 0.0421 |
| GPR182 | 5.3123 | 0.0107 | FAM166B | −5.9975 | 0.038 |
| CCDC74B | 5.2571 | 0.0489 | DTYMK | −5.9009 | 0.0255 |
| HPDL | 5.2215 | 0.0128 | CXCR2 | −5.8694 | 0.0155 |
| SHC3 | 5.1772 | 0.0392 | KLHDC1 | −5.7732 | 0.0391 |
| ZNF222 | 5.1663 | 0.0455 | PLIN1 | −5.742 | 0.029 |
| KCTD14 | 5.1346 | 0.0421 | KCNJ2 | −5.7133 | 0.0236 |
| C4orf46 | 5.0848 | 0.0216 | ASPN | −5.6593 | 0.0227 |
| CPLX2 | 5.0008 | 0.0333 | SUV39H2 | −5.5883 | 0.0335 |
| SYT2 | 4.9878 | 0.0383 | ROPN1B | −5.533 | 0.0381 |
| MAT1A | 4.9268 | 0.0432 | VNN1 | −5.4803 | 0.018 |
| FOXE1 | 4.8759 | 0.0339 | IFI27 | −5.4264 | 0.0349 |
| INA | 4.7583 | 0.0409 | KCNG2 | −5.3548 | 0.0268 |
| ALX1 | 4.6257 | 0.0328 | LAIR1 | −5.3473 | 0.0371 |
| KBTBD12 | 4.5979 | 0.0351 | P2RX5 | −5.3335 | 0.039 |
| GINS4 | 4.5679 | 0.0456 | CHRM4 | −5.2948 | 0.0336 |
| RGS11 | 4.5219 | 0.0141 | TOR4A | −5.2677 | 0.004 |
| DCDC2B | 4.5158 | 0.0323 | HIGD1B | −5.2371 | 0.042 |
| ANKRD53 | 4.4706 | 0.0298 | RGS2 | −5.1484 | 0.0134 |
| EBLN2 | 4.4504 | 0.0266 | RNF224 | −4.9675 | 0.0442 |
| COX6B2 | 4.3655 | 0.0257 | AURKA | −4.9118 | 0.0485 |
| CHRM5 | 4.3036 | 0.0389 | LGI2 | −4.8099 | 0.0284 |
| TTC34 | 4.274 | 0.0394 | SLC22A13 | −4.7851 | 0.0416 |
| ADPRM | 4.2277 | 0.0448 | MLC1 | −4.7144 | 0.0305 |
| C9orf66 | 4.2211 | 0.0339 | TLR3 | −4.7066 | 0.0429 |
| MAP1S | 4.1703 | 0.0454 | HHEX | −4.7002 | 0.0388 |
| CYP4F11 | 4.1295 | 0.0493 | C8orf48 | −4.6899 | 0.0382 |
| LY6G5B | 4.093 | 0.0488 | TIMM8A | −4.5289 | 0.0318 |
| HEATR4 | 3.9807 | 0.0423 | TTC25 | −4.4167 | 0.0396 |
| SHISA6 | 3.9742 | 0.0442 | KRT72 | −4.3577 | 0.0397 |
| TPST1 | 3.9197 | 0.0379 | KCNMB3 | −4.2805 | 0.0257 |
| KCTD19 | 3.9047 | 0.0402 | HAPLN4 | −4.2381 | 0.0472 |
| CDHR2 | 3.8518 | 0.0391 | CCDC69 | −4.203 | 0.0488 |
| ZNF454 | 3.8193 | 0.0491 | TMBIM4 | −4.1761 | 0.0273 |
| DGKG | 3.8179 | 0.0189 | BMP5 | −4.1521 | 0.0233 |
| TRIM45 | 3.7012 | 0.0495 | GPRC5A | −4.1494 | 0.0183 |
| PCYT1B | 3.6534 | 0.0363 | GPD2 | −4.1448 | 0.0444 |
| ZNF696 | 3.5396 | 0.0301 | ZNF668 | −4.1396 | 0.0428 |
| RNF165 | 3.536 | 0.0369 | SERPINB3 | −4.0734 | 0.0235 |
| RBM44 | 3.5063 | 0.0106 | PPP1R16B | −4.0259 | 0.0093 |
| PRICKLE4 | 3.4544 | 0.0447 | NTSR1 | −3.9405 | 0.0434 |
| PCDHAC1 | 3.3838 | 0.0156 | PTAFR | −3.9092 | 0.0477 |
| MAST1 | 3.3258 | 0.0467 | AVPR1A | −3.907 | 0.0044 |
| COL14A1 | 3.3194 | 0.0444 | STARD8 | −3.8533 | 0.0246 |
| ISY1-RAB43 | 3.2156 | 0.0306 | C15orf53 | −3.6751 | 0.0462 |
| SPRED3 | 3.2113 | 0.004 | ADCY7 | −3.6529 | 0.0156 |
| DET1 | 3.1417 | 0.0322 | PIK3R6 | −3.6311 | 0.0264 |
| CCDC168 | 3.0629 | 0.0279 | ZIC2 | −3.6198 | 0.0249 |
| FAM9C | 2.9715 | 0.0439 | ZNF490 | −3.5651 | 0.0493 |
| PDZD7 | 2.957 | 0.024 | CLDN14 | −3.5193 | 0.0385 |
| GPR179 | 2.9457 | 0.0181 | NUDT2 | −3.5151 | 0.0464 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| NPDC1 | 2.9016 | 0.0258 | FOXP3 | −3.4118 | 0.0275 |
| KIF12 | 2.9003 | 0.0157 | APBB1IP | −3.3841 | 0.0244 |
| DCHS1 | 2.7724 | 0.0288 | EIF3C | −3.3247 | 0.0213 |
| KIF7 | 2.7666 | 0.017 | ACTR5 | −3.2145 | 0.0319 |
| ZNF799 | 2.7127 | 0.0494 | RPS6KA5 | −3.1343 | 0.0376 |
| RPS6KL1 | 2.6129 | 0.04 | C4orf27 | −3.1257 | 0.0253 |
| ZNF717 | 2.5241 | 0.0163 | FUT2 | −3.0804 | 0.0348 |
| ARMC7 | 2.4962 | 0.0019 | LCE3E | −3.0756 | 0.0024 |
| ATHL1 | 2.3694 | 0.0467 | HIST3H2BB | −3.0463 | 0.0407 |
| B3GNT9 | 2.3402 | 0.0426 | ARC | −3.0248 | 0.0423 |
| GIN1 | 2.2823 | 0.0085 | SPRR2A | −3.0167 | 0.0345 |
| RNLS | 2.2603 | 0.0203 | DOCK11 | −2.9427 | 0.0164 |
| EFEMP2 | 2.2448 | 0.0377 | KRT78 | −2.8669 | 0.0053 |
| GDF11 | 2.2028 | 0.0292 | WAS | −2.8546 | 0.0369 |
| VAMP1 | 2.1104 | 0.0086 | RTL1 | −2.852 | 0.0458 |
| PITPNM2 | 2.0924 | 0.044 | TCEANC | −2.8089 | 0.011 |
| NUP35 | 2.0831 | 0.0019 | FAM25A | −2.6398 | 0.0004 |
| CDC25B | 2.068 | 0.0423 | G0S2 | −2.6281 | 0.037 |
| XPNPEP3 | 2.0478 | 0.0119 | CD3G | −2.5886 | 0.0351 |
| ANKRD9 | 2.0415 | 0.0129 | SPRR2G | −2.5758 | 0.027 |
| NID2 | 2.0359 | 0.0405 | GPN3 | −2.5708 | 0.0125 |
| TK2 | 2.0105 | 0.0346 | SEL1L3 | −2.5671 | 0.038 |
| SLC47A1 | 1.998 | 0.0381 | CSF1R | −2.5368 | 0.0412 |
| FAM20C | 1.9903 | 0.0498 | CETN3 | −2.4829 | 0.0161 |
| NSUN4 | 1.9577 | 0.0448 | STXBP6 | −2.468 | 0.0065 |
| ZDHHC1 | 1.9446 | 0.0171 | MSRB2 | −2.4649 | 0.0437 |
| EIF3CL | 1.9147 | 0.0137 | CD209 | −2.4462 | 0.0496 |
| ACACB | 1.9112 | 0.0473 | MRPL39 | −2.4296 | 0.0129 |
| FAM213B | 1.8976 | 0.0267 | NCOA7 | −2.38 | 0.0136 |
| GNB1L | 1.8789 | 0.01 | C9orf85 | −2.3763 | 0.0349 |
| NME6 | 1.8707 | 0.0097 | PTPMT1 | −2.3581 | 0.0248 |
| ZNF358 | 1.8663 | 0.0053 | COX14 | −2.3346 | 0.0071 |
| SOX8 | 1.8525 | 0.0332 | LCE3D | −2.2937 | 0.0431 |
| C19orf48 | 1.8457 | 0.013 | SLC43A2 | −2.2909 | 0.0474 |
| RAC3 | 1.8405 | 0.0318 | SLC20A1 | −2.2879 | 0.0421 |
| SMIM8 | 1.8085 | 0.0292 | MLF1 | −2.26 | 0.0347 |
| DDX51 | 1.7997 | 0.0428 | FAM185A | −2.2522 | 0.0245 |
| ZNF785 | 1.7908 | 0.0171 | MRPL15 | −2.2193 | 0.0185 |
| RRP8 | 1.7884 | 0.0409 | B3GALT4 | −2.2061 | 0.0213 |
| POLR2H | 1.786 | 0.0151 | TBC1D12 | −2.183 | 0.0436 |
| ARHGAP24 | 1.7854 | 0.0219 | FCHSD1 | −2.1791 | 0.031 |
| ARNT2 | 1.785 | 0.0093 | DNASE1L2 | −2.1662 | 0.0445 |
| PCDH12 | 1.7803 | 0.0248 | PNPLA1 | −2.156 | 0.0076 |
| IVD | 1.7686 | 0.0312 | ABHD17B | −2.1475 | 0.0047 |
| ZNF484 | 1.746 | 0.0095 | CARD16 | −2.1366 | 0.0288 |
| MARCH5 | 1.739 | 0.0152 | IL6R | −2.1301 | 0.0109 |
| TFAM | 1.7294 | 0.0052 | HIST1H4B | −2.1092 | 0.014 |
| MRPL14 | 1.7167 | 0.0295 | PTS | −2.0901 | 0.0276 |
| TSHZ1 | 1.7159 | 0.0484 | ANAPC13 | −2.0894 | 0.0188 |
| FEM1A | 1.7134 | 0.0187 | DCTN5 | −2.0889 | 0.001 |
| R3HCC1 | 1.7112 | 0.0105 | FAM110C | −2.0776 | 0.0038 |
| C1orf174 | 1.7009 | 0.0292 | GOLGA8F | −2.0534 | 0.0477 |
| IPMK | 1.6975 | 0.0123 | SPRR2E | −2.0439 | 0.0024 |
| ZNF500 | 1.6929 | 0.0455 | GNA12 | −2.0286 | 0.0443 |
| TUBGCP5 | 1.6922 | 0.0484 | ZNF584 | −2.0169 | 0.0115 |
| MR1 | 1.6913 | 0.0051 | GPX3 | −2.0139 | 0.0464 |
| FAM89B | 1.681 | 0.0222 | RIPK2 | −2.0049 | 0.0083 |
| TMEM80 | 1.677 | 0.0414 | LCE6A | −1.9922 | 0.0321 |
| SLC44A3 | 1.6556 | 0.0416 | RNF180 | −1.9829 | 0.0073 |
| PLTP | 1.6543 | 0.0335 | GNB5 | −1.9531 | 0.0465 |
| FASTKD2 | 1.6536 | 0.0098 | SDR9C7 | −1.9516 | 0.0005 |
| TYK2 | 1.6521 | 0.0414 | DUSP5 | −1.9484 | 0.0168 |
| CEP89 | 1.6498 | 0.0147 | ETS1 | −1.9476 | 0.0412 |
| ANAPC4 | 1.6404 | 0.0187 | PLA2G2F | −1.9275 | 0.0379 |
| TTYH1 | 1.6205 | 0.0301 | YOD1 | −1.9234 | 0.0003 |
| ZNF574 | 1.616 | 0.014 | TRAPPC1 | −1.9138 | 0.0339 |
| PARP2 | 1.6149 | 0.0364 | ZDHHC13 | −1.9113 | 0.0372 |
| NEU1 | 1.6133 | 0.0305 | MARVELD3 | −1.9109 | 0.0275 |
| STARD3 | 1.5994 | 0.046 | ZNF16 | −1.9062 | 0.0374 |
| CBX7 | 1.5991 | 0.0137 | PRELID3B | −1.8833 | 0.0175 |
| CBLC | 1.5975 | 0.0488 | TMLHE | −1.8685 | 0.0325 |
| ZNF529 | 1.5958 | 0.0115 | SLC36A1 | −1.8658 | 0.0376 |
| CADM1 | 1.5941 | 0.0097 | CCL22 | −1.8563 | 0.0346 |

TABLE 18-continued

Genes Significantly Modulated Between Baseline and Week 24 in Non-Responders

| Increased Expression from Baseline to Week 24 ||| Decreased Expression from Baseline to Week 24 |||
| --- | --- | --- | --- | --- | --- |
| Gene Symbol | Fold Change | Raw P Value | Gene Symbol | Fold Change | Raw P Value |
| ABCB6 | 1.5753 | 0.0179 | ZFAND2A | −1.8553 | 0.0436 |
| ZC2HC1A | 1.5687 | 0.0397 | MAP1LC3A | −1.8522 | 0.0095 |
| MTSS1L | 1.5593 | 0.0181 | RHOQ | −1.8521 | 0.0337 |
| LONRF1 | 1.5555 | 0.0374 | ARNTL | −1.8509 | 0.0325 |
| PAXBP1 | 1.5555 | 0.0102 | INPP5D | −1.8454 | 0.027 |
| SMO | 1.5445 | 0.0114 | SPTBN5 | −1.8452 | 0.0221 |
| THNSL2 | 1.543 | 0.0113 | PRSS3 | −1.8422 | 0.0492 |
| TULP3 | 1.5357 | 0.0378 | MPDU1 | −1.8281 | 0.0308 |
| CNGA1 | 1.524 | 0.0361 | MPST | −1.8255 | 0.0228 |
| PACS2 | 1.519 | 0.0117 | SMOX | −1.8246 | 0.0122 |
| RAB3IP | 1.5134 | 0.0007 | MRPL30 | −1.8185 | 0.0147 |
| TBC1D16 | 1.5078 | 0.0113 | NOS3 | −1.8178 | 0.0274 |
| ZNF316 | 1.5078 | 0.0084 | ARNTL2 | −1.8116 | 0.0408 |
| CDK4 | 1.5049 | 0.0196 | LIMS1 | −1.8077 | 0.0265 |
| CTBP2 | 1.501 | 0.0397 | BCKDK | −1.7907 | 0.0102 |
| NOL9 | 1.4991 | 0.0188 | ABHD12B | −1.783 | 0.003 |
| MEX3D | 1.4985 | 0.0228 | HIST1H4C | −1.7668 | 0.0292 |
| TC2N | 1.4963 | 0.0044 | SLC19A2 | −1.7647 | 0.0356 |
| NEIL1 | 1.4926 | 0.0479 | RAP1B | −1.764 | 0.0111 |
| TMEM181 | 1.4892 | 0.0037 | UBL3 | −1.7629 | 0.0069 |
| FZD8 | 1.4746 | 0.04 | NAA20 | −1.7564 | 0.0237 |
| MRPS16 | 1.4726 | 0.0412 | EXOC5 | −1.7555 | 0.0241 |
| PCNXL4 | 1.4664 | 0.032 | ZNF248 | −1.7545 | 0.0341 |
| TRIM8 | 1.4615 | 0.0303 | TBC1D23 | −1.7528 | 0.022 |
| DHRS3 | 1.4609 | 0.0161 | CCDC124 | −1.7484 | 0.0352 |
| RGL2 | 1.4604 | 0.0012 | RAB23 | −1.7364 | 0.0327 |
| EXOC3 | 1.4509 | 0.0025 | PAPL | −1.7334 | 0.0094 |
| PER2 | 1.4369 | 0.0293 | PHLDA2 | −1.7326 | 0.0389 |
| ASPH | 1.4367 | 0.0368 | TSSC1 | −1.7263 | 0.0443 |
| HKR1 | 1.4322 | 0.0451 | POLD3 | −1.726 | 0.0298 |
| ARL10 | 1.4309 | 0.0168 | MPV17 | −1.7246 | 0.036 |
| TASP1 | 1.4307 | 0.0355 | CEMIP | −1.7239 | 0.02 |
| RCN1 | 1.4224 | 0.0146 | GULP1 | −1.7222 | 0.0476 |
| TNS1 | 1.4221 | 0.0436 | NCCRP1 | −1.7216 | 0.0013 |
| REV1 | 1.4168 | 0.0298 | TM2D1 | −1.7173 | 0.0044 |
| BIN3 | 1.4116 | 0.0472 | MYO1B | −1.7131 | 0.0018 |
| RHOV | 1.4116 | 0.0186 | C2orf47 | −1.7098 | 0.0486 |
| PLAGL2 | 1.4073 | 0.0028 | RNASE7 | −1.6985 | 0.0398 |
| FAM53C | 1.4072 | 0.0213 | TMEM127 | −1.6948 | 0.0164 |
| SCAF1 | 1.4053 | 0.0016 | TMEM11 | −1.6876 | 0.0443 |
| TSPYL5 | 1.3949 | 0.0198 | NT5C3A | −1.6864 | 0.0087 |
| PDCD5 | 1.3899 | 0.0011 | ESD | −1.6832 | 0.0341 |
| MEX3C | 1.3871 | 0.0381 | GADD45A | −1.6793 | 0.015 |
| ADPRHL2 | 1.3855 | 0.0444 | AIM1 | −1.6698 | 0.038 |
| ZBTB4 | 1.3837 | 0.0237 | GCOM1 | −1.6691 | 0.0128 |
| SMPD4 | 1.3832 | 0.011 | ACTR10 | −1.6639 | 0.0274 |
| FAM189B | 1.383 | 0.0178 | AK9 | −1.6629 | 0.0471 |
| GYS1 | 1.3784 | 0.042 | FAM98A | −1.6616 | 0.007 |
| FRAT2 | 1.3756 | 0.0102 | TMEM86A | −1.6601 | 0.0072 |
| PKD1 | 1.374 | 0.0367 | MRPL27 | −1.6542 | 0.0028 |
| ARID2 | 1.3706 | 0.0329 | HERC6 | −1.6508 | 5.71E−05 |
| FGD1 | 1.3669 | 0.0188 | ERN1 | −1.6493 | 0.0114 |
| GPAA1 | 1.3609 | 0.038 | NAA10 | −1.648 | 0.0232 |
| MYSM1 | 1.3578 | 0.0212 | SLC10A6 | −1.6437 | 0.0277 |
| ZNF623 | 1.3561 | 0.0106 | RBPJ | −1.6436 | 0.029 |
| TOPBP1 | 1.3549 | 0.01 | LCE2C | −1.642 | 0.0318 |
| CACNB1 | 1.3537 | 0.0424 | SEMA7A | −1.6327 | 0.0033 |
| BTBD7 | 1.3428 | 0.0311 | RNGTT | −1.632 | 0.0064 |
| PEX14 | 1.3404 | 0.0399 | USP2 | −1.6284 | 0.0306 |
| STK35 | 1.3378 | 0.0185 | CHURC1 | −1.6274 | 0.0014 |
| NFXL1 | 1.3373 | 0.0184 | SPATS2L | −1.626 | 0.008 |
| PLEKHG5 | 1.3348 | 0.0384 | BZW1 | −1.6243 | 0.0034 |
| MAN2B2 | 1.3277 | 0.026 | ABHD5 | −1.6219 | 0.0132 |
| XPO7 | 1.3258 | 0.0498 | HK2 | −1.6217 | 0.0443 |
| GAS1 | 1.3212 | 0.0324 | AZGP1 | −1.6203 | 0.0214 |
| SNX17 | 1.3212 | 0.0206 | CASP7 | −1.6192 | 0.0045 |
| MAST2 | 1.3045 | 0.033 | SLC5A1 | −1.618 | 0.008 |
| TRAF3IP2 | 1.2978 | 0.0286 | RAP1GDS1 | −1.6172 | 0.0033 |
| UBE2I | 1.2935 | 0.0322 | TVP23B | −1.6152 | 0.0291 |
| IGF1R | 1.289 | 0.0067 | MRPS25 | −1.615 | 0.0317 |
| LDB1 | 1.2829 | 0.0019 | MINPP1 | −1.612 | 0.0296 |
| RIPK4 | 1.2752 | 0.0235 | CPA4 | −1.6102 | 0.0133 |
| SRRT | 1.2673 | 0.0313 | ATG9B | −1.6079 | 0.0419 |

TABLE 18-continued

Genes Significantly Modulated Between Baseline and Week 24 in Non-Responders

| Increased Expression from Baseline to Week 24 ||| Decreased Expression from Baseline to Week 24 |||
| --- | --- | --- | --- | --- | --- |
| Gene Symbol | Fold Change | Raw P Value | Gene Symbol | Fold Change | Raw P Value |
| TOM1L2 | 1.254 | 0.0306 | CNFN | −1.6073 | 0.02 |
| NOTCH3 | 1.2513 | 0.03 | UBB | −1.6053 | 0.0014 |
| SNRNP70 | 1.2481 | 0.046 | GNPTAB | −1.6027 | 0.039 |
| MBD6 | 1.246 | 0.0256 | SNRPG | −1.596 | 0.0494 |
| VPS36 | 1.2454 | 0.0256 | ARHGAP29 | −1.5928 | 0.0322 |
| ZNF207 | 1.2452 | 0.0386 | USF1 | −1.5874 | 0.0386 |
| KANSL1 | 1.2397 | 0.0313 | ZNF330 | −1.5849 | 0.0195 |
| HNRNPD | 1.2357 | 0.0209 | NBN | −1.583 | 0.0384 |
| RNMT | 1.2177 | 0.0422 | HIST1H1B | −1.5817 | 0.0218 |
| SMAD5 | 1.2141 | 0.0237 | PIM1 | −1.581 | 0.04 |
| ZFP36L1 | 1.2025 | 0.0203 | GSDMA | −1.5778 | 0.0068 |
| ATXN7L3 | 1.201 | 0.0141 | UBE2D3 | −1.5735 | 0.01 |
| SIN3B | 1.1983 | 0.0224 | CDC34 | −1.5732 | 0.0273 |
| IRX3 | 1.1959 | 0.0451 | PCNP | −1.568 | 0.0475 |
| EFS | 1.1946 | 0.0277 | SLC35E3 | −1.5657 | 0.0156 |
| PLCH2 | 1.1917 | 0.0243 | YWHAH | −1.5657 | 0.0098 |
| CIC | 1.1774 | 0.0061 | C18orf25 | −1.5611 | 0.0313 |
| CREBBP | 1.1736 | 0.0258 | RPRD1B | −1.5569 | 0.0442 |
| ZFP36L2 | 1.173 | 0.0168 | UBE2J1 | −1.5485 | 0.0292 |
| DOCK7 | 1.1723 | 0.0045 | MRPL32 | −1.5465 | 0.0406 |
| IQSEC1 | 1.162 | 0.048 | ECHDC1 | −1.5434 | 0.0362 |
| DDR1 | 1.1618 | 0.0261 | PDE12 | −1.5349 | 0.0472 |
| SUV420H1 | 1.1548 | 0.0457 | ZNF649 | −1.5338 | 0.0147 |
| MBD2 | 1.119 | 0.0409 | DNAJB1 | −1.5334 | 0.0017 |
| | | | CHIC2 | −1.5332 | 0.0359 |
| | | | CNST | −1.5303 | 0.0152 |
| | | | NUP107 | −1.5272 | 0.045 |
| | | | ZNF720 | −1.5207 | 0.0359 |
| | | | PLA2G4D | −1.5181 | 0.0315 |
| | | | STXBP3 | −1.518 | 0.0229 |
| | | | SSNA1 | −1.5168 | 0.0398 |
| | | | BAG5 | −1.5158 | 0.0015 |
| | | | PRKCH | −1.5157 | 0.01 |
| | | | ARHGAP30 | −1.5151 | 0.0477 |
| | | | PPP1R18 | −1.5143 | 0.0216 |
| | | | USP38 | −1.5138 | 0.0377 |
| | | | SLC31A2 | −1.5136 | 0.0419 |
| | | | NUB1 | −1.5101 | 0.0086 |
| | | | SEPT11 | −1.5075 | 0.0388 |
| | | | SUB1 | −1.5053 | 0.0269 |
| | | | TIMM21 | −1.4994 | 0.0417 |
| | | | MRPL49 | −1.4981 | 0.0257 |
| | | | DENR | −1.487 | 0.0274 |
| | | | TRABD | −1.4869 | 0.0348 |
| | | | VMP1 | −1.4868 | 0.0465 |
| | | | FNDC3A | −1.4825 | 0.0115 |
| | | | SIL1 | −1.4815 | 0.0127 |
| | | | MAP1LC3B | −1.4758 | 0.038 |
| | | | WWC1 | −1.4749 | 0.0404 |
| | | | POLR3B | −1.4745 | 0.0212 |
| | | | VSIG10L | −1.4732 | 0.0134 |
| | | | BLOC1S1 | −1.473 | 0.0469 |
| | | | SHPK | −1.4715 | 0.0309 |
| | | | PI4K2A | −1.4714 | 0.0311 |
| | | | TNIP1 | −1.471 | 0.0008 |
| | | | ZNF706 | −1.4695 | 0.0366 |
| | | | CORO1C | −1.4673 | 0.0345 |
| | | | PLEKHB2 | −1.4646 | 0.0055 |
| | | | ALDH7A1 | −1.4641 | 0.0251 |
| | | | TOMM5 | −1.4639 | 0.0399 |
| | | | ADTRP | −1.462 | 0.0229 |
| | | | SLC6A14 | −1.4614 | 0.0223 |
| | | | CSRNP1 | −1.4595 | 0.0091 |
| | | | FAF2 | −1.457 | 0.0056 |
| | | | MRPL44 | −1.4529 | 0.0283 |
| | | | UGCG | −1.4494 | 0.0216 |
| | | | SYNJ2 | −1.4479 | 0.0404 |
| | | | PDLIM2 | −1.4444 | 0.006 |
| | | | AK3 | −1.4361 | 0.0358 |
| | | | DERL1 | −1.4357 | 0.0305 |
| | | | TMEM179B | −1.4357 | 0.0194 |
| | | | SNF8 | −1.4332 | 0.0489 |
| | | | MGLL | −1.4306 | 0.0327 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| | | | GSE1 | −1.4247 | 0.0324 |
| | | | CIRH1A | −1.4201 | 0.0236 |
| | | | HEXA | −1.417 | 0.0329 |
| | | | SYNJ1 | −1.4159 | 0.0369 |
| | | | ZNF440 | −1.4142 | 0.0323 |
| | | | PPARD | −1.414 | 0.0131 |
| | | | HYOU1 | −1.4135 | 0.0046 |
| | | | ARL13B | −1.4122 | 0.0417 |
| | | | PLCXD1 | −1.4108 | 0.0348 |
| | | | CRCT1 | −1.4069 | 0.0325 |
| | | | PPP1R15B | −1.405 | 0.0255 |
| | | | TTYH3 | −1.4035 | 0.0153 |
| | | | GBA | −1.4003 | 0.0395 |
| | | | ARRDC4 | −1.3999 | 0.0042 |
| | | | DDX52 | −1.3964 | 0.0404 |
| | | | CFL1 | −1.3955 | 0.0493 |
| | | | RABGEF1 | −1.3923 | 0.0238 |
| | | | ARHGEF10L | −1.3921 | 0.042 |
| | | | GNPAT | −1.3896 | 0.0473 |
| | | | NFYA | −1.3888 | 0.0287 |
| | | | SFT2D2 | −1.388 | 0.0387 |
| | | | ZNF213 | −1.3874 | 0.0437 |
| | | | NADK | −1.3873 | 0.0021 |
| | | | SH3BP5L | −1.3827 | 0.0087 |
| | | | MXD1 | −1.382 | 0.0308 |
| | | | DHRS7 | −1.3803 | 0.0389 |
| | | | RAB24 | −1.3771 | 0.0378 |
| | | | LNX1 | −1.3769 | 0.0218 |
| | | | PSD4 | −1.373 | 0.0093 |
| | | | ATP6V1C2 | −1.3717 | 0.0136 |
| | | | TMED9 | −1.371 | 0.0377 |
| | | | PDCD7 | −1.3706 | 0.0474 |
| | | | H2AFY | −1.3699 | 0.049 |
| | | | ALAS1 | −1.3692 | 0.032 |
| | | | NCOA3 | −1.3678 | 0.023 |
| | | | SDCCAG8 | −1.3678 | 0.0196 |
| | | | KATNB1 | −1.3677 | 0.0328 |
| | | | AP5Z1 | −1.3664 | 0.0149 |
| | | | ADIPOR1 | −1.3654 | 0.0443 |
| | | | TMPRSS13 | −1.3611 | 0.0285 |
| | | | SNX9 | −1.3605 | 0.0224 |
| | | | PPP2CA | −1.3592 | 0.0465 |
| | | | GPR137B | −1.3585 | 0.0428 |
| | | | EHD1 | −1.3582 | 0.0131 |
| | | | DENND2C | −1.3558 | 0.0144 |
| | | | CHTF8 | −1.3535 | 0.0141 |
| | | | PLK3 | −1.349 | 0.0139 |
| | | | CTSB | −1.3444 | 0.0441 |
| | | | PIEZO1 | −1.3433 | 0.0008 |
| | | | ERH | −1.3384 | 0.0422 |
| | | | ITFG1 | −1.3382 | 0.0356 |
| | | | RND3 | −1.3368 | 0.0298 |
| | | | IRF2 | −1.3364 | 0.0324 |
| | | | PTPN2 | −1.3363 | 0.0424 |
| | | | FBXW11 | −1.3355 | 0.0431 |
| | | | ITSN2 | −1.3354 | 0.0054 |
| | | | MAP2K3 | −1.3315 | 0.0374 |
| | | | GTPBP2 | −1.3304 | 0.0303 |
| | | | SBSN | −1.3301 | 0.0467 |
| | | | LIMA1 | −1.3288 | 0.0293 |
| | | | EPG5 | −1.3268 | 0.0308 |
| | | | TWISTNB | −1.326 | 0.028 |
| | | | EPT1 | −1.3252 | 0.0184 |
| | | | SPIRE1 | −1.324 | 0.0058 |
| | | | LAMP2 | −1.3221 | 0.0175 |
| | | | COPB2 | −1.3193 | 0.0325 |
| | | | GAS6 | −1.3184 | 0.0451 |
| | | | LMTK3 | −1.3184 | 0.0421 |
| | | | BCR | −1.3173 | 0.0251 |
| | | | TCP11L2 | −1.3165 | 0.0246 |
| | | | AHCYL1 | −1.3145 | 0.0047 |
| | | | HMGN2 | −1.3145 | 0.0141 |
| | | | MYO9B | −1.3112 | 0.0113 |

TABLE 18-continued

Genes Significantly Modulated Between Baseline and Week 24 in Non-Responders

Increased Expression from Baseline to Week 24 | Decreased Expression from Baseline to Week 24

| Gene Symbol | Fold Change | Raw P Value | Gene Symbol | Fold Change | Raw P Value |
| --- | --- | --- | --- | --- | --- |
| | | | PPP2R2C | −1.3073 | 0.0332 |
| | | | ARPC5 | −1.3065 | 0.0351 |
| | | | ATP2C1 | −1.3047 | 0.0206 |
| | | | TBC1D20 | −1.3043 | 0.0417 |
| | | | MAPKAPK5 | −1.3018 | 0.0068 |
| | | | WWTR1 | −1.2981 | 0.0469 |
| | | | SDE2 | −1.2972 | 0.0283 |
| | | | NDUFA13 | −1.2936 | 0.0337 |
| | | | EDEMI | −1.2917 | 0.0304 |
| | | | HEATR5B | −1.2866 | 0.0276 |
| | | | CHMP4C | −1.2862 | 0.0302 |
| | | | CTTNBP2NL | −1.2817 | 0.0229 |
| | | | RSF1 | −1.2789 | 0.012 |
| | | | RPS26 | −1.2758 | 0.0385 |
| | | | PRMT2 | −1.2753 | 0.0261 |
| | | | RBM10 | −1.2741 | 0.0361 |
| | | | TAF7 | −1.2737 | 0.025 |
| | | | JARID2 | −1.2729 | 0.0219 |
| | | | PSMD3 | −1.2716 | 0.0312 |
| | | | COL5A2 | −1.2659 | 0.0478 |
| | | | ZNF212 | −1.2542 | 0.031 |
| | | | UBR1 | −1.2539 | 0.0462 |
| | | | IMMT | −1.2534 | 0.0354 |
| | | | TBC1D10B | −1.2483 | 0.0209 |
| | | | FNBP1 | −1.2453 | 0.0353 |
| | | | STAM2 | −1.2398 | 0.0137 |
| | | | PCLO | −1.2393 | 0.0119 |
| | | | TTC19 | −1.2369 | 0.0248 |
| | | | RAB7A | −1.2359 | 0.0361 |
| | | | EPS15 | −1.235 | 0.0398 |
| | | | PICALM | −1.2347 | 0.026 |
| | | | PELI1 | −1.2318 | 0.0416 |
| | | | CUL1 | −1.2268 | 0.0027 |
| | | | ENSA | −1.2222 | 0.0155 |
| | | | CYFIP1 | −1.2184 | 0.0182 |
| | | | KDM1B | −1.2178 | 0.0474 |
| | | | EPS8L1 | −1.2091 | 0.047 |
| | | | RTFDC1 | −1.209 | 0.0493 |
| | | | MARVELD2 | −1.2083 | 0.036 |
| | | | COPA | −1.2072 | 0.0353 |
| | | | KPNB1 | −1.2072 | 0.0224 |
| | | | ITGAV | −1.2026 | 0.0359 |
| | | | PCF11 | −1.1978 | 0.019 |
| | | | NDUFS1 | −1.1881 | 0.0323 |
| | | | ITPKC | −1.1866 | 0.0212 |
| | | | KHSRP | −1.1825 | 0.0257 |
| | | | PAPD4 | −1.1728 | 0.0378 |
| | | | DDX18 | −1.1521 | 0.0177 |
| | | | GMFG | −22.3167 | 0.0097 |
| | | | IL1RL1 | −22.1689 | 0.0074 |
| | | | NIPSNAP3B | −21.7911 | 0.0031 |
| | | | FMO2 | −19.3532 | 0.0037 |
| | | | LUZP6 | −18.3831 | 0.0373 |
| | | | TICAM2 | −17.0725 | 0.0078 |
| | | | RNF148 | −16.9574 | 0.0293 |
| | | | ABHD14A | −16.9299 | 0.0072 |
| | | | SIGLEC10 | −16.0127 | 0.0072 |
| | | | DEFB103B | −14.7613 | 0.0041 |
| | | | RHOF | −14.111 | 0.0338 |
| | | | RHCG | −13.9626 | 0.0246 |
| | | | CCL20 | −13.8396 | 0.0339 |
| | | | LCE5A | −13.4353 | 0.0063 |
| | | | C10orf128 | −13.3022 | 0.0129 |
| | | | IL37 | −13.122 | 0.0158 |
| | | | CYP27B1 | −12.6505 | 0.0006 |
| | | | SH3BGR | −12.366 | 0.0197 |
| | | | VNN3 | −11.7831 | 0.0073 |
| | | | PRR7 | −11.7235 | 0.0434 |
| | | | ADCY2 | −11.6259 | 0.0144 |
| | | | KBTBD8 | −10.5372 | 0.0222 |
| | | | CD28 | −10.3214 | 0.0352 |
| | | | SOX10 | −10.3179 | 0.001 |
| | | | CD36 | −10.1313 | 0.0169 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| | | | KRT3 | −9.945 | 0.0064 |
| | | | TRIM36 | −9.6633 | 0.0104 |
| | | | ARL4D | −9.5441 | 0.0273 |
| | | | IGFN1 | −9.3742 | 0.0091 |
| | | | S100A12 | −9.2963 | 0.0413 |
| | | | PROX1 | −8.9646 | 0.0106 |
| | | | FAM19A5 | −8.8138 | 0.0147 |
| | | | C19orf80 | −8.659 | 0.0157 |
| | | | APOBEC3A | −8.5652 | 0.0249 |
| | | | DLEU1 | −8.5213 | 0.0357 |
| | | | PARVG | −8.4144 | 0.0464 |
| | | | GSTT2B | −8.3303 | 0.0329 |
| | | | SLCO4C1 | −8.0891 | 0.0272 |
| | | | ENG | −7.819 | 0.0225 |
| | | | RCBTB2 | −7.7833 | 0.0232 |
| | | | GZMB | −7.7809 | 0.0456 |
| | | | OASL | −7.7308 | 0.0217 |
| | | | LY6K | −7.6642 | 0.0325 |
| | | | VMO1 | −7.5022 | 0.0422 |
| | | | LZTS1 | −7.4675 | 0.0335 |
| | | | TF | −7.3803 | 0.0431 |
| | | | AMDHD1 | −7.38 | 0.0478 |
| | | | SLFN12 | −7.303 | 0.0095 |
| | | | PPP1R14A | −7.2477 | 0.0419 |
| | | | MYPN | −7.1862 | 0.0238 |
| | | | JAKMIP1 | −7.0395 | 0.0191 |
| | | | AHRR | −6.9435 | 0.0297 |
| | | | LGALS2 | −6.8965 | 0.0396 |
| | | | TIGD3 | −6.7542 | 0.0288 |
| | | | GPRIN1 | −6.7215 | 0.0187 |
| | | | CHKB-CPT1B | −6.6251 | 0.039 |
| | | | NRN1 | −6.6135 | 0.0139 |
| | | | PIK3R5 | −6.6118 | 0.0383 |
| | | | SLAMF7 | −6.5562 | 0.0484 |
| | | | SRGN | −6.5542 | 0.0169 |
| | | | RNF113B | −6.434 | 0.0392 |
| | | | TRPV2 | −6.4053 | 0.0239 |
| | | | KRTAP5-1 | −6.2339 | 0.0342 |
| | | | TRAF5 | −6.1305 | 0.0317 |
| | | | PDE6A | −6.0672 | 0.0328 |
| | | | CD244 | −6.0509 | 0.0421 |
| | | | FAM166B | −5.9975 | 0.038 |
| | | | DTYMK | −5.9009 | 0.0255 |
| | | | CXCR2 | −5.8694 | 0.0155 |
| | | | KLHDC1 | −5.7732 | 0.0391 |
| | | | PLIN1 | −5.742 | 0.029 |
| | | | KCNJ2 | −5.7133 | 0.0236 |
| | | | ASPN | −5.6593 | 0.0227 |
| | | | SUV39H2 | −5.5883 | 0.0335 |
| | | | ROPN1B | −5.533 | 0.0381 |
| | | | VNN1 | −5.4803 | 0.018 |
| | | | IFI27 | −5.4264 | 0.0349 |
| | | | KCNG2 | −5.3548 | 0.0268 |
| | | | LAIR1 | −5.3473 | 0.0371 |
| | | | P2RX5 | −5.3335 | 0.039 |
| | | | CHRM4 | −5.2948 | 0.0336 |
| | | | TOR4A | −5.2677 | 0.004 |
| | | | HIGD1B | −5.2371 | 0.042 |
| | | | RGS2 | −5.1484 | 0.0134 |
| | | | RNF224 | −4.9675 | 0.0442 |
| | | | AURKA | −4.9118 | 0.0485 |
| | | | LGI2 | −4.8099 | 0.0284 |
| | | | SLC22A13 | −4.7851 | 0.0416 |
| | | | MLC1 | −4.7144 | 0.0305 |
| | | | TLR3 | −4.7066 | 0.0429 |
| | | | HHEX | −4.7002 | 0.0388 |
| | | | C8orf48 | −4.6899 | 0.0382 |
| | | | TIMM8A | −4.5289 | 0.0318 |
| | | | TTC25 | −4.4167 | 0.0396 |
| | | | KRT72 | −4.3577 | 0.0397 |
| | | | KCNMB3 | −4.2805 | 0.0257 |
| | | | HAPLN4 | −4.2381 | 0.0472 |
| | | | CCDC69 | −4.203 | 0.0488 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| | | | TMBIM4 | −4.1761 | 0.0273 |
| | | | BMP5 | −4.1521 | 0.0233 |
| | | | GPRC5A | −4.1494 | 0.0183 |
| | | | GPD2 | −4.1448 | 0.0444 |
| | | | ZNF668 | −4.1396 | 0.0428 |
| | | | SERPINB3 | −4.0734 | 0.0235 |
| | | | PPP1R16B | −4.0259 | 0.0093 |
| | | | NTSR1 | −3.9405 | 0.0434 |
| | | | PTAFR | −3.9092 | 0.0477 |
| | | | AVPR1A | −3.907 | 0.0044 |
| | | | STARD8 | −3.8533 | 0.0246 |
| | | | C15orf53 | −3.6751 | 0.0462 |
| | | | ADCY7 | −3.6529 | 0.0156 |
| | | | PIK3R6 | −3.6311 | 0.0264 |
| | | | ZIC2 | −3.6198 | 0.0249 |
| | | | ZNF490 | −3.5651 | 0.0493 |
| | | | CLDN14 | −3.5193 | 0.0385 |
| | | | NUDT2 | −3.5151 | 0.0464 |
| | | | FOXP3 | −3.4118 | 0.0275 |
| | | | APBB1IP | −3.3841 | 0.0244 |
| | | | EIF3C | −3.3247 | 0.0213 |
| | | | ACTR5 | −3.2145 | 0.0319 |
| | | | RPS6KA5 | −3.1343 | 0.0376 |
| | | | C4orf27 | −3.1257 | 0.0253 |
| | | | FUT2 | −3.0804 | 0.0348 |
| | | | LCE3E | −3.0756 | 0.0024 |
| | | | HIST3H2BB | −3.0463 | 0.0407 |
| | | | ARC | −3.0248 | 0.0423 |
| | | | SPRR2A | −3.0167 | 0.0345 |
| | | | DOCK11 | −2.9427 | 0.0164 |
| | | | KRT78 | −2.8669 | 0.0053 |
| | | | WAS | −2.8546 | 0.0369 |
| | | | RTL1 | −2.852 | 0.0458 |
| | | | TCEANC | −2.8089 | 0.011 |
| | | | FAM25A | −2.6398 | 0.0004 |
| | | | G0S2 | −2.6281 | 0.037 |
| | | | CD3G | −2.5886 | 0.0351 |
| | | | SPRR2G | −2.5758 | 0.027 |
| | | | GPN3 | −2.5708 | 0.0125 |
| | | | SEL1L3 | −2.5671 | 0.038 |
| | | | CSF1R | −2.5368 | 0.0412 |
| | | | CETN3 | −2.4829 | 0.0161 |
| | | | STXBP6 | −2.468 | 0.0065 |
| | | | MSRB2 | −2.4649 | 0.0437 |
| | | | CD209 | −2.4462 | 0.0496 |
| | | | MRPL39 | −2.4296 | 0.0129 |
| | | | NCOA7 | −2.38 | 0.0136 |
| | | | C9orf85 | −2.3763 | 0.0349 |
| | | | PTPMT1 | −2.3581 | 0.0248 |
| | | | COX14 | −2.3346 | 0.0071 |
| | | | LCE3D | −2.2937 | 0.0431 |
| | | | SLC43A2 | −2.2909 | 0.0474 |
| | | | SLC20A1 | −2.2879 | 0.0421 |
| | | | MLF1 | −2.26 | 0.0347 |
| | | | FAM185A | −2.2522 | 0.0245 |
| | | | MRPL15 | −2.2193 | 0.0185 |
| | | | B3GALT4 | −2.2061 | 0.0213 |
| | | | TBC1D12 | −2.183 | 0.0436 |
| | | | FCHSD1 | −2.1791 | 0.031 |
| | | | DNASE1L2 | −2.1662 | 0.0445 |
| | | | PNPLA1 | −2.156 | 0.0076 |
| | | | ABHD17B | −2.1475 | 0.0047 |
| | | | CARD16 | −2.1366 | 0.0288 |
| | | | IL6R | −2.1301 | 0.0109 |
| | | | HIST1H4B | −2.1092 | 0.014 |
| | | | PTS | −2.0901 | 0.0276 |
| | | | ANAPC13 | −2.0894 | 0.0188 |
| | | | DCTN5 | −2.0889 | 0.001 |
| | | | FAM110C | −2.0776 | 0.0038 |
| | | | GOLGA8F | −2.0534 | 0.0477 |
| | | | SPRR2E | −2.0439 | 0.0024 |
| | | | GNA12 | −2.0286 | 0.0443 |
| | | | ZNF584 | −2.0169 | 0.0115 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| | | | GPX3 | −2.0139 | 0.0464 |
| | | | RIPK2 | −2.0049 | 0.0083 |
| | | | LCE6A | −1.9922 | 0.0321 |
| | | | RNF180 | −1.9829 | 0.0073 |
| | | | GNB5 | −1.9531 | 0.0465 |
| | | | SDR9C7 | −1.9516 | 0.0005 |
| | | | DUSP5 | −1.9484 | 0.0168 |
| | | | ETS1 | −1.9476 | 0.0412 |
| | | | PLA2G2F | −1.9275 | 0.0379 |
| | | | YOD1 | −1.9234 | 0.0003 |
| | | | TRAPPC1 | −1.9138 | 0.0339 |
| | | | ZDHHC13 | −1.9113 | 0.0372 |
| | | | MARVELD3 | −1.9109 | 0.0275 |
| | | | ZNF16 | −1.9062 | 0.0374 |
| | | | PRELID3B | −1.8833 | 0.0175 |
| | | | TMLHE | −1.8685 | 0.0325 |
| | | | SLC36A1 | −1.8658 | 0.0376 |
| | | | CCL22 | −1.8563 | 0.0346 |
| | | | ZFAND2A | −1.8553 | 0.0436 |
| | | | MAP1LC3A | −1.8522 | 0.0095 |
| | | | RHOQ | −1.8521 | 0.0337 |
| | | | ARNTL | −1.8509 | 0.0325 |
| | | | INPP5D | −1.8454 | 0.027 |
| | | | SPTBN5 | −1.8452 | 0.0221 |
| | | | PRSS3 | −1.8422 | 0.0492 |
| | | | MPDU1 | −1.8281 | 0.0308 |
| | | | MPST | −1.8255 | 0.0228 |
| | | | SMOX | −1.8246 | 0.0122 |
| | | | MRPL30 | −1.8185 | 0.0147 |
| | | | NOS3 | −1.8178 | 0.0274 |
| | | | ARNTL2 | −1.8116 | 0.0408 |
| | | | LIMS1 | −1.8077 | 0.0265 |
| | | | BCKDK | −1.7907 | 0.0102 |
| | | | ABHD12B | −1.783 | 0.003 |
| | | | HIST1H4C | −1.7668 | 0.0292 |
| | | | SLC19A2 | −1.7647 | 0.0356 |
| | | | RAP1B | −1.764 | 0.0111 |
| | | | UBL3 | −1.7629 | 0.0069 |
| | | | NAA20 | −1.7564 | 0.0237 |
| | | | EXOC5 | −1.7555 | 0.0241 |
| | | | ZNF248 | −1.7545 | 0.0341 |
| | | | TBC1D23 | −1.7528 | 0.022 |
| | | | CCDC124 | −1.7484 | 0.0352 |
| | | | RAB23 | −1.7364 | 0.0327 |
| | | | PAPL | −1.7334 | 0.0094 |
| | | | PHLDA2 | −1.7326 | 0.0389 |
| | | | TSSC1 | −1.7263 | 0.0443 |
| | | | POLD3 | −1.726 | 0.0298 |
| | | | MPV17 | −1.7246 | 0.036 |
| | | | CEMIP | −1.7239 | 0.02 |
| | | | GULP1 | −1.7222 | 0.0476 |
| | | | NCCRP1 | −1.7216 | 0.0013 |
| | | | TM2D1 | −1.7173 | 0.0044 |
| | | | MYO1B | −1.7131 | 0.0018 |
| | | | C2orf47 | −1.7098 | 0.0486 |
| | | | RNASE7 | −1.6985 | 0.0398 |
| | | | TMEM127 | −1.6948 | 0.0164 |
| | | | TMEM11 | −1.6876 | 0.0443 |
| | | | NT5C3A | −1.6864 | 0.0087 |
| | | | ESD | −1.6832 | 0.0341 |
| | | | GADD45A | −1.6793 | 0.015 |
| | | | AIM1 | −1.6698 | 0.038 |
| | | | GCOM1 | −1.6691 | 0.0128 |
| | | | ACTR10 | −1.6639 | 0.0274 |
| | | | AK9 | −1.6629 | 0.0471 |
| | | | FAM98A | −1.6616 | 0.007 |
| | | | TMEM86A | −1.6601 | 0.0072 |
| | | | MRPL27 | −1.6542 | 0.0028 |
| | | | HERC6 | −1.6508 | 5.71E−05 |
| | | | ERN1 | −1.6493 | 0.0114 |
| | | | NAA10 | −1.648 | 0.0232 |
| | | | SLC10A6 | −1.6437 | 0.0277 |
| | | | RBPJ | −1.6436 | 0.029 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| | | | LCE2C | −1.642 | 0.0318 |
| | | | SEMA7A | −1.6327 | 0.0033 |
| | | | RNGTT | −1.632 | 0.0064 |
| | | | USP2 | −1.6284 | 0.0306 |
| | | | CHURC1 | −1.6274 | 0.0014 |
| | | | SPATS2L | −1.626 | 0.008 |
| | | | BZW1 | −1.6243 | 0.0034 |
| | | | ABHD5 | −1.6219 | 0.0132 |
| | | | HK2 | −1.6217 | 0.0443 |
| | | | AZGP1 | −1.6203 | 0.0214 |
| | | | CASP7 | −1.6192 | 0.0045 |
| | | | SLC5A1 | −1.618 | 0.008 |
| | | | RAP1GDS1 | −1.6172 | 0.0033 |
| | | | TVP23B | −1.6152 | 0.0291 |
| | | | MRPS25 | −1.615 | 0.0317 |
| | | | MINPP1 | −1.612 | 0.0296 |
| | | | CPA4 | −1.6102 | 0.0133 |
| | | | ATG9B | −1.6079 | 0.0419 |
| | | | CNFN | −1.6073 | 0.02 |
| | | | UBB | −1.6053 | 0.0014 |
| | | | GNPTAB | −1.6027 | 0.039 |
| | | | SNRPG | −1.596 | 0.0494 |
| | | | ARHGAP29 | −1.5928 | 0.0322 |
| | | | USF1 | −1.5874 | 0.0386 |
| | | | ZNF330 | −1.5849 | 0.0195 |
| | | | NBN | −1.583 | 0.0384 |
| | | | HIST1H1B | −1.5817 | 0.0218 |
| | | | PIM1 | −1.581 | 0.04 |
| | | | GSDMA | −1.5778 | 0.0068 |
| | | | UBE2D3 | −1.5735 | 0.01 |
| | | | CDC34 | −1.5732 | 0.0273 |
| | | | PCNP | −1.568 | 0.0475 |
| | | | SLC35E3 | −1.5657 | 0.0156 |
| | | | YWHAH | −1.5657 | 0.0098 |
| | | | C18orf25 | −1.5611 | 0.0313 |
| | | | RPRD1B | −1.5569 | 0.0442 |
| | | | UBE2J1 | −1.5485 | 0.0292 |
| | | | MRPL32 | −1.5465 | 0.0406 |
| | | | ECHDC1 | −1.5434 | 0.0362 |
| | | | PDE12 | −1.5349 | 0.0472 |
| | | | ZNF649 | −1.5338 | 0.0147 |
| | | | DNAJB1 | −1.5334 | 0.0017 |
| | | | CHIC2 | −1.5332 | 0.0359 |
| | | | CNST | −1.5303 | 0.0152 |
| | | | NUP107 | −1.5272 | 0.045 |
| | | | ZNF720 | −1.5207 | 0.0359 |
| | | | PLA2G4D | −1.5181 | 0.0315 |
| | | | STXBP3 | −1.518 | 0.0229 |
| | | | SSNA1 | −1.5168 | 0.0398 |
| | | | BAG5 | −1.5158 | 0.0015 |
| | | | PRKCH | −1.5157 | 0.01 |
| | | | ARHGAP30 | −1.5151 | 0.0477 |
| | | | PPP1R18 | −1.5143 | 0.0216 |
| | | | USP38 | −1.5138 | 0.0377 |
| | | | SLC31A2 | −1.5136 | 0.0419 |
| | | | NUB1 | −1.5101 | 0.0086 |
| | | | SEPT11 | −1.5075 | 0.0388 |
| | | | SUB1 | −1.5053 | 0.0269 |
| | | | TIMM21 | −1.4994 | 0.0417 |
| | | | MRPL49 | −1.4981 | 0.0257 |
| | | | DENR | −1.487 | 0.0274 |
| | | | TRABD | −1.4869 | 0.0348 |
| | | | VMP1 | −1.4868 | 0.0465 |
| | | | FNDC3A | −1.4825 | 0.0115 |
| | | | SIL1 | −1.4815 | 0.0127 |
| | | | MAP1LC3B | −1.4758 | 0.038 |
| | | | WWC1 | −1.4749 | 0.0404 |
| | | | POLR3B | −1.4745 | 0.0212 |
| | | | VSIG10L | −1.4732 | 0.0134 |
| | | | BLOC1S1 | −1.473 | 0.0469 |
| | | | SHPK | −1.4715 | 0.0309 |
| | | | PI4K2A | −1.4714 | 0.0311 |
| | | | TNIP1 | −1.471 | 0.0008 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| | | | ZNF706 | −1.4695 | 0.0366 |
| | | | CORO1C | −1.4673 | 0.0345 |
| | | | PLEKHB2 | −1.4646 | 0.0055 |
| | | | ALDH7A1 | −1.4641 | 0.0251 |
| | | | TOMM5 | −1.4639 | 0.0399 |
| | | | ADTRP | −1.462 | 0.0229 |
| | | | SLC6A14 | −1.4614 | 0.0223 |
| | | | CSRNP1 | −1.4595 | 0.0091 |
| | | | FAF2 | −1.457 | 0.0056 |
| | | | MRPL44 | −1.4529 | 0.0283 |
| | | | UGCG | −1.4494 | 0.0216 |
| | | | SYNJ2 | −1.4479 | 0.0404 |
| | | | PDLIM2 | −1.4444 | 0.006 |
| | | | AK3 | −1.4361 | 0.0358 |
| | | | DERL1 | −1.4357 | 0.0305 |
| | | | TMEM179B | −1.4357 | 0.0194 |
| | | | SNF8 | −1.4332 | 0.0489 |
| | | | MGLL | −1.4306 | 0.0327 |
| | | | GSE1 | −1.4247 | 0.0324 |
| | | | CIRH1A | −1.4201 | 0.0236 |
| | | | HEXA | −1.417 | 0.0329 |
| | | | SYNJ1 | −1.4159 | 0.0369 |
| | | | ZNF440 | −1.4142 | 0.0323 |
| | | | PPARD | −1.414 | 0.0131 |
| | | | HYOU1 | −1.4135 | 0.0046 |
| | | | ARL13B | −1.4122 | 0.0417 |
| | | | PLCXD1 | −1.4108 | 0.0348 |
| | | | CRCT1 | −1.4069 | 0.0325 |
| | | | PPP1R15B | −1.405 | 0.0255 |
| | | | TTYH3 | −1.4035 | 0.0153 |
| | | | GBA | −1.4003 | 0.0395 |
| | | | ARRDC4 | −1.3999 | 0.0042 |
| | | | DDX52 | −1.3964 | 0.0404 |
| | | | CFL1 | −1.3955 | 0.0493 |
| | | | RABGEF1 | −1.3923 | 0.0238 |
| | | | ARHGEF10L | −1.3921 | 0.042 |
| | | | GNPAT | −1.3896 | 0.0473 |
| | | | NFYA | −1.3888 | 0.0287 |
| | | | SFT2D2 | −1.388 | 0.0387 |
| | | | ZNF213 | −1.3874 | 0.0437 |
| | | | NADK | −1.3873 | 0.0021 |
| | | | SH3BP5L | −1.3827 | 0.0087 |
| | | | MXD1 | −1.382 | 0.0308 |
| | | | DHRS7 | −1.3803 | 0.0389 |
| | | | RAB24 | −1.3771 | 0.0378 |
| | | | LNX1 | −1.3769 | 0.0218 |
| | | | PSD4 | −1.373 | 0.0093 |
| | | | ATP6V1C2 | −1.3717 | 0.0136 |
| | | | TMED9 | −1.371 | 0.0377 |
| | | | PDCD7 | −1.3706 | 0.0474 |
| | | | H2AFY | −1.3699 | 0.049 |
| | | | ALAS1 | −1.3692 | 0.032 |
| | | | NCOA3 | −1.3678 | 0.023 |
| | | | SDCCAG8 | −1.3678 | 0.0196 |
| | | | KATNB1 | −1.3677 | 0.0328 |
| | | | AP5Z1 | −1.3664 | 0.0149 |
| | | | ADIPOR1 | −1.3654 | 0.0443 |
| | | | TMPRSS13 | −1.3611 | 0.0285 |
| | | | SNX9 | −1.3605 | 0.0224 |
| | | | PPP2CA | −1.3592 | 0.0465 |
| | | | GPR137B | −1.3585 | 0.0428 |
| | | | EHD1 | −1.3582 | 0.0131 |
| | | | DENND2C | −1.3558 | 0.0144 |
| | | | CHTF8 | −1.3535 | 0.0141 |
| | | | PLK3 | −1.349 | 0.0139 |
| | | | CTSB | −1.3444 | 0.0441 |
| | | | PIEZO1 | −1.3433 | 0.0008 |
| | | | ERH | −1.3384 | 0.0422 |
| | | | ITFG1 | −1.3382 | 0.0356 |
| | | | RND3 | −1.3368 | 0.0298 |
| | | | IRF2 | −1.3364 | 0.0324 |
| | | | PTPN2 | −1.3363 | 0.0424 |
| | | | FBXW11 | −1.3355 | 0.0431 |

TABLE 18-continued

Genes Significantly Modulated Between Baseline and Week 24 in Non-Responders

| Increased Expression from Baseline to Week 24 | | | Decreased Expression from Baseline to Week 24 | | |
|---|---|---|---|---|---|
| Gene Symbol | Fold Change | Raw P Value | Gene Symbol | Fold Change | Raw P Value |
| | | | ITSN2 | −1.3354 | 0.0054 |
| | | | MAP2K3 | −1.3315 | 0.0374 |
| | | | GTPBP2 | −1.3304 | 0.0303 |
| | | | SBSN | −1.3301 | 0.0467 |
| | | | LIMA1 | −1.3288 | 0.0293 |
| | | | EPG5 | −1.3268 | 0.0308 |
| | | | TWISTNB | −1.326 | 0.028 |
| | | | EPT1 | −1.3252 | 0.0184 |
| | | | SPIRE1 | −1.324 | 0.0058 |
| | | | LAMP2 | −1.3221 | 0.0175 |
| | | | COPB2 | −1.3193 | 0.0325 |
| | | | GAS6 | −1.3184 | 0.0451 |
| | | | LMTK3 | −1.3184 | 0.0421 |
| | | | BCR | −1.3173 | 0.0251 |
| | | | TCP11L2 | −1.3165 | 0.0246 |
| | | | AHCYL1 | −1.3145 | 0.0047 |
| | | | HMGN2 | −1.3145 | 0.0141 |
| | | | MYO9B | −1.3112 | 0.0113 |
| | | | PPP2R2C | −1.3073 | 0.0332 |
| | | | ARPC5 | −1.3065 | 0.0351 |
| | | | ATP2C1 | −1.3047 | 0.0206 |
| | | | TBC1D20 | −1.3043 | 0.0417 |
| | | | MAPKAPK5 | −1.3018 | 0.0068 |
| | | | WWTR1 | −1.2981 | 0.0469 |
| | | | SDE2 | −1.2972 | 0.0283 |
| | | | NDUFA13 | −1.2936 | 0.0337 |
| | | | EDEM1 | −1.2917 | 0.0304 |
| | | | HEATR5B | −1.2866 | 0.0276 |
| | | | CHMP4C | −1.2862 | 0.0302 |
| | | | CTTNBP2NL | −1.2817 | 0.0229 |
| | | | RSF1 | −1.2789 | 0.012 |
| | | | RPS26 | −1.2758 | 0.0385 |
| | | | PRMT2 | −1.2753 | 0.0261 |
| | | | RBM10 | −1.2741 | 0.0361 |
| | | | TAF7 | −1.2737 | 0.025 |
| | | | JARID2 | −1.2729 | 0.0219 |
| | | | PSMD3 | −1.2716 | 0.0312 |
| | | | COL5A2 | −1.2659 | 0.0478 |
| | | | ZNF212 | −1.2542 | 0.031 |
| | | | UBR1 | −1.2539 | 0.0462 |
| | | | IMMT | −1.2534 | 0.0354 |
| | | | TBC1D10B | −1.2483 | 0.0209 |
| | | | FNBP1 | −1.2453 | 0.0353 |
| | | | STAM2 | −1.2398 | 0.0137 |
| | | | PCLO | −1.2393 | 0.0119 |
| | | | TTC19 | −1.2369 | 0.0248 |
| | | | RAB7A | −1.2359 | 0.0361 |
| | | | EPS15 | −1.235 | 0.0398 |
| | | | PICALM | −1.2347 | 0.026 |
| | | | PELI1 | −1.2318 | 0.0416 |
| | | | CUL1 | −1.2268 | 0.0027 |
| | | | ENSA | −1.2222 | 0.0155 |
| | | | CYFIP1 | −1.2184 | 0.0182 |
| | | | KDM1B | −1.2178 | 0.0474 |
| | | | EPS8L1 | −1.2091 | 0.047 |
| | | | RTFDC1 | −1.209 | 0.0493 |
| | | | MARVELD2 | −1.2083 | 0.036 |
| | | | COPA | −1.2072 | 0.0353 |
| | | | KPNB1 | −1.2072 | 0.0224 |
| | | | ITGAV | −1.2026 | 0.0359 |
| | | | PCF11 | −1.1978 | 0.019 |
| | | | NDUFS1 | −1.1881 | 0.0323 |
| | | | ITPKC | −1.1866 | 0.0212 |
| | | | KHSRP | −1.1825 | 0.0257 |
| | | | PAPD4 | −1.1728 | 0.0378 |
| | | | DDX18 | −1.1521 | 0.0177 |

Table 19 lists differentially expressed genes that were stably expressed in responders throughout the study and were not significantly modulated by treatment between baseline and Week 24.

TABLE 19

Genes Stably Expressed Between Day 1 and Week 24

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| SERINC4 | 34.3284 | 0.0518 | ESD | −47.3843 | 0.0643 |
| FAM153C | 29.43 | 0.0795 | HIST1H2AK | −45.1381 | 0.0531 |
| ANGPTL3 | 26.1574 | 0.1792 | DCAF4 | −32.5166 | 0.1119 |
| ADCY7 | 23.0366 | 0.2193 | MRAP2 | −30.5134 | 0.0571 |
| NUGGC | 20.5734 | 0.0722 | SIRT3 | −29.7841 | 0.0816 |
| AGTRAP | 20.0111 | 0.1793 | C3orf49 | −23.1537 | 0.0517 |
| FOSL1 | 17.5836 | 0.1671 | IYD | −22.2703 | 0.1023 |
| BEST1 | 16.5446 | 0.1629 | TWIST2 | −18.1727 | 0.0595 |
| TBX19 | 15.0717 | 0.1436 | CSF1R | −17.8603 | 0.2654 |
| RGS16 | 14.0051 | 0.0856 | ZNF224 | −17.0106 | 0.1338 |
| ESRRG | 13.8518 | 0.0855 | CCDC77 | −15.6151 | 0.2115 |
| KCNRG | 13.8334 | 0.1162 | MANEA | −13.6223 | 0.1211 |
| KLB | 12.4857 | 0.0761 | ZNF619 | −13.2749 | 0.1456 |
| IL2RB | 10.8092 | 0.1694 | ZNF764 | −13.1932 | 0.1349 |
| COQ6 | 10.7709 | 0.1102 | MSRB2 | −12.9185 | 0.1888 |
| CILP2 | 10.7666 | 0.086 | HLCS | −12.7892 | 0.1489 |
| RARRES3 | 10.0574 | 0.1796 | TCEB3B | −11.6698 | 0.1256 |
| ZSCAN31 | 9.9201 | 0.1378 | SLC39A14 | −11.5582 | 0.133 |
| RGS9 | 9.873 | 0.2332 | PLSCR1 | −11.5506 | 0.1374 |
| FGFRL1 | 9.8481 | 0.1008 | CCDC78 | −11.3228 | 0.1061 |
| ABLIM2 | 9.6717 | 0.2161 | VEPH1 | −11.2508 | 0.059 |
| DNAJB5 | 9.3076 | 0.312 | VARS2 | −11.0178 | 0.1183 |
| PSG1 | 9.1933 | 0.195 | GAGE2E | −10.6926 | 0.1817 |
| EN1 | 9.1394 | 0.184 | THG1L | −10.688 | 0.0959 |
| SPRR3 | 9.12 | 0.2347 | CCDC105 | −10.3782 | 0.2109 |
| PILRB | 8.7256 | 0.0793 | ZNF77 | −10.3141 | 0.1357 |
| MRPS28 | 8.6524 | 0.1779 | KRT71 | −10.2566 | 0.1144 |
| CTAGE15 | 8.6356 | 0.2001 | FAM13C | −10.1912 | 0.1209 |
| C10orf128 | 8.4822 | 0.1446 | DRC3 | −9.7252 | 0.2144 |
| ZNF469 | 8.2243 | 0.086 | RPL36A | −9.7145 | 0.2232 |
| DENND1C | 8.0945 | 0.3416 | ERAP2 | −9.6026 | 0.154 |
| NHLH1 | 7.9637 | 0.1535 | PLD2 | −9.2801 | 0.2707 |
| HLA-DMA | 7.9418 | 0.2251 | BHLHE41 | −9.1793 | 0.2438 |
| CD3G | 7.7405 | 0.1815 | HBZ | −8.9457 | 0.2065 |
| ZNF597 | 7.6 | 0.1519 | DERL3 | −8.7066 | 0.152 |
| DUSP28 | 7.4942 | 0.2359 | LAMTOR5 | −8.5578 | 0.2044 |
| SGIP1 | 7.0389 | 0.1875 | TMEM14A | −8.4019 | 0.1953 |
| SLC9A4 | 6.9988 | 0.3613 | KCNAB3 | −8.2478 | 0.1873 |
| MTRNR2L3 | 6.9949 | 0.1884 | TMEM68 | −8.1349 | 0.2041 |
| WNT5A | 6.873 | 0.2695 | ACAD11 | −7.9298 | 0.1781 |
| CNGB1 | 6.6189 | 0.1883 | APLN | −7.9087 | 0.0998 |
| LAIR1 | 6.5911 | 0.1932 | PDE9A | −7.808 | 0.1511 |
| GOLGA8R | 6.5819 | 0.4926 | NFYB | −7.6596 | 0.2107 |
| FAM231D | 6.5529 | 0.3909 | CSNK1G3 | −7.4422 | 0.2146 |
| QTRTD1 | 6.4476 | 0.0698 | CDC27 | −7.3554 | 0.2263 |
| GGACT | 6.3922 | 0.2153 | SUPV3L1 | −7.245 | 0.1424 |
| TDRKH | 6.2265 | 0.302 | TMSB10 | −6.9475 | 0.3782 |
| C3 | 6.1916 | 0.1921 | NPIPB4 | −6.9423 | 0.2675 |
| KCNIP4 | 6.1543 | 0.2061 | ERMARD | −6.8012 | 0.1415 |
| CYP27B1 | 6.1044 | 0.1376 | PRPF40B | −6.7313 | 0.236 |
| LRRC37A3 | 6.0566 | 0.2476 | VBP1 | −6.6425 | 0.2802 |
| HCN4 | 5.8493 | 0.1417 | DDX55 | −6.4281 | 0.242 |
| PRR15 | 5.6279 | 0.1936 | NDUFB6 | −6.3519 | 0.2601 |
| SSC4D | 5.5912 | 0.1798 | DUSP23 | −6.2692 | 0.2681 |
| PADI3 | 5.5866 | 0.1831 | FBXO4 | −6.2466 | 0.207 |
| NEFH | 5.5755 | 0.201 | PHF1 | −6.1423 | 0.2155 |
| TMEM8A | 5.5413 | 0.5101 | STARD9 | −6.1174 | 0.1875 |
| MYCL | 5.5065 | 0.1456 | ETNPPL | −6.094 | 0.1817 |
| C1QTNF6 | 5.461 | 0.2211 | GTF2H3 | −6.0361 | 0.1908 |
| LRRC70 | 5.4331 | 0.0932 | ECE2 | −5.9855 | 0.1135 |
| S1PR2 | 5.3442 | 0.2721 | MPHOSPH10 | −5.9297 | 0.3449 |
| CUX2 | 5.3366 | 0.1895 | UTP23 | −5.8203 | 0.3474 |
| GAS2L3 | 5.1129 | 0.3695 | PSMB3 | −5.7926 | 0.3734 |
| NDOR1 | 5.0487 | 0.3877 | LRIG3 | −5.7089 | 0.3642 |
| NOP16 | 5.024 | 0.1491 | ZNF551 | −5.6873 | 0.147 |
| FUT2 | 4.8582 | 0.5052 | PHF10 | −5.6573 | 0.3747 |
| SLC25A25 | 4.738 | 0.3423 | FAM60A | −5.5425 | 0.3226 |

TABLE 19-continued

Genes Stably Expressed Between Day 1 and Week 24

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| SCARB1 | 4.7238 | 0.187 | PPP1R14B | −5.5217 | 0.407 |
| PIK3CG | 4.6587 | 0.1867 | BTN3A3 | −5.4241 | 0.2408 |
| FAM216A | 4.6515 | 0.1312 | PTGER1 | −5.3803 | 0.1808 |
| PRR5 | 4.6447 | 0.2381 | CDK2 | −5.32 | 0.3026 |
| RAD51B | 4.5065 | 0.3035 | TFAM | −5.3111 | 0.3205 |
| VOPP1 | 4.4705 | 0.0567 | PGRMC1 | −5.2664 | 0.3723 |
| SERTAD1 | 4.4197 | 0.2114 | KATNAL2 | −5.2088 | 0.287 |
| C9orf172 | 4.3974 | 0.4044 | COL11A1 | −5.1339 | 0.2327 |
| GPR27 | 4.2735 | 0.2146 | IFT43 | −5.0331 | 0.2865 |
| MUC4 | 4.24 | 0.1784 | SLC2A10 | −5.028 | 0.2656 |
| KBTBD8 | 4.1801 | 0.4819 | SYCP2 | −4.9532 | 0.2374 |
| ARHGAP30 | 3.9568 | 0.1496 | AP3M1 | −4.7944 | 0.3675 |
| TRUB2 | 3.8837 | 0.1049 | CASC4 | −4.7642 | 0.3695 |
| ARNTL | 3.8384 | 0.1 | MCPH1 | −4.6727 | 0.3028 |
| C1orf233 | 3.8091 | 0.36 | EIF2A | −4.6478 | 0.4098 |
| DNAH9 | 3.6983 | 0.4376 | RUNX2 | −4.2513 | 0.3311 |
| CXCL11 | 3.6945 | 0.3739 | PHTF1 | −4.2207 | 0.3946 |
| GTF2H2C | 3.6605 | 0.3008 | SEPSECS | −4.2127 | 0.3042 |
| ATP11A | 3.5782 | 0.2704 | NUP107 | −4.2013 | 0.2705 |
| CUEDC1 | 3.5752 | 0.1938 | NID2 | −4.1828 | 0.1903 |
| KCNMB1 | 3.5008 | 0.4613 | GTF2H5 | −4.1516 | 0.2765 |
| PRR7 | 3.4892 | 0.1896 | ZYG11A | −4.1329 | 0.3724 |
| FBXO42 | 3.4291 | 0.2361 | HSPA4L | −4.128 | 0.4198 |
| FAM124A | 3.378 | 0.3654 | FCER2 | −4.121 | 0.2084 |
| STK24 | 3.3537 | 0.2623 | HAUS5 | −4.1129 | 0.3442 |
| RCBTB2 | 3.3151 | 0.3744 | ARMC7 | −4.0945 | 0.4073 |
| GOLGA8Q | 3.2905 | 0.3739 | FBXO8 | −4.0786 | 0.4089 |
| ABCA7 | 3.2193 | 0.1371 | LIMA1 | −4.0571 | 0.3427 |
| APOLD1 | 3.1813 | 0.2989 | UGT1A6 | −3.9944 | 0.4743 |
| TEX264 | 3.1806 | 0.227 | POLR3GL | −3.9758 | 0.3695 |
| GRM3 | 3.1721 | 0.47 | PHIP | −3.9114 | 0.4104 |
| GALNT16 | 3.1416 | 0.4283 | C1orf123 | −3.8754 | 0.4586 |
| PAEP | 3.1052 | 0.3739 | C10orf62 | −3.8517 | 0.2469 |
| MIDN | 3.0971 | 0.2751 | OR7G1 | −3.7882 | 0.1842 |
| NUDT6 | 3.0822 | 0.3739 | IL6ST | −3.7675 | 0.4524 |
| TVP23C-CDRT4 | 3.0556 | 0.404 | RNF8 | −3.7619 | 0.2934 |
| CHRNB1 | 3.0434 | 0.2083 | GEMIN6 | −3.6995 | 0.3088 |
| GSTT2B | 3.0327 | 0.6084 | NPR3 | −3.6501 | 0.4355 |
| WSCD2 | 2.9828 | 0.3739 | MRPL50 | −3.6073 | 0.4044 |
| CECR5 | 2.9502 | 0.2933 | B3GNT4 | −3.5538 | 0.22 |
| HEATR5A | 2.8966 | 0.1039 | ZNF525 | −3.5313 | 0.1197 |
| MAPK3 | 2.8872 | 0.252 | XPO4 | −3.5195 | 0.3389 |
| DNAJC25 | 2.7894 | 0.5481 | KLHDC1 | −3.5157 | 0.2893 |
| TTYH2 | 2.7783 | 0.6172 | IFT88 | −3.5102 | 0.2742 |
| PROX1 | 2.7543 | 0.4706 | NUDT9 | −3.4451 | 0.4643 |
| NANOS1 | 2.7533 | 0.2919 | TARSL2 | −3.3939 | 0.4891 |
| IMPG2 | 2.7174 | 0.261 | TSPAN6 | −3.3845 | 0.4921 |
| MRPL27 | 2.6711 | 0.1835 | CSTF2 | −3.238 | 0.4491 |
| TAPT1 | 2.6433 | 0.1649 | WBSCR17 | −3.1432 | 0.2976 |
| FBRSL1 | 2.6305 | 0.225 | TMEM174 | −3.1396 | 0.1778 |
| ARMC9 | 2.6302 | 0.4374 | PSD2 | −3.1005 | 0.502 |
| EFR3B | 2.6266 | 0.4084 | LMLN | −3.0824 | 0.1291 |
| RNF166 | 2.6109 | 0.2916 | POLR1B | −3.0821 | 0.4797 |
| WNK1 | 2.5892 | 0.3235 | FECH | −3.0503 | 0.2444 |
| MSANTD4 | 2.5863 | 0.259 | LRRC8C | −3.0412 | 0.3776 |
| GPRC5A | 2.5842 | 0.6585 | GAA | −3.0326 | 0.4261 |
| HIST1H2AB | 2.5833 | 0.6394 | NAF1 | −2.971 | 0.4349 |
| CXCL10 | 2.5678 | 0.3739 | SCO2 | −2.9595 | 0.7006 |
| MAGEF1 | 2.5305 | 0.3842 | TMEM108 | −2.9127 | 0.5065 |
| HEXA | 2.503 | 0.1697 | STX7 | −2.9038 | 0.2808 |
| IL1RL1 | 2.4524 | 0.3739 | SPRY4 | −2.7701 | 0.4022 |
| BRINP2 | 2.4455 | 0.5524 | BMF | −2.745 | 0.2732 |
| NAA10 | 2.4343 | 0.1594 | CTPS1 | −2.7178 | 0.4494 |
| TAF6 | 2.4311 | 0.0976 | RNF2 | −2.6973 | 0.3165 |
| TICAM2 | 2.43 | 0.3739 | KLHL9 | −2.6271 | 0.487 |
| CTGF | 2.4076 | 0.519 | CLEC4E | −2.6141 | 0.3857 |
| JMJD6 | 2.3959 | 0.276 | CILP | −2.5985 | 0.6722 |
| SLC35E3 | 2.3844 | 0.1806 | MUC1 | −2.5194 | 0.2811 |
| JPH3 | 2.3689 | 0.5395 | CARD16 | −2.4854 | 0.6097 |
| RAB3B | 2.3307 | 0.3433 | TMC8 | −2.4762 | 0.2767 |
| H3F3C | 2.325 | 0.5232 | EVA1B | −2.4551 | 0.2752 |
| MMP25 | 2.3217 | 0.3739 | FAM89B | −2.4267 | 0.2174 |
| SELPLG | 2.3087 | 0.572 | KIF18A | −2.411 | 0.3753 |

TABLE 19-continued

Genes Stably Expressed Between Day 1 and Week 24

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| GJA3 | 2.3028 | 0.6892 | SLC41A2 | −2.4064 | 0.6077 |
| LDHD | 2.2804 | 0.3739 | EOGT | −2.3932 | 0.5402 |
| DOCK6 | 2.2514 | 0.3618 | ZNF34 | −2.3565 | 0.6014 |
| KDM6A | 2.2454 | 0.1988 | USP28 | −2.3453 | 0.5125 |
| ZNF124 | 2.2406 | 0.1454 | MRPL30 | −2.3409 | 0.6064 |
| NAV1 | 2.2328 | 0.4401 | CCBL1 | −2.3295 | 0.4185 |
| SEC16A | 2.2099 | 0.374 | GOLGA6D | −2.3232 | 0.2298 |
| TNFAIP8L1 | 2.1997 | 0.7021 | CCDC153 | −2.2569 | 0.6317 |
| MRPL24 | 2.1684 | 0.7528 | SCFD2 | −2.2518 | 0.5973 |
| CRY2 | 2.1667 | 0.4047 | SYT12 | −2.2414 | 0.5919 |
| DENND6A | 2.1648 | 0.1827 | RARS2 | −2.2399 | 0.1675 |
| MTCH1 | 2.1562 | 0.3584 | HSF4 | −2.2397 | 0.4843 |
| NUMA1 | 2.1528 | 0.2922 | MTHFD1 | −2.2305 | 0.1436 |
| SEMA4G | 2.1505 | 0.6416 | ACVR1C | −2.2172 | 0.6208 |
| C15orf65 | 2.1386 | 0.1793 | DNHD1 | −2.1827 | 0.2773 |
| AMOTL2 | 2.1319 | 0.3229 | FUBP1 | −2.1687 | 0.2808 |
| SNRK | 2.1261 | 0.1386 | PDGFRL | −2.1564 | 0.603 |
| RANBP9 | 2.1232 | 0.3506 | MAST2 | −2.1536 | 0.1942 |
| RNF113A | 2.1184 | 0.085 | P3H3 | −2.1322 | 0.6975 |
| TOB2 | 2.0962 | 0.3623 | PRKAR2B | −2.1287 | 0.6693 |
| SPATA5L1 | 2.0888 | 0.6004 | SS18L2 | −2.1095 | 0.6267 |
| HRNR | 2.0402 | 0.3811 | METTL20 | −2.1019 | 0.6083 |
| MAP1A | 2.0315 | 0.3767 | HNRNPD | −2.0951 | 0.3784 |
| CMTM4 | 2.0212 | 0.2153 | ASB1 | −2.0551 | 0.2544 |
| NDC1 | 2.0151 | 0.3282 | CDK4 | −2.0245 | 0.2923 |
| PUSL1 | 2.0097 | 0.2397 | APLF | −2.0171 | 0.3156 |
| SYNJ1 | 1.9876 | 0.0633 | TFR2 | −2.0111 | 0.4138 |
| PPP1R37 | 1.9796 | 0.228 | RBPMS2 | −1.9965 | 0.5721 |
| PRMT6 | 1.9643 | 0.7787 | ZSCAN16 | −1.9784 | 0.6451 |
| GNB5 | 1.961 | 0.7344 | ARHGAP5 | −1.9623 | 0.3827 |
| PLA2G4C | 1.9518 | 0.3739 | SHMT2 | −1.9486 | 0.5957 |
| C4orf27 | 1.8958 | 0.6437 | RFX7 | −1.9378 | 0.6311 |
| TNFRSF8 | 1.8873 | 0.3739 | SLC5A6 | −1.9304 | 0.5922 |
| SLC22A18 | 1.8713 | 0.2434 | SARM1 | −1.9262 | 0.5968 |
| RARB | 1.8708 | 0.6754 | RNPC3 | −1.9255 | 0.2359 |
| ZC3H11A | 1.8698 | 0.2458 | SMPD2 | −1.9034 | 0.6971 |
| ZBTB46 | 1.8681 | 0.6633 | WAS | −1.8976 | 0.7233 |
| DAXX | 1.8643 | 0.0535 | NLRP2 | −1.8924 | 0.755 |
| NDFIP2 | 1.859 | 0.4237 | MLH1 | −1.8922 | 0.6326 |
| ZNF91 | 1.8552 | 0.0999 | CDC42EP5 | −1.882 | 0.5718 |
| DHFR | 1.8495 | 0.4613 | GRIP1 | −1.8766 | 0.4968 |
| BLOC1S1 | 1.8131 | 0.2349 | PDCD7 | −1.8491 | 0.6721 |
| SLA2 | 1.8034 | 0.7068 | RAB2B | −1.8441 | 0.6726 |
| FBXO2 | 1.7992 | 0.8145 | USP47 | −1.8253 | 0.436 |
| C1orf109 | 1.7809 | 0.4762 | PAAF1 | −1.8155 | 0.514 |
| CD3E | 1.7791 | 0.3739 | CHST15 | −1.8092 | 0.2302 |
| TEX14 | 1.7603 | 0.3739 | PLXND1 | −1.7959 | 0.1847 |
| CUZD1 | 1.759 | 0.3739 | DNAJC4 | −1.7745 | 0.2067 |
| AGFG1 | 1.7551 | 0.2009 | ARHGAP19-SLIT1 | −1.773 | 0.7896 |
| ZNF555 | 1.7534 | 0.7649 | INTS2 | −1.7696 | 0.5495 |
| TNPO1 | 1.7483 | 0.1871 | POU5F1B | −1.7681 | 0.5998 |
| PLIN1 | 1.7401 | 0.3739 | ORAOV1 | −1.7294 | 0.6659 |
| NKX3-2 | 1.7255 | 0.6319 | IARS2 | −1.7082 | 0.3135 |
| KAT6B | 1.7106 | 0.3438 | GLRX5 | −1.7067 | 0.3309 |
| DVL1 | 1.7097 | 0.3346 | LIN52 | −1.7056 | 0.4296 |
| NEK3 | 1.7075 | 0.7615 | MAK16 | −1.703 | 0.0719 |
| C20orf27 | 1.7055 | 0.8231 | TMX3 | −1.6985 | 0.7365 |
| DISC1 | 1.7042 | 0.7978 | SUMF1 | −1.6964 | 0.2343 |
| ZNF286B | 1.7019 | 0.7519 | MLKL | −1.6873 | 0.5389 |
| WNT4 | 1.6975 | 0.5715 | RNF34 | −1.6802 | 0.4231 |
| GPR34 | 1.6935 | 0.8137 | BTF3L4 | −1.6797 | 0.2736 |
| RNF167 | 1.6858 | 0.3763 | PDE5A | −1.6733 | 0.7035 |
| RBM23 | 1.6704 | 0.19 | MRPS10 | −1.6705 | 0.3746 |
| PEPD | 1.6565 | 0.5091 | BACE1 | −1.6702 | 0.7311 |
| MCC | 1.6426 | 0.5683 | HNRNPLL | −1.6604 | 0.3086 |
| SCAF1 | 1.6323 | 0.385 | CDC5L | −1.6466 | 0.3951 |
| LYPLA2 | 1.6236 | 0.1253 | CCDC174 | −1.6461 | 0.4577 |
| UBE2K | 1.6227 | 0.1321 | TATDN2 | −1.6456 | 0.3546 |
| EFR3A | 1.6123 | 0.2674 | LIPH | −1.6288 | 0.5124 |
| PTK2B | 1.6073 | 0.4028 | CKS1B | −1.6266 | 0.7369 |
| HIST4H4 | 1.5911 | 0.8254 | CNDP1 | −1.6189 | 0.8338 |
| ANKRD13B | 1.5851 | 0.8084 | VPS36 | −1.6136 | 0.4226 |

TABLE 19-continued

Genes Stably Expressed Between Day 1 and Week 24

| Genes Increased But Not Significant ||| Genes Decreased But Not Significant |||
|---|---|---|---|---|---|
| Gene Symbol | Fold Change | Raw P Value | Gene Symbol | Fold Change | Raw P Value |
| SDF2L1 | 1.5827 | 0.8375 | TMEM158 | −1.6135 | 0.5804 |
| AIMP2 | 1.5808 | 0.0887 | IQGAP1 | −1.6109 | 0.5146 |
| TM7SF3 | 1.5639 | 0.0593 | SEZ6L2 | −1.6078 | 0.5077 |
| RAB30 | 1.547 | 0.4934 | PPP1R12A | −1.6055 | 0.4244 |
| TBC1D22A | 1.5369 | 0.448 | ZNF266 | −1.6029 | 0.1865 |
| SLMAP | 1.5335 | 0.2042 | MROH7 | −1.5865 | 0.7363 |
| ARFRP1 | 1.5193 | 0.0729 | BIN2 | −1.5796 | 0.6686 |
| TMEM170B | 1.5059 | 0.6892 | ZNF397 | −1.5785 | 0.3393 |
| PIGV | 1.505 | 0.4766 | FBXL4 | −1.5774 | 0.7773 |
| TRIM28 | 1.5043 | 0.274 | TRIM11 | −1.5759 | 0.2122 |
| INTS3 | 1.5041 | 0.0505 | GPR89B | −1.5544 | 0.8646 |
| LZTS1 | 1.5017 | 0.7977 | FEZ1 | −1.5533 | 0.8327 |
| CTF1 | 1.4977 | 0.8095 | HIVEP1 | −1.5526 | 0.3101 |
| UQCC2 | 1.4965 | 0.2955 | VWA5B2 | −1.5496 | 0.8079 |
| TRPM2 | 1.4962 | 0.3739 | DNAJA3 | −1.5487 | 0.5153 |
| REXO1 | 1.4924 | 0.4688 | YWHAZ | −1.5479 | 0.4545 |
| RNF180 | 1.4747 | 0.6686 | ZNF765 | −1.5444 | 0.3564 |
| NPAS3 | 1.4731 | 0.7784 | MED1 | −1.5396 | 0.0896 |
| C1orf74 | 1.4728 | 0.8286 | CAPG | −1.5363 | 0.1149 |
| AHRR | 1.465 | 0.7263 | CYP4V2 | −1.5251 | 0.1835 |
| MAN2C1 | 1.4567 | 0.0758 | PRKAA1 | −1.5203 | 0.7775 |
| EED | 1.4553 | 0.8591 | MRPL14 | −1.5169 | 0.4042 |
| PRKG1 | 1.4537 | 0.3739 | CCP110 | −1.5123 | 0.5009 |
| ITGB1 | 1.4492 | 0.4447 | SFMBT1 | −1.5056 | 0.2177 |
| PSME3 | 1.4428 | 0.4053 | PDLIM7 | −1.5018 | 0.7639 |
| ANKRD2 | 1.4367 | 0.9091 | IQCG | −1.4874 | 0.7796 |
| ARHGEF5 | 1.4325 | 0.2892 | PCCA | −1.4865 | 0.5448 |
| SKA1 | 1.428 | 0.6767 | BCL2L12 | −1.4692 | 0.7604 |
| RALBP1 | 1.4273 | 0.3882 | HNRNPK | −1.4474 | 0.2774 |
| CD2AP | 1.4177 | 0.1421 | MPLKIP | −1.441 | 0.4332 |
| DNMT3A | 1.4149 | 0.4164 | BUB3 | −1.4396 | 0.2793 |
| ZNF43 | 1.414 | 0.4897 | IFNAR1 | −1.4359 | 0.3819 |
| DCTN4 | 1.4113 | 0.4838 | SKAP2 | −1.4226 | 0.4894 |
| FAM96B | 1.4038 | 0.3508 | H2AFV | −1.4218 | 0.6944 |
| GLCCI1 | 1.3978 | 0.5703 | RNF148 | −1.4114 | 0.8068 |
| SRSF12 | 1.3959 | 0.8318 | METTL7A | −1.4017 | 0.2471 |
| PHF8 | 1.3895 | 0.4124 | GBP3 | −1.3999 | 0.5036 |
| MDM4 | 1.3893 | 0.3667 | XK | −1.3803 | 0.7933 |
| CD5 | 1.3884 | 0.853 | SAP18 | −1.3779 | 0.2244 |
| PDIA5 | 1.3863 | 0.8711 | ENOSF1 | −1.3736 | 0.3875 |
| WTAP | 1.3809 | 0.1579 | HINT1 | −1.3666 | 0.4126 |
| CAMK2D | 1.3749 | 0.1579 | GINS1 | −1.3548 | 0.7736 |
| PHLPP1 | 1.3741 | 0.7485 | CALU | −1.3433 | 0.1939 |
| GID4 | 1.3721 | 0.6957 | GLOD4 | −1.3325 | 0.5928 |
| ZNF133 | 1.372 | 0.5126 | OVCH2 | −1.3293 | 0.8758 |
| CNNM3 | 1.3706 | 0.2288 | GORAB | −1.3221 | 0.8934 |
| TMEM70 | 1.3609 | 0.3956 | C11orf49 | −1.3125 | 0.3291 |
| AVPR1A | 1.3591 | 0.3739 | DNAJC13 | −1.3096 | 0.4011 |
| LZTS2 | 1.3571 | 0.4819 | SLIT3 | −1.3076 | 0.4018 |
| KMT2C | 1.3569 | 0.3679 | RDH11 | −1.3014 | 0.602 |
| TGIF2 | 1.3531 | 0.8395 | KCNJ1 | −1.2995 | 0.8641 |
| ARL13B | 1.3521 | 0.1725 | BIRC2 | −1.2987 | 0.3168 |
| FAXC | 1.3426 | 0.8393 | PEX26 | −1.2922 | 0.7017 |
| AKAP10 | 1.319 | 0.5513 | TMED7 | −1.2914 | 0.0691 |
| CD2BP2 | 1.3178 | 0.6314 | HCFC2 | −1.2816 | 0.6402 |
| ACAN | 1.3116 | 0.3739 | SPEN | −1.2785 | 0.4115 |
| CACNA1F | 1.3099 | 0.8943 | RAB11FIP2 | −1.2759 | 0.5278 |
| IL17B | 1.305 | 0.9142 | ZNF865 | −1.267 | 0.5754 |
| VPS33A | 1.2993 | 0.4692 | CLASRP | −1.2664 | 0.1703 |
| BBS9 | 1.2922 | 0.6281 | PLCE1 | −1.2662 | 0.6246 |
| STK16 | 1.2893 | 0.5004 | MRPL33 | −1.257 | 0.6843 |
| FAM219A | 1.2855 | 0.6483 | FLOT2 | −1.2564 | 0.6178 |
| SPTLC1 | 1.2852 | 0.3364 | ZNF780A | −1.2522 | 0.7068 |
| PAF1 | 1.2823 | 0.4648 | DCAF17 | −1.2447 | 0.718 |
| RNF41 | 1.2814 | 0.7961 | ALKBH3 | −1.2358 | 0.6155 |
| RNASEH1 | 1.2812 | 0.4092 | LSAMP | −1.2332 | 0.8476 |
| IKZF5 | 1.2766 | 0.1381 | IPO8 | −1.2249 | 0.5669 |
| C12orf29 | 1.2735 | 0.4177 | RPS6KB1 | −1.2148 | 0.5212 |

TABLE 19-continued

Genes Stably Expressed Between Day 1 and Week 24

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| RAB22A | 1.2722 | 0.3945 | ZSCAN1 | −1.2134 | 0.9296 |
| RFNG | 1.2708 | 0.6642 | C11orf57 | −1.2087 | 0.4954 |
| DDB1 | 1.2706 | 0.1924 | IMMT | −1.2053 | 0.6593 |
| INO80D | 1.2508 | 0.4856 | ABCA2 | −1.2051 | 0.7005 |
| TARDBP | 1.2486 | 0.1398 | CNOT7 | −1.1995 | 0.5429 |
| PRPF18 | 1.2444 | 0.2087 | MCFD2 | −1.1991 | 0.6668 |
| APOBEC3G | 1.2442 | 0.7607 | SH3BGR | −1.1988 | 0.9125 |
| PPIAL4G | 1.2426 | 0.8817 | ASAH1 | −1.1987 | 0.5587 |
| MEA1 | 1.2345 | 0.6167 | NHSL2 | −1.1949 | 0.7177 |
| ST6GALNAC6 | 1.2293 | 0.4843 | C1QL1 | −1.1899 | 0.9282 |
| TRIM66 | 1.2138 | 0.2418 | PMF1 | −1.1896 | 0.7797 |
| CGGBP1 | 1.2061 | 0.275 | PLXNA3 | −1.1891 | 0.6238 |
| UBTF | 1.2001 | 0.5212 | FBXO48 | −1.185 | 0.8748 |
| RUFY1 | 1.1823 | 0.515 | CCDC117 | −1.1845 | 0.5684 |
| ANKHD1 | 1.1809 | 0.591 | PMPCB | −1.1787 | 0.5688 |
| SLC25A44 | 1.1757 | 0.6893 | PALD1 | −1.1739 | 0.6174 |
| MAPK7 | 1.1678 | 0.6886 | PAFAH1B2 | −1.1689 | 0.7234 |
| NMRK1 | 1.1673 | 0.6635 | TAF1L | −1.1551 | 0.919 |
| LDHAL6A | 1.145 | 0.7744 | PRPF4 | −1.1498 | 0.6006 |
| SLFN12 | 1.1371 | 0.9183 | SMC1A | −1.1481 | 0.5563 |
| SMIM5 | 1.1305 | 0.765 | ZNF638 | −1.1466 | 0.5843 |
| DCXR | 1.1294 | 0.7353 | DENND1A | −1.1447 | 0.7931 |
| TRIP11 | 1.1237 | 0.2552 | SDCCAG8 | −1.143 | 0.7603 |
| SHCBP1 | 1.1225 | 0.3253 | KDM5A | −1.1363 | 0.3314 |
| IGFN1 | 1.1199 | 0.8295 | TGOLN2 | −1.1327 | 0.5785 |
| CAB39L | 1.1072 | 0.8469 | TAOK3 | −1.104 | 0.6469 |
| SRC | 1.1072 | 0.5551 | TRA2A | −1.101 | 0.2225 |
| FOXO1 | 1.1054 | 0.6213 | ZNF444 | −1.1002 | 0.8229 |
| TANK | 1.1047 | 0.7836 | CNTN4 | −1.0998 | 0.7783 |
| ZNF787 | 1.0984 | 0.5444 | ARID2 | −1.0958 | 0.8084 |
| DLEU1 | 1.096 | 0.9565 | OXSR1 | −1.0947 | 0.5115 |
| HMMR | 1.0897 | 0.3739 | PAPD4 | −1.0946 | 0.7857 |
| EXOC5 | 1.0815 | 0.8585 | ANKS1A | −1.0933 | 0.5991 |
| AVL9 | 1.074 | 0.5527 | SAR1A | −1.0872 | 0.7106 |
| TBC1D8B | 1.0706 | 0.8034 | DNAJC8 | −1.0817 | 0.709 |
| ATP5E | 1.0675 | 0.8835 | FAM50A | −1.0776 | 0.7436 |
| ACBD6 | 1.0629 | 0.892 | MEF2A | −1.0722 | 0.732 |
| PCNXL4 | 1.0628 | 0.7428 | SWAP70 | −1.0719 | 0.8245 |
| EDC4 | 1.0599 | 0.9017 | FBXO25 | −1.0697 | 0.8649 |
| RAB3IL1 | 1.0581 | 0.3739 | HMGCL | −1.0684 | 0.8143 |
| WDR33 | 1.0578 | 0.7285 | EDARADD | −1.0652 | 0.3739 |
| TAS1R3 | 1.0521 | 0.9485 | DCAF15 | −1.0498 | 0.8502 |
| ARID3B | 1.0478 | 0.9345 | NBAS | −1.0482 | 0.8536 |
| BRAT1 | 1.0445 | 0.9268 | OR10A4 | −1.0478 | 0.9812 |
| PRR21 | 1.0425 | 0.9631 | MZF1 | −1.0398 | 0.9022 |
| FHL2 | 1.0395 | 0.9208 | COX7A2 | −1.0389 | 0.9275 |
| LRP11 | 1.0388 | 0.8197 | TMEM208 | −1.0371 | 0.9409 |
| REXO2 | 1.0385 | 0.8612 | SERINC1 | −1.0329 | 0.8602 |
| EIF2AK4 | 1.0361 | 0.9097 | C3orf58 | −1.0285 | 0.9443 |
| ATP11B | 1.0356 | 0.8862 | CPSF2 | −1.0267 | 0.9367 |
| CDK16 | 1.0342 | 0.6506 | POLR2E | −1.0177 | 0.9419 |
| MOAP1 | 1.0256 | 0.9396 | RNF20 | −1.0155 | 0.9624 |
| RFC4 | 1.0201 | 0.9903 | CSAG1 | −1.0119 | 0.9945 |
| ZNRF1 | 1.0196 | 0.9534 | C9orf64 | −1.0033 | 0.9978 |
| CHMP6 | 1.0111 | 0.9771 | | | |

Example 9: Identification of Genes that Predict Responsiveness to Treatment with Ruxolitinib Robust drug response genomic signatures were identified by selecting biomarkers from the RNA-Seq data in Examples 7 and 8. Specifically, baseline genes were selected from Example 7 if there was an absolute fold change greater than 2.0 and p<0.05 between the expression in responders and non-responders. The resulting genes were further analyzed to select those genes that were not significantly (less than absolute fold change of 1.5 and p>0.05) modulated between baseline and week 24. Table 20 illustrates the genes that met this criteria.

TABLE 20

Genes Differentially Expressed in the Skin Biopsies of Responders Compared to Non-Responders and not Significantly Modulated Between Baseline and Week 24

| Increased in Responders at Baseline | Increased in Non-Responders at Baseline |
|---|---|
| OVCH2 | SLFN12 |
| ANKRD2 | DLEU1 |
| KCNJ1 | EDARADD |
| TAS1R3 | SH3BGR |

TABLE 20-continued

Genes Differentially Expressed in the Skin Biopsies
of Responders Compared to Non-Responders and not Significantly
Modulated Between Baseline and Week 24

| Increased in Responders at Baseline | Increased in Non-Responders at Baseline |
|---|---|
| PPIAL4G | IGFN1 |
| ZSCAN1 | APOBEC3G |
| CACNA1F | TRPM2 |
| IL17B | RNF148 |
| C1QL1 | HMMR |
| OR10A4 | SKA1 |
| TAF1L | AHRR |
| STK16 | LDHAL6A |
| RFNG | SHCBP1 |
| CSAG1 | GBP3 |
| PRR21 | RFC4 |
| NHSL2 | CTF1 |
| ZNF787 | RAB3IL1 |
| ZNRF1 | GINS1 |
| PALD1 | CD5 |
| ZNF444 | PRKG1 |
| FAM219A | SRSF12 |
| TMEM208 | FAXC |
| NMRK1 | PDIA5 |
| ARID3B | TGIF2 |
| MPLKIP | EED |
| CAB39L | GORAB |
| ALKBH3 | NPAS3 |
| PLCE1 | AVPR1A |
| C12orf29 | C9orf64 |
| LSAMP | C1orf74 |
| SMIM5 | ACAN |
| UQCC2 | RNF180 |
| FAM96B | BCL2L12 |
| GID4 | XK |
| AKAP10 | IQCG |
| HMGCL | ZNF43 |
| C11orf49 | |

Example 10: Identification of Genes Differentially Expressed in Patients with Vitiligo that are Responders to Treatment with Ruxolitinib Cream Using non-invasive skin tape, skin tissue was collected from one hundred and twenty-three subjects with vitiligo enrolled in a study of ruxolitinib cream (INCB018424) for the treatment of subjects with a clinical diagnosis of vitiligo, depigmented areas including at least 0.5% of the total body surface area on the face, and at least 3% of the total body surface area on nonfacial areas affected using the palmar (or handprint) method (palm plus 5 digits). All subjects consented to the skin tissue collection and met the inclusion and exclusion criteria outlined in the clinical protocol. Once collected, skin tissue was processed from the non-invasive skin tape into ribonucleic acid (RNA) for further analysis and subsequently analyzed using RNA sequencing. Samples were separated into to two groups based on clinical response to treatment with topical INCB018424. Specifically, samples were classified as "responder" (alternatively referred to as "early responder") or "non-responder" (alternatively referred to as "late responder") based on their therapeutic response at Week 24 of treatment ("F-VASI" refers to facial-vitiligo area and severity index). Individuals were topically applied INCB018424 either once or twice daily at dose strengths of 0.15%, 0.5%, or 1.5%. Twice daily applications were at least 10 hours apart in a cream formulation.

One hundred and twenty-six genes were identified from Examples 7 and 8 and evaluated in RNA from each subject using the Illumina HiSeq 4000 system. See Table 21. Data was then aligned and quality controlled in OmicSoft Array Studio using the Human Genome B38 library. The Fragments Per Kilobase of transcript per Million (FPKM) mapped reads (the relative expression of a transcript) were generated and used in all downstream analysis.

TABLE 21

Targeted Analysis of 126 Genes

| ACAN | CAB39L | EGF | IL17B | NHSL2 | S100A1 | XK |
|---|---|---|---|---|---|---|
| ACVR1C | CACNA1F | FAM219A | IL17RB | NMRK1 | SELPLG | ZNF43 |
| ADAM21 | CCNI2 | FAM96B | IL23 | NPAS3 | SerpinF1 | ZNF444 |
| ADAMTS13 | CCR4 | FAXC | IL1RL1 | OR10A4 | SH3BGR | ZNF787 |
| AHRR | CCR5 | GBP3 | IL-1RL2 | OVCH2 | SHCBP1 | ZNRF1 |
| AKAP10 | CD28 | GID4 | IL32 | PALD1 | SKA1 | ZSCAN1 |
| ALKBH3 | CD3E | GINS1 | IL36A | PCDHB5 | SLFN12 | |
| ALPK3 | CD5 | GORAB | IL4I1 | PDIA5 | SMIM5 | |
| ANKRD2 | CNTF | GPR61 | IQCG | PDE9A | SOCS5 | |
| APOBEC3G | CSAG1 | GPR89B | KCNJ1 | PI3KCG | SRSF12 | |
| ARID3B | CTF1 | HLA-DQB2 | KRT16 | PLCE1 | STK16 | |
| AurKA | CXCL9 | HMGCL | KRT33A | PPIAL4G | TAF1L | |
| AVPR1A | CXCL10 | HMMR | LDHAL6A | PRKG1 | TAS1R3 | |
| BCL2L12 | CXCL11 | IFI6 | LSAMP | PRR21 | TBC1D3 | |
| BCL7B | CXCL8 | IFNA | MAKPK12 | PTPN22 | TGIF2 | |
| C11orf49 | CXCR4 | IFNB | MMP25 | RAB3IL1 | TICAM2 | |
| C12orf29 | dkk2 | IFNG | MMP28 | RFC4 | TMEM208 | |
| C1orf74 | DLEU1 | IGFN1 | MPLKIP | RFNG | TNFAIP8L1 | |
| C1QL1 | EDARADD | IL15 | MT1E | RNF148 | TRPM2 | |
| C9orf64 | EED | IL17A | NLRP1 | RNF180 | UQCC2 | |

RNA samples that did not have measureable gene expression in any of the 126 genes outlined in Table 21 were removed from further analysis. A total of 52 baseline RNA samples were available for analysis with 27 early responders and 25 late responders across the three treatment arms (0.5% QD, 1.5% BID, 1.5% QD). Twenty-five genes were increased and 11 genes were decreased at baseline in responders compared to non-responders (Table 22).

TABLE 22

Differentially Expressed Genes in the Skin Biopsies of Responders Compared to Non-Responders

| Up-regulated in Responders vs. Non-Responders at Baseline | | | Down-regulated in Responders vs. Non-Responders at Baseline | | |
|---|---|---|---|---|---|
| Gene Symbol | Fold Change | Raw P-value | Gene Symbol | Fold Change | Raw P-value |
| PPIAL4G | 2.946 | 0.0015 | STK16 | −16.642 | 1.19E−06 |
| CD5 | 2.7957 | 0.013 | RFNG | −9.1603 | 4.34E−05 |
| IFI6 | 2.2036 | 0.0803 | ZNRF1 | −8.1509 | 0.0002 |
| CCR4 | 1.7699 | 0.0093 | ARID3B | −7.1425 | 0.0012 |
| CNTF | 1.5962 | 0.0103 | WSB2 | −5.7202 | 0.0057 |
| CD28 | 1.5816 | 0.0652 | JAK1 | −4.9886 | 0.0131 |
| RAB3IL1 | 1.5178 | 0.0134 | IL1RL2 | −3.3798 | 0.0063 |
| C1QL1 | 1.4941 | 0.0808 | PALD1 | −3.2885 | 0.0274 |
| VCAM1 | 1.4707 | 0.0378 | S100A1 | −2.5712 | 0.0829 |
| ACAN | 1.4153 | 0.0471 | BCL2L12 | −2.2394 | 0.0716 |
| ETS1 | 1.4103 | 0.0668 | FAM219A | −1.796 | 0.0975 |
| GPR61 | 1.4101 | 0.0566 | TSHZ1 | −1.6083 | 0.0705 |
| IFNG | 1.3952 | 0.0597 | | | |
| KCNJ1 | 1.3898 | 0.0674 | | | |
| PDE9A | 1.3878 | 0.0532 | | | |
| NPAS3 | 1.3709 | 0.0801 | | | |
| AVPR1A | 1.3704 | 0.0677 | | | |
| PRKG1 | 1.3694 | 0.0653 | | | |
| CSAG1 | 1.3646 | 0.0876 | | | |
| APOBEC3G | 1.3633 | 0.0676 | | | |
| LDHAL6A | 1.3522 | 0.0993 | | | |
| ZSCAN1 | 1.3521 | 0.0993 | | | |
| HMMR | 1.3416 | 0.0991 | | | |
| IL15 | 1.3367 | 0.0739 | | | |
| SHCBP1 | 1.3109 | 0.099 | | | |

What is claimed is:

1. A method of treating a human subject having, suspected of having, or at risk of developing vitiligo, comprising:
   measuring in a biological sample obtained from the human subject a reduced concentration, as compared to a control, of at least one protein selected from the group consisting of SCF, CPA2, P4HB, SPARCL1, ST2, SCF, CNDP1, TRAIL, KIRREL2, EGFR, ISLR2, PPP3R1, FCGR3B, MMP-3, IL-18BP, Flt3L, PPY, LTA4H, ITGB2, PTN, GPNMB, SIRPB1, PLTP, PSP-D, COMP, PAMR1, VASN, F11, IL10, CA3, CXCL10, Notch 3, NCAM1, PROC, CLEC14A, IL-12B, IL10, CD40, and IFN-gamma, and/or an increased concentration, as compared to a control, of at least one protein selected from the group consisting of SERPINA12, GHRL, PREB, IL-20RA, and PON2; and
   administering a JAK inhibitor to the human subject;
   wherein the JAK inhibitor is ruxolitinib, or a pharmaceutically acceptable salt thereof.

2. The method of claim 1, wherein the JAK inhibitor is administered to the human subject at least once a day for a period of at least 12 weeks.

3. The method of claim 1, wherein the JAK inhibitor is administered to the human subject at least two times each day for a period of at least 12 weeks.

4. The method of claim 1, wherein the JAK inhibitor is topically administered to the human subject.

5. The method of claim 1, wherein ruxolitinib is topically administered to the human subject in a cream comprising at least 0.15% ruxolitinib.

6. The method of claim 1, wherein ruxolitinib is topically administered to the human subject in a cream comprising at least 1.5% ruxolitinib.

7. The method of claim 1, wherein ruxolitinib is topically administered to the human subject in a cream comprising 1.5% ruxolitinib.

8. The method of claim 1, wherein ruxolitinib is topically administered to the human subject at least two times each day in a cream comprising 1.5% ruxolitinib.

\* \* \* \* \*